(12) United States Patent
Lum et al.

(10) Patent No.: US 7,763,243 B2
(45) Date of Patent: Jul. 27, 2010

(54) IN SITU IMMUNIZATION

(75) Inventors: Lawrence G. Lum, Coventry, RI (US); Gerald Elfenbein, Franklin, MA (US)

(73) Assignee: Roger Williams Medical Center, Providence, RI (US)

( * ) Notice: Subject to any disclaimer, the term of this patent is extended or adjusted under 35 U.S.C. 154(b) by 1504 days.

(21) Appl. No.: 10/222,960

(22) Filed: Aug. 16, 2002

(65) Prior Publication Data

US 2003/0185823 A1 Oct. 2, 2003

Related U.S. Application Data

(60) Provisional application No. 60/313,164, filed on Aug. 17, 2001.

(51) Int. Cl.
*A61K 35/12* (2006.01)
*A61K 39/44* (2006.01)

(52) U.S. Cl. .................................. 424/93.71; 424/178.1

(58) Field of Classification Search ........................ None
See application file for complete search history.

(56) References Cited

U.S. PATENT DOCUMENTS

2002/0146396 A1* 10/2002 Albert et al. ............. 424/93.21
2003/0082194 A1* 5/2003 Gaiger et al. ............ 424/184.1

FOREIGN PATENT DOCUMENTS

| JP | 11-511746 | 12/1999 |
|----|-----------|---------|
| WO | WO 88/03565 | 5/1988 |
| WO | WO 96/37208 | 11/1996 |
| WO | WO 97/29183 | 8/1997 |
| WO | WO 00/78348 A1 | 12/2000 |

OTHER PUBLICATIONS

Sad et al, Journal of Experimental Medicine, 1995, vol. 182, pp. 1505-1515.*
Abstract of Wheeler (Salud p'ublica de M'exico, (Jul.-Aug. 1997) 39 (4) 283-7).*
Efferson et al (Anticancer research, 2005, vol. 25, pp. 715-724).*
Bachman et al (Journal of Immunology, 2005, vol. 175, pp. 4677-4685).*
Sen et al (Journal of Hematotherapy & Stem Cell Research, Apr. 10, 2001).*
Reese et al (Stem Cells, 1997, vol. 15, pp. 1-8).*
Van Gool et al (Journal of Experimental Medicine, 1994, vol. 179, pp. 715-720).*
Uberti et al (Clinical Immunology and Immunopathology, 1994 vol. 70, pp. 234-240).*
Abstract of Trevor et al (Tumor Targeting, 2000 vol. 4, pp. 245-256).*
Hoffman et al (International Journal of Cancer, 2005, vol. 115, pp. 98-104).*
Manzke et al (Int J of Cancer, 2001, vol, 91, pp. 508-515.).*

Lamers et al., "Optimization of Culture Conditions for Activation and Large-Scale Expansion of Human T Lymphocytes for Bispecific Antibody-Directed Cellular Immunotherapy" Int. J. Cancer 51: 973-979 (1992).
Canevari et al., "Bispecific Antibody Targeted T Cell Therapy of Ovarian Cancer: Clinical Results and Future Directions" J. Hematother. 4:423-427 (1995).
Canevari et al., "Regression of Advanced Ovarian Carcinoma by intraperitoneal Treatment With Autologous T Lymphocytes Retargeted by a Bispecific Monoclonal Antibody" J. Natl. Cancer Inst. 87: 1463-1469 (1995).
Bolhuis et al., "Adoptive Immunotherapy of Ovarian Carcinoma with BS-Mab-Targeted Lymphocytes: A Multicenter Study" Int. J. Cancer Supp. 7, 78-81 (1992).
M. Fanger et al., Bispecific Antibodies,*Critical Reviews in Immunology*, 12(3,4):101-124 (1992).
P. Dong et al, *Vaccine Design: The Subunit and Adjuvant Approach*, Chapter 27, pp. 625-643, 1995.
M. Shalaby et al., Development of Humanized Bispecific Antibodies Reactive with Cytotoxic Lymphocytes and Tumor Cells Overexpressing the HER2 Protooncogene, *J. Exp. Med.*, vol. 175, pp. 217-225, 1992.
R. Koelemij et al., Administration of BiMAb-Retargeted T Cells in a Rat Hepatic Metastases Colon Tumour Model Results in T.Cell Tumour Infiltration Independent of the Route of Administration, *Scan d. J. Immunol.* 53, 277-281, 2001.

(Continued)

*Primary Examiner*—Karen A Canella
(74) *Attorney, Agent, or Firm*—Townsend and Townsend and Crew LLP

(57) ABSTRACT

The arming of activated T cells (ATC) with BiAbs can overcome major barriers for successful adoptive immunotherapy. The BiAb approach takes the advantage of the targeting specificity of monoclonal antibodies and the cytotoxic capacity of T cells to lyse tumors. Arming of ATC with BiAb makes every T cell an antigen-specific CTL and infusions of such cells will markedly increase the effective precursor frequency of CTL in the cancer patient. Furthermore, the ability of such armed ATC to kill multiple times without rearming with BiAb, secrete tumoricidal cytokines, secrete chemokines, and survive in patients for up to 8 days after the last infusion or in Beige/SCID mice for over 13 weeks after cessation of treatment. The persistence of cells in the Beige/SCID after infusion show long-term survival capability in the host. Restimulation of armed ATC after 3 cycles of cytotoxicity with tumor cells resulted in the secretion of interferon gamma indicating the development of tumor specific immune responses in the population of cells that have been exposed multiple times to antigen. In summary, armed ATC can act as a cytotoxic "drug", kill multiple times (direct killing), divide after killing (increasing the effector:target ratio in vivo), secrete tumoricidal cytokines (indirectly killing), secrete chemokines at the tumor site (recruit naïve T cells and antigen-presenting cells to immunize the patient to tumor lysate) and persist in patients and animal models for weeks to months (long-term survival).

81 Claims, 53 Drawing Sheets

OTHER PUBLICATIONS

H. Bohlen et al., Lysis of Malignant B Cells From Patients With B-Chronic Lymphocytic Leukemia by Autologous T Cells Activated With CD3×CD19 Bispecific Antibodies in Combination With Bivalent CD28 Antibodies, *Blood*, vol. 82, No. 6, pp. 1803-1812, 1993.

M. Brandl et al., Bispecific antibody fragments with CD20×CD28 specificity allow effective autologous and allogeneic T-cell activation against malignant cells in peripheral blood and bone marrow cultures from patents with B-cell lineage leukemia and lymphoma, *Experimental Hematology 27*, pp. 1264-1270, 1999.

Lum, Lawrence G., et al., "Activated T-Cell and Bispecific Antibody Immunotherapy for High-Risk Breasts Cancer," Acta Haematol 2001, vol. 105, pp. 130-136.

Lawrence G. Lum, et al.; "Activated T-Cell and Bispecific Antibody Immunotherapy for High-Risk Breast Cancer"; Acta Haematol; 2001; vol. 105; pp. 130-136.

Cor H. J. Lamers et al.; "Local But No Systemic Immunomodulation by Intraperitoneal Treatment of Advanced Ovarian Cancer with Autologous T Lymphocytes Re-Targeted by a Bi-specific Monoclonal Antibody"; Int. J. Cancer; vol. 73; (1997); pp. 211-219.

Shalaby, M.R. et al., "Bispecific HER2×CD3 Antibodies Enhance T-Cell Cytotocicity in Vitro and Localize to HER2-Overexpresssing Xenografts in Nude Mice," Clinical Immunology and Immunopatholgy, vol. 74, No. 2, (1995) pp. 185-192.

Staerz, U.D. et al. "Hybrid antibodies can target sites for attack by T cells," Nature, vol. 314, No. 6012, (1985) pp. 628-631.

* cited by examiner

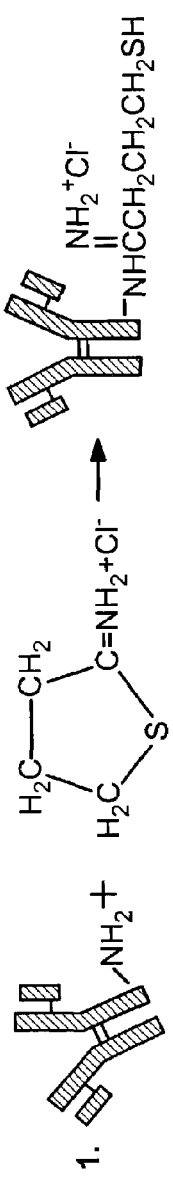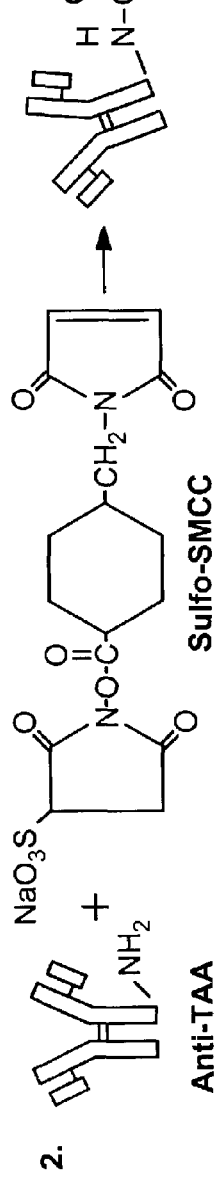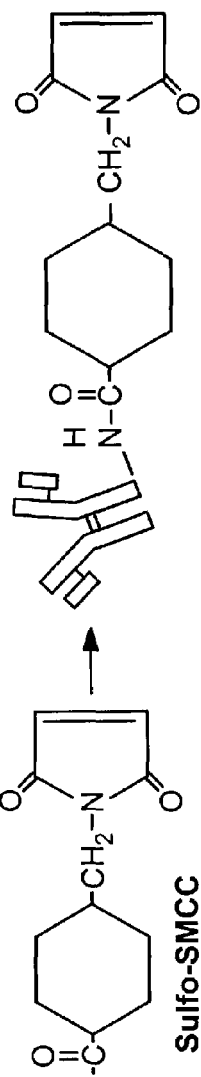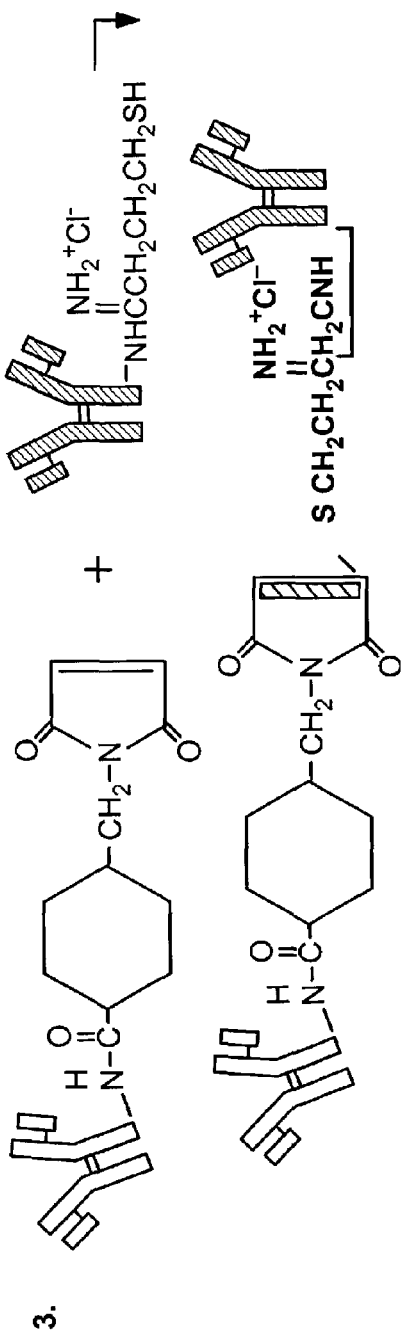
FIG. 1

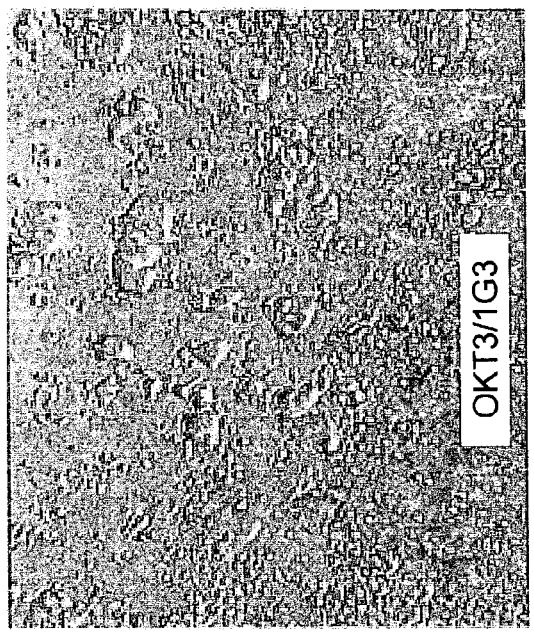
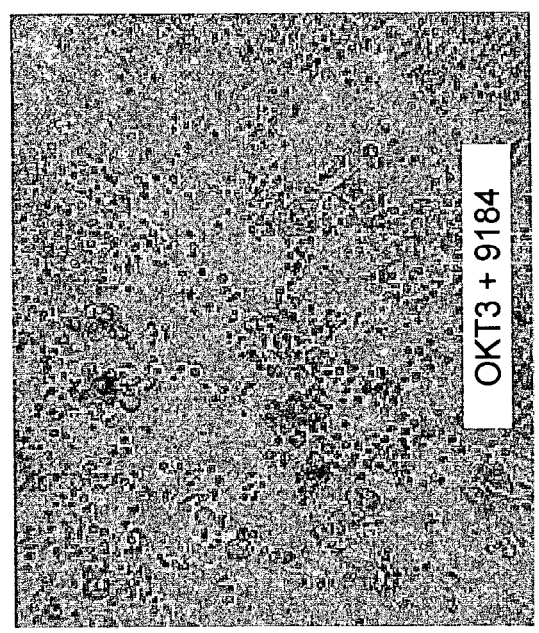
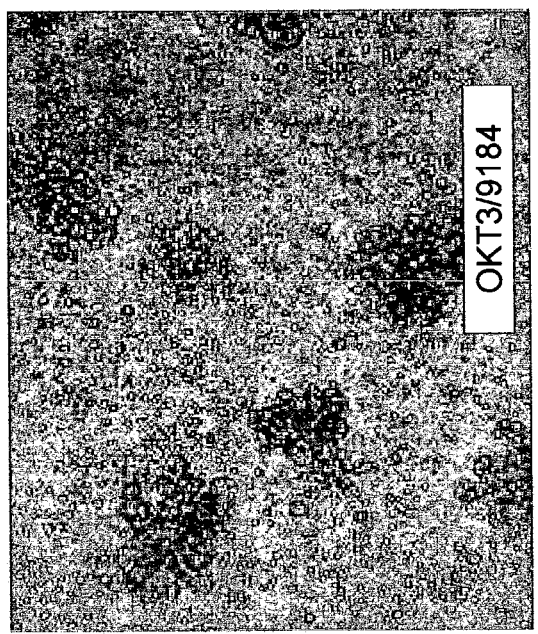
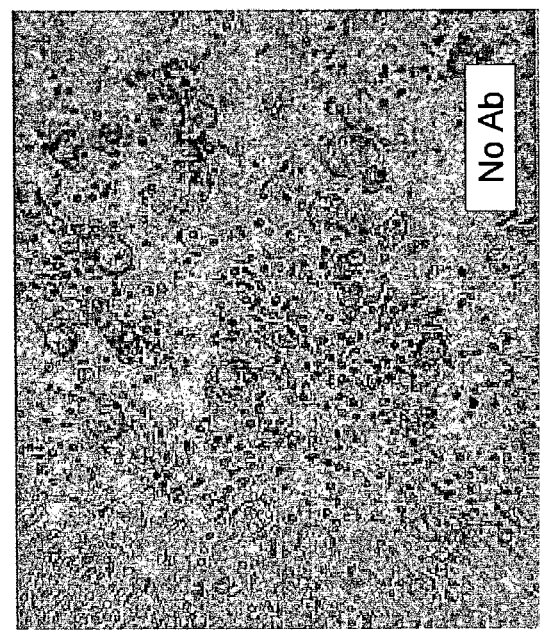
FIG. 3

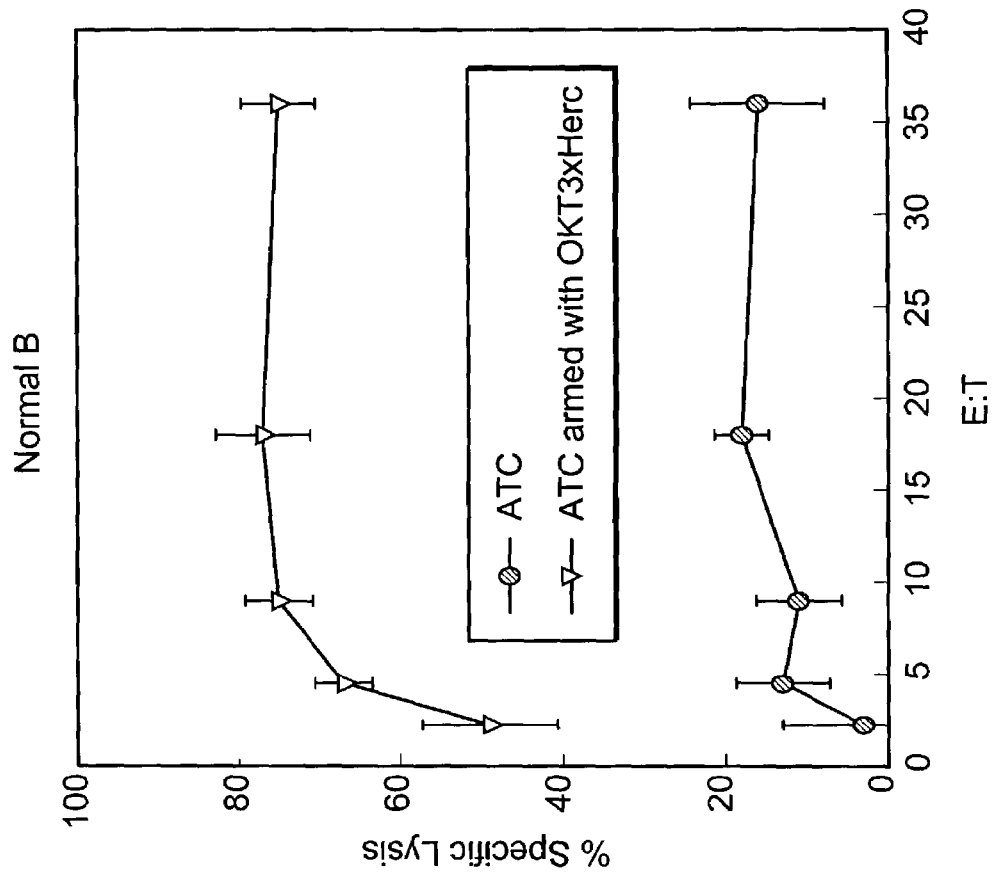
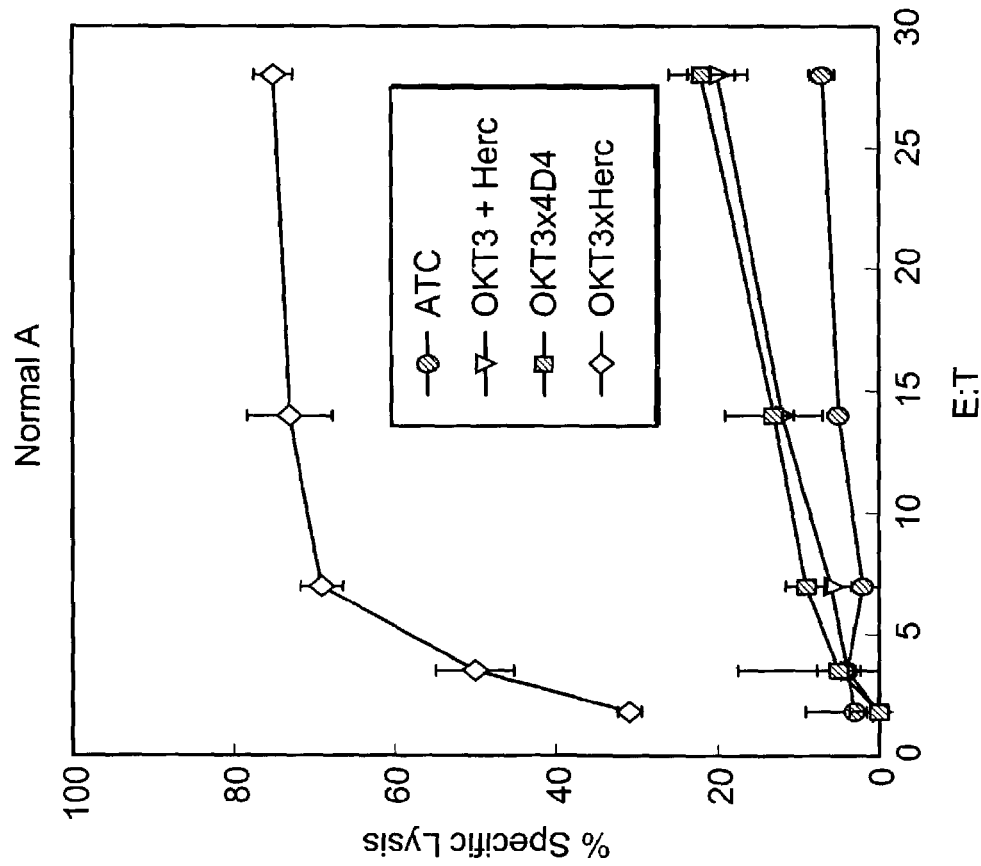
FIG. 17B
FIG. 17A

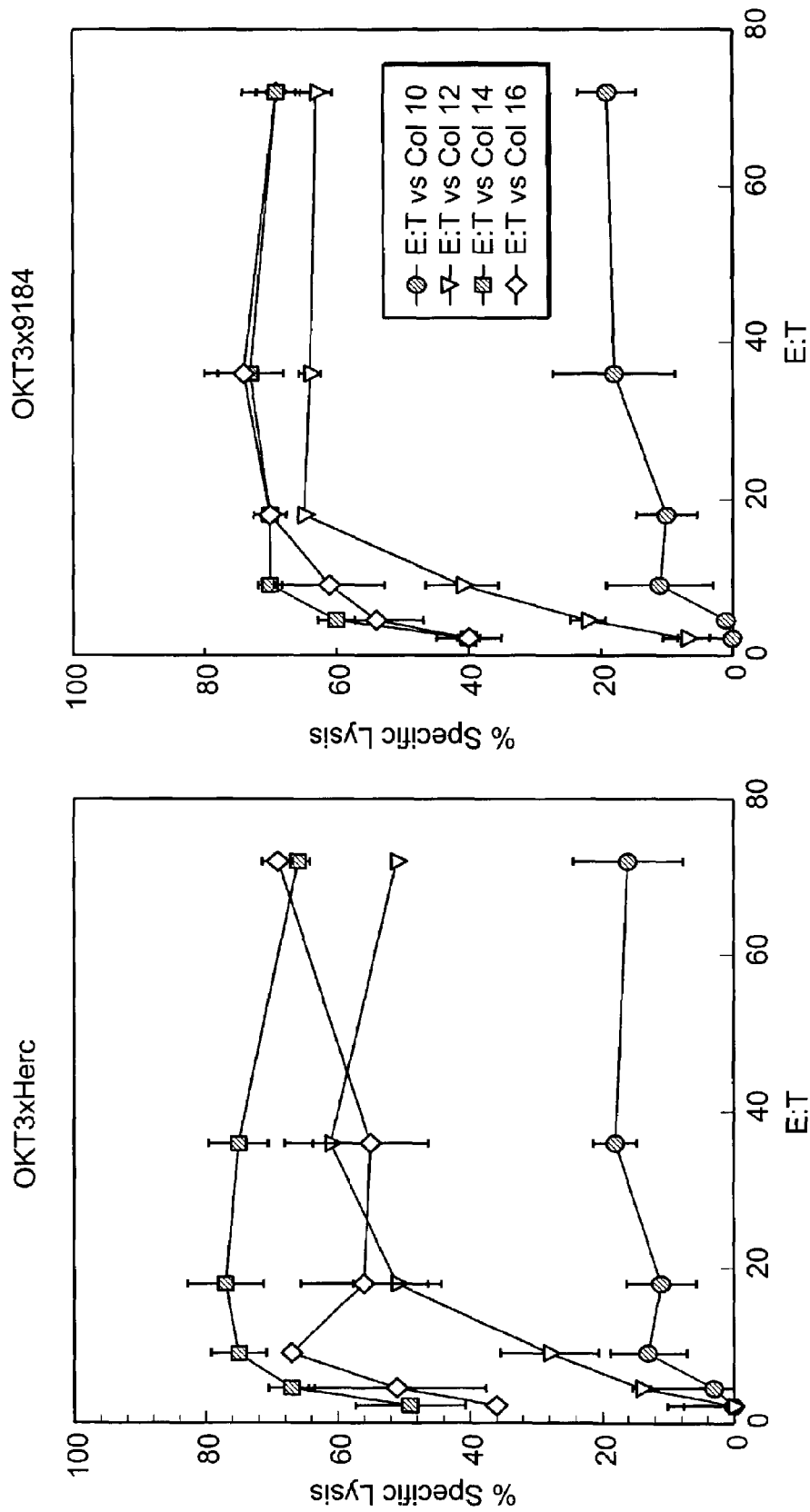

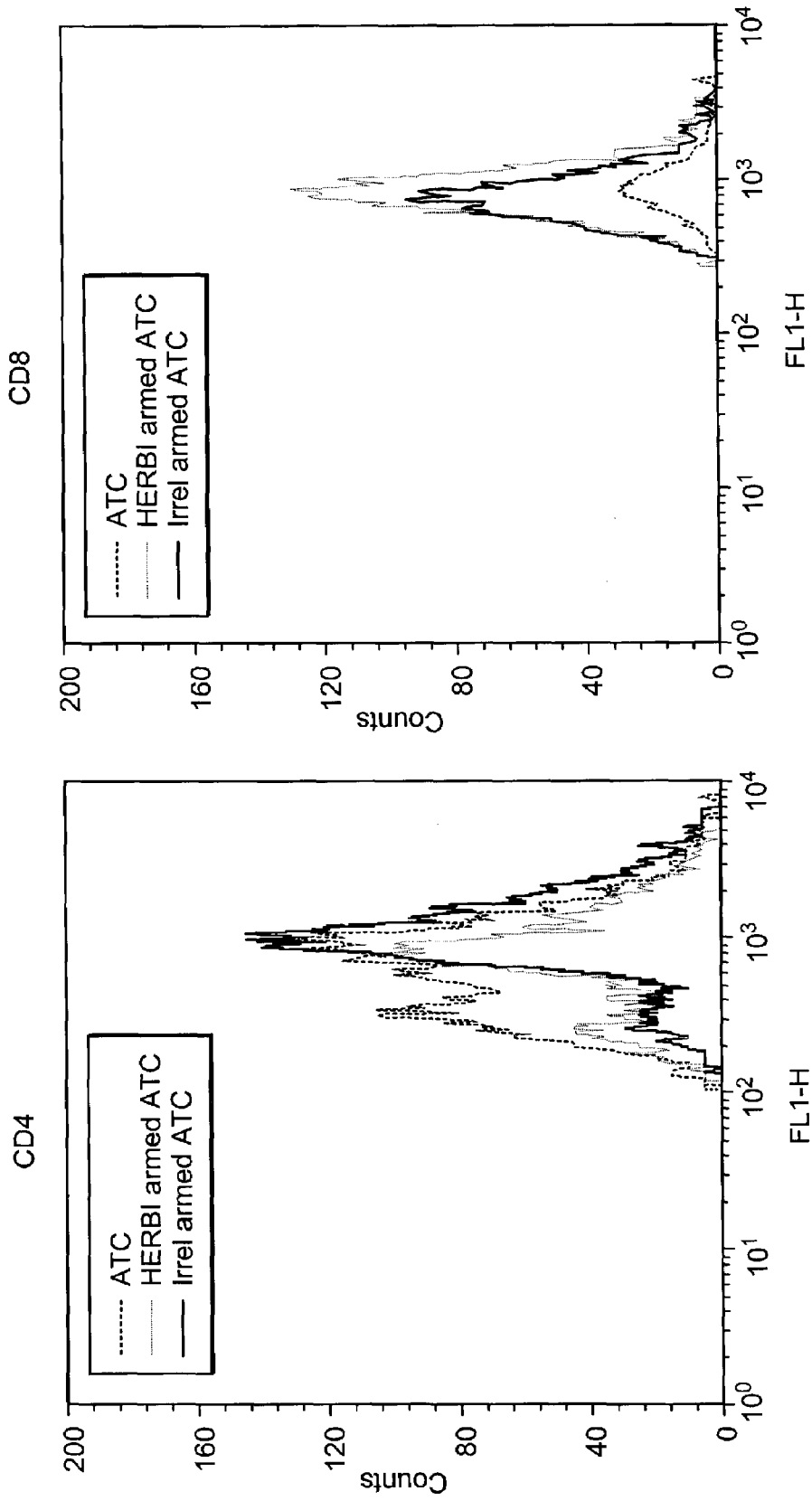

IN SITU IMMUNIZATION

This application claims priority to U.S. Provisional Application Ser. No. 60/313,164 filed Aug. 17, 2001, the entirety of which is incorporated by reference herein.

BACKGROUND OF THE INVENTION

1. Field of the Invention

The present invention provides for compositions and methods for a T-cell based immunotherapy for malignancies or other disease characterized by abnormal cellular proliferation. In particular, the invention relates to in vivo activated T cells armed with chemically heteroconjugated bispecific monoclonal antibodies generated against tumor antigens. The invention provides for treatment using autologous, related HLA-identical, partially-related HLA-mismatched, or allogeneic T cells from patients diagnosed with such malignancies such as breast cancer, prostate cancer, renal tumors, or other malignancies, and the generation of antigen-specific long-term memory T cells. The advantages of the present invention are that antibodies can be generated against tumor specific antigens of choice, and the method uses the patient's autologous, activated T cells armed with the targeting specificity of the bispecific antibody for combating the tumor.

2. Background

With early detection, most malignancies can be treated by conventional surgery, chemotherapy, or radiotherapy. In contrast, it is nearly impossible for the immune system to reject bulky or metastatic disease. The challenge then is to identify antigen specific or non-specific systems that will improve clinical responses in the treatment of advanced cancers and hematologic malignancies.

The key challenge in immunotherapy is to induce the immune system of a cancer patient to make a specific immune response to autologous tumors. A few tumor-specific antigens, such as HER-2/neu, malignant melanoma, and p53 are well-characterized and are known to induce in vitro and in vivo specific immune responses. Although adoptively transferred T cells can eliminate or reduce lethal tumor burdens in animals, adapting this principle in humans has been problematic. Moreover, while dramatic clinical responses have been observed in some patients with renal cell carcinoma and malignant melanoma who received treatment with tumor infiltrating lymphocytes, the success of murine models did not translate into higher cure rates in large trials of patients with renal carcinoma and malignant melanoma.

Previous approaches taken included expansion of tumor infiltrating lymphocytes (TIL) that display cytotoxic activity directed at autologous tumor antigens using IL-2, and reinfusion of the TIL into patients with renal carcinoma (RCC) and metastatic melanoma (MM). TIL are $CD3^+$ cells that display activated natural killer cell (ANK) activity, but are more effective killers than ANK-on a per cell basis.[19] TIL have been reported to traffic to metastatic melanoma lesions.[20] Trials using TIL and high dose IL-2 in patients with advanced RCC, MM, and other advanced tumors have obtained clinical responses ranging from 13 to 60% with most reports ranging between 15-20%.[22-25] The higher responses may be due to differences in patient selection as well as laboratory processing differences.

However, this therapeutic approach has major drawbacks. One limitation of TIL therapy are the toxicities related to high dose IL-2 infusions which restrict the use of IL-2 in patients who have poor performance status.[26-28] The major toxicities of IL-2 are fluid gain and capillary leak leading to respiratory distress and hypotension often requiring vasopressor support and ICU monitoring.[26] Other side effects include fever, chills, malaise, diarrhea, increased creatinine, mental status changes, cardiac arrhythmias, and rashes.[27;28] Although high doses of TIL alone can be infused without toxicities,[29] the efficacy of TIL is thought to be linked to co-administration of high dose IL-2. Subsequent studies suggest that high dose IL-2 alone is equivalent to high dose IL-2 in combination with TIL therapy.

Another drawback to this approach is that the rate of positive clinical responses from the combination of TIL and high dose IL-2 is still unacceptably low. Unfortunately, the anti-tumor activity exhibited by TIL has not been a consistent observation in larger clinical series.[19] Therefore, new approaches to generate tumor specific CTL and methods to specifically target tumors are needed to improve clinical responses.

There is a need in the art to provide for immunotherapeutic approaches that need to include strategies that address the above issues and other issues.

SUMMARY OF THE INVENTION

The present invention combines the cytotoxic capability of T cells and the specificity of antibodies to augment the cytotoxic capacity of T cells to lyse tumor cells. The present invention further provides compositions and methods for treatment of tumors on an individual patient basis by arming activated autologous T cells with bispecific antibodies specific for a certain tumor antigen. If the tumor antigen changes in a patient, the bispecific antibody used to arm the activated T cell can be replaced with a bispecific antibody that is specific for the new antigen. Furthermore, long term antigen-specific T cells are generated by the methods and compositions disclosed in the present invention.

The present invention is advantageous in that the arming of T cells with bispecific antibodies significantly increases the chances of overcoming some of the major barriers for successful adoptive immunotherapy, such as for example, tumor escape. This approach, increases the precursor frequency of CTL directed to specific tumors, and improves specific binding and enrichment of effector cells at the tumor site, as well as augmenting tumoricidal activity.

In general the invention provides for the arming of activated r cells (ATC) with a bispecific antibody (BiAb) which targets a tumor antigen. The present approach is advantageous in that it combines the specificity of the antibody directed at CD3 (T cell receptors, TCR) and a tumor antigen to augment the cytotoxic capacity of T cells to lyse, for example, $Her2^+$ prostate tumors. In this illustrative example, the BiAb bridge between the ATC and the $Her2^+$ target redirects the cytotoxicity of T cells to the Her2+ targets, while bypassing major histocompatibility restrictions. The present invention bypasses the toxic side effects of co-administered chemokines, such as IL-2, as ATC from normal subjects and cancer patients are first grown in low dose IL-2 (100 IU/ml) and then armed with the BiAb, for example, anti-CD3 x anti-Her2 (Her2Bi). These ATC target and kill $Her2^+$ breast, prostate, and pancreatic carcinoma cell lines. The invention also provides for immunotherapy (IT) comprising multiple infusions of bispecific antibody armed ATC, IL-2, and granulocyte-macrophage colony stimulating factor (GM-CSF).

Another major advantage of the present invention is that only nanogram amounts of bispecific antibodies are needed to produce the desired cytotoxic effect, because the cytotoxicity is very specifically directed and localized towards the tumor. Other advantages of the present invention are the use of autologous patient cells, thereby, avoiding any graft-versushost-reaction complications; reinfused cells can be washed so that there in no carry over of antibodies or cytokines; and bispecific antibodies can-be produced against an emergent new tumor antigen during the progression of the disease.

In a preferred embodiment, a patient suffering from cancer is treated according to the method of the invention which comprises the steps of isolating the patient's peripheral blood mononuclear cells. The patient's T cells are activated by ex vivo stimulation with either soluble anti-CD3 monoclonal antibody, or anti-CD3 and anti-CD28 monoclonal antibodies attached to a solid support. The activated T cells are expanded in the presence of about 100 IU/ml of IL-2. Once a suitable number of activated T cells is achieved, for example, between about 1-10 billion activated T cells, the T cells are armed with bispecific antibodies. The bispecific antibodies are capable of binding to the T cell receptor complex of a T cell, to tumor-associated antigens on a tumor cell, and to Fc-receptors of accessory cells via the Fe part of the antibody. The cytotoxic activity is tested in vitro against tumor cells and an appropriate arming dose of bispecific antibodies is determined, based on the cytotoxic activity. The patient is then reinfused with a composition of the autologous cells, which comprises the activated T cells armed with a bispecific antibody, immunocompetent naïve or mature T cells, immunocompetent naïve or mature B cells, and dendritic cells.

In another preferred embodiment the bispecific antibody is comprised of two monoclonal antibodies, chemically heteroconjugated to form the bispecific antibody, preferably in a 1:1 ratio. The preferred specificity of the bispecific antibody is for tumor antigens, for example $Her2^+$ and the T cell receptor complex. Most preferred T cell receptor antigens are the CD3 and CD28. In one aspect of the invention, the monoclonal antibodies forming the bispecific antibody are humanized monoclonal antibodies or are genetically engineered, using methods well known to one of skill in the art.

In another preferred embodiment, the autologous, activated T cells are armed with at least about 0.5 ng antibody per million T cells, more preferably at least about 10 ng antibody per million T cells, most preferably to at least about 100 ng antibody per million T cells. The arming dose, however, is optimized for each individual patient by titrating a frozen aliquot of the patients activated T cells to achieve a percent specific cytotoxicity level at an effector to target ratio of 25:1 of at least about 30% against a tumor target.

In another preferred embodiment, the infusing dose of armed T cells is preferably about 2 billion, more preferably about 10 billion, most preferably at least about 40 billion armed T cells. In one aspect of the invention, the patient receives at least about four infusions, more preferably about six infusions, most preferably at least about 10 infusions.

In another preferred embodiment the activated T cell is either CD3/CD8 positive and/or a CD3/CD4 positive cell. In one aspect of the invention the armed T cells from a patient can be co-administered with other forms of therapy. The autologous T cells can be transduced with vectors coding for chemokines thereby producing a high concentration of localized of chemokines. The invention is thus, also suitable for treating immunosuppressed patients.

In another preferred embodiment, patients which have been treated with ATC or COACT, induces immunological memory to the specific antigen recognized by the infused T cells. The memory T cells preferably exhibit a mature or secondary immune response so that the immune response is more rapid and more specific as compared to a naïve or primary immune response. Memory cells are easily identifiable, e.g. by flow cytometric analysis.

In another preferred embodiment, the ATC or COACT are able to carry out multiple cycles of tumor cell killing. That is, the same cell, can target and kill tumor cells more than once after infusion into the patient.

In another preferred embodiment, multiple exposure of the anti-CD3 activated polyclonal T cell population induces the development of antigen specific T cell clones, for example HER2/neu. Preferably, the induction of antigen specific clones directed at a specific tumor antigen allows for the maturation of the cellular response so as to induce the production of T cells that recognize antigens on the tumor that are yet undefined and unknown.

In another preferred embodiment, the ATC or COACT are infused into the patient in the absence of antigen presenting cells, for example, dendritic cells.

Other aspects of the invention are disclosed infra.

BRIEF DESCRIPTION OF DRAWINGS

FIG. 1 is a diagram illustrating the steps for heteroconjugating OKT3 with the anti-tumor associated antigen MAb (anti-TAA) (9184).

FIG. 3 shows an overnight culture, whereby, rosetting of ATC armed with Her2Bi with MCF-7 or PC-3 cells is shown.

FIG. 17 is a graph showing the ability of ATC from two normal subjects to lyse SK-BR-3 targets.

FIG. 18 is a graph showing the comparative arming doses between OKT3 x 9184 and OKT3 x Herc.

FIG. 22 summarizes data as spots/million armed ATC.

FIG. 28 shows the data for the normal (NL) and FIG. 29 shows the data for the patient (PT).

FIG. 36 are results from a flow cytometry assay showing the numbers of CFDA-SE+cells within the CD4 or CD8 subsets that had been armed with OKT3 x Herceptin, OKT3 x Rituxan, or left unarmed. CD4+ population showed evidence of cell division with a very distinct population of cells that had divided and showed reduce intensity whereas the CD4+ cells armed with OKT3 x Rituxan and unarmed ATC did not show as many cells that had divided and exhibited half as much staining intensity.

DETAILED DESCRIPTION OF THE INVENTION INCLUDING PREFERRED EMBODIMENTS THEREOF

Figure 2:
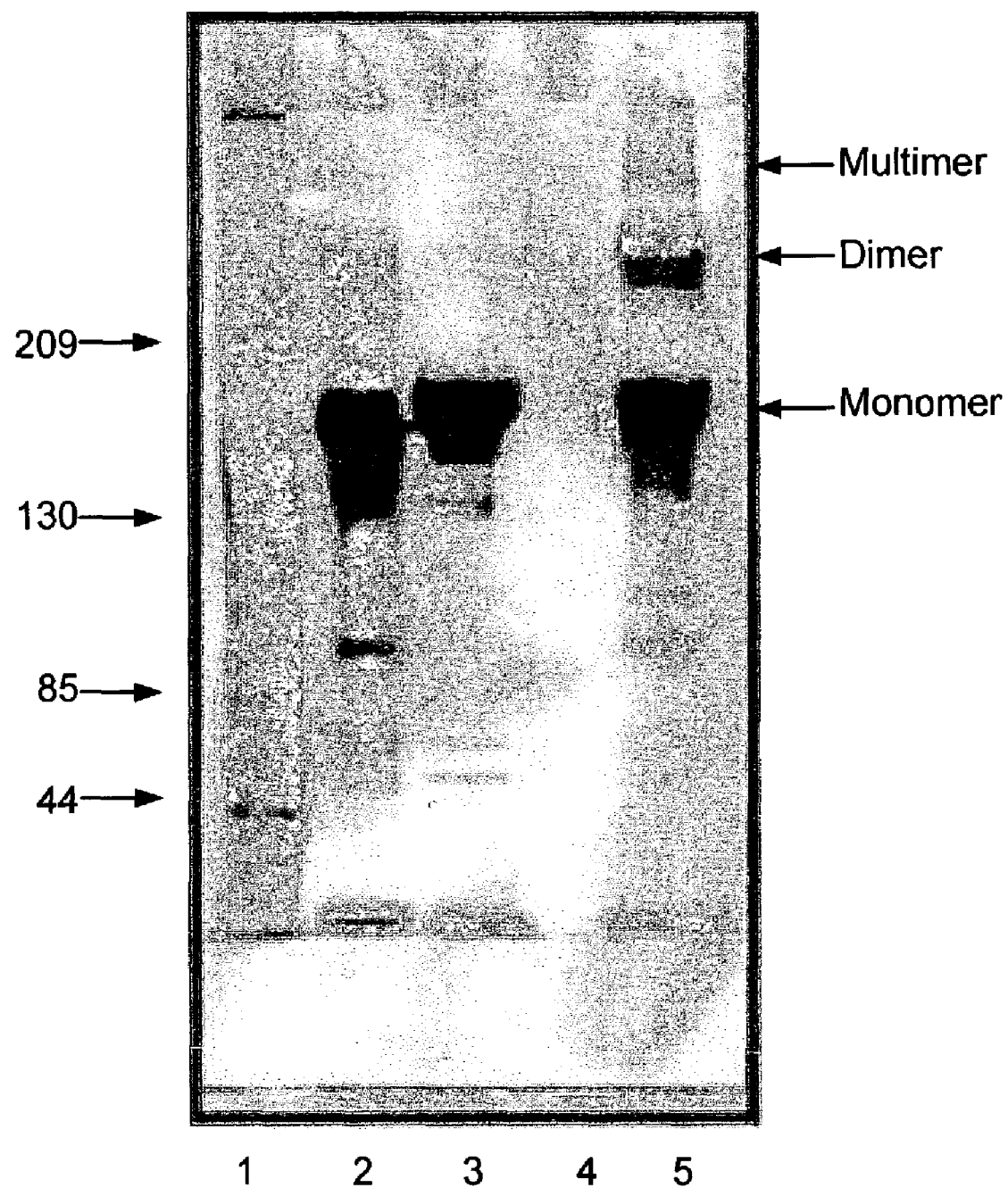
FIG. 2 shows the analysis of the heteroconjugation product on a non-reducing SDS gel electrophoresis using a 2-15% gradient.
Figure 4A:
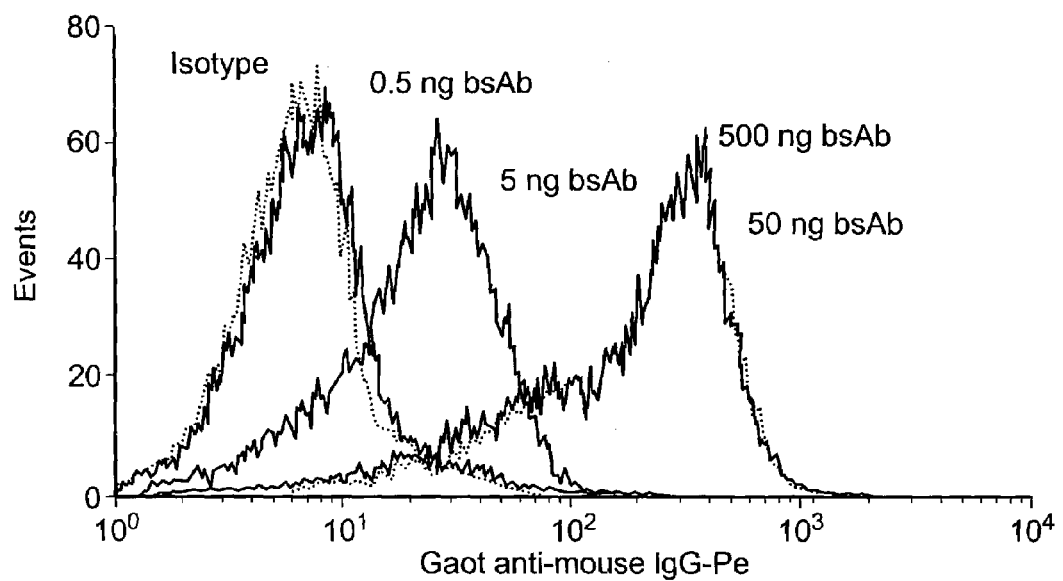
FIG. 4A-E shows a histogram illustrating the binding of IgG1 (9184 portion of Her2Bi) to SK-BR-3 and MCF-7 cells, respectively.
Figure 4B:
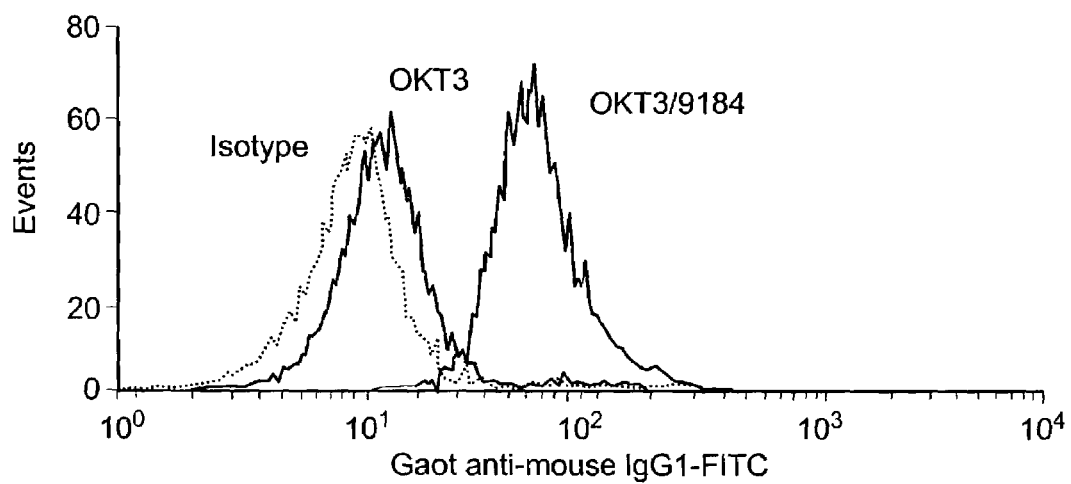
Figure 4C:
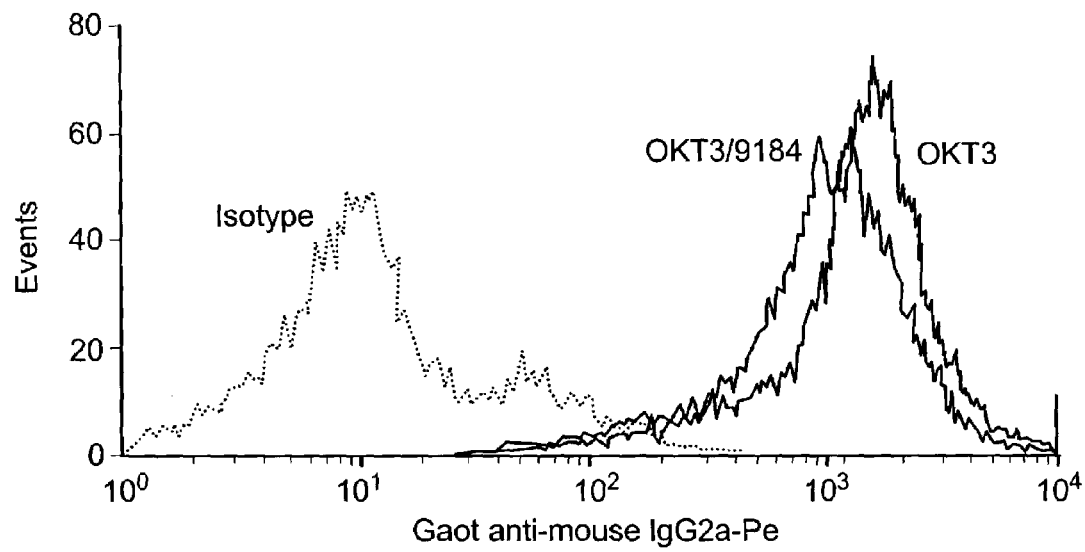
Figure 4D:
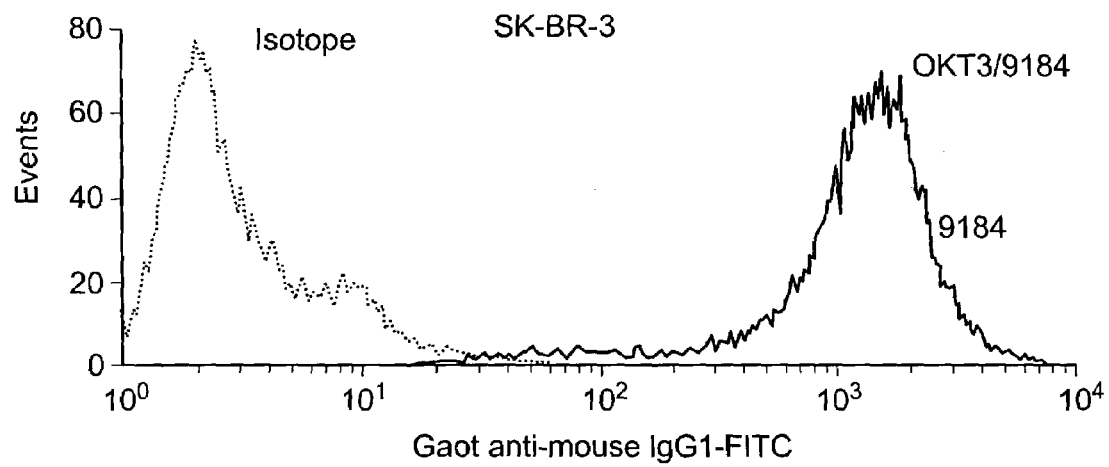
Figure 4E:
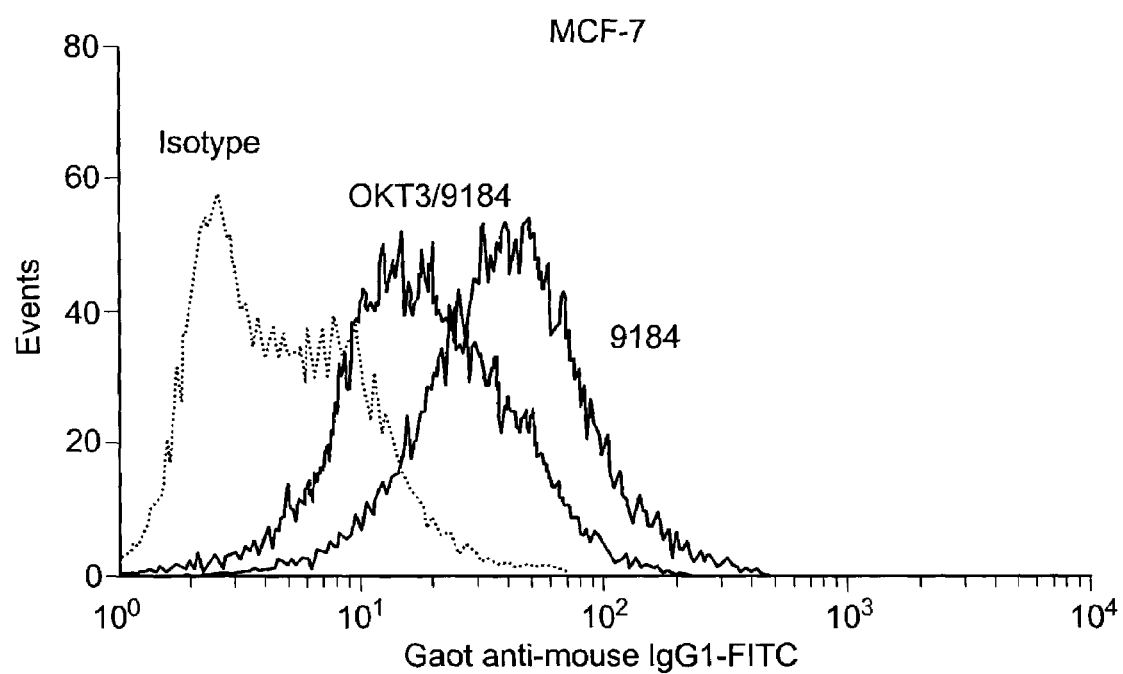
Figure 5C:
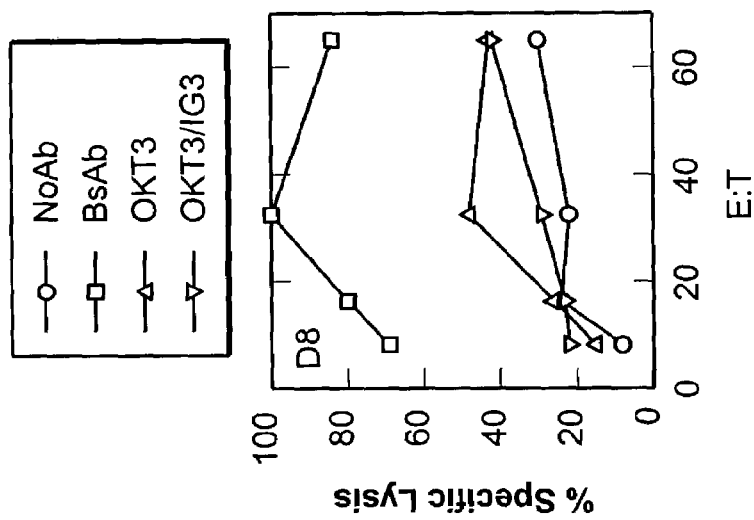
FIG. 5 is a graph showing the development of specific cytotoxicity directed at MCF-7 by armed ATC, fresh PBMC or ATC from normal subjects.
Figure 5B:
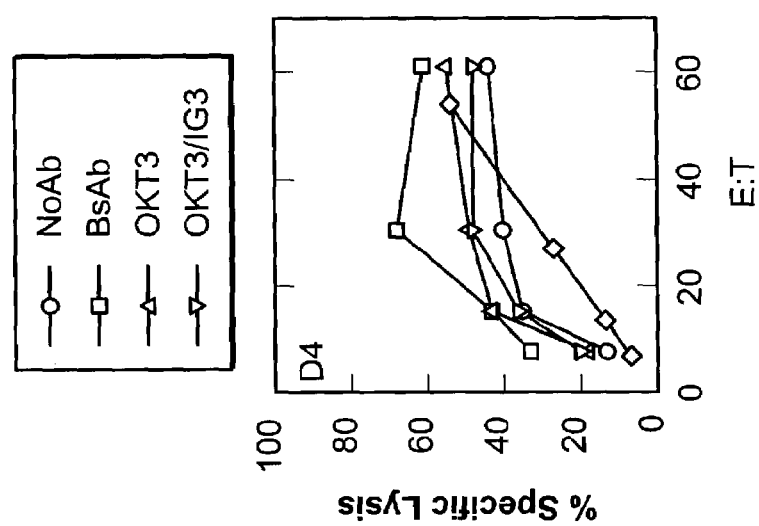
Figure 5A:
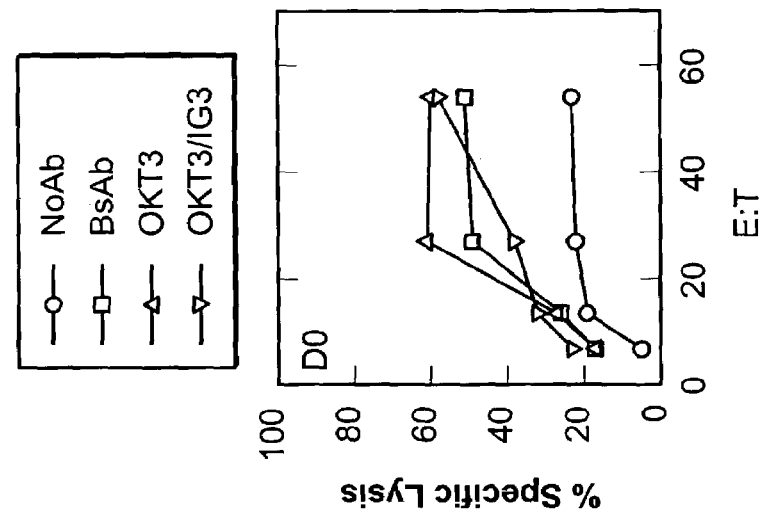
Figure 5F:
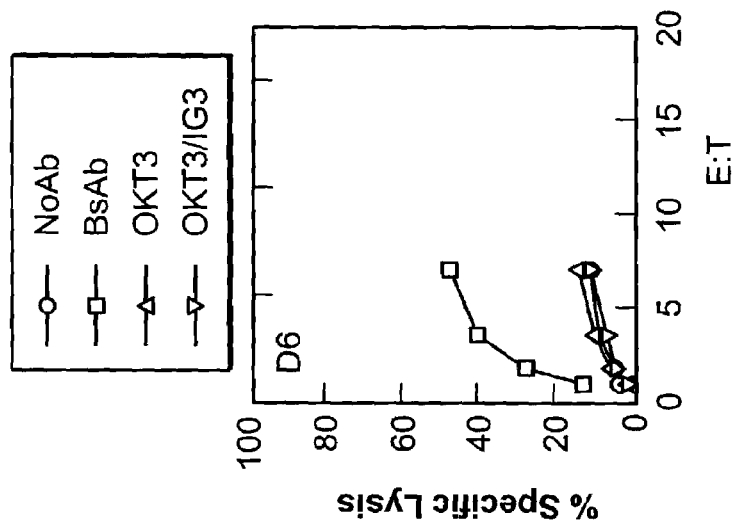
Figure 5E:
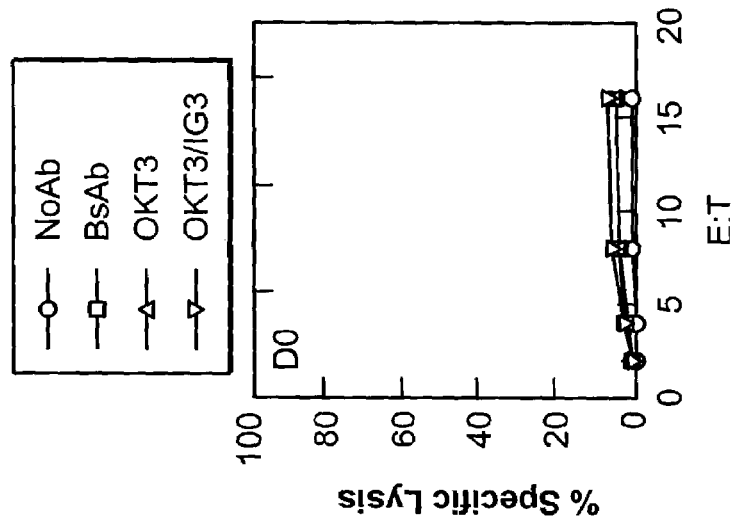
Figure 5D:
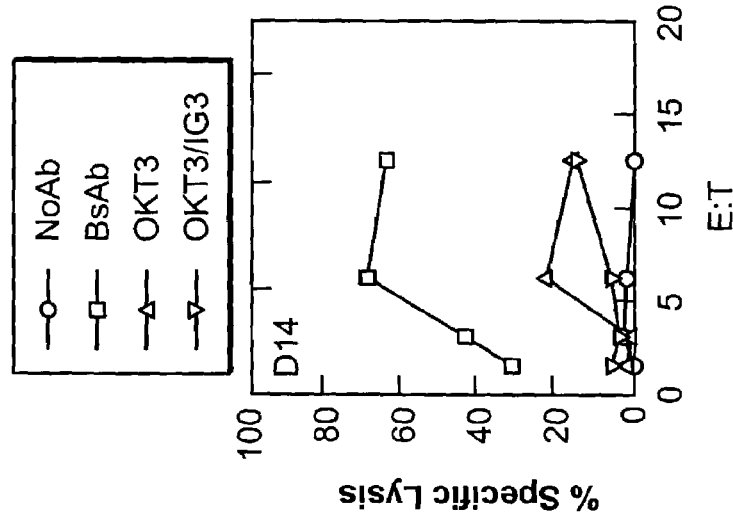
Figure 5I:
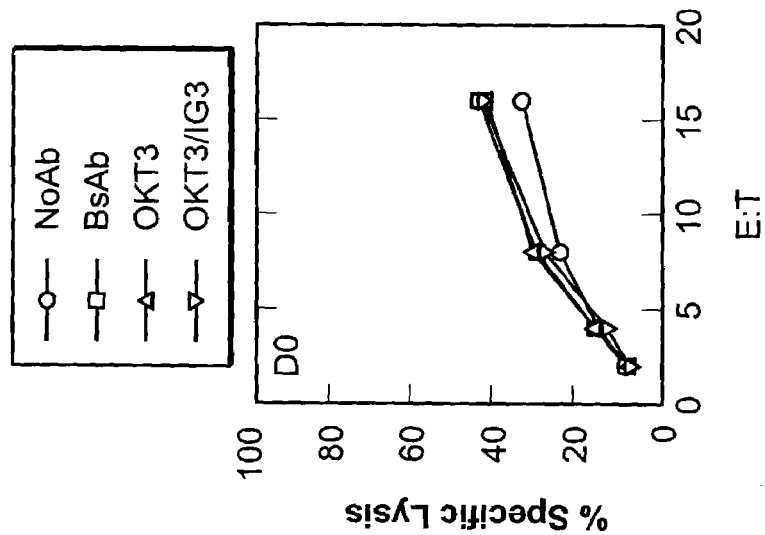
Figure 5H:
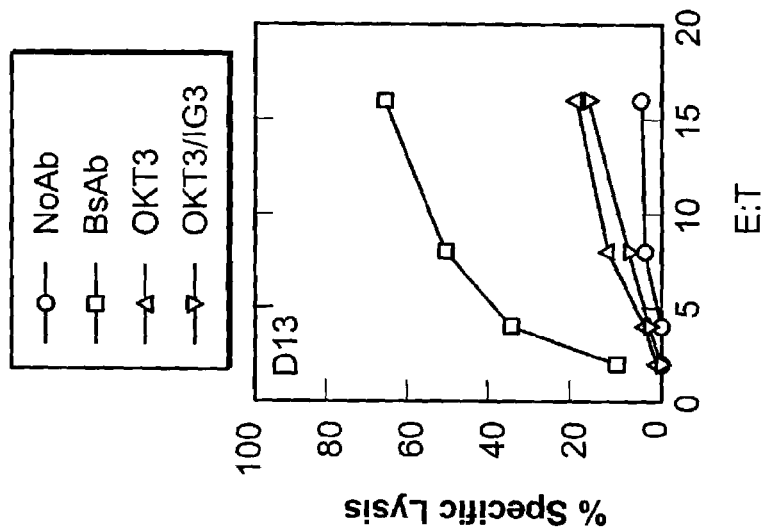
Figure 5G:
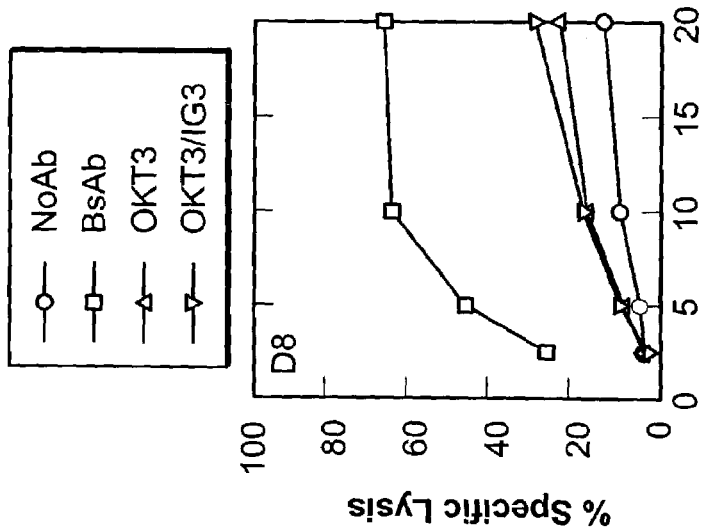
Figure 5L:
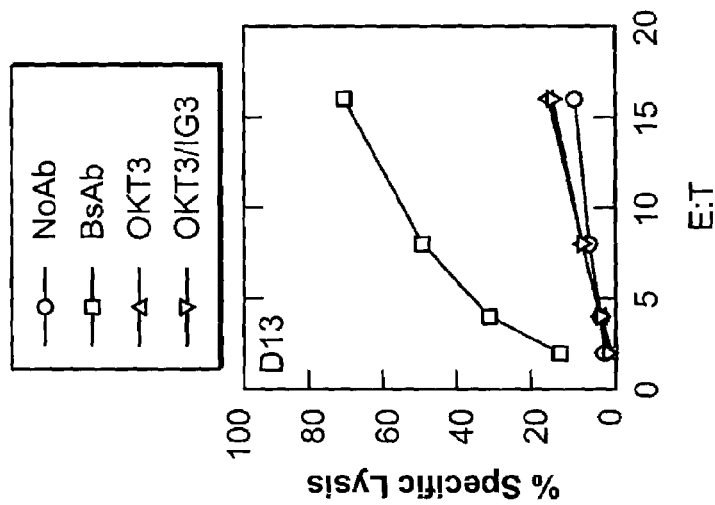
Figure 5K:
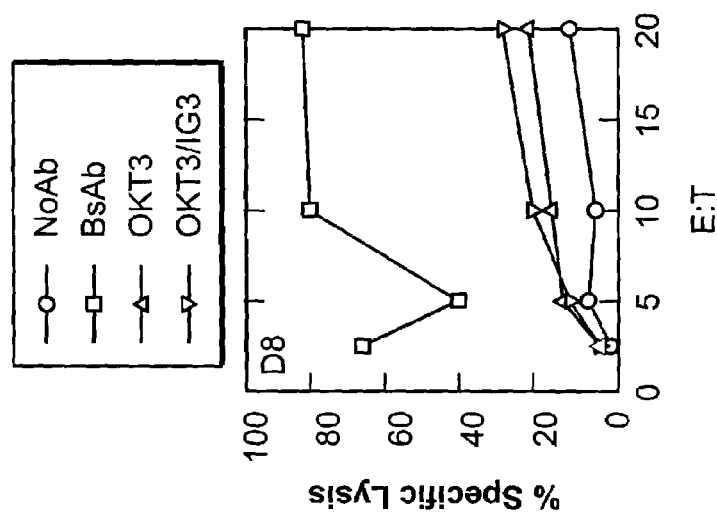
Figure 5J:
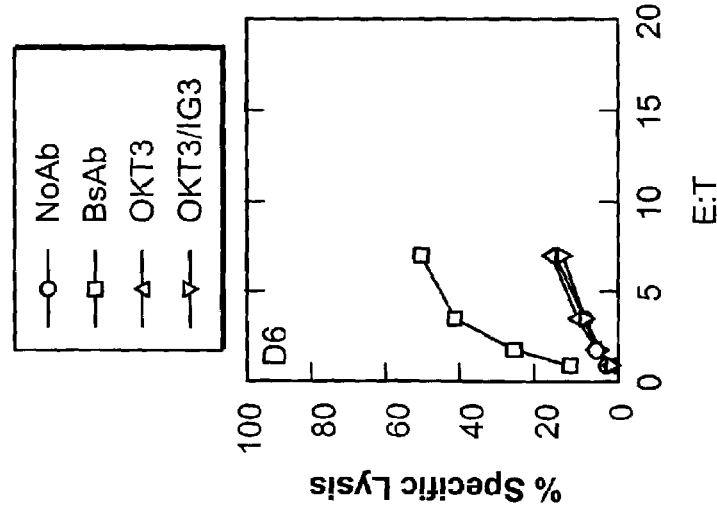

The present invention provides novel compositions and methods for the treatment of tumors. The compositions comprise activated T cells armed with bispecific antibodies specifically capable of binding to tumor antigens ultimately resulting in the destruction of the tumor. The present invention is advantageous in that it uses a patient's own T cells, activates the patient's T cells ex vivo and arms the T cells with antibodies specific for the patients tumor. The reinfusion of the patients own activated and armed T cells with a composition comprising naïve T and B cells as well as powerful antigen presenting cells such as dendritic cells provides for an increase in the patients own precursor cytotoxic cellular pool of cells and induction of long-term memory T cells.

Before the present modified T-cells, compositions and methods of treatment are described, it is to be understood that this invention is not limited to particular cell lines, excipients or method steps described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a T-cell" includes a plurality of such T-cells and reference to "the antibodies" includes reference to one or more antibodies and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention.

In general, the present invention provides for a "drug" which is comprised of anti-CD3 activated T cells (ATC) or anti-CD3 and anti-CD28 co-activated T cells (COACTS) armed with chemically heteroconjugated anti-CD3 (OKT3) x anti-Her-2/neu (9184) or anti-CD3 (OKT3) x anti-Her2/neu (Herceptin) bispecific monoclonal antibodies (BiAb). ATC are produced by ex vivo stimulation with soluble OKT3 (about 10-20 ng/ml) and cultured in at least about 100 to about 600 IU/ml IL-2. COACTS are produced by coactivation with anti-CD3 (OKT3)/anti-CD28 (9.3) monoclonal antibodies co-immobilized on beads. ATC or COACTS are armed with pretitrated doses of bispecific antibodies (BiAb) based on functional cytotoxicity directed at Her-2$^+$ tumor cells. The non-binding monoclonal antibodies or heteroconjugates are washed away from the armed ATC or COACTS.

ATC or COACTS armed with BiAb will be interchangeably referred to as "the drug" for the purposes of this disclosure. This drug provides specific anti-tumor effect for patients who have Her2/neu+ tumors such as breast, renal, prostate, and other HER2 tumors. However, this antigen is merely an illustrative example and is not meant to be construed as limiting in any way. Any antibody raised against an individual patients tumor may be used. This has the major advantage of monitoring any antigenic changes of the tumor, allowing for tailoring treatment on an individual or disease progression stage. The other major advantage of the present invention is that neither ATC or COACTS have caused dose-limiting cell-based toxicities. Furthermore, no monoclonal antibodies are infused in patients thereby, removing any risk of toxic side-effects.

In a preferred embodiment, the ATC or COACTs undergo multiple cycles of tumor antigen recognition and tumor cell killing. The ability of these ATC or COACTs to kill multiple cells is shown in the examples which follow. Assays used to identify the ATC and/or COACTs and determine their ability to kill tumor cells is discussed in great detail infra and in the examples which follow. For example, an armed T cell which is targeted to tumor antigens such as, for example, Her2$^+$ tumors, can be identified by labeling the T cell with a fluorescent marker, or secondary antibody that is detectable by flow cytometry or other methods well-known to one of ordinary skill in the art. Examples of labels for detection of the armed T cells include but not limited to, green fluorescent proteins, avidins and the like. As an illustrative example, biopsies from a tumor to which tumor specific T cells armed with bispecific antibodies and labeled with a detectable marker, are used to confirm the presence of the armed T cells at the site of the tumor. The biopsied tissue is processed by methods well known in the art and prepared for use in cell detection assays.

Figure 44:
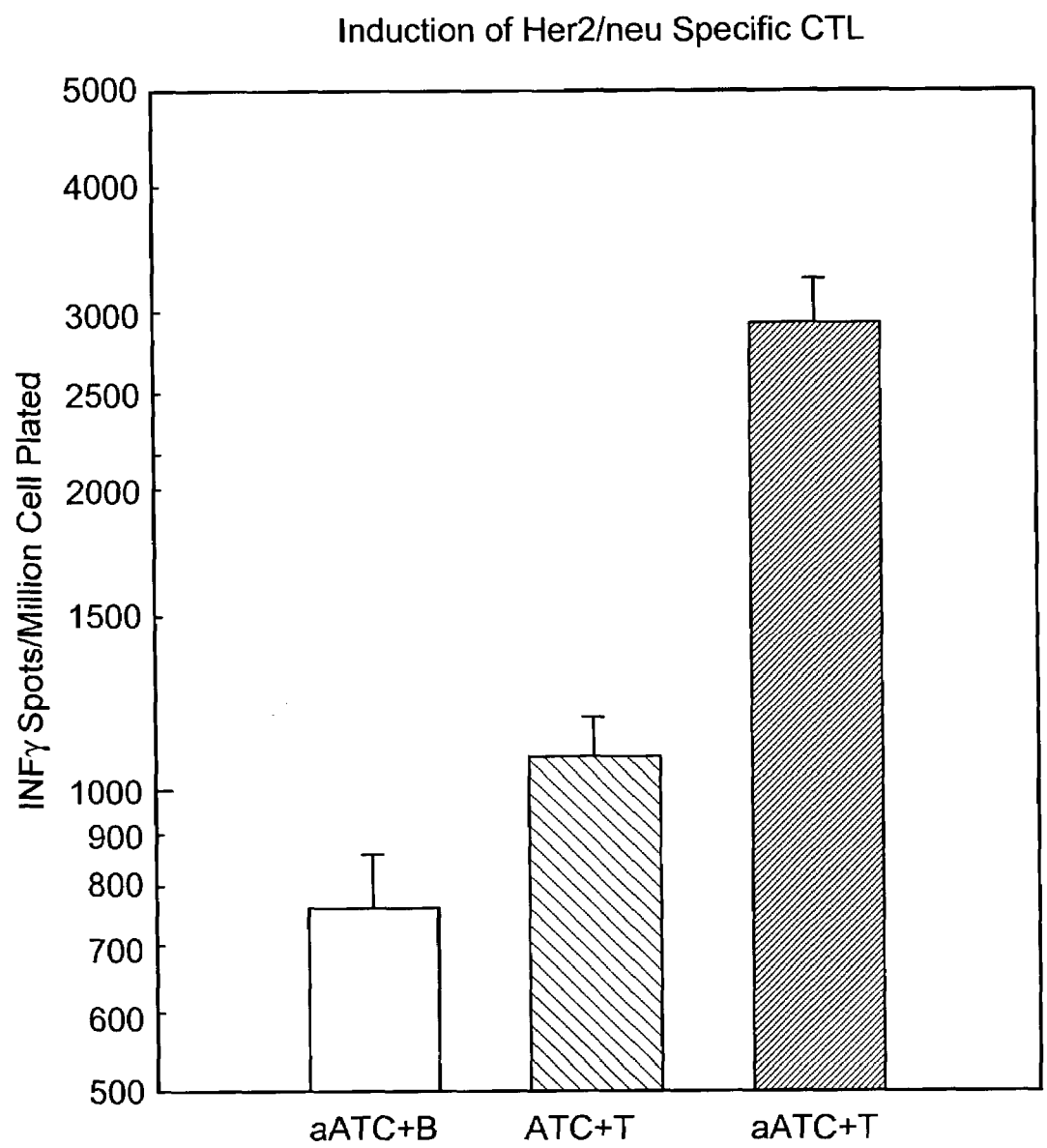
FIG. 44 is a bar graph showing the number of IFN gamma ELISPOTS from ATC (unarmed activated T cells that had been exposed 3 times to SK-BR-3), unarmed ATC that were exposed to a human EBV-driven B cell lines (a B cell line would not express HER2/neu receptors; only the final time), and aATC (armed ATC that were exposed to SK-BR-3 three times and then exposed a fourth time in this assay). The assay was performed on day 20 after arming. No additional arming was performed from the initial arming with 50 ng/million.

In another preferred embodiment, multiple exposure of the anti-CD3 activated polyclonal T cell population induces the development of antigen specific T cell clones, for example HER2/neu. As an illustrative example which is not meant to be construed or limiting in any way, the data shown in FIG. 44 show the number of IFN gamma ELISPOTS from ATC (unarmed activated T cells that had been exposed 3 times to SK-BR-3), unarmed ATC that were exposed to a human EBV-driven B cell lines (a B cell line would not express HER2/neu receptors; only the final time), and aATC (armed ATC that were exposed to SK-BR-3 three times and then exposed a fourth time in this assay). The assay was performed on day 20 after arming. No additional arming was performed from the initial arming with 50 ng/million. Without wishing to be bound by theory, subpopulations of armed ATC were primed to HER2/neu and have become memory cells as measured by their ability to respond vigorously to rechallenge to HER2/neu antigen on the SK-BR-3 cells. Furthermore, the results suggest that multiple exposure of the anti-CD3 activated polyclonal T cell population has selected or induced the development of HER2/neu specific T cell clones.

Preferably, the induction of antigen specific clones directed at a specific tumor antigen allows for the maturation of the cellular response so as to induce the production of T cells that recognize antigens on the tumor that are yet undefined and unknown.

In another preferred embodiment, the ATC or COACT are infused into the patient without any antigen presenting cells, for example, dendritic cells. As discussed in the Examples which follow, the armed T cells are administered to a patient without any dendritic cells in the culture system. Without wishing to be bound by theory, one very real possibility is that activated T cells can act as professional antigen presenting cells since they upregulate class II upon activation and may act together with the crosslinked tumor antigen in the presence of cytokine and chemokines produced by the reactivation process to induce antigen specific CTL. Class II upregulation may provide the necessary help from CD4 helper cells in the polyclonal mixture to provide the signals needed to induce antigen-specific CTL.

In another preferred embodiment, the present invention has the advantage of activating "by-stander" T cells, not just specifically one particular stimulating antigen, thus a bigger immune response is produced leading to the production of more lymphokines and subsequently greater immunoglobulin production by B cells.

Another advantage of the present invention is the maintenance of the peripheral pool of memory T cells ($CD45RO^+$) as memory T cells can be expanded (proliferated) without the need of specific antigenic stimulation to maintain the clonal size. Also the naive T cell repertoire ($CD45RA^+$) can be maintained, as the present invention allows the proliferation of naive T cells and/or precursor cells. For example, to evaluate the frequency of resting T cells with memory phenotype that could be stimulated by cytokines to grow, limiting dilution experiments can be performed. $CD45RO^+$ $CD4^+$ resting T cells can be cultured with IL-2 alone or in combination with TNF-$\alpha$ and IL-6, in the presence of autologous irradiated macrophages and anti-DR antibodies to prevent autoreactive responses.

A "precursor cell" can be any cell in a cell differentiation pathway that is capable of differentiating into a more mature cell. As such, the term "precursor cell population" refers to a group of cells capable of developing into a more mature cell. A precursor cell population can comprise cells that are totipotent, cells that are pluripotent and cells that are stem cell lineage restricted (i.e. cells capable of developing into less than all hematopoietic lineages, or into, for example, only cells of erythroid lineage). As used herein, the term "totipotent cell" refers to a cell capable of developing into all lineages of cells. Similarly, the term "totipotent population of cells" refers to a composition of cells capable of developing into all lineages of cells. Also as used herein, the term "pluripotent cell" refers to a cell capable of developing into a variety (albeit not all) lineages and are at least able to develop into all hematopoietic lineages (e.g., lymphoid, erythroid, and thrombocytic lineages). For example, a pluripotent cell can differ from a totipotent cell by having the ability to develop into all cell lineages except endothelial cells. A "pluripotent population of cells" refers to a composition of cells capable of developing into less than all lineages of cells but at least into all hematopoietic lineages. As such, a totipotent cell or composition of cells is less developed than a pluripotent cell or compositions of cells. As used herein, the terms "develop", "differentiate" and "mature" all refer to the progression of a cell from the stage of having the potential to differentiate into at least two different cellular lineages to becoming a specialized cell. Such terms can be used interchangeably for the purposes of the present application.

As used herein, the term "population" refers to cells having the same or different identifying characteristics. The term "lineage" refers to all of the stages of the development of a cell type, from the earliest precursor cell to a completely mature cell (i.e. a specialized cell).

Systemic memory T cells are characterized according to the cell surface expression of certain known antigens. Typically these cells are positive for CD4, and lack expression of CD45RA, and integrin $\alpha 4\beta 7$. They are further characterized by expression of CCR4. A subset of cells of interest are common leukocyte antigen positive ($CLA^+$). Verification of the identity of the cells of interest may be performed by any convenient method, including antibody staining and analysis by fluorescence detection, ELISA, etc., reverse transcriptase PCR, transcriptional amplification and hybridization to nucleic acid microarrays, etc.

Some memory T cells associated with the skin are known to express CLA, and such cells are of particular interest for treatment with the present methods, particularly to modulate the trafficking, or homing of these cells to cutaneous tissues, for treatment, for example of melanomas.

Other systemic memory cells are triggered to adhere to endothelial ICAM-1, by LFA-1 binding. These adhesion molecules are implicated directly in graft rejection, psoriasis, and arthritis. A CCR4 blocking agent that prevents triggering of LFA-1 mediated adhesion is useful in the inhibition of graft rejection by preventing the accumulation of memory T cells at the site of graft implantation; preventing intra-islet infiltration by T cells to inhibit development of insulin-dependent diabetes mellitus; blocking infiltration of T cells into the central nervous system to treat multiple sclerosis and other demyelinating diseases; blocking the accumulation of T cells in the synovial joints of patients suffering from rheumatoid arthritis; accumulation of memory T cells to influence immune responsiveness, and the like. Thus, the drug (ATC, COACT) of the invention allows for treatments of diseases other than tumors as the bispecific antibody can be specific for any desired epitope.

In accordance with the invention, T cells from patients are, preferably activated ex vivo either by soluble anti-CD3 antibody, or are co-activated by using anti-CD3 and anti-CD28 monoclonal antibodies, either by soluble or immobilized on a solid support. A preferred solid support are plastics, or any surface upon which antibodies can be immobilized, or beads, such as, for example, Dynal beads. Once activated, T cells are armed with a bispecific antibody. The location and movements through the patient's body of these activated T cells can be monitored by using a labeled antibody that binds to a desired molecule on the surface of the activated T cell or directed to a portion of the bispecific antibody, such as for example, the $F_c$ region. Monitoring of the cells is achieved by using the flow cytometry methods of the invention. The T cells can also be labeled by agents which are detectable by any imaging techniques known in the art.

By "patient" herein is meant a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

The terms "treatment", "treating", and the like are used herein to generally mean obtaining a desired pharmacological and/or physiological effect. The effect may be prophylactic in terms of completely or partially preventing a disease or symptom thereof and/or may be therapeutic in terms of a partial or complete cure of a disease and/or adverse effect attributed to the disease. In general, methods of the invention involve treating diseases generally referred to as cancer and may be applied to a variety of different types of cancers by utilizing antibodies which specifically bind antigens known to be present on the surfaces of cancer cells of the type of cancer being treated. "Treatment" as used herein covers any treatment of such a disease in a mammal, particularly a human, and includes:

(a) Preventing and/or diagnosing the disease in a subject which may be predisposed to the disease but has not yet been diagnosed as having it;

(b) Inhibiting the disease, i.e. arresting it's development; and/or (c) Relieving the disease, i.e. causing regression of the disease.

The invention is directed towards treating patients with cancer and is particularly directed towards treating types of cancer which are not generally treatable by normal surgical methodologies. More specifically, "treatment" is intended to mean providing a therapeutically detectable and beneficial effect on a patient suffering from cancer. That effect can include stimulating the patient's own immune system to aid in treating the cancer.

Although a variety of types of cancer can be treated the antibodies attached to the T-cells will generally determine the type of cancer which can be treated. The antibodies must have a sufficiently high level of binding affinity to antigens on the cancer cells which are being targeted. As used herein in order to consider the antibodies to be "specific" or have a sufficiently high binding affinity, e.g. the antibodies will have a binding affinity of about $10^{-7}$ moles/liter, or about $10^{-8}$ to about $10^9$ moles/liter and may be up to $10^{-11}$ moles/liter or higher for the epitope of interest which is preferably specific to the cell surface of the cancer being targeted. It will be understood by those skilled in the art that the term "specific" as used in connection with binding affinity refers to such a high affinity binding, and is not intended to mean that the binding affinity can not bind to other molecules as well. One may find cross-reactivity with different epitopes, e.g. to relatedness of an antigen sequence for structure, or the structure of the antibody binding pocket itself. Antibodies demonstrating such cross-reactivity are still considered specific for the purposes of the present invention.

"Immune cells" as used herein, is meant to include any cells of the immune system that may be assayed, including, but not limited to, B lymphocytes, also called B cells, T lymphocytes, also called T cells, natural killer (NK) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor-infiltrating (TIL) cells, gene modified immune cells including hybridomas, drug modified immune cells, and derivatives, precursors or progenitors of the above cell types.

"Activity", "activation" or "augmentation" is the ability of immune cells to respond and exhibit, on a measurable level, an immune function. Measuring the degree of activation refers to a quantitative assessment of the capacity of immune cells to express enhanced activity when further stimulated as a result of prior activation. The enhanced capacity may result from biochemical changes occurring during the activation process that allow the immune cells to be stimulated to activity in response to low doses of stimulants.

Immune cell activity that may be measured include, but is not limited to, (1) cell proliferation by measuring the cell or DNA replication; (2) enhanced cytokine production, including specific measurements for cytokines, such as IFN-γ, GM-CSF, or TNF-α; (3) cell mediated target killing or lysis; (4) cell differentiation; (5) immunoglobulin production; (6) phenotypic changes; (7) production of chemotactic factors or chemotaxis, meaning the ability to respond to a chemotactin with chemotaxis; (8) immunosuppression, by inhibition of the activity of some other immune cell type; and, (9) apoptosis, which refers to fragmentation of activated immune cells under certain circumstances, as an indication of abnormal activation.

As used herein, the terms "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

Several different ways, to assess maturity and cell differentiation, are available. For example, one such method is by measuring cell phenotypes. The phenotypes of immune cells and any phenotypic changes can be evaluated by flow cytometry after immunofluorescent staining using monoclonal antibodies that will bind membrane proteins characteristic of various immune cell types.

A second means of assessing cell differentiation is by measuring cell function. This may be done biochemically, by measuring the expression of enzymes, mRNA's, genes, proteins, or other metabolites within the cell, or secreted from the cell. Bioassays may also be used to measure functional cell differentiation or measure specific antibody production directed at a patient's tumor, tumor cell lines or cells from fresh tumors.

As used herein, "fresh tumors" refer to tumors removed from a host by surgical or other means.

As mentioned above, T cells from patients are, preferably activated ex vivo either by soluble anti-CD3 antibody, or are co-activated by using anti-CD3 and anti-CD28 monoclonal antibodies, either by soluble or immobilized on a solid support. A preferred solid support are plastics, or any surface upon which antibodies can be immobilized, or beads, such as, for example, Dynal beads. Once activated, T cells are armed with a bispecific antibody.

Bispecific antibodies are able to bind to the T cell receptor complex of the T cell with one binding arm and to tumor-associated antigens on the tumor cell with the second binding arm. Thereby, they activate T cells which kill tumor cells by releasing cytokines. Moreover, there is the possibility that T cells recognize tumor-specific antigens via their receptor during activation by bispecific antibodies and that, a long-lasting immunization is initiated. Of particular importance in this regard is the intact Fc portion of the bispecific antibody which mediates the binding to accessory cells such as monocytes/macrophages/dendritic cells and causes these cells to become cytotoxic themselves and/or at the same time to transduce important co-stimulatory signals to the T cell.

Bispecific antibodies (BiAbs) have been used for targeting drugs, pro-drug activation, and immune recruitment strategies.[96] They can directly mediate cytotoxicity to the tumor by specifically targeting the T cells to a tumor. BiAbs have been modified to bear enzymes for the conversions of circulating inactive pro-drug to active drug at the tumor site. Infused BiAbs have been used to recruit and redirect immune effector cells to target tumor cells in vivo, and/or arm effector T cells after ex vivo expansion for immunotherapy.

Intact bispecific antibodies are composed of two antibody semi-molecules (one H and one L immunoglobulin chain each) each representing a specificity, and in addition have, like normal antibodies, a Fc portion performing the well-known effector functions. A particularly preferred method for the preparation of bispecific antibodies, of the present invention, is by chemical heteroconjugation, as described in the Examples which follow. It should be understood that other methods of preparation are also useful if they lead to the intact bispecific antibodies according to the above definition required according to the invention.

The immunoglobulins can have two pairs of light chain/heavy chain complexes, typically at least one chain comprising mouse complementarity determining regions functionally joined to human framework region segments. For example, mouse complementarity determining regions, with or without additional naturally-associated mouse amino acid residues, can be used to produce human-like antibodies capable of binding to Her $2^+$ type tumors.

The intact bispecific antibodies used in the present invention carry a functional Fc part Contrary to bispecific F(ab)2 fragments which do not include a functional Fc part the intact bispecific antibodies of the present invention are able to bind not only to T cells but also accessory cells which are also known as Fc-receptor positive cells (e.g. monocytes, macrophages, dendritic cells). The binding of the cells plays an essential role in providing an efficient, direct tumor destruction which is 10-1000 times higher compared to the efficiency of the method used by Kaneko, T. et al. *Blood* (Mar. 1, 1993) 81 (5): 1333-1341; and Kaneko, T. et al. *Leukemia and Lymphoma* (1994) 14: 219-229; Kaneko, T. et al, *Bone Marrow Transplantation* (1994) 14: 213-217. The intact bispecific antibodies of the present invention enable an optimal co-stimulation of T cells. Particularly preferred surface antigens for optimal co-stimulation are CD3 and/or CD28 and particular secreted cytokines (like IL-2, IL-6, IL-12, TNF-alpha).

Arming activated T cells using the intact bispecific antibodies of the present invention, efficiently directs destruction of tumor cells by T cells. The presence of accessory cells, such as dendritic cells, may cause such cells to be, also, bound by the bispecific antibody of the present invention during the arming process. Dendritic cells from a cancer patient can thus, be stimulated to uptake, process and present parts of the tumor.

The immune mechanisms leading to destruction of target tumor cells are at least partially understood. A population of cytolytic T cells have been identified which carry the CD8+ antigenic determinant on their surfaces. These cells require CD4+ helper lymphocytes for activation, which is a complex event mediated by antigen processing and presentation in association with the major histocompatibility complexes. Antigen processing assures that only cells targeted to the tumor antigens will be activated.

Monoclonal antibodies directed to various markers on subpopulations of T lymphocytes have been used to activate immune effector cells. OKT3 antibody administered by injection, for example, meets with CD3, and can cause a whole array of immune effects including release of IL-2, TNF-alpha, GM-CSF, MIP1α, RANTES, and/or IL-6, tissue damage, and either activation or suppression of T cell activity. More recently, OKT3 specificity has been combined with a antitumor specificity in a bispecific antibody. Link, et al., *Blood*, 81: 3343 (1993) showed that a bispecific antibody having one arm of OKT3 and the other arm directed to a B-cell malignant antigen was able to induce cytotoxicity of target tumor cells. Interestingly, the T-cell activation was without regard to the natural specificity of the T cell, and required the presence of the tumor cells. Thus, in the simultaneous binding of tumor cell and effector cell by the same antibody, the T cells are effectively recruited from the general T cell population, and retargeted to destroy the tumor cells.

It has also been shown by Weiner, *Int. J. Cancer*, Supplement 7, 63 (1992) that the action of the bispecific antibody is enhanced by co-administration of IL-2, so that combinational therapy resulted in management of a 100 to 1000 times greater tumor load than with the anti-tumor monoclonal antibody alone. Alternatively, the co-stimulus observed in the use of the bispecific antibody may be provided through binding of the Fc domain of the antibody to the Fc monocyte receptor, which in turn provide the co-stimulus, possibly through binding of the B7 family of membrane proteins to CD28. Preactivation ex vivo of cytotoxic T cells with co-administration of bispecific F(ab') has also been reported (Mezzanzanice, et al., *Cancer Res.,* 51:5716 (1991)).

However, the present invention differs from the prior art in that the T cells are activated and then armed with bispecific antibodies whose specificity is directed against a tumor antigen, like for example Her2+ tumors, prior to re-infusion into the patient.

In a preferred embodiment, the cellular composition of the reinfusion is comprised of naïve T and B cells and accessory cells such as dendritic cells. Dendritic cells are powerful antigen presenting cells. Without wishing to be bound by theory, a composition of cells which include dendritic cells, for example between about 5×105 to about 2×106 dendritic cells would provide a powerful antigen presenting cell so that the dose of armed T cells and/or naïve immunocompetent T cells could be reduced depending on the patient's prognosis. Thus, these stimulate tumor specific T cell responses from the pool of naïve T cells.

Monoclonal antibodies used in the production of bispecific antibodies are available from commercial sources, for example anti-CD3 monoclonal antibody (OK-T3) is available from OrthoBiotech. Monoclonal antibodies specific for tumor antigens such as Her2+, (Herceptin®) can be purchased from Genentech, S.F., Calif.

Monoclonal antibodies may also be produced in the laboratory. Thus, in selecting an antibody specific for a common antigenic determinant displayed on the cell surface of cancers of a defined cell type, a mixture of cells is prepared, the mixture comprising cells from individual cell lines derived from a plurality of-cancer cells of defined tissue type. This mixture of whole cells is then injected into a laboratory animal such as a mouse, according to a conventional immunization protocol to immunize the animal with the heterologous human tumor cells. Reactive B cells are then harvested from the animal, preferably the disrupted spleens, and fused with myeloma cells to form hybridomas. By maintaining the cell density below a critical level in which a statistical distribution function predicts one or two hybridomas per well, the likelihood of obtaining isolated single hybridomas is improved.

After cloning and outgrowth, supernatant medium containing the secreted monoclonal antibodies is removed. The screenings can then be carried out, first, by contacting the mixture of cancer cells of the defined tissue, and a mixture of cancer cells of a different tissue type, with the monoclonal antibody under conditions conducive to binding of the antibody to cells displaying the target antigenic determinant. A fluorescent dye that recognizes the antibody is then added and the cells are then evaluated in a flow cytometer to determine which cells have detectable dye and which do not. The cell types are distinguished by a log scale of emission light intensity. Thus, the cells are ranked into a first class having labeled antibody bound to the surfaces thereof and into a second class having no labeled antibody bound, thereby showing a bimodal distribution of cells in flow cytometry.

The second screen involves further screening tests on the cells showing a bimodal distribution in which individual cells of prostate cancer and other cells of cancer origin are labeled with the monoclonal antibody. Thus, each cancer cell type is individually tested with the labeled antibody to identify antibody with binding specificity for the cancer cells derived from the tissue of interest. Those antibodies which demonstrate unambiguous reactivity with, for example, prostate cancer-derived cells and no reactivity with nonprostate-derived cells are further tested. The cancer tissue types for which this method is intended in its therapeutic application include all those derived or arising from body organs unessential for viability such as ovary, breast, certain endocrine glands (thyroid), testicle, as well as prostate.

The third screening test is performed upon the monoclonal antibodies passing both the first and second screen, and involves determining the binding specificity of the labeled antibody for tissue sections derived from a plurality of cancers of defined cell type, together with controls of normal tissue sections from nonhomologous tissue.

The term "derived" as it applies herein means the cells were obtained by subculture of tumors isolated from patients. It also applies to cell lines established from non-solid tumors of the lymphatic system. The techniques for routine subculture of tumor cells are well known in the art, and include the use of growth factors, nutrients, support matrices; and hormones, as required for the particular tissue type. The techniques for immunization of experimental animals and subsequent cell fusion of splenic B cells to produce hybridomas, and their subsequent culture are conventional. The basic protocol utilized in the practice of the present invention is set forth in detail in Current Protocols in Immunology, vol. 1, J. E. Coligan, et al., eds., John Wiley & Sons: 1991, hereby incorporated by reference.

It is important in applying these protocols to the isolation of hybridomas according to the present invention, that a proper dilution of fused cells occurs, so that a substantial number of wells in the 96 well trays contain about 1-2 clones, and preferably, not more. At dilutions sufficiently great to attain this objective, some 6 to 12 percent of wells will contain 0 clones.

Screening by flow cytometry has several key advantages. First, it is important that a stable cell surface antigen be identified. By selecting only those antibodies that bind whole cells, the likelihood of choosing a stable surface component antigen is enhanced. The term "stable" means in the context of antibody/cellular interactions, that the target molecule is preferably a constitutive cell membrane glycoprotein integral to the structure and integrity of the membrane, and not a transient resident of the cell which is shed, displaced, or antigenically modified during the cell cycle.

A second advantage to screening by flow cytometry, is that the bimodal profile indicates that some cells bind the fluorophore labeled antibody and not others, which is a threshold indication of specificity. If only a single fluorescent peak is observed, this means that some antigen common to both the tumor cells and the non-prostate cells has been identified by the antibody. Two peaks mean that either one or more subsets of tumor cells have a unique antigen, one or more subsets of tumor cells but not all share an antigen with the non-tumor cells, or that the tumor cells have an antigen not shared by normal cells. Another advantage of this method of pre-selection is that the techniques of labeling cells and preparing them for flow cytometry are well known, and may be carried out routinely.

Bispecific antibodies have been utilized in a variety of therapeutic applications. U.S. Pat. No. 5,601,819 (Wong) discloses the use of a combinational CD3, and CD28 or interleukin 2 receptor bispecific antibody to selectively cause proliferation and destruction of specific T cell subsets. Belani, et al. showed that bispecific IgG functions in a B cell lymphoma model to retarget the specificity of T cells in low dose, and to cause nonspecific T cell activation with systemic cytokine production at higher doses. It was found that bsF (ab')2 was also capable of retargeting T-cell mediated lysis by activated T cells. Thus, in many applications portions of antibodies, such as enzyme digested fragments, will mediate the effects otherwise observed for the intact antibody. These fragments necessarily contain the complementarity determining regions (CDRs) of the variable light and heavy chain antibody domains, and may be integrated with other protein fragments to form a bispecific antigen binding protein construct. This construct will minimally contain the CDRs including the interspersed constant framework beta sheet portions. These regions are easily identified following routine cloning and sequencing procedures, as disclosed in U.S. Pat. Nos. 5,530,101 and 5,585,089, hereby incorporated by reference. Cloning may be facilitated by PCR primers complementary to conserved sequences flanking the functional variable regions.

Useful bispecific antibodies combining a CDR specific for an effector cell and the CDR for a tissue specific antigen may also be humanized, either by replacing the light and heavy chain constant regions of the murine antibody with their human counterparts, or by grafting the CDRs onto a human antibody. Methods for carrying out these procedures are contained in U.S. Pat. Nos. 5,530,101 and 5,585,089. The immune construct of the present invention may also be bispecific single chain antibodies, which are typically recombinant polypeptides consisting of a variable light chain portion covalently attached through a linker molecule to the corresponding variable heavy chain portion, as disclosed in U.S. Pat. Nos. 5,455,030, 5,260,203, and 4,496,778, hereby incorporated by reference. A more complex construct for a single chain bispecific antibody also containing an Fc portion is provided in detail in U.S. Pat. No. 5,637,481. The principal advantage of constructs of this type is that only one species of antibody is produced, rather than three separate antibody types in the fused cell hybrid-hybridoma, which require further purification.

Other methods can be utilized in producing bispecific antibodies. A particular preferred method in the present invention is by chemical heteroconjugation of two monoclonal antibodies. Monoclonal antibodies, in addition to the described methods of production may be purchased from a commercial source. Chemical heteroconjugates can be created by the chemical linking of either intact antibodies or antibody fragments of different specificities. The preferred method for chemical heteroconjugation is described in the example section which follows and the method is schematically shown in FIG. 1.

Bispecific antibodies may also be created by disulfide exchange, which involves enzymatic cleavage and reassociation of the antibody fragments. Glennie et al., "Preparation and Performance of Bispecific F(ab')$_2$ Antibody Containing Thioether Linked Fab' Fragments", *J. Immunol.* 139: 2367-2375 (1987). Another method is the creation of F(ab')$_2$ connected via a shortened Fc to the leucine zipper region of the transcription factors Fos and Jun. Kostelny et al., "Formation of a Bispecific Monoclonal Antibody by the Use of Leucine Zippers", *J. Immunol.* 148: 1547-53 (1992).

Bispecific antibodies are also produced by hybrid-hybridomas. Hybrid-hybridomas are created by fusing two hybridoma cell lines together so that the resulting hybrid-hybridoma contains two productive light chain alleles. Hybrid-hybridomas secrete individual bispecific IgG molecules which are monovalent for each of the two distinct antigens recognized by antibodies produced by the parent hybridomas. However, hybrid-hybridomas produce both bispecific antibodies and monospecific antibodies for each of the two antigens recognized by the parent hybridomas. Further, light chain/heavy chain fidelity does not always occur. In all, there are 10 possible heavy and light chain combinations that could be produced by the hybrid-hybridoma cell line. Only one of these is the desired bispecific antibody. Some degree of purification of the bispecific component is therefore necessary prior to the use of such bispecific antibodies. A preferred method of purification is protein A immunoaffinity chromatography followed by HPLC purification.

In order that the invention may be more completely understood, several definitions are set forth. As used herein, the term "immunoglobulin" refers to a protein consisting of one or more polypeptides substantially encoded by immunoglobulin genes. The recognized immunoglobulin genes include the kappa, lambda, alpha, gamma (IgG$_1$, IgG$_2$, IgG$_3$, IgG$_4$), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH—terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, and F(ab')$_2$, as well as bifunctional hybrid antibodies (e.g., Lanzavecchia et al., *Eur. J Immunol.* 17, 105 (1987)) and in single chains (e.g., Huston et al., *Proc. Natl. Acad. Sci. U.S.A.*, 85, 5879-5883 (1988) and Bird et al., *Science,* 242, 423-426 (1988), which are incorporated herein by reference). (See, generally, Hood et al., "Immunology", Benjamin, N.Y., 2nd ed. (1984), and Hunkapiller and Hood, *Nature,* 323, 15-16 (1986), which are incorporated herein by reference).

An immunoglobulin light or heavy chain variable region consists of a "framework" region interrupted by three hypervariable regions, also called CDR's. The extent of the framework region and CDR's have been precisely defined (see, "Sequences of Proteins of Immunological Interest," E. Kabat et al., U.S. Department of Health and Human Services, (1983); which is incorporated herein by reference). The sequences of the framework regions of different light or heavy chains are relatively conserved within a species. As used herein, a "human framework region" is a framework region that is substantially identical (about 85% or more, usually 90-95% or more) to the framework region of a naturally occurring human immunoglobulin. The framework region of an antibody, that-is the combined framework regions of the constituent light and heavy chains, serves to position and align the CDR's. The CDR's are primarily responsible for binding to an epitope of an antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. A typical therapeutic chimeric antibody is thus a hybrid protein composed of the variable or antigen-binding domain from a mouse antibody and the constant or effector domain from a human antibody, although other mammalian species may be used.

As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor."Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human. One says that the donor antibody has been "humanized", by the process of "humanization", because the resultant humanized antibody is expected to bind to the same antigen as the donor antibody that provides the CDR's.

It is understood that the humanized antibodies may have additional conservative amino acid substitutions which have substantially no effect on antigen binding or other immunoglobulin functions. By conservative substitutions are intended combinations such as gly, ala; val, ile, leu; asp, glu; asn, gln; ser, thr; lys, arg; and phe, tyr.

Humanized immunoglobulins, including humanized antibodies, have been constructed by means of genetic engineering. Most humanized immunoglobulins that have been previously described have comprised a framework that is identical to the framework of a particular human immunoglobulin chain, the acceptor, and three CDR's from a non-human donor immunoglobulin chain.

A principle is that as acceptor, a framework is used from a particular human immunoglobulin that is unusually homologous to the donor immunoglobulin to be humanized, or use a consensus framework from many human antibodies. For example, comparison of the sequence of a mouse heavy (or light) chain variable region against human heavy (or light) variable regions in a data bank (for example, the National Biomedical Research Foundation Protein Identification Resource) shows that the extent of homology to different human regions varies greatly, typically from about 40% to about 60-70%. By choosing as the acceptor immunoglobulin one of the human heavy (respectively light) chain variable regions that is most homologous to the heavy (respectively light) chain variable region of the donor immunoglobulin, fewer amino acids will be changed in going from the donor immunoglobulin to the humanized immunoglobulin. Hence, and again without intending to be bound by theory, it is believed that there is a smaller chance of changing an amino acid near the CDR's that distorts their conformation. Moreover, the precise overall shape of a humanized antibody comprising the humanized immunoglobulin chain may more closely resemble the shape of the donor antibody, also reducing the chance of distorting the CDR's.

Typically, one of the 3-5 most homologous heavy chain variable region sequences in a representative collection of at least about 10 to 20 distinct human heavy chains will be chosen as acceptor to provide the heavy chain framework, and similarly for the light chain. Preferably, one of the 1-3 most homologous variable regions will be used. The selected acceptor immunoglobulin chain will most preferably have at least about 65% homology in the framework region to the donor immunoglobulin.

In many cases, it may be considered preferable to use light and heavy chains from the same human antibody as acceptor sequences, to be sure the humanized light and heavy chains will make favorable contacts with each other. Regardless of how the acceptor immunoglobulin is chosen, higher affinity may be achieved by selecting a small number of amino acids in the framework of the humanized immunoglobulin chain to be the same as the amino acids at those positions in the donor rather than in the acceptor.

Humanized antibodies generally have at: least three potential advantages over mouse or in some cases chimeric antibodies for use in human therapy:
1) Because the effector portion is human, it may interact better with the other parts of the human immune system (e.g., destroy the target cells more efficiently by complement-dependent cytotoxicity (CDC) or antibody-dependent cellular cytotoxicity (ADCC)).
2) The human immune system should not recognize the framework or constant region of the humanized antibody as foreign, and therefore the antibody response against such an antibody should be less than against a totally foreign mouse antibody or a partially foreign chimeric antibody.

Antibodies can also be genetically engineered. Particularly preferred are humanized immunoglobulins that are produced by expressing recombinant DNA segments encoding the heavy and light chain CDR's from a donor immunoglobulin capable of binding to a desired antigen, such as the human T cell CD3 complex, attached to DNA segments encoding acceptor human framework regions.

The DNA segments typically further include an expression control DNA sequence operably linked to the humanized immunoglobulin coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the humanized light chains, heavy chains, light/heavy chain dimers or intact antibodies, binding fragments or other immunoglobulin forms may follow (see, S. Beychok, Cells of Immunoglobulin Synthesis, Academic Press, New York, (1979), which is incorporated herein by reference).

Human constant region DNA sequences can be isolated in accordance with well known procedures from a variety of human cells, but preferably immortalized B-cells (see, Kabat op. cit. and WP87/02671). The CDR's for producing preferred immunoglobulins of the present invention will be similarly derived from monoclonal antibodies capable of binding to the predetermined antigen, such as the human T cell receptor CD3 complex, and produced by well known methods in any convenient mammalian source including, mice, rats, rabbits, or other vertebrates, capable of producing antibodies. Suitable source cells for the constant region and framework DNA sequences, and host cells for immunoglobulin expression and secretion, can be obtained from a number of sources, such as the American Type Culture Collection ("Catalogue of Cell Lines and Hybridomas," sixth edition (1988) Rockville, Md., U.S.A., which is incorporated herein by reference).

Other "substantially homologous" modified immunoglobulins to the native sequences can be readily designed and manufactured utilizing various recombinant DNA techniques well known to those skilled in the art. For example, the framework regions can vary at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis (see, Gillman and Smith, Gene, 8, 81-97 (1979) and S. Roberts et al., Nature, 328, 731-734 (1987), both of which are incorporated herein by reference).

Substantially homologous immunoglobulin sequences are those which exhibit at least about 85% homology, usually at least about 90%, and preferably at least about 95% homology with a reference immunoglobulin protein.

Alternatively, polypeptide fragments comprising only a portion of the primary antibody structure may be produced, which fragments possess one or more immunoglobulin activities (e.g., complement fixation activity). These polypeptide fragments may be produced by proteolytic cleavage of intact antibodies by methods well known in the art, or by inserting stop codons at the desired locations in vectors known to those skilled in the art, using site-directed mutagenesis.

As stated previously, the DNA sequences can be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors contain selection markers, e.g., tetracycline or neomycin resistance, to permit detection of those cells transformed with the desired DNA sequences (see, e.g., U.S. Pat. No. 4,704, 362, which is incorporated herein by reference).

*E. coli* is one prokaryotic host useful particularly for cloning the DNA sequences of the present invention. Other microbial hosts suitable for use include bacilli, such as *Bacillus subtilus*, and other enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention (see, Winnacker, "From Genes to Clones," VCH Publishers, New York, N.Y. (1987), which is incorporated herein by reference). Eukaryotic cells are actually preferred, because a number of suitable host cell lines capable of secreting intact immunoglobulins have been developed in the art, and include the CHO cell lines, various COS cell lines, HeLa cells, preferably myeloma cell lines, etc, and transformed B-cells or hybridomas. Expression vectors for these cells can include expression control sequences, such as an origin of replication, a promoter, an enhancer (Queen et al., *Immunol. Rev.*, 89, 49-68 (1986), which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, SV40, Adenovirus, cytomegalovirus, Bovine Papilloma Virus, and the like.

The vectors containing the DNA segments of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (See, generally, Maniatis et al., Molecular Cloning: A Laboratory Manual, Cold Spring Harbor Press, (1982), which is incorporated herein by reference.)

Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like (see, generally, R. Scopes, "Protein Purification", Springer-Verlag, N.Y. (1982)). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally) or in developing and performing assay procedures, immunofluorescent staining, and the like. (See, generally, Immunological Methods, Vols. I and II, Lefkovits and Pernis, eds., Academic Press, New York, N.Y. (1979 and 1981)).

Other suitable techniques involve in vitro exposure of lymphocytes to the antigenic polypeptides or alternatively to selection of libraries of antibodies in phage or similar vectors. See, Huse et al. (1989) "Generation of a Large Combinatorial Library of the Immunoglobulin Repertoire in Phage Lambda," *Science* 246:1275-1281; and Ward et al. (1989) *Nature* 341:544-546, each of which is hereby incorporated herein by reference. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567. These patents are incorporated herein by reference.

The antibodies of this invention can also be used for affinity chromatography in isolating a protein or antigenic target. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified antigen will be released.

The antibodies may also be used to screen expression libraries for particular expression products, for example anti-CD3 or any other molecule that can activate a T cell and be used in arming the ATC. Usually the antibodies used in such a procedure will be labeled with a moiety allowing easy detection of presence of antigen by antibody binding.

Antibodies raised against, for example, a CD3 complex will also be useful to raise anti-idiotypic antibodies.

The preparation and characterization of the preferred phage-displayed random peptide libraries have been described elsewhere. See, for example, Kay, B. K. et al. in *Gene* (1992) 128:59-65, for a description of the preparation of the phage-displayed random peptide library known as TSAR-9, more below. In particular, by cloning degenerate oligonucleotides of fixed length into bacteriophage vectors, recombinant libraries of random peptides can be generated which are expressed at the amino-terminus of the pIII protein on the surface of M13 viral particles. (There are 3-5 copies of the pIII-fusion on the surface of each particle.) Consequently, these libraries can be screened by isolating viral particles that bind to targets. The isolates can be grown up overnight, and the displayed peptide sequence responsible for binding can be deduced by DNA sequencing.

These libraries have approximately >$10^8$ different recombinants, and nucleotide sequencing of the inserts suggests that the expressed peptides are indeed random in amino acid sequence. These libraries are referred to herein as TSAR libraries, where TSAR stands for Totally Synthetic Affinity Reagents. The preparation of the TSAR libraries are described further in U.S. Pat. No. 6,432,920.

A preferred pharmaceutical composition of the present invention comprises the use of the monoclonal antibodies, which are either commercially available or produced by the methods described above. The monoclonal antibodies are preferably chemically heteroconjugated to produce the bispecific antibody of interest. These bispecific antibodies are then used to "arm" the activated T cells.

In one embodiment, the bispecific antibody remains bound to the T cell after the armed cell has killed a tumor target, thereby allowing the armed T cell to kill multiple target tumors, i.e. the bispecific antibody does not become unbound from the armed T cell, once the armed T cell has contacted and killed a tumor target. The armed T cell, once it has killed one tumor target can engage another tumor target for which the armed T cell is specific, kill the second tumor target and proceed to engage another tumor target etc. Preferably, the armed T cell performs multiple rounds of target cell killing. This is discussed in detail in the Examples which follow.

As used herein, a "target cell" is any cell comprising antigens that the armed T cell binds to. The target cell is not limited to tumor antigens but can include for example, viral antigens, infectious disease organism antigens and the like.

As used herein, "arming" is the binding of the bispecific antibody portion specific for the T cell antigen of interest, that is the T cell receptor complex antigens such as CD3 and/or CD3 and CD28. The second portion of the bispecific antibody is the antibody which is specific for the tumor antigen of choice, thereby targeting the activated T cell to the specific tumor antigen.

While various procedures involving the use of antibodies have been applied in the treatment of tumors, few if any successful attempts using cytotoxic T-cells have been recorded. Theoretically, cytotoxic T-cells would be the preferable means of treating tumors. However, no procedures have been available to specifically activate cytotoxic T-cells. In contrast to antibodies, the T-cell receptors on the surface of CD8 cells cannot recognize foreign antigens directly. Antigen must first be presented to the T cell receptor.

The present invention provides a detailed description of activation of T cells as described in the examples which follow.

The presentation of antigen to CD8 T-cells is accomplished by major histocompatibility complex (MHC) molecules of the Class I type. The major histocompatibility complex (MHC) refers to a large genetic locus encoding an extensive family of glycoproteins which play an important role in the immune response. The MHC genes, which are also referred to as the HLA (human leukocyte antigen) complex, are located on chromosome 6 in humans. The molecules encoded by MHC genes are present on cell surfaces and are largely responsible for recognition of tissue transplants as "non-self". Thus, membrane-bound MHC molecules are intimately involved in recognition of antigens by T-cells.

MHC products are grouped into three major classes, referred to as I, II, and III. T-cells that serve mainly as helper cells express CD4 and primarily interact with Class II molecules, whereas CD8-expressing cells, which mostly represent cytotoxic effector cells, interact with Class I molecules.

Class I molecules are membrane glycoproteins with the ability to bind peptides derived primarily from intracellular degradation of endogenous proteins. Complexes of MHC molecules with peptides derived from viral, bacterial and other foreign proteins comprise the ligand that triggers the antigen responsiveness of T-cells. In contrast, complexes of MHC molecules with peptides derived from normal cellular products play a role in "teaching" the T-cells to tolerate self-peptides, in the thymus. Class I molecules do not present entire, intact antigens; rather, they present peptide fragments thereof, "loaded" onto their "peptide binding groove".

As used herein, "allogeneic" is used to refer to immune cells derived from non-self major histocompatibility complex donors. HLA haplotypes/allotypes vary from individual to individual and it is often helpful to determine the individual's HLA type. The HLA type may be determined via standard typing procedures and the peripheral blood lymphocytes (PBLs) purified by Ficoll gradients.

As will be recognized by those in the art, the term "host compatible" or "autologous" cells means cells that are of the same or similar haplotype as that of the subject or "host" to which the cells are administered.

As used herein, "partially-mismatched HLA", refers to HLA types that are between about 20 to 90% compatible to the host's HLA type.

For many years, immunologists have hoped to raise specific cytotoxic cells targeting viruses, retroviruses and cancer cells. While targeting against viral diseases in general may be accomplished in vivo by vaccination with live or attenuated vaccines, no similar success has been achieved with retroviruses or with cancer cells. Moreover, the vaccine approach has not had the desired efficacy in immunosuppressed patients. At least one researcher has taken the rather non-specific approach of "boosting" existing CD8 cells by incubating them in vitro with IL-2, a growth factor for T-cells. However, this protocol (known as LAK cell therapy) will only allow the expansion of those CD8 cells which are already activated. As the immune system is always active for one reason or another, most of the IL-2 stimulated cells will be irrelevant for the purpose of combating the disease. In fact, it has not been documented that this type of therapy activates any cells with the desired specificity. Thus, the benefits of LAK cell therapy are controversial at best, and the side effects are typically so severe that many studies have been discontinued.

The presentation of Class I MHC molecules bound to peptide alone has generally been ineffective in activating CD8 cells. In nature, the CD8 cells are activated by antigen-presenting cells, such as, for example, dendritic cells, which present not only a peptide-bound Class I MHC molecule, but also a costimulatory molecule. Such costimulatory molecules include B7 which is now recognized to be two subgroups designated as B7.1 and B7.2. It has also been found that cell adhesion molecules such as integrins assist in this process.

Dendritic cells are antigen-presenting cells that are found in all tissues and organs, including the blood. Specifically, dendritic cells present antigens for T lymphocytes, i.e., they process and present antigens, and stimulate responses from naive and memory T cells. In addition to their role in antigen presentation, dendritic cells directly communicate with non-lymph tissue and survey non-lymph for an injury signal (e.g., ischemia, infection, or inflammation) or tumor growth. Once signaled, dendritic cells initiate the immune response by releasing IL-1 which triggers lymphocytes and monocytes.

When the CD8 T-cell interacts with an antigen-presenting cell, such as a dendritic cells, having the peptide bound by a Class I MHC and costimulatory molecule, the CD8 T-cell is activated to proliferate and becomes an effector T-cell. See, generally, Janeway and Travers, Immunobiology, published by Current Biology Limited, London (1994), incorporated by reference.

Accordingly, what is needed and which the present invention provides, is a means to activate T-cells so that they proliferate and become cytotoxic. The present invention is also useful as the activation is done in vitro and the activated cytotoxic T-cells reintroduced into the patient. Activation is achieved by the crosslinking of the T cell receptor complex (anti-CD3 and anti-CD28 antibodies) which increase the effectiveness of the activation.

The present invention also provides for the involvement of antigen presenting cells as the reinfused composition of cells is comprised of armed activated T cells, naïve T and B cells and dendritic cells. Besides the capacity of being powerful antigen presenting cells, the dendritic cells can also bind to the Fc portion of the bispecific antibody, thereby forming a complex of armed T cells bound to the tumor and dendritic cells bound to the Fc portion of the bispecific antibody. Therefore, an extremely powerful, localized immune response is theoretically produced by the engagement of antigen presenting cells such as dendritic cells at the tumor site.

Chemokines and cytokines also play a powerful role in the development of an immune response. The role of chemokines in leukocyte trafficking is reviewed by Baggiolini (1998) *Nature* 392:565-8, in which it is suggested that migration responses in the complicated trafficking of lymphocytes of different types and degrees of activation will be mediated by chemokines. The use of small molecules to block chemokines is reviewed by Baggiolini and Moser (1997) *J. Exp. Med.* 186:1189-1191.

The role of various specific chemokines in lymphocyte homing has been previously described. For example, Campbell et al. (1998) *Science*, showed that SDF-1 (also called PBSF), 6-C-kine (also called Exodus-2), and MIP-3beta (also called ELC or Exodus-3) induced adhesion of most circulating lymphocytes, including most CD4+ T cells; and MIP-3alpha (also called LARC or Exodus-1) triggered adhesion of memory, but not naive, CD4+ T cells. Tangemann et al. (1998) *J. Immunol.* 161:6330-7 disclose the role of secondary lymphoid-tissue chemokine (SLC), a high endothelial venule (HEV)-associated chemokine, with the homing of lymphocytes to secondary lymphoid organs. Campbell et al. (1998) *J. Cell Biol* 141(4):1053-9 describe the receptor for SLC as CCR7, and that its ligand, SLC, can trigger rapid integrin-dependent arrest of lymphocytes rolling under physiological shear.

Preferably, the ATC or COACT induce memory T cells from naïve or pluripotent stem cells. Immature and mature T cells are readily identifiable by markers and can be detected by flow cytometric analysis. A review of the biology of memory T cells may be found in Dutton et al. (1998) *Ann. Rev Immunol* 16:201-23. Memory cells express a different pattern of cell surface markers, and they respond in several ways that are functionally different from those of naive cells. Human memory cells are $CD45RA^-$, $CD45RO^+$. In contrast to naive cells, memory cells secrete a full range of T cell cytokines.

Mature B cells can be measured in immunoassays, for example, by cell surface antigens including CD19 and CD20 with monoclonal antibodies labeled with fluorochromes or enzymes may be used to these antigens. B cells that have differentiated into plasma cells can be enumerated by staining for intracellular immunoglobulins by direct immunofluorescence in fixed smears of cultured cells.

Several different ways, to assess maturity and cell differentiation, are available. For example, one such method is by measuring cell phenotypes. The phenotypes of immune cells and any phenotypic changes can be evaluated by flow cytometry after immunofluorescent staining using monoclonal antibodies that will bind membrane proteins characteristic of various immune cell types.

A second means of assessing cell differentiation is by measuring cell function. This may be done biochemically, by measuring the expression of enzymes, mRNA's, genes, proteins, or other metabolites within the cell, or secreted from the cell. Bioassays may also be used to measure functional cell differentiation or measure specific antibody production directed at a patient's tumor, tumor cell lines or cells from fresh tumors.

As used herein, "fresh tumors" refer to tumors removed from a host by surgical or other means.

Immune cells express a variety of cell surface molecules which can be detected with either monoclonal antibodies or polyclonal antisera. Immune cells that have undergone differentiation or activation can also be enumerated by staining for the presence of characteristic cell surface proteins by direct immunofluorescence in fixed smears of cultured cells.

In vitro T cell cytotoxic assays are well known to those skilled in the art. In general, cytotoxicity is measured in a 5 hr $^{51}$Sodium chromate ($^{51}$Cr) release assay. In particular, a 20 hr $^{51}$Cr-release assay is preferred. Tumor cells, also referred to herein as "target cells" are plated in flat-bottomed microtiter plates and incubated at 37° C. overnight. The targets are washed and labeled the next day with $^{51}$Cr at 37° C. $^{51}$Cr is taken up by the target cells, either by endocytosis or pinocytosis, and is retained in the cytoplasm. The wells containing tumor cells are washed, and then armed or unarmed ATC, referred to as "effector cells" are plated at different E:T ratios and incubated overnight at 37° C. Cytolysis is a measure of the $^{51}$Cr released from the target cells into the supernatant due to destruction of the target cells by the effector cells. The microtiter plates are centrifuged at 1000 rpm for 10 minutes and an aliquot of about 50 μl to about 100 μl is removed and the level of radioactivity is measured the next day by a gamma counter and the percent specific lysis calculated.

Percent specific lysis is measured by using the formula:

($^{51}$Cr released from the target cells)–(spontaneous $^{51}$Cr released from the target cells)/(maximum $^{51}$Cr released from the target cells)–(spontaneous $^{51}$Cr released from the target cells)×100

The spontaneous $^{51}$Cr released from the target cells is measured with tumor cells to which no effector cells have been added. Maximum $^{51}$Cr released from the target cells is obtained by adding, for example, 1M HCl and represents the total amount of $^{51}$Cr present in the cytoplasm of the target cell.

All of the cytotoxicity assays shown in this application are conducted without the addition of IL-2 for 18 to 20 hours. The redirected cytotoxicity mediated by armed ATC or COACTS occurs in presence of serum and complement and in the absence of IL-2. Therefore, the infused armed T cells are likely to kill tumor for at least 18 to 20 hours in the absence of IL-2.

Serum and complement do not affect cytotoxicity mediated by armed ATC. Armed ATC were not lysed in the presence of fresh PBMC and rabbit complement or high concentrations of fresh human serum. This result suggests that armed ATC are not lysed in vivo by complement fixation and lysis via Fc-receptor mediated antibody dependent cellular cytotoxicity.

Other cytotoxicity assays such as the labeling of target cells with tritiated thymidine ($^3$H-TdR) may also be used. $^3$H-TdR is taken up by target cells into the nucleus of the cell. Release of $^3$H-TdR is a measure of cell death by DNA fragmentation. The assay is conducted as above except the incubation period is at least about 48 hours and 50 μl to about 100 μl of the supernatant is measured by a beta-counter in the presence of at least about 1 ml of scintillation fluid. Calculation of percent specific lysis is performed using the above formula The following definitions are used throughout the application:

The term "fluorescent component" or "fluorescent label" or "labeled" refers to a component capable of absorbing light and then re-emitting at least some fraction of that energy as light over time. The term includes discrete compounds, molecules, naturally fluorescent proteins and macro-molecular complexes or mixtures of fluorescent and non-fluorescent compounds or molecules. The term "fluorescent component" or "fluorescent label" also includes components that exhibit long lived fluorescence decay such as lanthanide ions and lanthanide complexes with organic ligand sensitizes, that absorb light and then re-emit the energy over milliseconds. Other labels include different fluorochromes and fluorescent proteins such as green fluorescent protein. Fluorochromes which may find use in a multicolor analysis include phycobiliproteins, e.g., phycoerythrin and allophycocyanins; fluorescein and Texas red.

Activated T Cells (ATC) are a heterogeneous population of human lymphocytes predominantly T lymphocytes of CD8 phenotype that have been triggered to proliferate after stimulation with OKT3 and grown in low doses of IL-2. ATC has been safe given in combination with subcutaneous or continuous infusion of IL-2 at low doses of 300,000 IU/m$^2$/day and GM-CSF at doses as high as 250 µg/m$^2$/day or as low as 125 µg/m$^2$/twice weekly. ATC may also be administered with other immune augmenting cytokines or chemokines, such as for example, IL-12.

Preferably, reinfused ATC or COACT are administered to a patient twice a week for about four weeks. The skilled practitioner will be able to determine the correct times and doses depending on the age, sex, body weight and condition of the patient.

Murmonab OKT3: OKT3 (OrthoClone OKT3) has been extensively characterized in both preclinical and clinical testing. OKT3 is a murine IgG2a MAb directed at human CD3 and is commercially available from OrthoBiotech, Raritan, N.J. It is purchased in 5 mg vials containing 5 ml of bacteriostatic water. It is used to produce ATC, coat Dynal beads for the production of COACTS, and produce chemical heteroconjugate with 9184 or Herceptin®.

IL-2 Proleukin: Proleukin (recombinant IL-2) is purchased from Chiron, Emeryville, Calif. It is approved for the treatment of renal cell carcinoma. The clinical grade drug is used to expand T cells in culture. It is currently being used in this laboratory to expand ATC and COACTS.

COACTS are a heterogeneous population of human T cells, roughly 50% of the CD4+ phenotype, that have been triggered to proliferate and differentiate with coimmobilized OKT3 and 9.3 Mabs. COACTS are grown with or without low doses of IL-2 up to 14 days. Only the COACTS are infused into patients. IL-2, OKT3, 9.3, and the beads are not present in the final product. OKT3 is coimmobilized with 9.3 (anti-CD28 monoclonal antibody) to costimulate T cells.

Murm 9.3 is a mouse Mab of the IgG2a isotype directed at the CD28 receptor on human T cells. The 9.3 Mab was produced under clinical grade condition by Abbott-Biotech. The antibody is coimmobilized with OKT3 on Dynal beads to activate T cells during culture. The antibody is not infused into patients. The monoclonal antibody is removed when the beads are removed.

The BiAb: OKT3 x 9184 or OKT3 x Herc [either designated as Her2Bi] are used to arm ATC so that the non-MHC restricted cytotoxicity exhibited by ATC can be redirected by the bispecific antibody to lyse targets expressing a specific target antigen. ATC armed with Her2bi are designated ATC armed with Her2Bi.

Clinical grade 9184 Mab: Clinical material, GMP 9184 (anti-Her-2/neu), is supplied in vials containing 1 mg by Nexell Corporation, Irving, Calif. 9184 has been extensively characterized by Nexell and has been used for purging of stem cell products in the European market.

Anti-Her2/neu monoclonal antibody (9184, Nexell Corporation). Anti-Her2 (9184 monoclonal provided as a study drug by Nexell Corporation is a murine IgG1 monoclonal antibody directed at Her2/neu. The binding characteristics and its ability to mediate redirected cellular cytotoxicity towards MCF-7, SK-BR-3 and PC-3 have been well documented in our preclinical studies.

Her2/neu is a tumor associated antigen (TAA) on prostate cancers. Her2/neu (Her2) belongs to the epidermal growth factor receptor family of tyrosine kinases. The Her2/neu oncogene encodes an 185 kDa transmembrane receptor with significant sequence homology to class I receptor tyrosine kinase family.[145] Her2 is over-expressed in breast, ovarian, lung, gastric, oral,[146] and prostate cancers.[142-144] The over-expression of Her2 makes it an ideal target. The expression of Her2/neu on prostate cancer, however, is controversial. There are reports that suggest that expression of Her2/neu on prostate cancers is low or absent,[142;147;148] or high.[144]

Herceptin®: Herceptin® (Genentech, SF, Calif.) has been extensively characterized in preclinical and clinical trials. The Mab is commercially available for in vivo use for the treatment of stage IV breast cancer in combination with Taxol.[161]

OKT3: Clinical grade OKT3 obtained commercially will be heteroconjugated to 9184 or Herceptin® to produce OKT3 x 9184 or OKT3 x Herc, respectively.

Armed T Cells (The "Drug"):

Armed ATC are ATC grown for 6-14 days and armed with Her2Bi (OKT3 x 9184 or OKT3 x Herc).

Armed COACTS are COACTS grown for 6-14 days and armed with Her2Bi (OKT3 x 9184 or OKT3 x Herc).

For certain therapeutic applications, a DNA expression vector encoding a desired cytokine, such as, for example, IL-12, chemokine, or any other immune-augmenting molecule of the invention can be introduced into immune cells of the present invention such as, for example, T cells.

The term "vector" as used herein (including "expression vector") means any nucleic acid sequence of interest capable of being incorporated into a host cell resulting in the expression of a nucleic acid of interest. Vectors can include, e.g., linear nucleic acid sequences, plasmids, cosmids, phagemids, and extrachromosomal DNA. Specifically, the vector can be a recombinant DNA. Also used herein, the term "expression", or "gene expression", is meant to refer to the production of the protein product of the nucleic acid sequence of interest, including transcription of the DNA and translation of the RNA transcript.

These can include vectors, liposomes, naked DNA, adjuvant-assisted DNA, gene gun, catheters, etc. Vectors include chemical conjugates such as described in WO 93/04701, which has a targeting moiety (e.g. a ligand to a cellular surface receptor), and a nucleic acid binding moiety (e.g. polylysine), viral vector (e.g. a DNA or RNA viral vector), fusion proteins such as described in PCT/US95/02140 (WO 95/22618) which is a fusion protein containing a target moiety (e.g. an antibody specific for a target cell) and a nucleic acid binding moiety (e.g. a protamine), plasmids, phage etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. Viral vectors can be chosen to introduce the cytokine or chemokine to cells of choice. Such vectors include pox vectors such as orthopox or avipox vectors, herpesvirus vectors such as herpes simplex I virus (HSV) vector (Geller, A. I et al, *J. Neurochem.*, 64:487(1995); Lim, F., et al., in DNA Cloning: Mammalian Systems, D. Glover, Ed. (Oxford Univ. Press, Oxford, England) (1995); Geller, A. I. et al., *Proc. Natl. Acad. Sci. USA* 87:1149 (1990)) Adenovirus vectors (LeGal LaSalle et al., *Science*, 259:988 (1993); Davidson, et al., *Nat. Genet.* 3:219 (1993); Yang et al., *J. Virol.* 69:2004 (1995)) and Adeno-associated virus vectors (Kaplitt, M. G. et al., *Nat. Genet.* 8:148 (1994)).

Pox viral vectors introduce the gene into the cells cytoplasm. Avipox virus vectors result in only short term expression of the nucleic acid. Adenovirus vectors, adeno-associated virus vectors and herpes simplex virus vectors are preferred for introducing the nucleic acid into neural cells. The adenovirus vector results in a shorter term expression (about 2 months) than adeno-associated virus (about 4 months), which in turn is shorter than HSV vectors. The vectors can be introduced by standard techniques, e.g. infection, transfection, transduction or transformation. Examples of modes of gene transfer include for example, naked DNA calcium phosphate precipitation, DEAE dextran, electroporation, protoplast fusion, lipofection, cell microinjection and viral vectors.

In a preferred embodiment, armed ATC are used in the treatment of hormone refractory prostate cancer (HRPC) and other patients with Her2+ tumors. However, the present invention allows for treatment of all types of tumors as a bispecific antibody can be generated with specificity for a tumor present in an individual patient. The present invention is advantageous in that it allows for use of autologous T cells and monoclonal antibody generation for a specific tumor present in an individual patient. Thus, treatment can be tailored for each individual patient and allows for changes in treatment if the tumor antigen changes, by generation of new monoclonal antibodies against the new tumor antigen. The new tumor specific antibody can then be heteroconjugated to the T cell activating antibody to form a new bispecific antibody, specific for the new tumor antigen and then used to arm the autologous ATC or COACT and reinfused into the patient.

In particular, the invention provides for determination of an individual patient's maximum tolerated dose (MTD) of armed ATC, involving patients with HRPC as well as determining the effectiveness of the arming strategy on an individual patient basis.

Preferably, the protocol for treatment of a patient requires the isolation of peripheral blood mononuclear cells (PBMC). PBMC's are isolated on a Ficoll-Hypaque gradient. PBMC's from each patient are activated as described in the examples which follow and then cryopreserved. Twice per week, ATC or COACTS are thawed, washed, armed with Her2bi, and infused into the patient. Preferably, there are four dose levels in the dose escalation schedule of armed ATC. The dose levels are at least about 2, 3, 5, and 8 billion armed ATC/infusion (total dose range of about 20-80 billion armed ATC/infusion). Patients are started on a very low dose (determination of doses are described in the examples which follow). If cell-based toxicity occurs, the dose level is decreased.

In accordance with the invention, suitable dose ranges of armed ATC/infusion are between about 2.5 billion armed ATC to about 40 billion armed ATC. Infusions of the present invention are administered at least about twice per week for at least about four weeks. A preferred armed ATC/infusion dose is at least about 2.5 billion, more preferably about 10 billion, most preferably about 40 billion armed ATC/infusion.

Toxicities are discussed infra. If the patient shows no signs of cell-based toxicity then the dose level is advanced to the next dose level. Preferably, at least about ten infusions are given to each patient. About two doses are infused per week for two weeks and about one dose per week for about 6 weeks. The patients also receive subcutaneous IL-2, or other immune augmenting cytokines, such as IL-12, of at least about 300,000 IU/m²/day, preferably on a daily basis beginning about 3 days before the first infusion and until about 1 week after the last infusion of armed ATC or COACTS.

Preferred dose ranges of IL-2 are at least about 50,000 IU/m²/day, more preferably about 150,000 IU/m²/day, most preferably about 300,000 IU/m²/day.

Preferred dose ranges of IL-12, or other immune augmenting cytokines or chemokines, are at least about 50,000 IU/m²/day, more preferably about 150,000 IU/m²/day, most preferably about 300,000 IU/m²/day. These doses may vary depending on the age, sex, condition, size, weight etc, of a patient, as determined by a practitioner well-skilled in the art.

GM-CSF is administered at a dose of about 125 µg/m², administered at least about twice per week beginning about 3 days before the first infusion and until about 1 week after the last infusion of armed ATC or COACTS. A preferred dose range of GM-CSF is at least about 50 µg/m², more preferably about 100 µg/m², and most preferably about 125 µg/m². Tumor and immune evaluations are performed at about 0, 3, 6, 9 and 12 months. If clinical response occurs, the patient is retreated at the next dose level. [111]Indium labeling of armed and unarmed ATC or COACTS can be used to determine trafficking of armed and unarmed ATC or COACTS. The trafficking procedure is usually conducted after the MTD has been determined.

The above procedure is an example of how the treatment protocol is used for patients with hormone refractory prostate cancer, but can be modified according to the type of tumor to be treated. The amount of armed ATC or COACTS administered to the patient will also vary depending on the condition of the patient and should be determined via consideration of all appropriate factors by the practitioner. Preferably, however, about $1 \times 10^6$ to about $1 \times 10^{12}$, more preferably about $1 \times 10^8$ to about $1 \times 10^{11}$, and even more preferably, about $1 \times 10^9$ to about $1 \times 10^{10}$ armed ATC or COACTS cells are utilized for adult humans. These amounts will vary depending on the age, weight, size, condition, sex of the patient, the type of tumor to be treated, the route of administration, whether the treatment is regional or systemic, and other factors. Those skilled in the art should be readily able to derive appropriate dosages and schedules of administration to suit the specific circumstance and needs of the patient.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8 cells via intravenous infusion is appropriate.

As used herein, determination of whether immunotherapy with armed ATC or COACTS can induce clinical remissions (CR) is measured by a 50% reduction of the appropriate tumor antigen. For example, clinical remission in a patient with hormone refractory prostate cancer is defined by a 50% reduction in the serum PSA level, which is determined by conventional ELISAs.

As used herein, determination of whether immunotherapy with armed ATC or COACTS can improve overall survival (OS), is defined as the length of time from day of entry into immunotherapy treatment until death.

As used herein, determination of whether immunotherapy with armed ATC COACTS can improve progression free survival (PFS), is defined as the length of time from day of entry into immunotherapy treatment until progression of disease.

In the present invention, there have been no dose-limiting toxicities of IL-2 given at doses of 300,000 IU/m²/day (continuous infusion or subcutaneously) and GM-CSF at 125 µg/kg/day given subcutaneously when given in combination with multiple doses of ATC after PBSCT for stage IIIb/IV breast cancer. Based on the clinical toxicities seen with the use of Herceptin alone or in combination with chemotherapy[159], ATC armed with ng amounts of BiAb do not produce dose-limiting cell-based toxicities. One can expect the side effects that are seen with the infusion of monoclonal antibodies such as fever, chills, low blood pressure, wheezing, and shortness of breath that can be treated by decreasing the dose level and time between infusions or by administration of antihistamines, for example, Benedryl™.

In a preferred embodiment, for the activation of ATC or COACTS, anti-T cell receptor monoclonal antibodies are preferably used. Preferred antibodies used to activate T cells, OKT3 for the production of ATC and OKT3/9.3 coated on a solid support, such as Dynal beads, to produce COACTS. Both ATC and COACTS are thoroughly washed during the harvest procedure to remove any medium components.

The production of ATC preferably involves a single pulse of antibody, followed by washing the cell product free of any remaining antibody prior to cell infusion, as discussed in the examples which follow.

The preferred production of COACTS only involves the Dynal beads bearing the coimmobilized antibodies OKT3 and 9.3, which are removed on about day 4 of in vitro culture. The minimum release criteria for the COACTS is preferably, at least about less than 25 beads/$3\times10^6$, more preferably at least about less than 50 beads/$3\times10^6$ cells, and most preferably at least about less than 100 beads/$3\times10^6$.

The activation method described herein, differs from the prior art in that the present invention directly cross-links the T cell receptor with a monoclonal antibody and expands the activated T cells in low dose IL-2 as described in the examples which follow. For example, autolymphocyte therapy (ALT) involves infusions of autologous PBMC produced by cultures containing extracts of autologous tumor and conditioned media (CM) derived from PBMC stimulated with OKT3.[50] Preclinical studies in C57BL/6J mice using tumor extracts from Lewis lung carcinoma and B16 melanoma showed that splenocytes can be stimulated to expand CD44+ memory CTL and respond to tumor challenge.[51;52] Subsequent studies using ALT generated cytotoxic effector cells could be obtained from PBMC grown in CM produced by OKT3-stimulated PBMC instead of autologous tumor. This procedure differs from the present invention in that ALT is distinguished from anti-CD3 activated T cells (ATC) based on differences in the activation method. ALT is indirectly activated via supernatants from OKT3-stimulated PBMC. In contrast, ATC are prepared by directly cross linking the T cell receptor (TCR) with OKT3 and expanding the T cells in low dose IL-2.

Anti-CD3 activated T cells (ATC): Cross linking of the T cell receptor (TCR) with anti-CD3 monoclonal-antibody (MAb) leads to T cell proliferation, cytokine synthesis, and immune responses.[54-57] ATC are produced by OKT3 stimulation of PBMC in the presence of low doses of IL-2 (at least about 5-100 IU/ml). ATC have a variety of clinical applications. ATC have activated NK and NK-like cytotoxic properties, produce tumoricidal cytokines, and can serve as vehicles that can deliver targeting antibodies or gene products. Preclinical studies show that ATC can be expanded from PBMC or bone marrow from normals and patients with malignancy and mediate non-MHC restricted cytotoxicity.[62-72] In vitro studies showed that human ATC exhibited non-MHC restricted cytotoxicity to Daudi cells (ANK sensitive targets), K562 cells (NK sensitive targets), leukemic blasts,[73;74] neuroblastomas,[63] and autologous plasma cells in multiple myeloma.[75] In addition, ATC produce immunologically active or tumoricidal cytokines such as IFNγ, TNFα, or GM-CSF.

Anti-CD3/Anti-CD28 coactivated T Cells (COACTS): Cross linking of the TCR with anti-CD3 triggers a signaling cascade resulting in T cell proliferation, cytokine synthesis, and immune responses.[54-57] However, optimal activation and proliferation requires costimulation of CD28 receptors on T cells with anti-CD28 or B7 molecules (CD80 and CD86).[79-83] These interactions enhance proliferation and stabilization of mRNAs for IL-2, IFNγ, TNFα, and granulocyte-macrophage colony stimulating factor (GM-CSF).[84] Costimulation of the CD28 receptor also leads to enhanced production of beta chemokines RANTES, MIP1-α and MIP1-β[85] The enhanced secretion of chemokines at the tumor site may augment recruitment of effector cells.

In one preferred embodiment, ATC or COACTS can be transduced with vectors coding for chemokines to deliver locally, high concentrations of cytokines which recruit other effector cells, trigger T cell proliferation and enhance a localized immune response. Methods for transduction are well known in the art.

A "vector" is a composition which can transduce, transfect, transform or infect a cell, thereby causing the cell to express nucleic acids and/or proteins other than those native to the cell, or in a manner not native to the cell. A cell is "transduced" by a nucleic acid when the nucleic acid is translocated into the cell from the extracellular environment. Any method of transferring a nucleic acid into the cell may be used; the term, unless otherwise indicated, does not imply any particular method of delivering a nucleic acid into a cell. A cell is "transformed" by a nucleic acid when the nucleic acid is transduced into the cell and stably replicated. A vector includes a nucleic acid (ordinarily RNA or DNA) to be expressed by the cell. A vector optionally includes materials to aid in achieving entry of the nucleic acid into the cell, such as a viral particle, liposome, protein coating or the like. A "cell transduction vector" is a vector which encodes a nucleic acid capable of stable replication and expression in a cell once the nucleic acid is transduced into the cell.

Anti-CD3/anti-CD28 coactivated T cells (COACTS) exhibit in vitro anti-tumor activity directed at a variety of tumor cell lines.[86] COACTS produce $Th_1$-type cytokine profiles[79;87] and may survive longer in vivo due to induction of the cell survival gene $Bcl-x_1$, which confers resistance to apoptosis.[88;89]

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Materials and Methods

Components used for ATC or COACTS.

Orthoclone OKT3 (muromonab-CD3). OKT3 is purchased from Ortho-Biotech (Raritan, N.J.). OKT3 is supplied as a sterile solution in packages of 5 ampoules (NDC 59676-101-01) containing 5 mg of muromonab-CD3. Proleukin® (Aldesleukin, IL-2). Proleukin® (recombinant IL-2) is purchased from Chiron (Emeryville, Calif.). ATC are expanded in the presence of low dose IL-2 (100 IU/ml) in RPMI 1640 (BioWhittaker) supplemented with 2-5% human serum (BioWhittaker). RPMI 1640 (BioWhittaker) is supplemented with 2 mM L-glutamine (BioWhittaker), and 50 µg/ml gentimicin (BioWhittaker).

"Armed ATC" or "Armed COACTS" are the best descriptive names for the armed and activated T cells. The chemically heteroconjugated anti-CD3 x anti-Her2 (either OKT3×9184 or OKT3 x Herceptin®) is referred to as Her2bi. Therefore, ATC armed with anti-CD3 x anti-Her2/neu BiAb are designated Her2bi armed ATC or COACTS. OKT3 x Herceptin® has been abbreviated to OKT3 x Herc.

Preparation of Anti-CD3 x Anti-Her2 Bispecific Antibody.

Equimolar concentrations of OKT3 and anti-Her2 (9184 or Herceptin) are conjugated. OKT3 is reacted with Traut's reagent at room temperature (RT) for 1 hr and 9184, Herceptin, or control irrelevant antibodies are reacted with sulphosuccinimidyl 4-(N-maleimidomethyl) cyclohexane-1-carboxylate at RT. Both Mabs are purified on 10 DG columns (Biorad) in PBS to remove unbound cross linker. The crosslinked Mabs are mixed at equimolar ratios and conjugated at 4° C. overnight. At these concentrations, dimer formation is optimal and multimer formation is minimized. The reactants, products, and purified fractions of the heteroconjugation reaction are visualized by SDS non-reducing PAGE and Coomassie blue staining. The final products OKT3×9184 or OKT3 x Herc are cleared for final use only after 7 days of bacteria and fungal cultures, PCR for mycoplasma (ATCC, Catalog #90-1001K), and assay for endotoxin (BioWhittaker, Catalog #50-6470) are all negative.

Each bispecific antibody heteroconjugate lot (previous testing negative for bacteria, fungi, Mycoplasma, and endotoxin) is tested by a dose-titration arming of normal cryopreserved ATC or COACTS against PC-3, MCF-7, and/or SK-BR-3 target cells prior to release. Multiple vials of pretested normal donors have been expanded for 14 days, cryopreserved in aliquots for lot testing as well as providing normal controls in the evaluation of the armed patient ATC. Each lot must exhibit a dose-titration effect with increased specific cytotoxicity at the same E/T ratio when as the arming dose of the Her2Bi is increased. The arming dose range of each lot is determined by such a titration. The lot is rejected if a % specific cytotoxicity of at least about 50% of PC-3, MCF-7 or SK-BR-3 at an E/T of 25:1 can not be attained after a 20 hr cytotoxicity assay with an arming dose of 50 ng/million ATC or COACTS.

Preparation, Culture, Arming and Cryopreservation of ATC or COACTS.

Peripheral blood mononuclear cells (PBMC) from normal subjects and cancer patients are isolated by Ficoll-Hypaque (Lymphoprep from Nycomed Pharma, Oslo, Norway). PBMC are activated on plates coated with 2 µg/ml immobilized OKT3 or 20 ng/ml of soluble OKT3 (Ortho Biotech, Inc., Raritan, N.J.).[67;68] COACTS are produced from PBMC or a leukopheresis product by co-stimulating the PBMC with beads co-coated with OKT3 and 9.3 Mabs for 4 days. After 4 days of culture, the beads are removed and the cultures continued for an additional 10 days. Unless otherwise indicated, ATC or COACTS are grown for 14 days in RPMI 1640 medium (BioWhittaker, Walkersville, Md.) supplemented with antibiotics, L-glutamine, 100 IU/ml of IL-2 (Chiron Corp., Emeryville, Calif.), and 10% fetal calf serum FCS (Hyclone, Logan, Utah) or human serum (BioWhittaker) as indicated. Cells are counted and maintained at $10^6$/ml. Viability is determined by trypan blue exclusion. T cells are grown from normal subjects or cancer patients. The T cells are washed, counted, and incubated ("armed") with BiAb at the indicated doses ($10^6$ T cells for 1 hr at 4° C. in 125 µl of media). The T cells are washed twice in complete medium prior to testing.

Activation, Culture, Cryopreservation, Thawing, and Washing of ATC.

In brief, lymphocytes are obtained by leukopheresis, cultured at a density of $1-3\times10^6$ cells/ml in RPMI 1640 medium supplemented with 2 mM of L-glutamine, 100 IU/ml of IL-2, 10-20 ng/ml of OKT3-, and 2% pooled human serum-. Cells are cultured for a maximum of 14 days. The ATC are counted, split, and/or fed every 3-4 days with complete medium based on cell concentration No additional OKT3 is added. After culture, ATC are harvested and washed using the Fenwal Cell harvester, and cryopreserved in 10% DMSO and 20% protein (albumin or autologous plasma) using controlled rate freezing and storage in liquid nitrogen. No exogenous IL-2, OKT3, or other culture reagents (e.g. medium components) are present in the final cryopreserved product.

Activation, Culture, Bead Removal, Cryopreservation, Thawing, and Washing of COACTS.

In brief, lymphocytes are obtained by leukopheresis, cultured at a density of $1-3\times10^6$ cells/ml in Ex vivo 15 medium supplemented with 2 mM of L-glutamine, 100 IU/ml of IL-2, and 2% pooled human serum-. PBMC from the leukopheresis produce are cocultured with Dynal beads with coimmobilized GMP grade OKT3 and 9.3 in order to coactivate the T cells. The beads are removed using the MagSep device after 4 days of culture and the COACTS are put back into culture. The COACTS are counted, split, and/or fed every 3-4 days with complete medium containing 100 IU/ml of IL-2 final. After culture, COACTS are harvested and washed using the Fenwal Cell harvester, and cryopreserved in 10% DMSO and 20% protein (albumin or autologous plasma) using controlled rate freezing and storage in liquid nitrogen. No exogenous IL-2, OKT3, culture reagents (e.g. beads or medium components) are present in the final cryopreserved product.

Initiation, Splitting, and Harvest of ATC Cultures.

PBMC at a concentration of $1\times10^6$ mononuclear cells/ml are activated with 20 ng/ml of soluble OKT3 in RPMI 1640 supplemented with L-glutamine, gentimicin, 100 IU/ml of IL-2, and 2% human serum in Stericel Multiple Container Sets. The activated T cells are counted split, and fed based on their expansion rate. After 6-14 days of culture, the ATC are harvested. If the amount of ATC to be harvested is 1 to 10 liters, procedures well-known in the art will be used for small volume T cell harvest & Cryopreservation. For volumes exceeding 10 liters, the ATC are harvested using a Fenwal Cell Harvesting System. Cryopreservation of unarmed or armed ATC is conducted using commercial human serum.

Anti-CD3 (OKT3) and anti-CD28 (9.3) monoclonal antibodies immobilized on beads are used to cross link cellular receptors. OKT3 is purchased from Ortho-Biotech (Raritan, N.J.). 9.3 antibody, lot #3-309-900411 was produced for Dr. Carl June by Abbott Biotech. OKT3 and 9.3 are linked to paramagnetic, polystyrene Dynabeads via tosyl chemistry in a 1:1 stoichiometry as per the manufacturer's protocol. The magnetic beads and the monoclonal antibodies linked to the beads are all produced under GMP conditions for clinical use.

COACTS are expanded in RPMI 1640 or X VIVO 15 supplemented with 2-5% human serum.

Initiation of Cultures Using OKT3/9.3 Coated Beads in 3 L Bags.

The procedure for seeding PBMC and stimulating PBMC with soluble OKT3 (20 ng/ml) in the presence of 100 IU/ml of IL-2 to produce ATC is modified to incorporate the introduction of OKT3/9.3 coated. The PBMC are counted, beads are added at a ratio of 3:1 (beads/cells), and the mixed in seeded into 3 L gas-permeable bags supplied by Nexell Therapeutics Inc (Irving, Calif.).

After the removal of beads on day 4 of culture using the MaxSep, the COACTS are placed back into culture in the conditioned medium. The COACTS are harvested, washed, and concentrated using a Fenwal Cell Harvester (Baxter).

Infusion Product Free of Carryover Cytokines.

The infused cell product does not contain exogenous cytokines. Data show that the IL-2 used in culture is undetectable by ELISA after 1 wash of ATC in 50 ml tube. Before washing of the cultured ATC, 3.5 IU/ml of IL-2 was detected. In a second experiment, duplicate 50 ml tubes spiked with 1200, 600, and 300 IU of IL-2/ml had no detectable IL-2 after 1 wash. The ELISA is sensitive to 50 pg/ml (<1 IU/ml). Since both ATC and COACTS are washed equally, COACTS do have any biologically significant cytokines after the harvest/wash.

Components to Produce OKT3×9184 or OKT3 x Herceptin®.

This application uses two BiAbs. Both BiAbs target Her2/neu use the chemical heteroconjugation process to produce the combination of anti-CD3 x anti-Her2/neu.

OKT3 x 9184 consists of clinical grade Orthoclone OKT3 (muromonab, IgG2a murine Mab directed at CD3 is purchased from Ortho-Biotech, Raritan, N.J.) chemically heteroconjugated to clinical grade 9184 (IgG1 murine Mab directed at Her2/neu is a gift from Nexell, Corporation, Irving, Calif.).

OKT3 x Herceptin® (OKT3 x Herc), consists of clinical grade OKT3 (IgG2a murine monoclonal antibody directed at CD3) chemically heteroconjugated to clinical grade Herceptin® (trastzumab, a humanized IgG1 Mab directed at Her2/neu is purchased from Genentech, San Francisco, Calif.).

Traut's Buffer: Traut's Buffer (pH 8) consists of Triethanolamine (Sigma Ultra #T9534), 1.5 M NaCl (Sigma), 1 mM EDTA (Disodium Dihydrate) (Sigma)

Sulphosuccinimidyl 4-(N-maleimidomethyl) cyclohexane-1-carboxylate: Sulpho-SMCC (SMCC buffer, Pierce #22322) is purchased from Pierce, Rockford, Ill.

Heteroconjugation Products: Equimolar quantities of OKT3 crosslinked with Traut's buffer and Sulpho-SMCC crosslinked 9184, Herceptin, or Rituxan are incubated overnight at 4° C. A non-reducing SDS gel is performed to identify the presence of monomer, dimer, or multimer. The material is sterile filtered and quality control by sterility, endotoxin, and Mycoplasma testing using standard procedures and release criteria (Limulus Amebocyte Lysate, Bio-Whittaker Catalog #50-6470; Mycoplasma detection kit, ATCC, Catalog #90-1001K).

ATC Armed with OKT3 x 9184 or OKT3 x Herc.

ATC are thawed after cryopreservation, armed with a pretitrated dose ranging from 5-100 ng of unpurified chemically heteroconjugated Her2Bi per million ATC, washed free of non-binding antibodies, and infused into the patients.

COACTS Armed with OKT3 x 9184 or OKT3 x Herc.

COACTS are thawed after cryopreservation, armed with a pretitrated dose ranging from 5-100 ng of unpurified chemically heteroconjugated Her2Bi per million, and washed free of non-binding antibodies. The armed COACTS are infused into the patients. There have been no toxicities or side effects attributed to antibody or bead carryover in patients who received up to $60 \times 10^9$ COACTS.

Specific Arming Dose for Each Patient.

The optimal arming dose is determined for each patient based on titration of a frozen aliquot of the patient's ATC or COACTS cell product. The arming dose is adjusted to achieve a % specific cytotoxicity level at an E/T of 25:1 of at least 30% on PC-3, SK-BR-3, or MCF-7 cells. The arming dose for each patient is recorded on the arming worksheet for each patient. Table 1, below, is an illustrative example of a treatment schedule and is not meant to limit or construe the invention in any way.

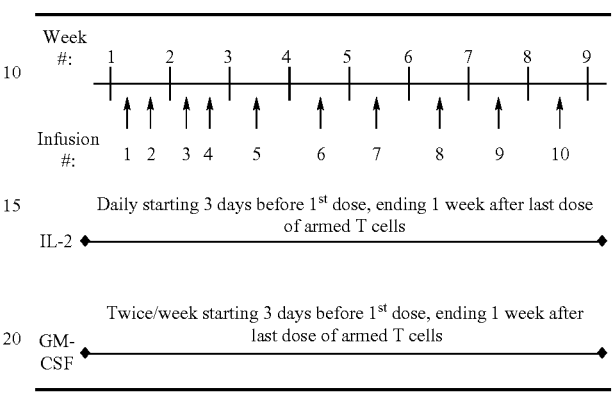

The treatment includes subcutaneous injections of IL-2 beginning 3 days before the first armed ATC or COACTS infusion at a dose of $3 \times 10^5$ IU/m²/day. IL-2 will be given until-7 days after the last dose of armed ATC or COACTS.

The treatment includes subcutaneous injections of 125 μg/m² of GM-CSF twice per week for 8 weeks beginning 3 days before the first armed ATC infusions and ending 7 days after the last dose of armed ATC or COACTS.

ATC infusions in the presence of low dose IL-2 in refractory cancers (SLMC BRM 94-01, BRM 95-02) and the combination of PBSCT for metastatic breast cancer (BRM 95-03) followed by ATC infusions, continuous infusion IL-2 (about $3 \times 10^5$ IU/m²/day for about 65 days), and GM-CSF injections (between about day 5 and about day 21 after PBSCT) have not induced life-threatening autologous graft-versus-host disease or autoimmune syndrome. The grade III skin rashes induced by the combination of ATC, IL-2, and GM-CSF may or may not have been autologous graft-versus-host disease or autoimmune syndromes (GVHD). Patients may develop an "autologous or syngeneic" GVHD skin rash due to dysregulated or overactive T cells. Two of 23 patients who received PBSCT and ATC developed skin rashes thought to be related to autologous GVHD but could have been related to chemotherapy agents such as Taxol. No treatment was required and the skin rashes spontaneously resolved. The rashes were not treated with steroids. No patient has suffered irreversible toxicities due to the syndrome.

Arming of the Clinical Product.

From 3 to 10 billion (20% more than the targeted amount is processed to account for washing and processing losses) cryopreserved ATC or COACTS are thawed, washed, resuspended in plasmanate containing 2% albumin, and armed in centrifuge tubes by incubating for 1 hr at 4° C. The Her2Bi is washed twice in plasmanate containing 2% albumin, and transferred into a transfer bag for infusion into the patient. An aliquot is removed for viability, sterility and cytotoxicity testing.

Tumor Cell Lines and Monoclonal Antibodies.

The breast cancer lines MCF-7 cells and SK-BR-3 are purchased from ATCC Rockville, Md. OKT3 is purchased from OrthoBiotech. The 9184 is an anti-Her2/neu, IgG1 provided by Nexell. Herceptin® is purchased from Genentech, SF, Calif.), Rituxan (anti-CD20) is purchased from Genentech. T84.55 hybridoma (anti-carcinoembryonic antigen) is purchased from ATCC, Rockville, Md. IG3 (anti-prostate specific membrane antigen) is a gift from Alton Boynton of Northwest Biotherapeutics, Seattle, Wash.

Table 2 summarizes the binding and functional characteristics of the two bispecific antibodies, OKT3 x 9184 and OKT3 x Herc, for rosetting, flow cytometry, and cytotoxicity.

TABLE 2

| Cell Lines | MCF-7 | SK-BR-3 | PC-3 |
|---|---|---|---|
| Rosetting | | | |
| OKT3 x 9184 | 4+ | 4+ | 3+ |
| OKT3 x Herc | 4+ | 4+ | 3+ |
| Flow Cytometry | | | |
| OKT3 x 9184 | 1+ | 4+ | 2+ |
| OKT3 x Herc | 1+ | 4+ | 2+ |
| Specific Cytotoxicity | | | |
| OKT3 x 9184 | 3+ | 4+ | 4+ |
| OKT3 x Herc | 4+ | 4+ | 4+ |

Prostate Carcinoma, Breast carcinoma, and Other Her2/neu+ Tumors.

The patients undergo leukopheresis for lymphocytes for generating ATC. At the designated times for infusions, ATC are thawed, washed, armed with Her2bi, and infused. There are four dose levels in the dose escalation schedule of armed ATC. Each dose level has 3 patients. The dose levels are 2, 3, 5, and 8 billion/infusion (total dose of 20-80 billion). If cell-based toxicity occurs, three additional patients will be added to the same dose level before advancing to the next dose level. Ten infusions are given to each patient. Two doses are infused per week for two weeks and one dose per week for the subsequent 6 weeks. The patients receive subcutaneous IL-2 (300,000 $IU/m^2$/day) daily beginning 3 days before the first infusion and until 1 week after the last infusion of armed ATC. GM-CSF is given at a dose of 125 μg/$m^2$ twice per week beginning 3 days before the first infusion and until 1 week after the last infusion of armed ATC. Tumor and immune evaluations are performed at 0, 3, 6, 9 and 12 month after the first armed ATC infusion. $^{111}$Indium labeling of armed and unarmed ATC is conducted in selected patients with measurable disease to determine if arming of ATC improves trafficking to tumor sites.

Adverse events are scored using the NCI immunotherapy toxicity scoring system. A 50% decline in the PSA level is considered an objective response. PSA levels, Her2/neu receptor levels, IFNγ ELISPOTS by PBMC before and after infusions, IFNγ ELISPOTS responses to autologous tumor (if available), cytokine secretion, phenotyping of PBMC, T cell proliferation, and HAMA responses are evaluated at the designated time points.

Administration of low dose subcutaneous (SQ) IL-2 ($2\times10^5$ $IU/m^2$/day) for 90 days resulted in no grade III toxicities. None of the patients experienced pulmonary capillary leak syndrome, severe hypotension, oliguria, azotemia, or hyperbilirubinemia.[162] The most frequent toxicities included fatigue, fever, and nausea. None of the patients had to stop their SQ IL-2 therapy due to side effects. Therefore, it is unlikely that major toxicities associated with the low dose SQ IL-2 occur, although death due to high dose IL-2 is a known toxicity.

GM-CSF is a colony stimulating factor. Known Side Effects and Toxicities: Patients receiving GM-CSF (Leukine-Sagra-mostim) have experienced fever 60-90 min after administration (duration 1-4 hrs); chills; nausea; vomiting; diarrhea; fatigue; weakness; headache; decreased appetite; thrombosis; rapid or irregular heartbeat or other heart problems; feeling of faintness; facial flushing; pain in the bones, muscles, chest, abdomen, or joints; local reaction at the site of injection; rashes; and kidney and liver dysfunction. Eosinophilia or other blood component abnormalities may occur. There have been infrequent reports of fluid accumulation or worsening of preexisting fluid accumulation in the extremities, in the lungs, and around the heart which may result in breathing problems or heart failure. Rarely, patients have developed acute allergic reactions. There have also been reports of low blood pressure, hypoxia, transient loss of consciousness, and difficulty in breathing after the first injection of Sargramostim. These signs may or may not recur with additional injections of Sargramostim. Patients with prior heart, lung, kidney, or liver problems may have worsening of their symptoms following administration of Sargramostim. There may be other side effects that could occur.

Infusions of Her2bi Armed ATC.

The ATC infusions are conducted on an outpatient basis in the BMT unit. All appropriate assurances for identification of product, patient, sterility, etc. are performed prior to reinfusion. Frozen ATC are thawed, washed, and then armed with a pretitrated dose of Her2bi. The armed ATC are washed 3 times and resuspended in infusion medium. The time for Her2bi armed ATC infusions varies from patient to patient, but the dose of armed ATC (up to 8 billion) is given over 30 min. All patients are observed for a least 1 hr after an infusion. Vital Signs (T, P, R, and BP) are obtained before and every 15 min until the end of the observation period. All vitals are recorded on the patient's immunotherapy toxicity scoring flowchart. If stable, the patient can be discharged home.

Determination of Maximum Tolerated Dose (MTD)

The endpoints for the Phase I trial are defined as: 1) reaching the maximum tolerated dose of armed ATC or 2) reaching the technical limit of cell product expansion. Three patients are entered at each dose level. Each patient receives ten infusions per course of treatment. The dose levels are 2, 3, 5, and 8 billion per infusion. The first three patients will receive ten infusions of $2\times10^9$ for a total dose of $2\times10^{10}$ armed ATC (1st dose level); the $2^{nd}$ three patients will receive ten infusions of $3\times10^9$ for a total dose of $3\times10^{10}$ armed ATC ($2^{nd}$ dose level); the $3^{rd}$ three patients will receive ten infusions of $5\times10^9$ for a total dose of $5\times10^{10}$ armed ATC; and the $4^{th}$ three patients will receive ten infusions of $8\times10^9$ for a total dose of $8\times10^{10}$ armed ATC. The cell dose is increased until the MTD is reached. Two doses are infused per week for the first two weeks and one dose per week for the subsequent 6 weeks.

Dose Modification for Her2bi Armed ATC or COACTS.

If there is persistent grade 3 or more severe toxicity at any time, the treatment will be held until toxicity improves to grade 0 or 1. If the toxicities continue at the reduced dose of armed ATC or COACTS, the IL-2 will be stopped and the armed ATC or COACTS will be continued at the reduced dose. If grade 3 or more severe toxicity again occurs, the armed ATC or COACTS infusions will be stopped. Toxicity is assessed daily for 2 days after each reinfusion and weekly between treatment courses for unresolved toxicities. Patients who develop non-hematological grade 4 toxicity will be required to discontinue treatment.

Armed ATC or COACTS toxicities are toxicities that occur during the armed ATC or COACTS infusions and up to 12 hrs after the infusions. Delayed clinical manifestations such as GVHD of the skin, liver, or gut or other autoimmune disease are considered as delayed toxicities of the infusions for purposes of dose-escalation. However, systemic infection due to infusion of a contaminated cell product is not considered a product-related toxicity in the determination of the MTD.

Toxicity Grading—The NCI Common Toxicity Scale.
- If Grade I-II toxicities occur, the patient may continue with the infusion schedule.
- If Grade III toxicity occurs, the "drug" will be held until the toxicity decreases to Grade I or II, then the infusion will be restarted. If Grade III or IV toxicity occurs after the restart, the "drug" infusions will be stopped.
- If Grade IV toxicity occurs, the patient is scored as having Grade IV toxicity and the next infusion is reduced to the previous dose. If the previous dose causes Grade IV toxicity, then the "drug" will be stopped.
- If Grade IV toxicity occurs in 1 of 3 patients at a specific dose level, an additional 3 patients must be entered at that cell-dose level for a total of 6 patients at that dose level. If 2 of 6 patients at a cell-dose level develop Grade IV toxicity, this dose is defined as the MTD. The next 3 patients will be given 66% (two-thirds) of the previous cell-dose level. For the purposes of evaluation for dose-escalation, each patient at the same dose level must have received at least 4 of 6 infusions.

Radioactively Indium Labeled Armed T Cells

The amount of radioactivity put onto the armed T cells is similar to that used in bone scans.

After the MTD is determine, approximately 6 patients with measurable disease will be entered into the trafficking study. Each patient receives unarmed $^{111}$Indium labeled ATC, scanned for tumor localization every 24 hrs for at least 72 hrs. After the disappearance of the label on scanning, the same patient receives the same amount of $^{111}$Indium labeled Her2Bi armed ATC to determine if there are significant differences in amount of labeling at tumor sites. Both unarmed and the Her2Bi armed ATC are labeled with $^{111}$Indium. After the MTD for Her2Bi armed ATC has been determined, selected patients will be studied with infusions of $^{111}$Indium labeled unarmed ATC. ATC are thawed, washed free of freezing medium, armed or left unarmed with the optimal concentration of Her2bi for 1 hr at 4° C., washed free of excess arming antibody, and then labeled with $^{111}$Indium using standard nuclear medicine labeling methodology. Planar whole-body imaging is performed at 4, 24, 48, and 72 hrs with a gamma camera (Picker Prism 2000, Picker International, Cleveland, Ohio) equipped with general purpose medium energy collimators. The patients are followed until the label can no longer be detected. Imaging time is approximately 30 min with a target of 500 k counts to be acquired at 4 hrs.

Stage IV Breast Cancer Treatments

Women with stage IV breast cancer are entered into a phase I dose escalation trial comprised of increasing doses of the bispecific antibody OKT3 x Herceptin (HER2Bi) armed, activated T cells (armed ATC). ATC are expanded for 14 days from a leukopheresis product, armed with HER2Bi, cryopreserved and infused in 8 divided doses. Escalating doses of armed-ATC are given until the maximum tolerated dose is determined or the maximum technically attainable dose has been reached. Three patients at each dose level receive doses of 2.5, 5.0, 10, 20, and 40 billion armed-ATC twice/week for 4 weeks. If there is a grade 3 non-hematological toxicity in one patient at any dose level, then the cohort will be expanded to six patients at that dose level. The dose is escalated to the next level only if no more patients in the expanded cohort tolerate therapy without developing grade 3 non-hematological toxicity. Low dose IL-2 (about 300,000 IU/m²/day) and GM-CSF (about 150 µg/m² twice per week) are started one day prior to the first armed-ATC infusion and end 7 days after the last dose of armed ATC.

After the maximum tolerated dose (MTD) is determined in the phase I setting, a phase II clinical trial using the MTD is performed in 33 patients with 2+ or 3+ HER2/neu over-expressing breast cancer tumors. This allows for defining the toxicity profile; determine clinical responses; evaluation of overall and progression free survival; sequential evaluation of clinical and immune parameters. Selected patients with HER2/neu positive tumors in the phase I and II parts of the clinical trials are given $^{111}$Indium-labeled unarmed and armed ATC to determine the survival rate of the armed ATC and localization of armed ATC to metastasized tumor sites.

ELISA Assay for Cytokines.

Armed or unarmed ATC or COACTS are cultured with or without PC-3, MCF-7, or SK-BR-3 as appropriate. ATC or COACTS are armed with OKT3 x 9184 or OKT3 x Her and irrelevant controls (OKT3, 9184, Herc, and/or OKT3 x Rituxan) at concentrations paralleling the concentrations used for the clinical arming process. Armed ATC or COACTS are cocultured at E/T of 10:1 or 5:1 for 24 hrs. The target and effector cells are adjusted to insure a plating concentration of 1×10⁶ of T cells. The supernatants are tested by ELISA and the amount of cytokine produced is expressed at pg/million armed ATC or COACTS/24 hrs.

ELISPOTS for Single Cell Secretion IFNγ.

Armed or unarmed ATC or COACTS are cultured with or without PC-3, MCF-7, or SK-BR-3 as appropriate. ATC or COACTS are armed with OKT3 x 9184 or OKT3 x Her and irrelevant controls (OKT3, 9184, Herc, and/or OKT3 x Rituxan) at concentrations paralleling the concentrations used for the clinical arming process. Armed ATC or COACTS are cocultured at E/T of 10:1 or 5:1 for 24 hrs. The target and effector cells are adjusted to insure a plating concentration of 1×10⁶ of T cells. The T cells in these cultures are harvested leaving the target cells on the flat-bottomed well. The T cells are counted and plated onto ELISPOT wells (Millipore Corp.) and the number of spots are enumerated using a dissecting microscope 24 hrs later. The number of IFN γ spots are expressed as IFNγ secreting cells/million armed ATC or COACTS.

$^{111}$Indium Oxine Labeling of Her2Bi Armed or Unarmed ATC.

A sample of ATC or Her2Bi armed ATC are labeled with $^{111}$Indium Oxine (Amersham Healthcare, Arlington Heights, Ill.) using a modification of standard method.[163; 164] Approximately 2×10⁵ COACTS are washed and resuspended in buffered, glucose-containing medium and 700 µCi of $^{111}$Indium Oxine is mixed with the sample. The labeled cells are then mixed with the remainder of the ATC dose and re-infused into the patient.

Cytotoxicity Assay.

Cytotoxicity is measured in a 20 hr $^{51}$Cr-release assay. Tumor cells are plated in flat-bottomed microtiter plates and incubated at 37° C. overnight. The targets are washed and labeled the next day with $^{51}$Cr at 37° C. The wells containing tumor cells are washed, and armed or unarmed ATC are plated at different E:T ratios and incubated overnight at 37° C. The next day, the plates are counted in a gamma counter and the percent specific lysis calculated.

All of the cytotoxicity assays shown in this application were conducted without the addition of IL-2 for 18 to 20 hours. The redirected cytotoxicity mediated by armed ATC or COACTS occurs in presence of serum and complement and in the absence of IL-2. Therefore, the infused armed T cells are likely to kill tumor for at least 18 to 20 hours in the absence of IL-2.

Serum and complement do not affect cytotoxicity mediated by armed ATC. Armed ATC were not lysed in the presence of fresh PBMC and rabbit complement or high concentrations of fresh human serum. This result suggests that armed ATC would not be lysed in vivo by complement fixation and lysis via Fc-receptor mediated antibody dependent cellular cytotoxicity.

Institutional Review Board.

The protocol entitled "Targeting of Her2/neu Prostate Carcinoma in Men With Hormone Refractory Prostate Cancer Using Activated T Cells Armed With Anti-CD3 x Anti-Her2/neu Bispecific Monoclonal Antibodies" and its consent form has been approved by the Roger Williams Hospital Institutional Review Board. The IRB will monitor the study and IRB approval will be obtained before changes of the protocol are initiated. All unanticipated problems involving risks to human subjects or other problems will be reported to the IRB.

The treatment plan will be according to the protocol(s), the therapy involved in the specific protocols and alternative forms of therapy will be presented to patients by the Investigators or their designees. The risk and hazards of the procedure will be fully explained to the patient. The protocols will contain the specific details and the consent forms.

Summary of Preclinical Work

The preclinical studies show: The optimal time interval for arming ATC begins around day 4 and persists up to day 14 after activation of ATC or COACTS. The saturating arming dose of OKT3 x 9184 or OKT3 x Herc needed for optimal cytotoxicity is around 50 ng/$10^6$ ATC or COACTS. Bispecific antibody mediated cytotoxicity is enriched in the dimer fraction based on parallel studies done using OKT3 x T84.66 (anti-CEA). Tumoricidal cytokine secretion by normal and patient ATC is induced by specific binding to tumor antigen; 5) cryopreservation prior to armed normal or patient ATC. OKT3 x 9184 armed normal ATC lyse PC-3, MCF-7 and SK-BR-3 tumor targets. Increasing the arming dose of OKT3 x 9184 increases the % specific cytotoxicity directed at MCF-7, SK-BR-3 and PC-3 targets. Flow cytometry shows that OKT3 x 9184 binds to MCF-7, SK-BR-3 and PC-3 cells. Arming ATC with OKT3 x Herc significantly enhances targeting of MCF-7, SK-BR-3 and PC-3 targets. Doses of OKT3 x Herc and OKT3 x 9184 for arming ATC are similar for targeting MCF-7 and PC-3 targets. Binding of ATC armed with OKT3x9184 or OKT3xHerc to SK-BR-3 induces IFNγ secretion. OKT3 x 9184 or OKT3 x Herc armed normal ATC are comparable in killing PC-3. Armed patient T cells remain cytotoxic to PC-3 after freeze/thaw. Cytotoxicity mediated by ATC armed with OKT3 x Herc is not inhibited by soluble Herceptin®. Clinical toxicities and efficacy were evaluated in a SCID mouse model showing that OKT3 x anti-CEA armed ATC could prevent the growth of LS174T colon carcinoma cells in 10% of the SCID mice injected in an Winn assay without any clinical toxicities when given subcutaneously. Although there was no clinical benefit, I.V. tail vein injections and intraperitoneal injections of armed ATC did not cause morbidity or mortality in SCID mice. Cytokine secretion by normal ATC armed with OKT3 x 9184 or OKT3 x Herc is induced by binding to PC-3. Transgene cytokine and endogenous cytokine secretion can be reinduced by targeting of IL-2 gene transduced-ATC. Clinical scale-up of arming process shows no differences in the arming doses needed for specific cytotoxicity in both normal and patient ATC. Anti-CD3/anti-CD28 coactivated T cells from a normal can be armed with OKT3 x 9184 and exhibit specific cytotoxicity directed at MCF-7. Cryopreservation had little affect on specific cytotoxicity directed at Her2+MCF-7 or PC-3 targets using both OKT3 x 9184 or OKT3 x Herc. Cancer patients COACTS and ATC armed with OKT3 x 9184 have comparable specific cytotoxicity activity against MCF-7 targets.

Example 1

Chemical Conjugation of OKT3 x 9184.

FIG. 1 shows the steps for heteroconjugating OKT3 with the anti-tumor associated antigen MAb (anti-TAA) (9184). OKT3 (1-5 mg) in 50 mM NaCl, 1 mM EDTA, pH 8.0 is reacted with a 5 fold molar excess of Traut's reagent (2-iminothiolane HC1); (Pierce, Rockford, Ill.) at room temperature for 1 hr (STEP, FIG. 1). 1-5 mgs of 9184 in 0.1 M sodium phosphate, 0.15 M NaCl at pH 7.2, is reacted, in a separate reaction, with a 4 fold M excess of sulphosuccinimidyl 4-(N-maleimidomethyl) cyclohexane-1-carboxylate (Sulpho-SMCC from Pierce, Rockford, Ill.) at room temperature for 1 hr (STEP 2). Both Mabs are purified on PD-10 columns (Pharmacia, Uppsala, Sweden) in PBS to remove unbound crosslinker. The crosslinked Mabs are mixed immediately at equimolar ratios and conjugated at 4° C. overnight (STEP 3). Protein quantitation is done with a BCA Protein Assay Kit (Pierce, Rockford, Ill.). The heteroconjugation product is analyzed by non-reducing SDS gel electrophoresis using a 2-15% gradient gel (OWL Scientific, Woburn, Mass.). Coomassie blue staining is used to visualize proteins in the gel. Densitometric analysis is performed using the Gel Doc 1000 System (Bio-Rad, Hercules, Calif.). Densitometric quantitation of lane 5 of the gel showed ~67% monomer, ~23% dimer, and ~10% multimer fractions (FIG. 2). Lane 1, high molecular weight marker; lane 2, 10 μg of OKT3 was loaded; lane 3, 10 g of 9184 was loaded; lane 4, blank; lane 5, 30 μg of Her2Bi was loaded. The unconjugated OKT3 and 9184 (monomer), dimer of OKT3 x 9184, and multimers of OKT3 x 9184 are indicated in lane 5.

Other anti-CD3 heteroconjugates are made with an irrelevant anti-prostate specific membrane antigen (anti-CD3 x IG3), Herceptin® (anti-CD3 x Herc), Rituxan (anti-CD3 x Rit), T84.66 (anti-CD3 x T84.66) are produced using the same procedure.

Example 2

Rosetting of ATC Armed with Her2Bi with MCF-7 or PC-3 Cells.

All of the arming is always expressed as ng per million ATC using the entire heteroconjugate unless otherwise stated. Unarmed ATC (lower left, FIG. 3), ATC armed with 50 ng of Her2Bi (upper left), ATC armed with 50 ng of irrelevant OKT3/IG3 (upper right), or ATC treated with a mixture of 250 ng of nonconjugated OKT3+250 ng of non-conjugated 9184 (lower right) are cultured with MCF-7 cells overnight at 37° C. An overnight culture at an effector-to-target (E/T) ratio from 90:1 to 3:1 would consistently rosette with MCF-7 or PC-3 cells.

Example 3

Binding of Her2Bi to ATC.

Phycoerythrin (PE)-conjugated goat anti-mouse IgG2a and IgG or fluorescein isothiocyanate (FITC)-conjugated goat anti-mouse IgG1 (Caltag Laboratories, Inc., Burlingame, Calif.) is used to detect binding of Her2Bi. Binding is determined by incubating $10^6$ ATC with the sample at the stated concentration of Her2Bi for 1 hr at 4° C., washing twice with PBS containing 1% BSA, and incubating for 30 mins in the dark with PE or FITC conjugated goat-anti-mouse to determine the amounts of OKT3 (IgG2a) or 9184 (IgG1) on the surface of the ATC. Binding of Her2Bi to PC-3, MCF-7, and SK-BR-3 were determined by incubating 106 MCF-7 or SK-BR-3 with 1 μg BiAb for 1 hr at 4° C. The cells are washed and incubated with goat anti-mouse IgG1-FITC.

In order to quantitate binding, the mean fluorescence intensity (MFI) is determined for increasing doses of Her2Bi used to arm ATC (FIG. 4, Panel A). One million ATC were armed with 0, 0.5, 5, 50 and 500 ng of Her2Bi. Panel A shows that 9184 (an IgG1) portion of Her2Bi was detected in increasing amounts on the surface of ATC with directly conjugated goat anti-mouse IgG allotype specific antibody. An arming dose of 0.5 ng could still be detected about the background staining for the isotype control.

Dual staining was performed using anti-IgG1 and anti-IgG2a specific reagents to demonstrate specific binding of the Her2Bi. In order to specifically detect the IgG1 portion (9184) of Her2Bi, ATC armed with 50 ng of Her2Bi are stained with goat anti-mouse IgG1-FITC for 9184. To detect the IgG2a portion of Her2Bi (OKT3), armed ATC are stained with goat anti-mouse IgG2a-PE for OKT3. The MFI for an arming dose of 5 ng was 82 with 38% of the ATC being positive. At a dose of 50 ng, the MFI was 223 with 93% being positive. Binding did not increase when the arming dose was further increased to 500 ng. Based on these data, 50 ng is selected as the saturating arming dose. The MFIs for 9184 and OKT3 were 68 and 1050, respectively. Over 95% of ATC stained with IgG1-FITC and IgG2a-PE clearly indicated binding of Her2Bi.

Example 4

Detection of Her2/neu Receptors on MCF-7 and SK-BR-3 Cells.

MCF-7 or SK-BR-3 are incubated with 1 μg Her2Bi or 9184, washed, and stained with IgG1-FITC. The histogram shows binding of IgG1 (9184 portion of Her2Bi) to SK-BR-3 and MCF-7, respectively. Both 9184 and Her2Bi were detected with goat anti-mouse IgG1-PE with an MFI of 1133 on 97% of SK-BR-3 cells which expresses high numbers of Her2/neu receptors (Panel D, FIG. 4). Irrelevant OKT3/IG3 did not bind to SK-BR-3 (not shown). MCF-7 cells ($10^6$) were incubated with 1 μg Her2Bi or 1 μg of 9184. The tumor cells were washed and stained with IgG1-FITC. The histograms show the binding of IgG1-FITC to MCF-7. 9184 and Her2Bi were detected on only 64% and 48% of MCF-7 cells with MFIs of 28 and 35 (Panel E) confirming the barely detectable expression of Her2/neu receptors on MCF-7 cells.[158]

Example 5

The Development of Specific Cytotoxicity Directed at MCF-7.

Cytotoxicity was measured in a $^{51}$Cr-release assay. Tumor cells are plated in a flat-bottomed microtiter plate at a cell concentration of $4\times10^4$/well. The plates are incubated at 37° C. overnight, washed once, labeled with $^{51}$Cr (2 μCi/well) (Amersham, Arlington Heights, Ill.) for 4 hrs at 37° C., washed 3 times and ATC are plated in triplicate at four effector to target ratios (E/T). After overnight culture, 100 μl aliquot of the culture supernatant is removed for gamma counting on a COBRA-II gamma counter (Packard, Downers Grove, Ill.). The % specific lysis=(cpm test−cpm spontaneous)/(cpm max−cpm spontaneous)×100. Spontaneous release is determined by incubation of targets with media alone; and maximum release is determined by lysing the targets in 1% Triton-X 100 (Sigma Chemical Co., St. Louis, Mo.).

To define the development of redirected cytotoxicity mediated by armed ATC, fresh PBMC or ATC from the three normal subjects were armed with 50 ng of Her2Bi and tested for cytotoxicity against MCF-7 cells on the days indicated in FIG. 5. Each set of horizontal panels shows data for 3 separate normal subjects. PBMC were tested on day 0 (D0) and ATC were left unarmed (•, no antibody) or armed with 50 ng of Her2Bi (■) 50 ng of OKT3xIG3 (▲), on day 4 (D4), day 6 (D6), day 8 (D8), day 13 or day 14 (D13 or D14).

Lysis of MCF-7 cells by armed fresh (inactivated) PBMC prior to culture was consistently <10% at all E/T and ATC armed with 50 ng of Traut-crosslinked OKT3 or irrelevant OKT3 x IG3 exhibited 30% specific lysis as all time points and E/T's tested. Arming after 6 days of culture consistently enhanced specific cytotoxicity.

ATC armed with Her2Bi are so potent that they bind and kill MCF-7, breast cancer cell line that expresses very few Her2/neu receptors. Our data indicate that our new binding and cytotoxicity assays may be more sensitive than classic immunohistochemical staining for Her2/neu. MCF-7 cells are consistently killed by Her2Bi armed ATC even though flow cytometry barely detects the presence of Her2/neu on the surface of MCF-7 (FIG. 4, panel E). Our data suggest that even very low expression of Her2/neu on prostate cancer cells may be targeted and lysed in vivo.

Example 6

Specific Cytotoxicity Directed at MCF-7 Increases with Arming Doses and E/T.

Figure 6:
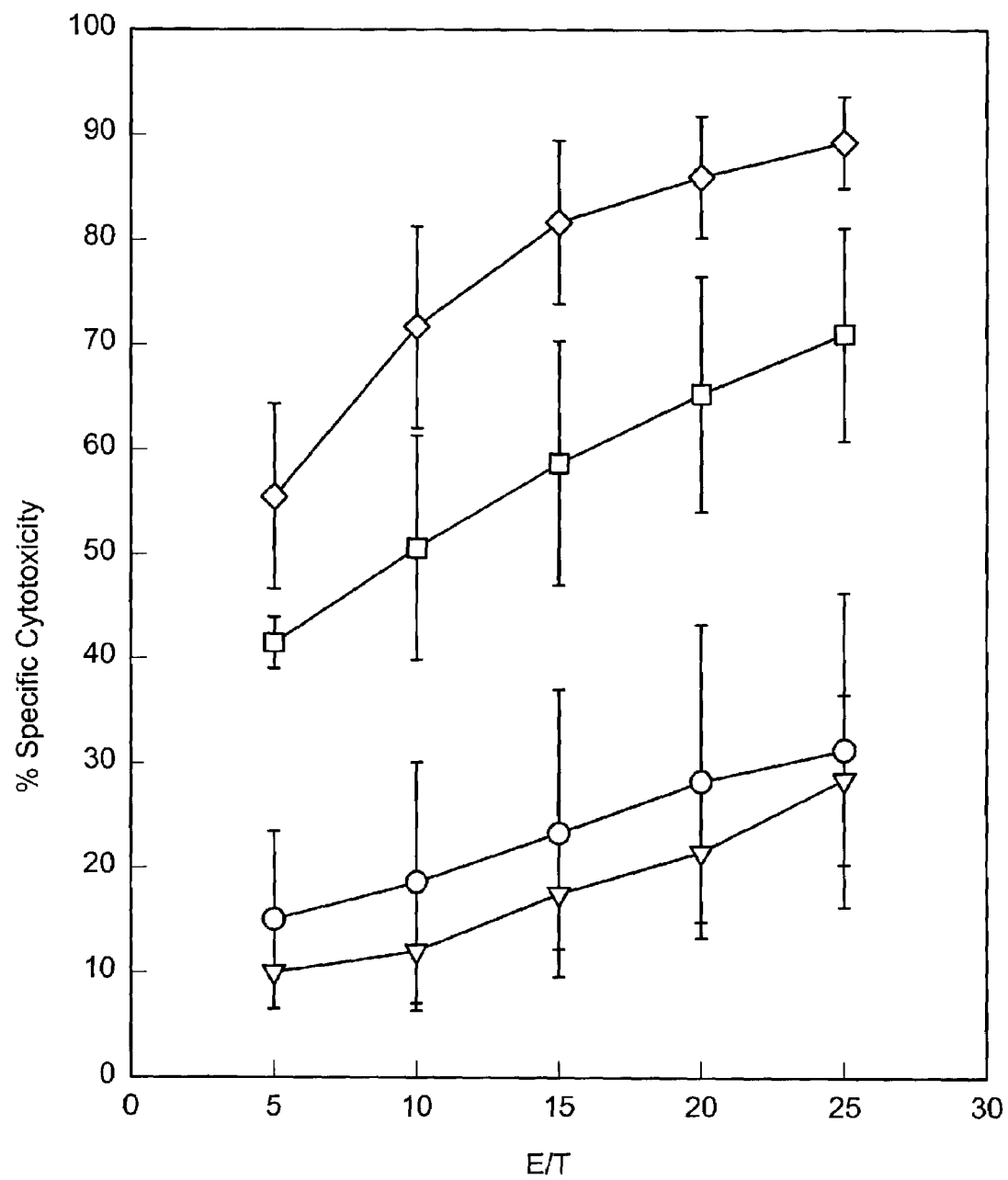
FIG. 6 shows composite titration curves for unarmed ATC and ATC armed with 0.5, 5.0, and 50.0 ng of Her2Bi at E/T between 5 and 25. Each curve represents the interpolated mean % (±SEM) specific cytotoxicity of 3 experiments directed at MCF-7 targets.

In order to determine the optimal arming dose range for Her2Bi, dose titration studies are performed at E/T from 5:1 to 25:1. FIG. 6 shows composite titration curves for unarmed ATC and ATC armed with 0.5, 5.0, and 50.0 ng of Her2Bi at E/T between 5 and 25. Each curve represents the interpolated mean % (±SEM) specific cytotoxicity of 3 experiments directed at MCF-7 targets. Each dose titration curve shows the interpolated mean of data using ATC from 3 normal subjects at the indicated E/T. Unarmed (▼) or ATC armed with 0.5 (●), 5.0 (■), and 50 (♦). Increasing the arming doses of Her2Bi led to increasing mean % specific cytotoxicity. ATC armed with 25-500 ng of irrelevant OKT3 x IG3 or OKT3 exhibited % specific cytotoxicity similar to that of unarmed ATC (data not shown).

Example 7

Enriched T Cell Subsets were Tested to Determine the T Cell Subsets for Specific Cytotoxicity.

Figure 7:
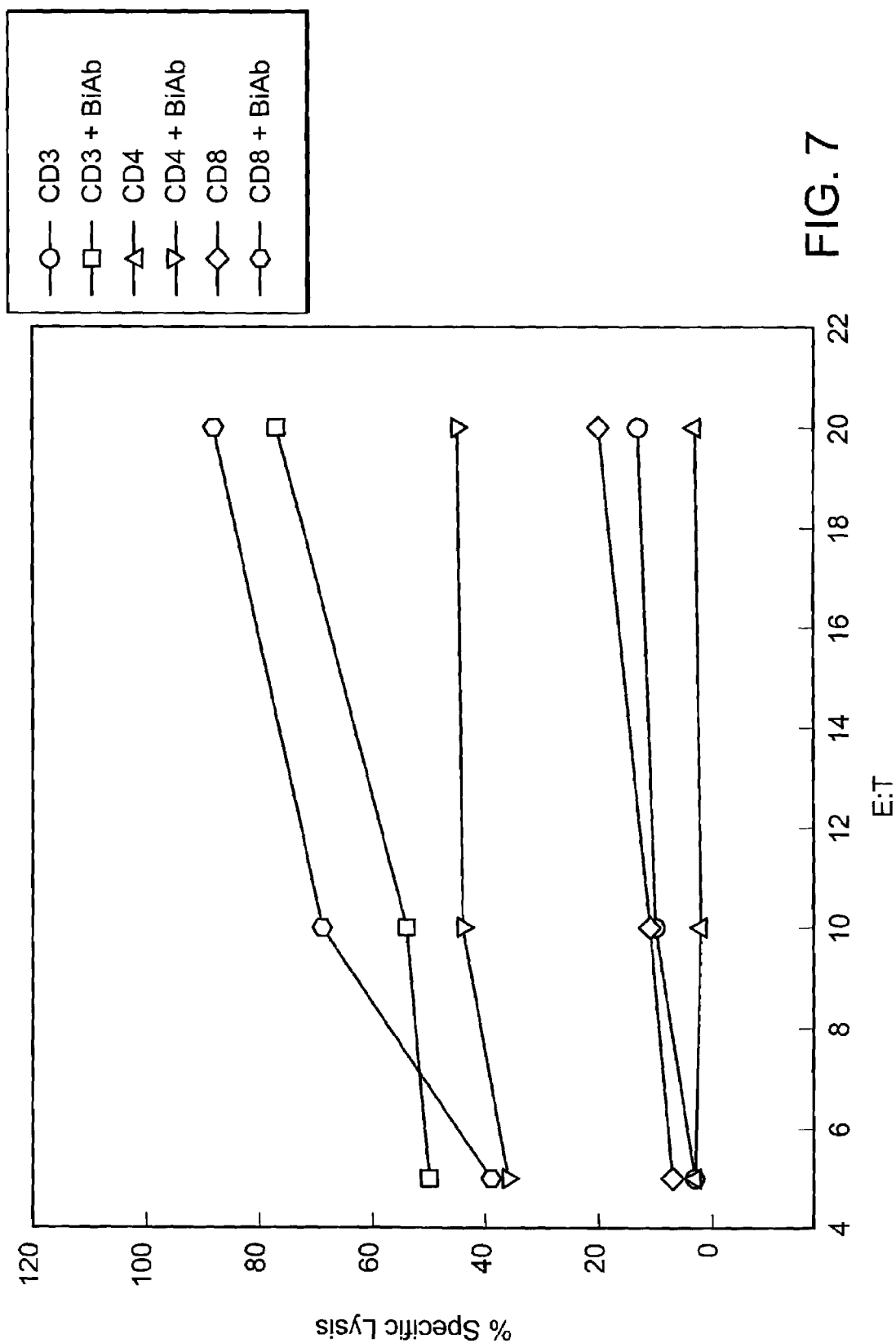
FIG. 7 shows a the results from a cytotoxic assay illustrating the cytotoxic activity of enriched T cell subsets to determine the T cell subsets for specific cytotoxicity.

Dynabeads-450 CD4 (DYNAL, Lake Success, N.Y.) are used with DETACHaBead methodology for the positive selection of CD4 cells and the negative selection of CD8 cells (CD4-depleted). The phenotype of the ATC and ATC subsets after separation is determined by FACS analysis. The CD4-selected cells were 99% CD4+ and the CD4− depleted cells were 94% CD8+. Unfractionated CD3+, CD4+ and CD8+ cells were armed with 50 ng Her2Bi and tested for their ability to mediate redirected cytotoxicity against MCF-7 cells (FIG. 7). At all E/T, the % specific cytotoxicity for armed CD3+, CD4+, and CD8+ cells were consistently higher than the unarmed CD3, CD4, and CD8 populations and hierarchy of cytotoxicity was CD8>CD3>CD4+ cells.

Example 8

Armed ATC Bind and Exhibit Cytotoxicity for More than 2 Days.

Figure 8A:
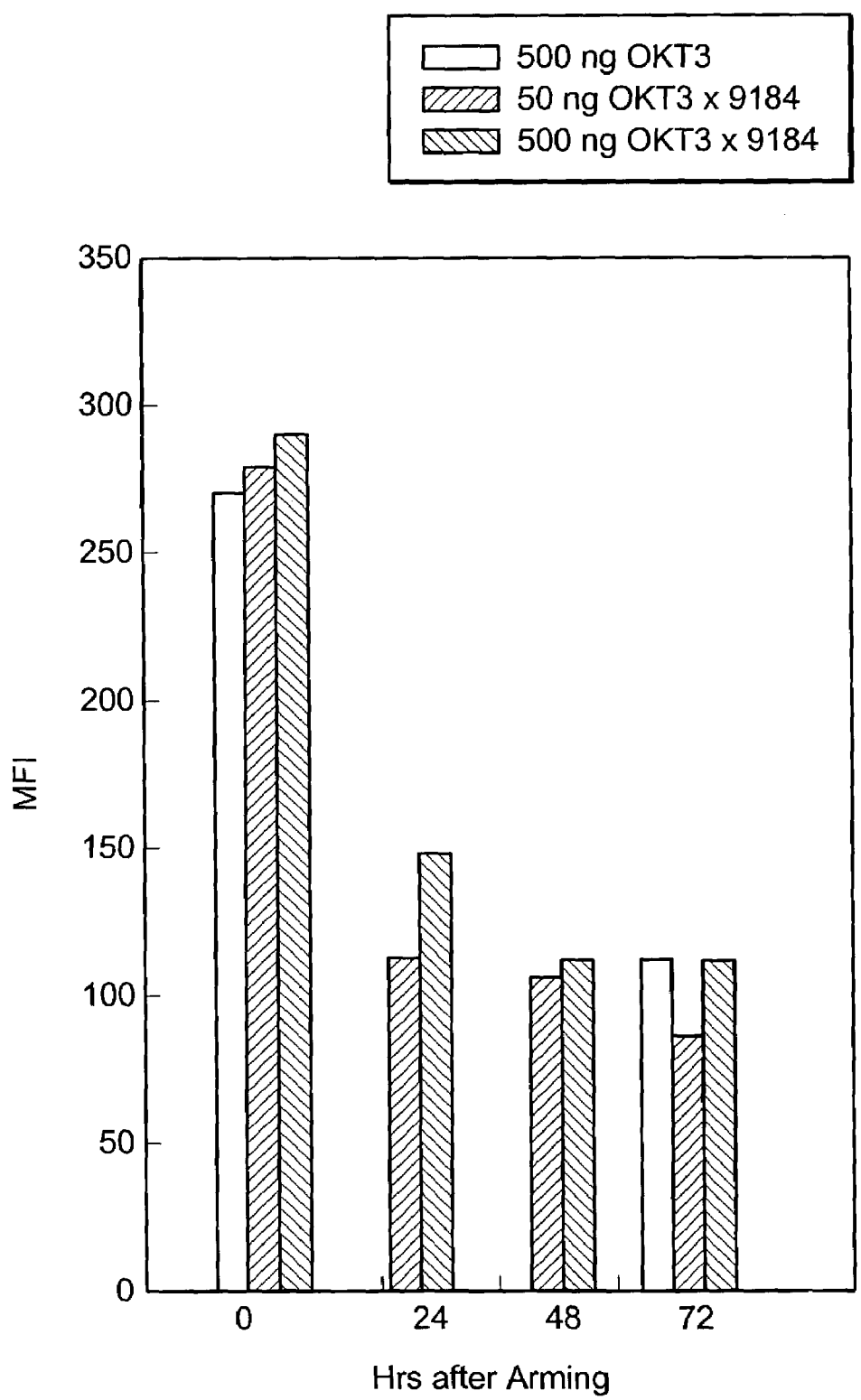
FIG. 8 is a bar graph showing how long ATC remain armed and continue to kill tumor cells.
Figure 8B:
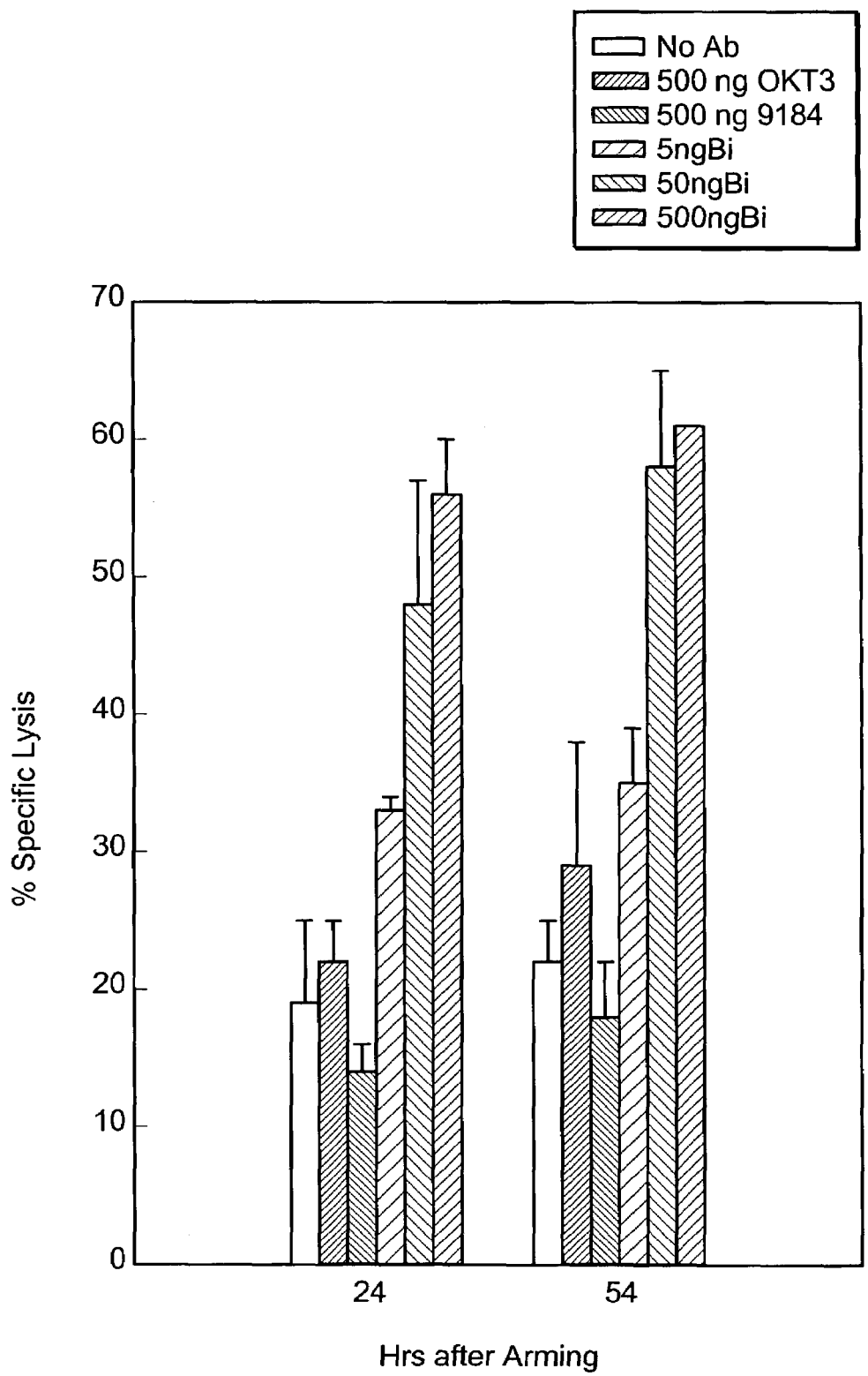

To determine how long ATC remain armed and continue to kill tumor cells, flow cytometry and cytotoxicity assays are performed at 24-hr intervals after arming. ATC from a normal subject was armed with 0, 50 and 500 ng of Her2Bi. The Her2Bi is detected using goat anti-mouse IgG-PE (FIG. 8, Panel A). The results show that although there was a rapid decrease in binding after 24 hrs, the remaining Her2Bi was stable and detectable after 72 hrs. Her2Bi binding paralleled that of OKT3. These studies show that hetero-conjugation did not impair binding of the anti-CD3 partner in Her2Bi. ATC armed with as little as 5 ng Her2Bi exhibited 33±1% lysis of MCF-7 cells 24 hrs after arming. ATC armed with Her2Bi continued to kill MCF-7 targets up to 54 hrs and a % specific lysis of 35±4% was seen at an E/T of 24:1. At higher arming doses of 50 and 500 ng, % specific lysis was >48% with no decrease in cytotoxicity after 54 hrs. ATC armed with 500 ng parental OKT3 or 9184 did not exhibit cytotoxicity above background. These results show that Her2Bi redirected cytotoxicity persists for 54 hrs.

Example 9

Enriched BiAb Activity in the Dimer-Enriched Fraction.

Figure 9:
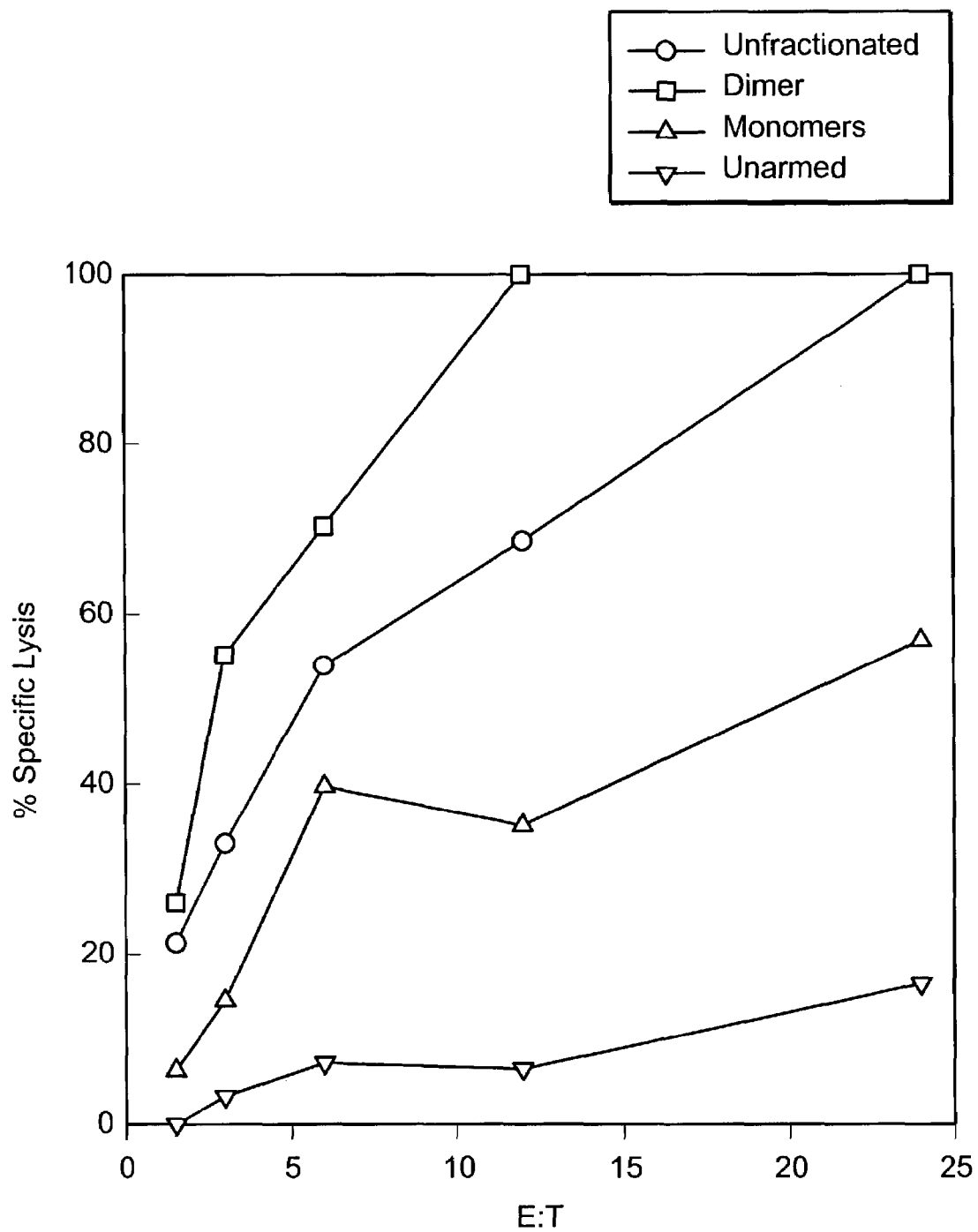
FIG. 9 shows the results of a cytotoxic assay from the fraction responsible for binding and targeting CEA. The dimer and multimer containing fractions are separated from the monomer fractions using a Sephacryl 300 column and testing each fraction after adjusting all protein concentrations to the same for % specific cytotoxicity directed at LS174T.
Figure 10A:
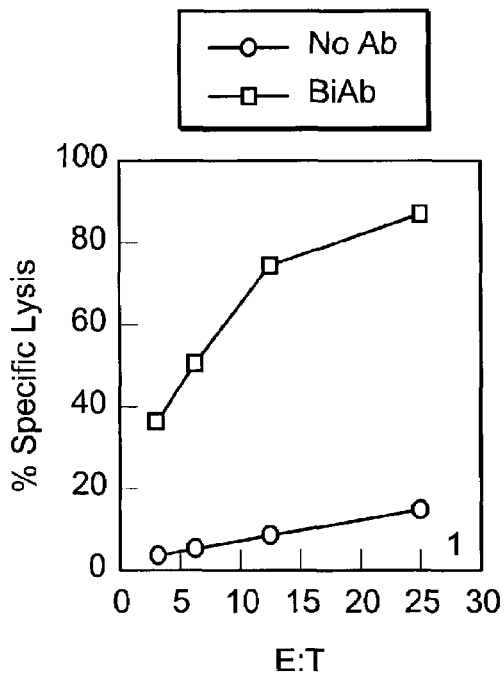
FIG. 10 are graphs which summarize data from 10 normal subjects armed with 50 ng of OKT3x9184 per $10^6$ ATC.
Figure 10B:
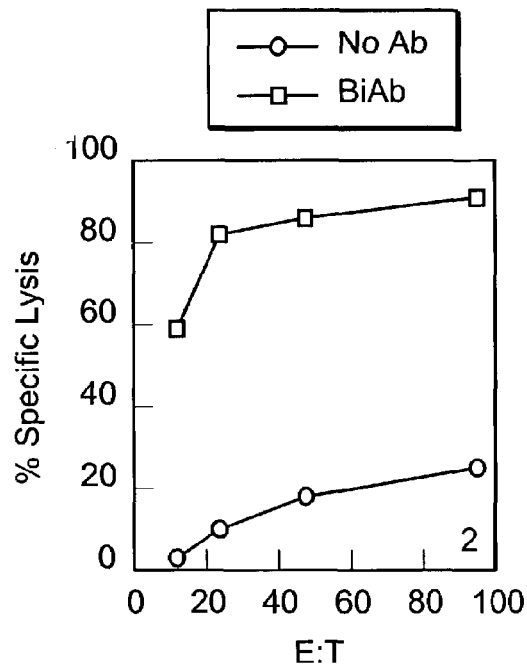
Figure 10C:
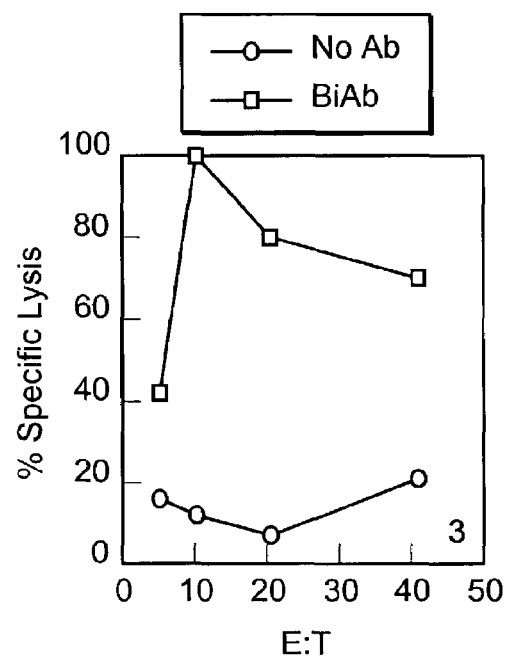
Figure 10D:
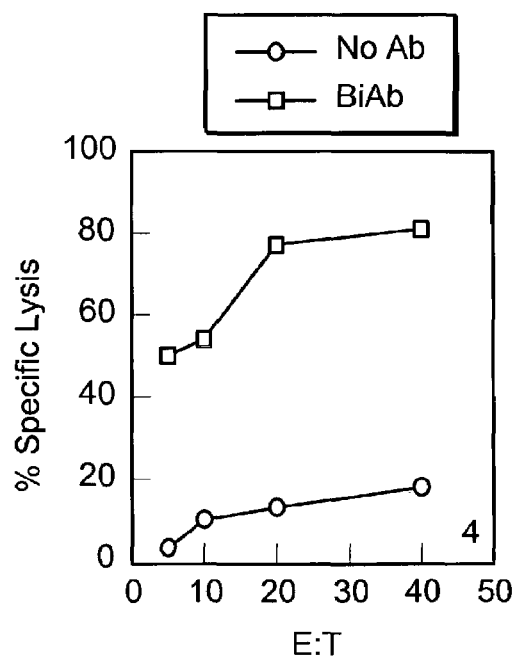
Figure 10E:
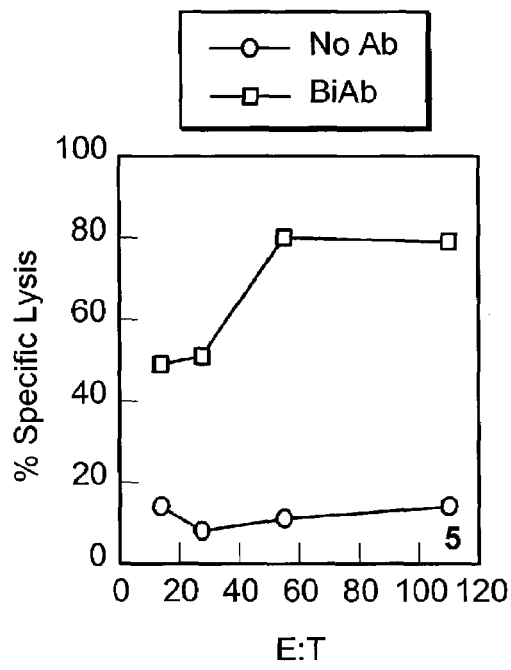
Figure 10F:
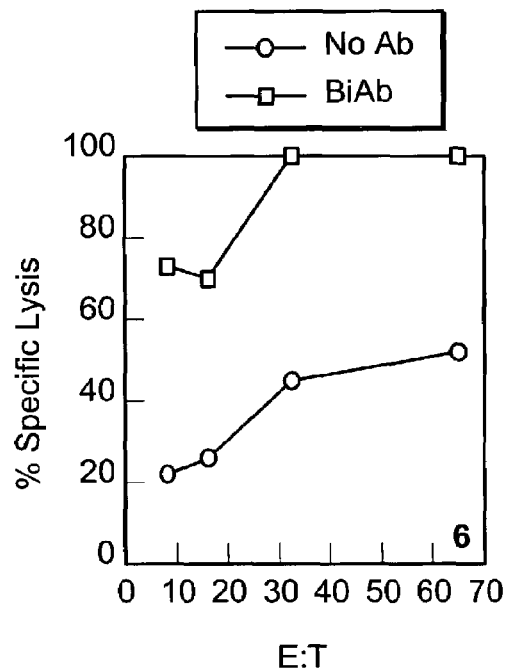
Figure 10G:
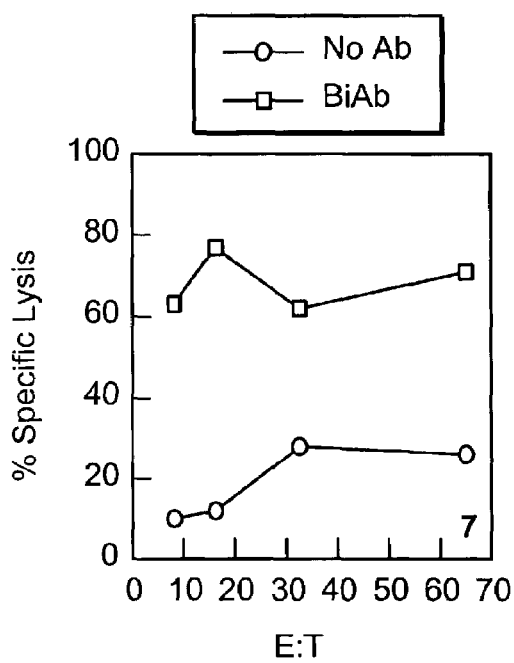
Figure 10H:
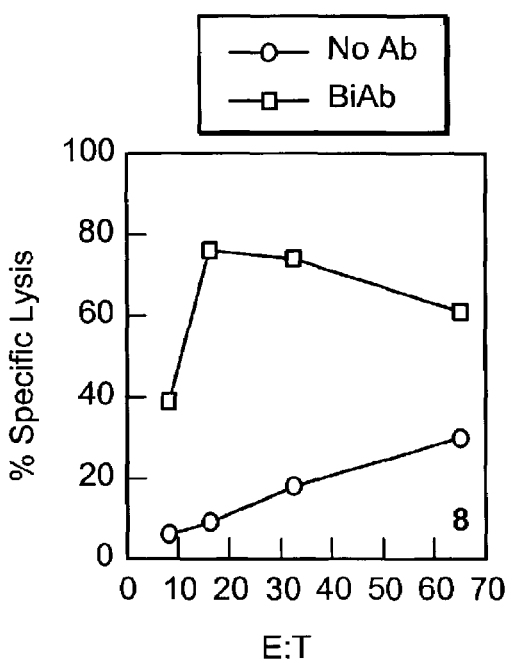
Figure 10I:
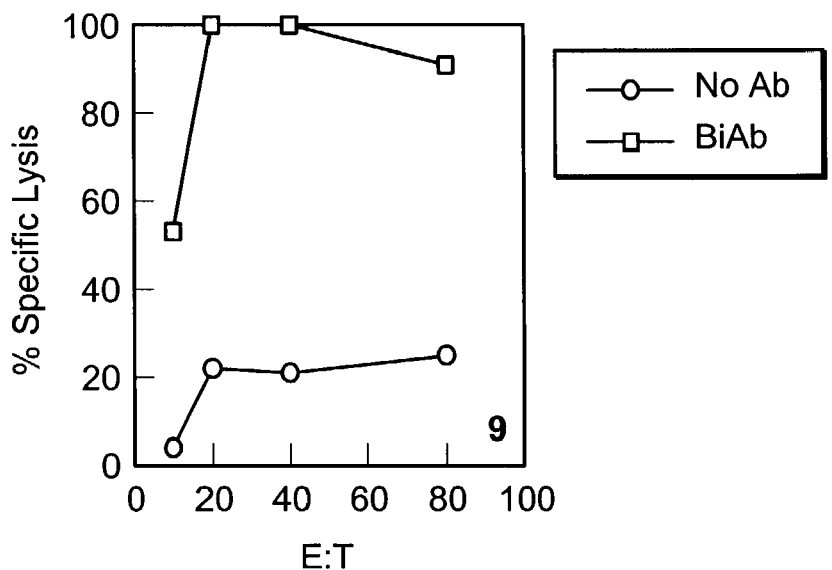
Figure 10J:
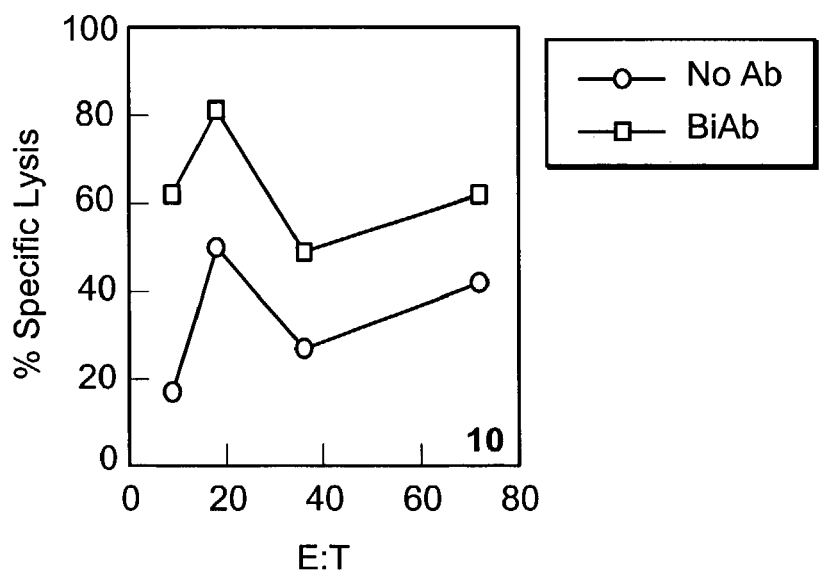
Figure 11A:
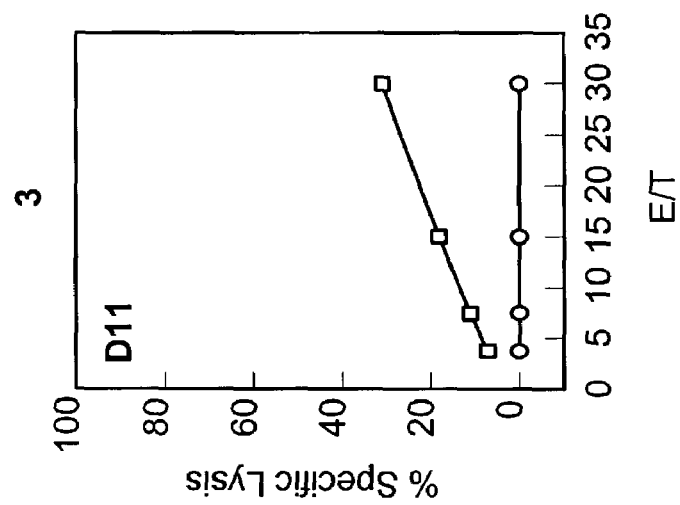
FIG. 11 are graphs showing in vivo ATC mediated cytotoxicity. ATC from cancer patients that had been cryopreserved using control rate freezing on the day of culture indicated on each panel, were thawed and armed with Her2Bi. ATC were tested for cytotoxicity directed at MCF-7.
Figure 11B:
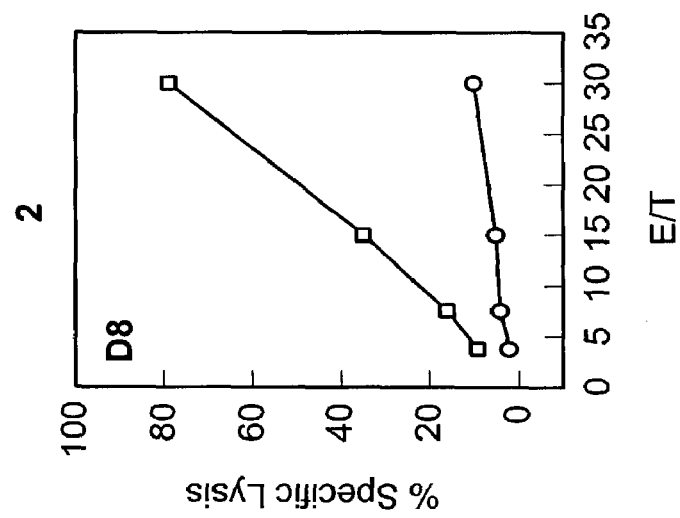
Figure 11C:
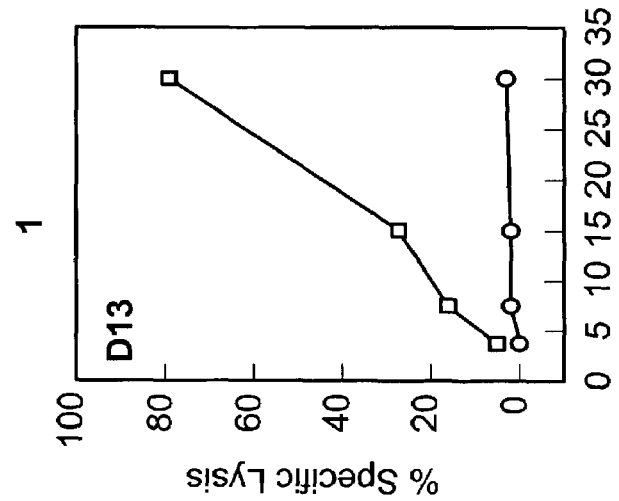
Figure 11F:
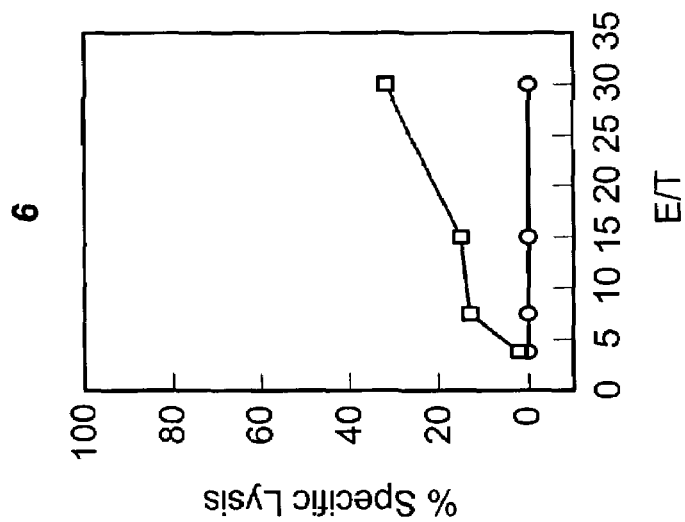
Figure 11E:
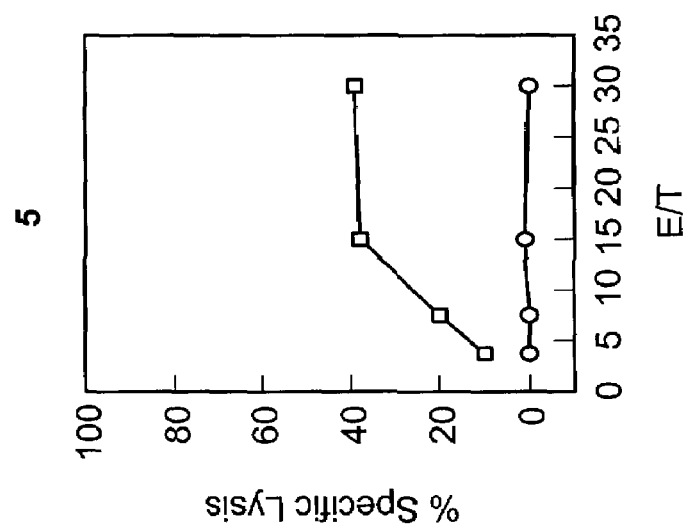
Figure 11D:
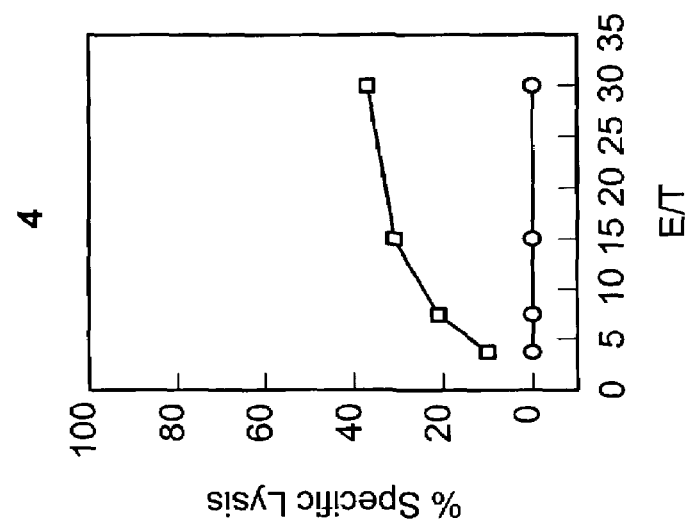

OKT3 x T94.66 (anti-CEA) heteroconjugates were produced to arm ATC to kill $CEA^+$ LS174T colon carcinoma cells. To confirm the fraction responsible for binding and targeting CEA, the dimer and multimer containing fractions are separated from the monomer fractions using a Sephacryl 300 column and testing each fraction after adjusting all protein concentrations to the same for % specific cytotoxicity directed at LS174T E/T (FIG. 9). The solid squares show the dimer fraction; the solid circles indicate the unfractionated material; the upward pointing solid triangles indicate the monomer fraction; and the downward pointing solid triangles indicate unarmed ATC. ATC were armed with 50 ng of each fraction. The dimer-enriched fraction was enriched for cytotoxicity above that seen for the unfractionated heteroconjugate whereas the monomer fraction is relatively depleted of cytotoxicity.

Example 10

Her2Bi Armed ATC from 10 Normal Control Subjects.

FIG. 10 summarizes data from 10 normal subjects armed with 50 ng of OKT3x9184 per $10^6$ ATC. At an E/T of 20:1, the mean increases in % specific lysis of MCF-7 cells by armed ATC from 10 normal subjects and 6 patients were 59∀11% and 32∀9%, respectively. These means were significantly higher than unarmed ATC at an E/T of 20:1 (P<0.001 for normal subjects, paired student's t test). Specific cytotoxicity was not different from ATC alone when ATC were armed with 50 ng of unconjugated OKT3, 50 ng of unconjugated 9184, or 50 ng of OKT3 x IG3 (data not shown).

Example 11

In vivo ATC Mediated Cytotoxicity

ATC from cancer patients that had been cryopreserved using control rate freezing on the day of culture indicated on each panel (FIG. 11), were thawed and armed with Her2Bi. ATC were tested for cytotoxicity directed at MCF-7. The patients with renal cell carcinoma (3) had no prior chemotherapy whereas the patients with breast cancer (2) and lymphoma (1) had prior chemotherapy. The % specific cytotoxicity for 6 patients increased by 32±19%. Arming with Her2Bi significantly increased % specific cytotoxicity mediated by patient ATC (P<0.0004, paired student's t test). The results indicate that there was no difference between those who received chemotherapy and those who did not receive chemotherapy.

Example 12

Cytokine Secretion Induced by Binding to SK-BR-3 Tumor Cells.

Figure 12:
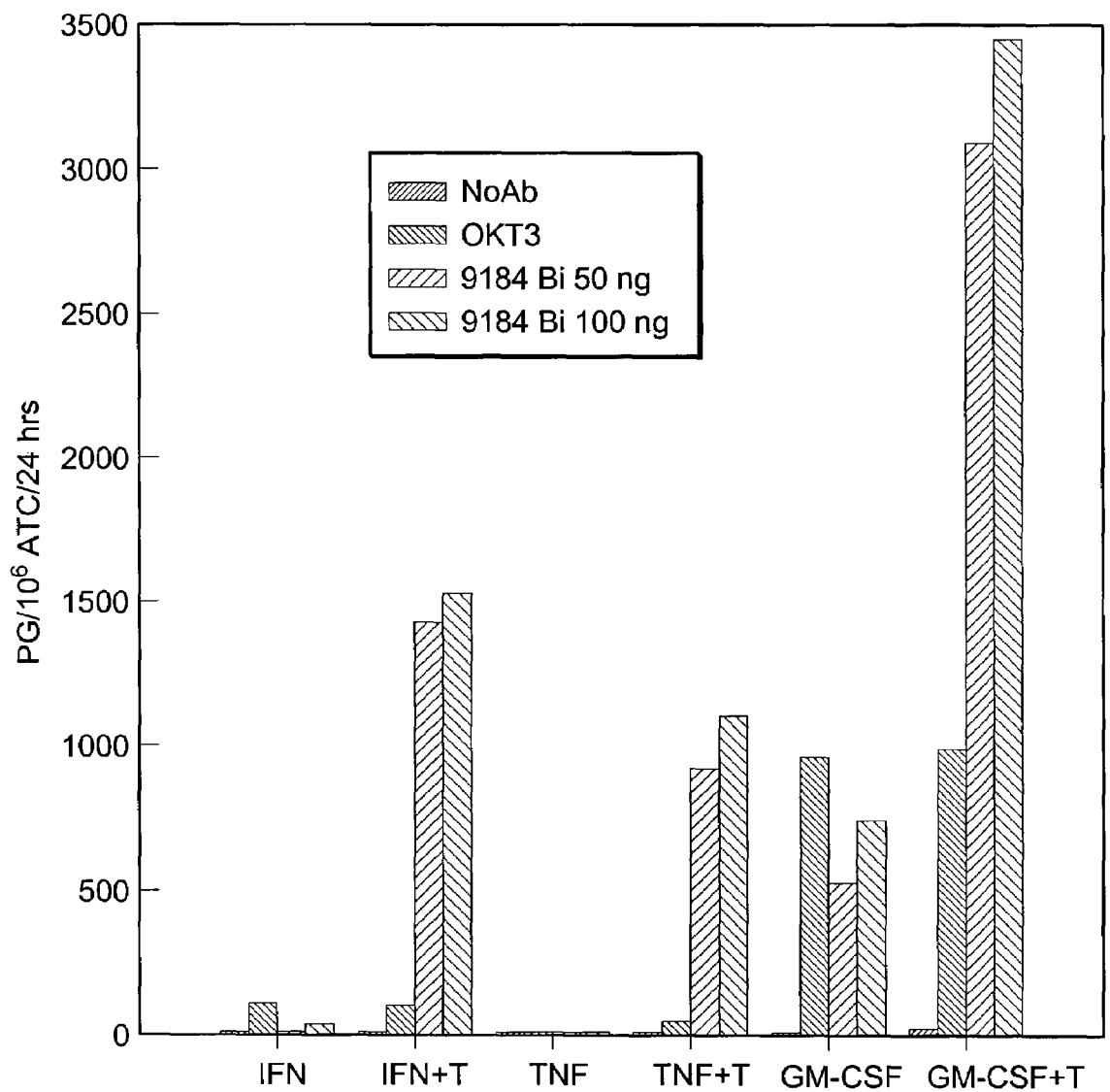
FIG. 12 shows a bar graph illustrating cytokine secretion induced by binding of ATC to SK-BR-3 tumor cells.

Since secretion of interferon-$\gamma$ (IFN$\gamma$), tumor necrosis factor-$\alpha$ (TNF$\alpha$) and GM-CSF are hypothesized to provide antitumor effects, experiments were conducted to test whether binding of armed ATC to SK-BR-3 would induce IFN$\gamma$, TNF$\alpha$ and GM-CSF secretion (FIG. 12). Tumor cells were plated at a concentration of $2\times10^5$ per well in a 24-well plate and incubated overnight t 37° C. The next day unarmed and armed ATC ($2\times10^6$/well) were co-cultured with tumor cells (T) in a total volume of 2 ml. Culture supernatants for each sample were pooled and tested for IFN$\gamma$, TNF$\alpha$, and GM-CSF by ELISA (R&D Systems, Minneapolis, Minn.). All values are reported in $\mu g/ml/10^6$ ATC/24 hrs. Unarmed or ATC armed with doses of irrelevant OKT3 x IG3 up to 500 ng, or 9184 in the presence or absence of tumor did not induce any IFN$\gamma$ or TNF$\alpha$ (data not shown). Background was <5 pg. When ATC armed with Her2Bi (at both the 50 and 100 ng doses) were co-cultured with SK-BR-3, the cultures markedly increased their production of IFN$\gamma$, TNF$\alpha$ and GM-CSF above background. Stimulation of ATC with Trauts-crosslinked OKT3 control produced 110 ng of IFN$\gamma$ in the absence or presence of tumor and <50 pg of TNF$\alpha$ in the absence or presence of SK-BR-3. Similar results were obtained using MCF-7 and PC-3.

Example 13

In vitro Cytotoxicity Mediated Against Various Tumor Cell Lines

Figure 15:
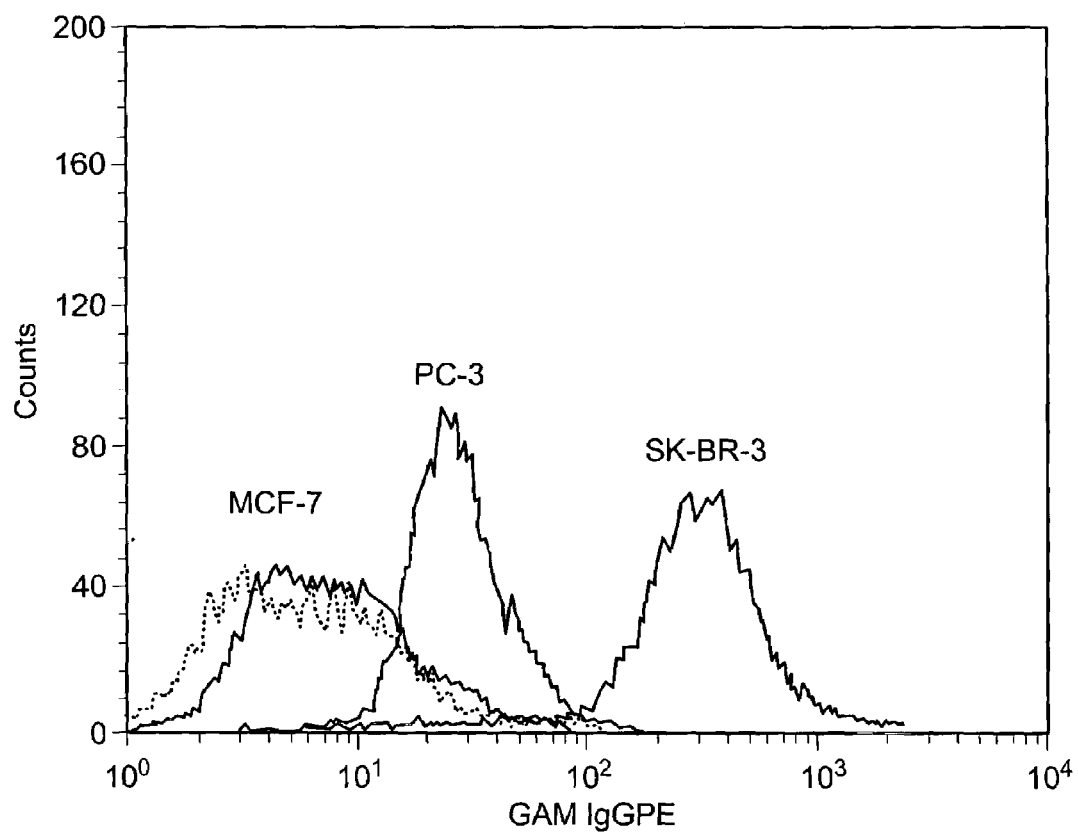
FIG. 15 shows flow cytometry results obtained from Her2BiAb binding to PC-3, MCF-7 and SK-BR-3 cells.

Arming of ATC or COACTS with Her2Bi significantly enhanced lysis of the HER2+ tumor targets MCF-7, SK-BR-3, and PC-3. We investigated the MCF-7 breast carcinoma lines as a model target that expresses low numbers of HER2 receptors (HER2r), the SK-BR-3 breast cancer line as a model target that expresses high numbers of HER2r, and the PC-3 prostate carcinoma cell line (intermediate numbers of HER2r as the organ specific target for this clinical trial. The results using the MCF-7 model provide a strong rationale for targeting even weakly positive tumors using Her2Bi armed ATC. Binding studies show that PC-3 have more HER2 receptors on their surface than MCF-7 (FIG. 15). Her2Bi was found to remain on armed ATC for over 72 hours and continue to mediate redirected cytotoxicity for more than 54 hours.

Figure 13B:
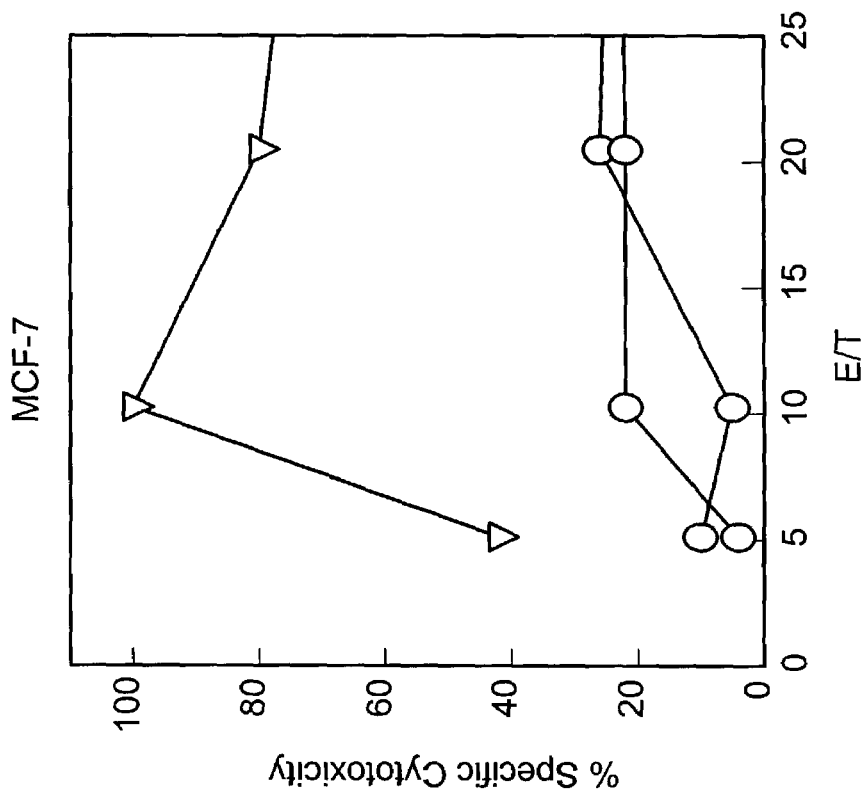
FIG. 13 shows a graph illustrating in vitro cytotoxicity mediated by armed ATC or COACTS with Her2Bi against various tumor $HER2^+$ tumor targets.
Figure 13A:
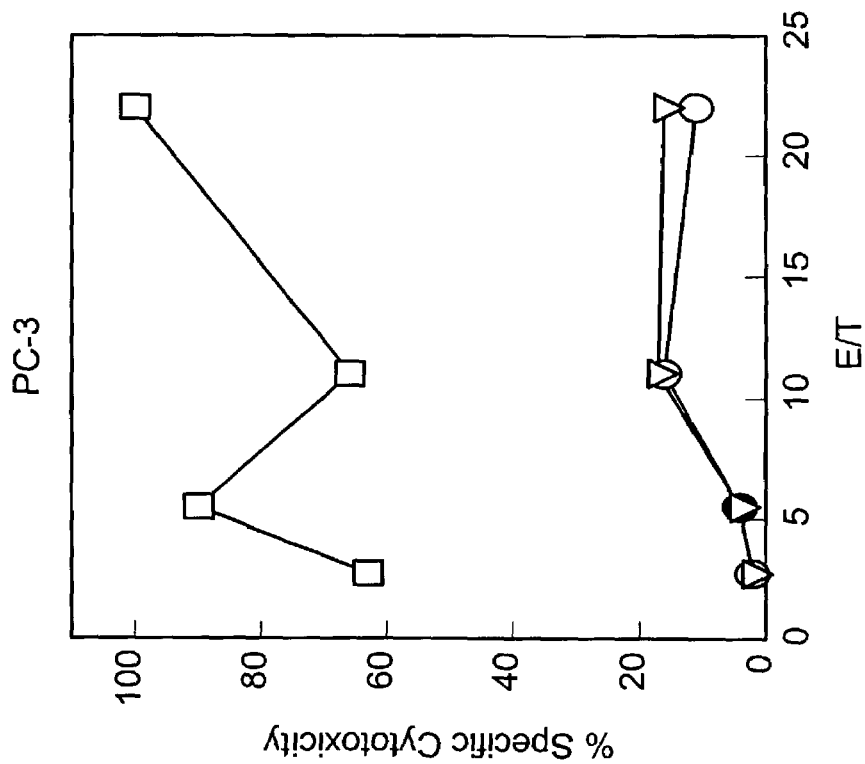

Her2Bi armed ATC were tested against PC-3 (left panel) and MCF-7 (right panel) in FIG. 13. ATC were left unarmed (−), armed with 50 ng OKT3/IG3 (▼), or Her2Bi (■). The E/T-titrations show that armed ATC are cytotoxic for both PC-3 and MCF-7 carcinoma cell lines. At low E/T ratios, the % specific cytotoxicity appears to be higher for PC-3 than MCF-7 cells. These results are consistent with the flow cytometry findings that show PC-3 carcinoma cells have more Her2 receptors on their surface than MCF-7 cells.

Figure 14:
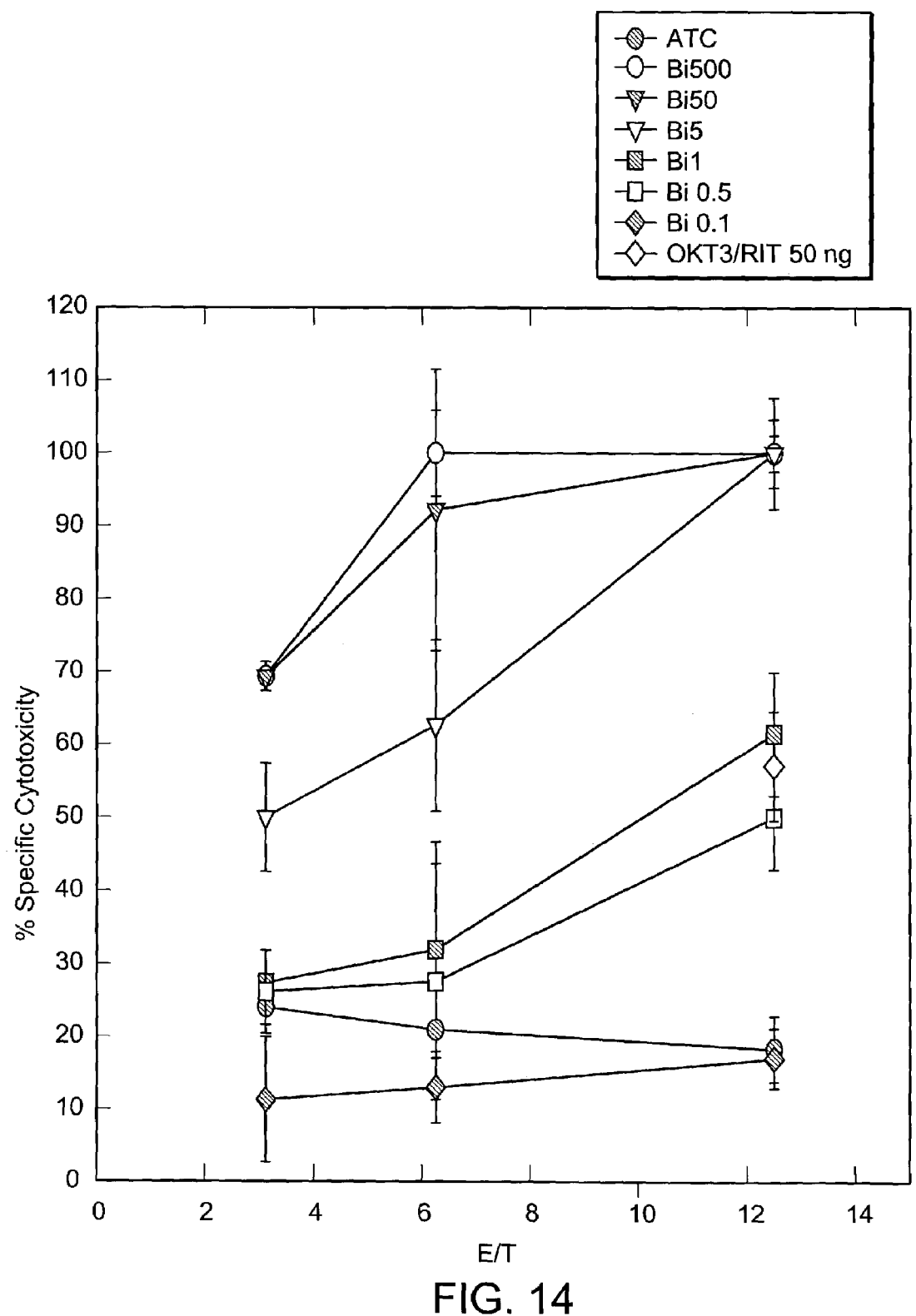
FIG. 14 is a graph showing increasing arming doses of OKT3 x 9184, increases the % specific cytotoxicity directed at PC-3, by armed ATC.

FIG. 14 indicates that increasing the arming dose of OKT3 x 9184 increases the % specific cytotoxicity directed at PC-3. ATC alone or ATC armed with 0.1, 0.5, 1.0, 5, 50, and 500 ng of Her2Bi as indicated in FIG. 14 and tested against PC-3.

The irrelevant BiAb was OKT3 x Rit. Cytotoxicity directed at PC-3 was near optimal at a dose of 50 ng. Similar results were obtained on ATC from 3 normal subjects in similar titration curves.

FIG. 15 illustrates the results obtained using flow cytometry. The data show that Her2Bi binds to PC-3 cells. PC-3, MCF-7 and SK-BR-3 were treated with 1 µg of OKT3 x 9184 or OKT3 and subsequently stained with PE-conjugated goat anti-mouse IgG antibodies to determine the level of expression of Her2 receptors on PC-3 in comparison to MCF-7 (low expression) and SK-BR-3 (high expression). FIG. 15 shows clear binding of OKT3x9184 to PC-3 and SK-BR-3 cells and the expected very low binding to MCF-7.

Example 14

OKT3xHerc Cytotoxicity Directed at SK-BR-3 Targets.

Figure 16:
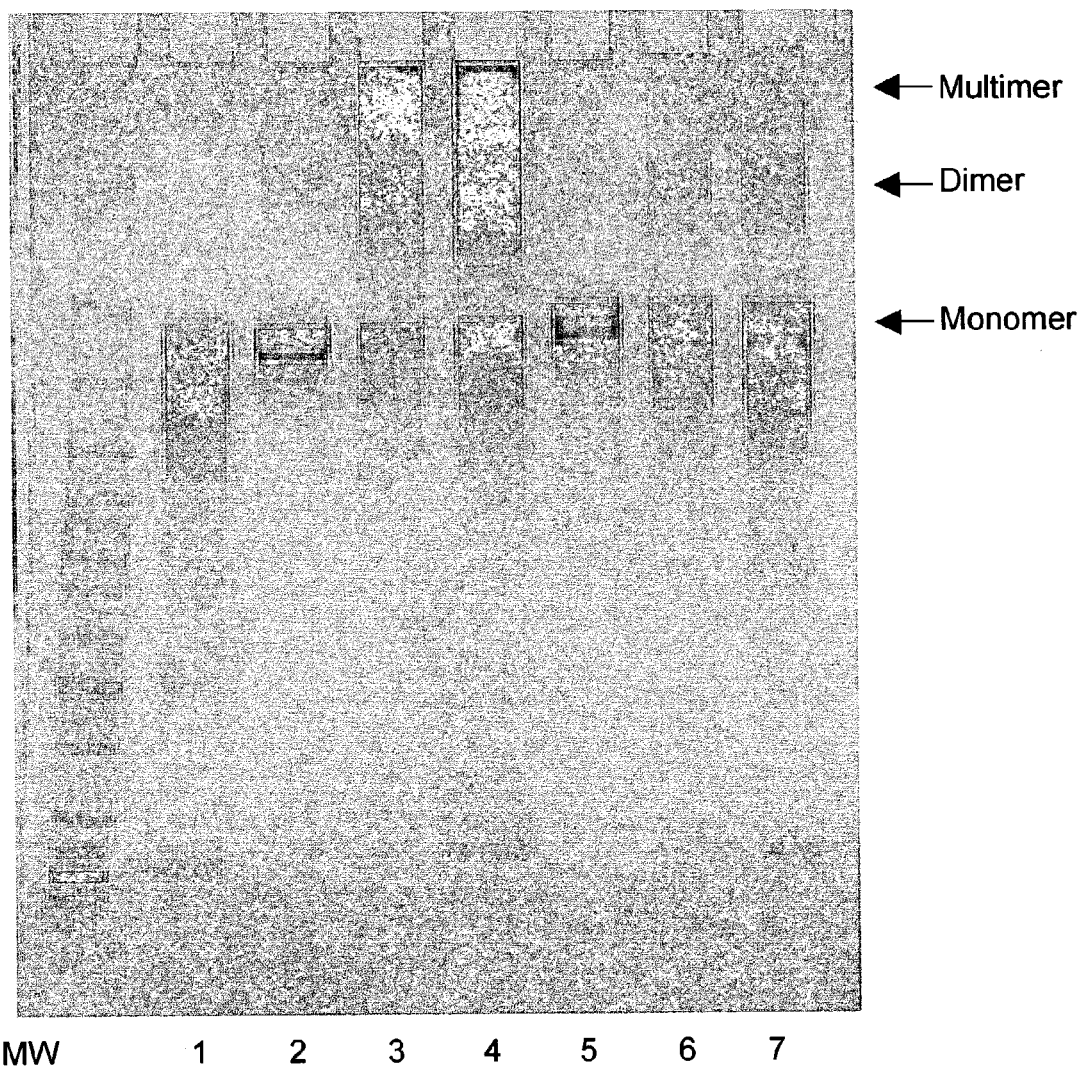
FIG. 16 is a gel showing the results of the chemical conjugation of OKT3 x Herc, using the scheme in FIG. 1. BCA protein is quantitated and analyzed by non-reducing SDS gel electrophoresis using a 2-15% gradient gel and Coomassie blue staining is used to visualize proteins in the gel.

As described earlier in FIG. 1, heteroconjugating OKT3 with Herceptin® is conducted in an identical manner. OKT3 (2 mg) in 50 mM NaCl, 1 mM EDTA, pH 8.0 is reacted with a 5 fold molar excess of Traut's reagent. Herceptin (2 mgs) in 0.1 M sodium phosphate, 0.15 M NaCl at pH 7.2 is reacted with a 4 fold molar excess of Sulpho-SMCC at room temperature for 1 hr (STEP 2). Both monoclonal antibodies (Mabs) are purified on PD-10 columns in PBS to remove unbound crosslinker. The crosslinked Mabs are mixed immediately at equimolar ratios and conjugated at 4° C. overnight (STEP 3). BCA protein is quantitated and analyzed by non-reducing SDS gel electrophoresis using a 2-15% gradient gel (FIG. 16). Coomassie blue staining is used to visualize proteins in the gel. Lane 1, high molecular weight marker; lane 2, OKT3 (4 µg); lane 3, 9184 (4 µg); lane 4, OKT3 x 9184 (4 µg); lane 5, OKT3 x 9184 (8 µg); lane 6, Herc (4 µg); lane 7, OKT3 x Herc (4 µg); and lane 8, OKT3 x Herc (8 µg). The proportion of dimers in lanes 3, 4,6 and 7 as measured by densitometric quantitation was 27, 27, 21 and 21%, respectively.

FIG. 17 shows the ability of ATC from two normal subjects to lyse SK-BR-3 targets. ATC from normal (A) were tested unarmed; armed with 50 ng of OKT3 x Herc; armed with the irrelevant OKT3x4D4, a monoclonal antibody raised against prostate specific membrane antigen (gift from Alton Boynton); or, a mix of 50 ng of unconjugated OKT3 and 50 ng of unconjugated Herc. Normal (B) was tested in the same manner. Only the unarmed ATC and ATC armed with 50 ng of OKT3 x Herc are shown.

Example 15

Comparative Arming Doses.

In order to determine arming dose differences between OKT3 x 9184 and OKT3 x Herc, ATC are armed with increasing doses of OKT3 x Herc and OKT3x9184. Both BiAbs are effective in arming ATC to kill SK-BR-3 targets (see FIG. 18). FIG. 18 shows that the OKT3 x Herc may be slightly less effective than OKT3x9184 at the 5 and 50 ng arming doses for specific cytotoxicity directed at SK-BR-3 targets at the lower E:T ratios. These differences may be due to experimental variation in these assays. The important observation is that arming at 50-500 ng/$10^6$ ATC markedly enhances the ability of ATC to lyse SK-BR-3 targets.

Example 16

IFN Secretion by Armed ATC

Figure 19:
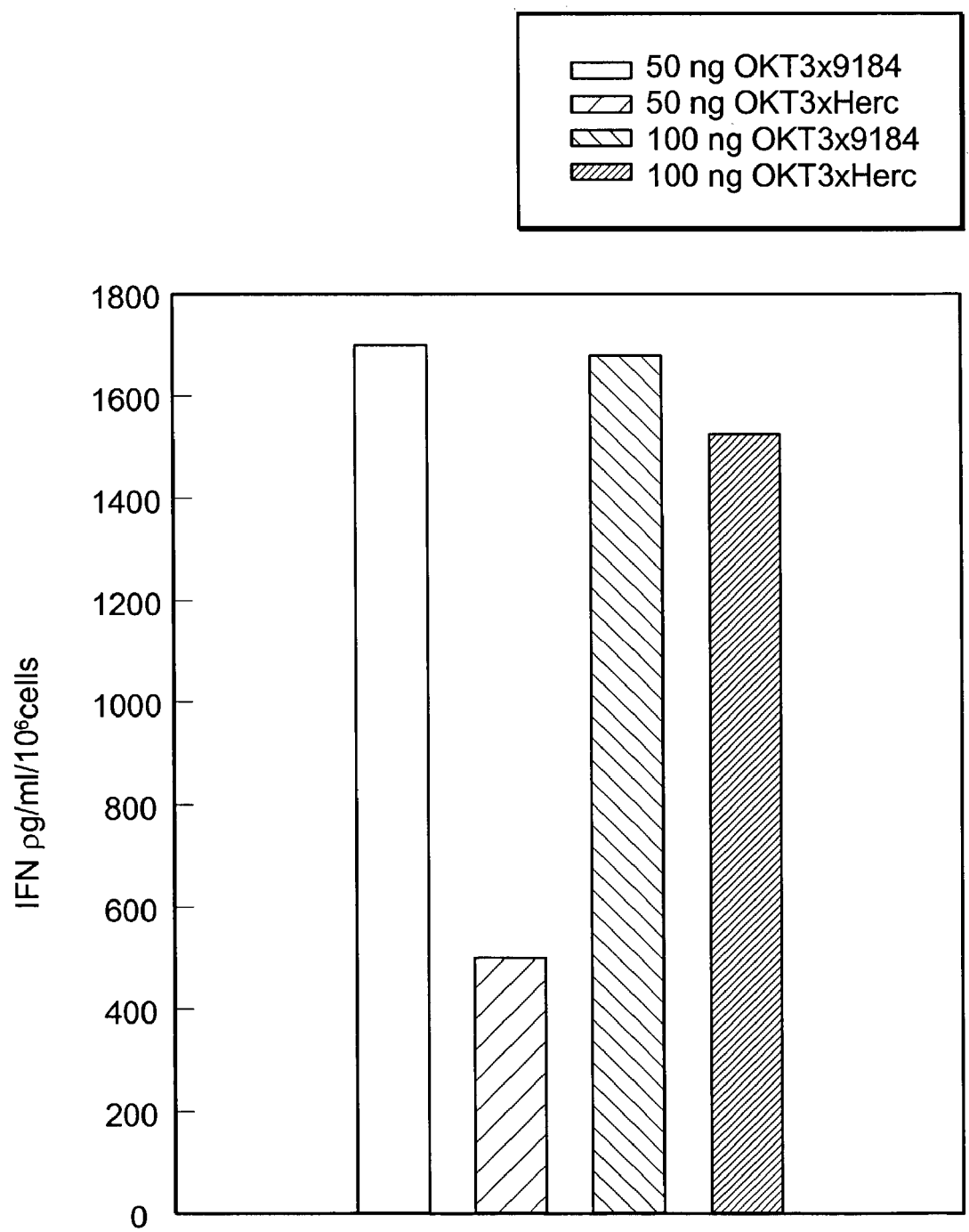
FIG. 19 is a bar graph showing interferon-γ secretion by armed ATC after 24 hrs of culture with target cells.

Normal ATC are armed with 50 or 100 ng of OKT3x9184 or OKT3xHerc respectively and cocultured with SK-BR-3 targets at a E:T of 10:1 and culture supernatants were tested for IFNγ secretion after 24 hrs of culture (FIG. 19). Arming with irrelevant OKT3xIG3 or a mixture of OKT3+9184 or OKT3+Herc as control induced less than 200 pg of IFNγ/ml/$10^6$ ATC. At an arming dose of 100 ng for both BiAbs, there were comparable induction of IFNγ secretion. At an arming dose of 50 ng, the binding of ATC armed with OKT3 x Herc induced less IFNγ than the binding of ATC armed with OKT3 x 9184. However, this may be due to experimental differences.

In order to determine how low an E:T would be effective in stimulating IFNγ upon binding of ATC armed with 50 ng of OKT3 x Herc, 24 hr culture supernatants derived from armed ATC, cocultured with SK-BR-3 targets at E:T ratios of 5:1, 2.5:1, 1.25:1, and 0.625:1, were tested. E:T ratios as low as 2.5:1 show an increase over background levels seen using no antibody (ATC alone), a mixed of soluble OKT3 and Herc, or arming with the irrelevant OKT3xIG3 BiAb. Based on these titration experiments, all cytokine secretion studies were done with E/T ratios between 5:1 and 10:1.

Example 17

Comparison of Cytolytic Capabilities of Her2Bi or OKT3 x Herc Armed Normal ATC Using PC-3 Targets.

Figure 20:
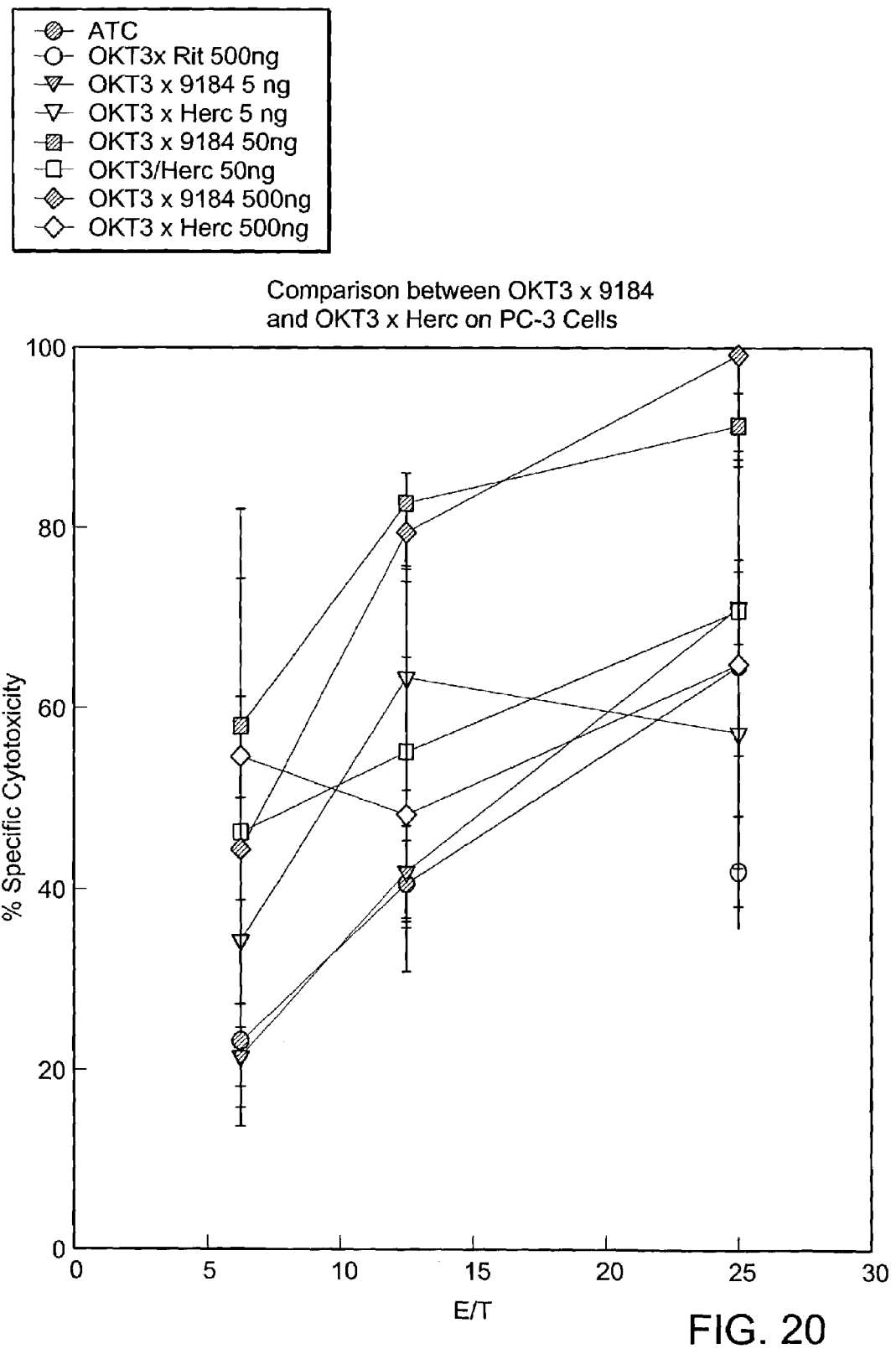
FIG. 20 is a graph showing the comparison of cytolytic capabilities of Her2Bi or OKT3 x Herc armed normal ATC using PC-3 targets.

FIG. 20 shows a direct comparison between OKT3 x 9184 and OKT3 x Herc at arming doses of 5, 50, and 500 ng. ATC armed with 500 ng of irrelevant OKT3 x Rit is shown as a control at the highest E/T ratio. These data show that both OKT3 x 9184 and OKT3 x Herc exhibit similar trends in titration for PC-3 cells. In this experiment, the cytotoxicity curves for the OKT3 x 9184 dose titrations are higher than those seen for ATC armed with comparable dose of OKT3 x Herc.

Figure 21:
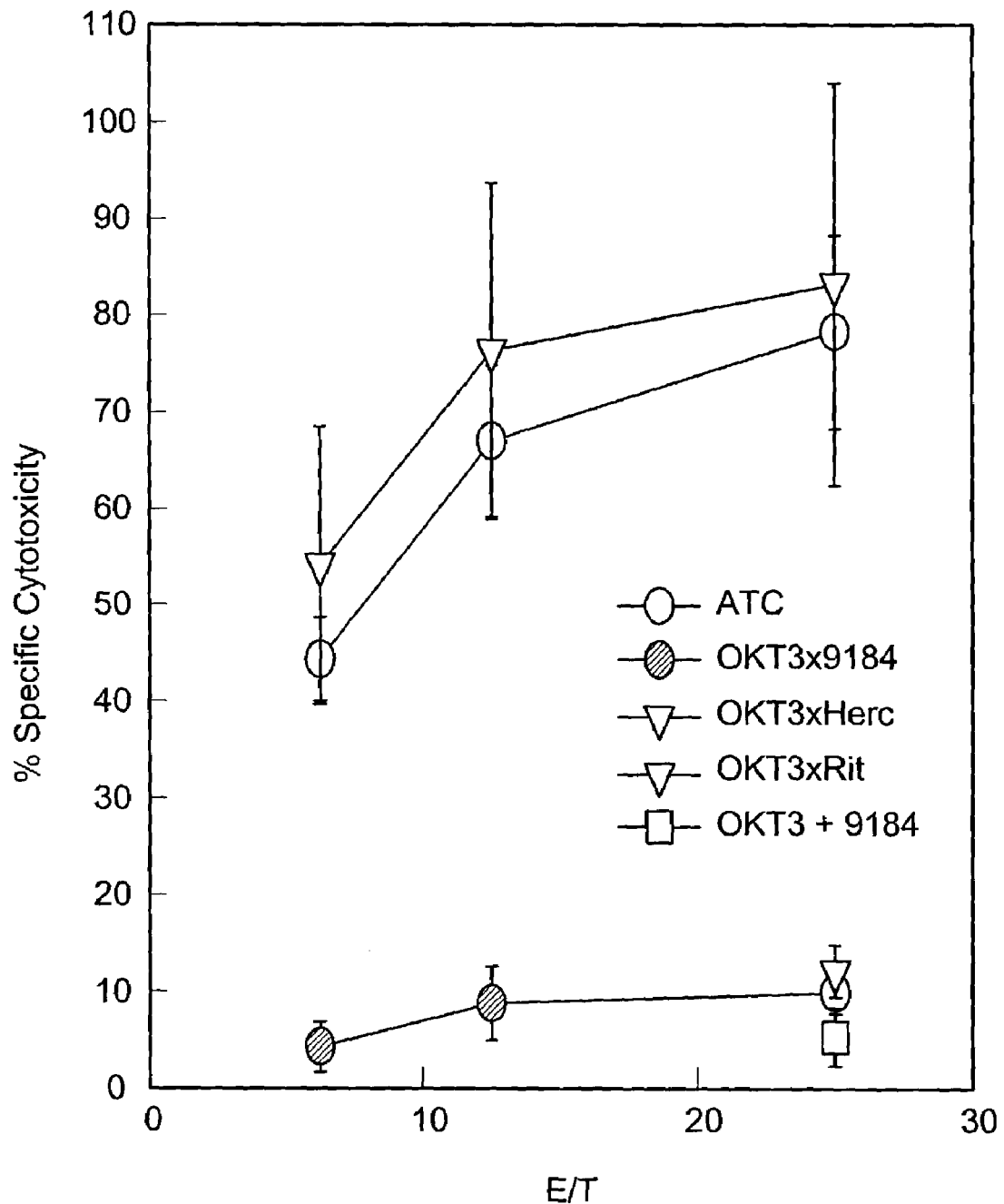
FIG. 21 is a graph showing that armed patient T cells remain cytotoxic to PC-3 after freeze/thawing.

Armed patient T cells remain cytotoxic to PC-3 after freeze/thaw. OKT3 x 9184 armed ATC from a patient with cancer were expanded for 14 days after anti-CD3 activation, cryopreserved, thawed, armed with 50 ng/$10^6$ ATC, and then tested for specific cytotoxicity (FIG. 21). ATC were armed with 50 ng of OKT3 x 9184 (○), of OKT3 x Herc ( ), or OKT3 x Rit (∇). A mix of soluble OKT3+9184 (■) was also used as a control. These data show that frozen and thawed ATC can be armed and mediate cytotoxicity directed at PC-3.

Example 18

IFNγ ELISPOTS Produced by Normal ATC Armed with OKT3 x 9184 upon Binding with PC-3 Cells.

Figure 22:
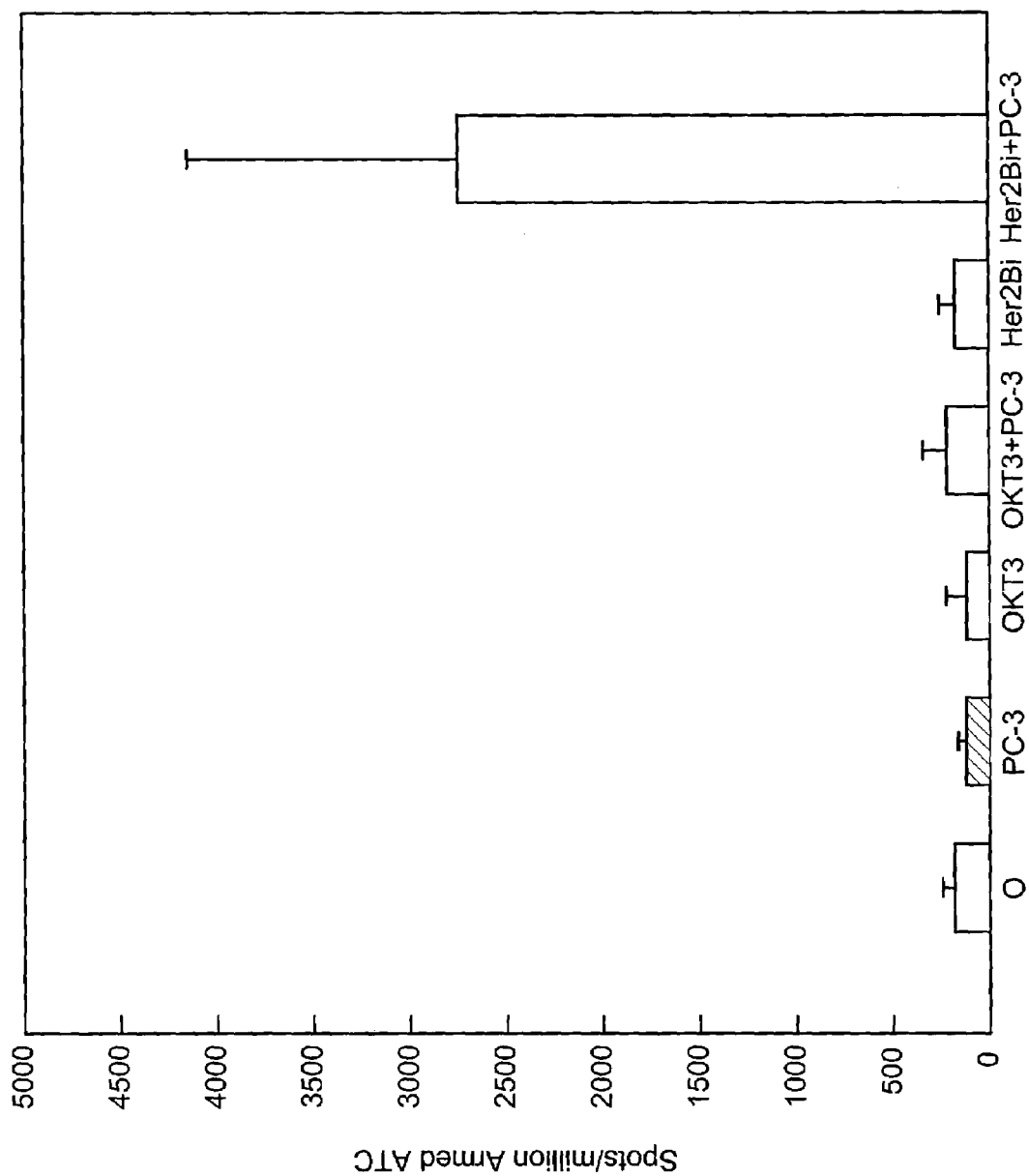
FIG. 22 is a bar graph showing IFNγ ELISPOTS produced by normal ATC armed with OKT3 x 9184 upon binding with PC-3 cells.

In order to determine the frequency of the number of armed ATC that produce IFNγ when exposed to PC-3 cells bearing Her2/neu, ATC armed with 50 ng/million of OKT3 x 9184 are placed onto plates containing 40,000 PC-3 cells per flat bottomed microwell for 4 hrs at an effector to target ratio of 10:1. After 4 hrs, the effectors are removed and plated into Millipore multiscreen nitrocellulose HA plates that are precoated with monoclonal 7-B6-1 anti-human IFNγ antibodies. The plates are developed and the number of ELISPOTS are counted using a dissecting microscope. FIG. 22 summarizes the spots/million armed ATC for ATC alone (O), ATC mixed with PC-3 (PC-3), ATC restimulated with 50 ng of soluble OKT3 (OKT3), ATC stimulated with 50 ng of OKT3 and PC-3 (OKT3+PC-3), ATC armed with OKT3 x 9184 without tumor (Her2Bi), and ATC armed with OKT3 x 9184 mixed with PC-3 (Her2Bi+PC-3). Note the error bars indicate ±1 SD of triplicate counts. There is a clear and brisk response of armed ATC to engagement with PC-3 cells via the Her2Bi bridge.

Figure 24:
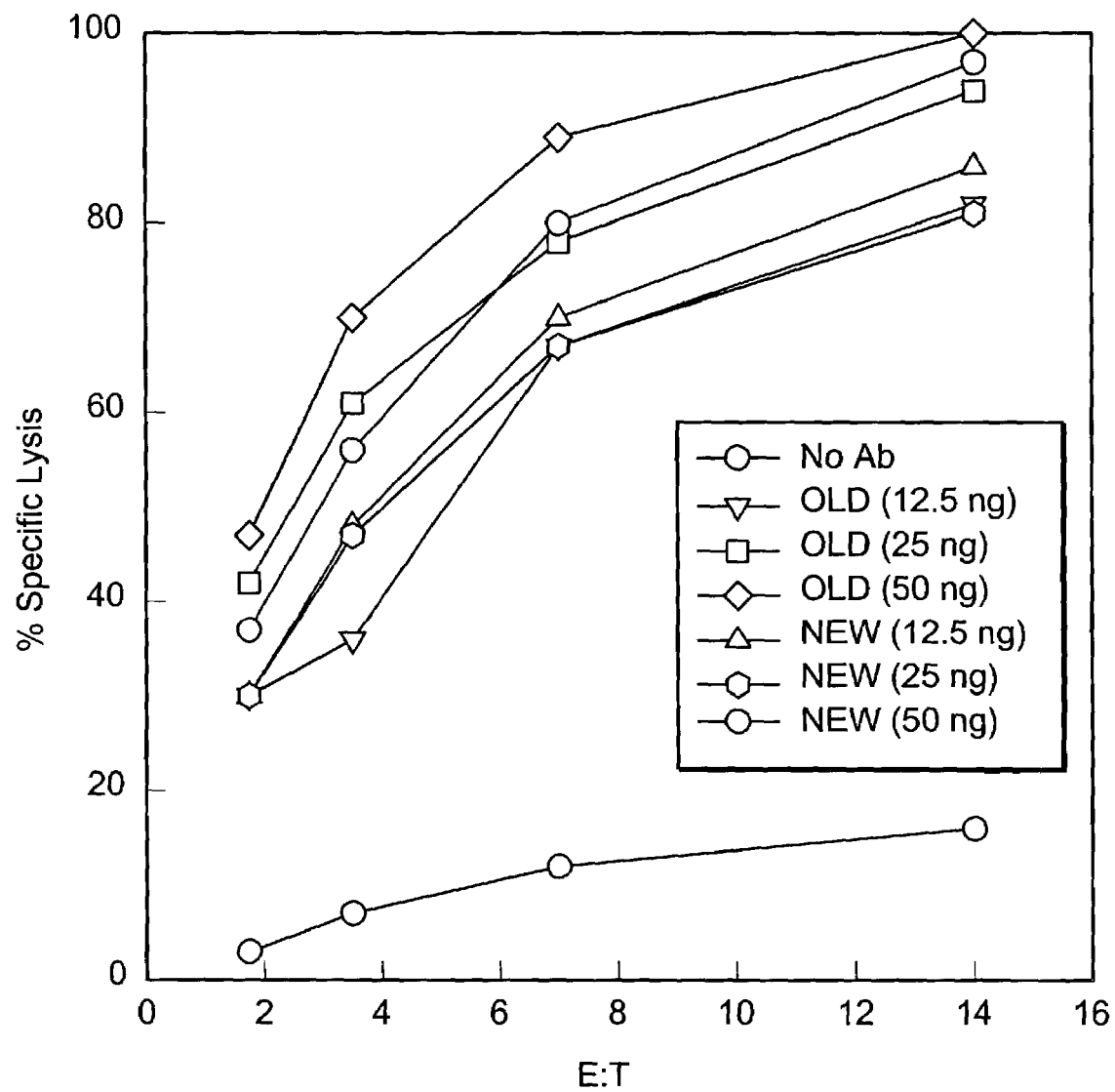
FIG. 24 is a graph illustrating that ATC armed with old and new lots of OKT3 x 9184, are stable for at least 11 months.

Old and new lots of OKT3 x 9184 stable for at least 11 months. There was no difference in the arming and specific cytotoxicity mediated by two batches of OKT3 x 9184 produced Dec. 9, 1997 (old) and Nov. 5, 1998 (new). FIG. 24 shows ATC armed with 12.5, 25, and 50 ng of old or new OKT3×9184. The dose titration curves at each dose overlap.

Figure 23:
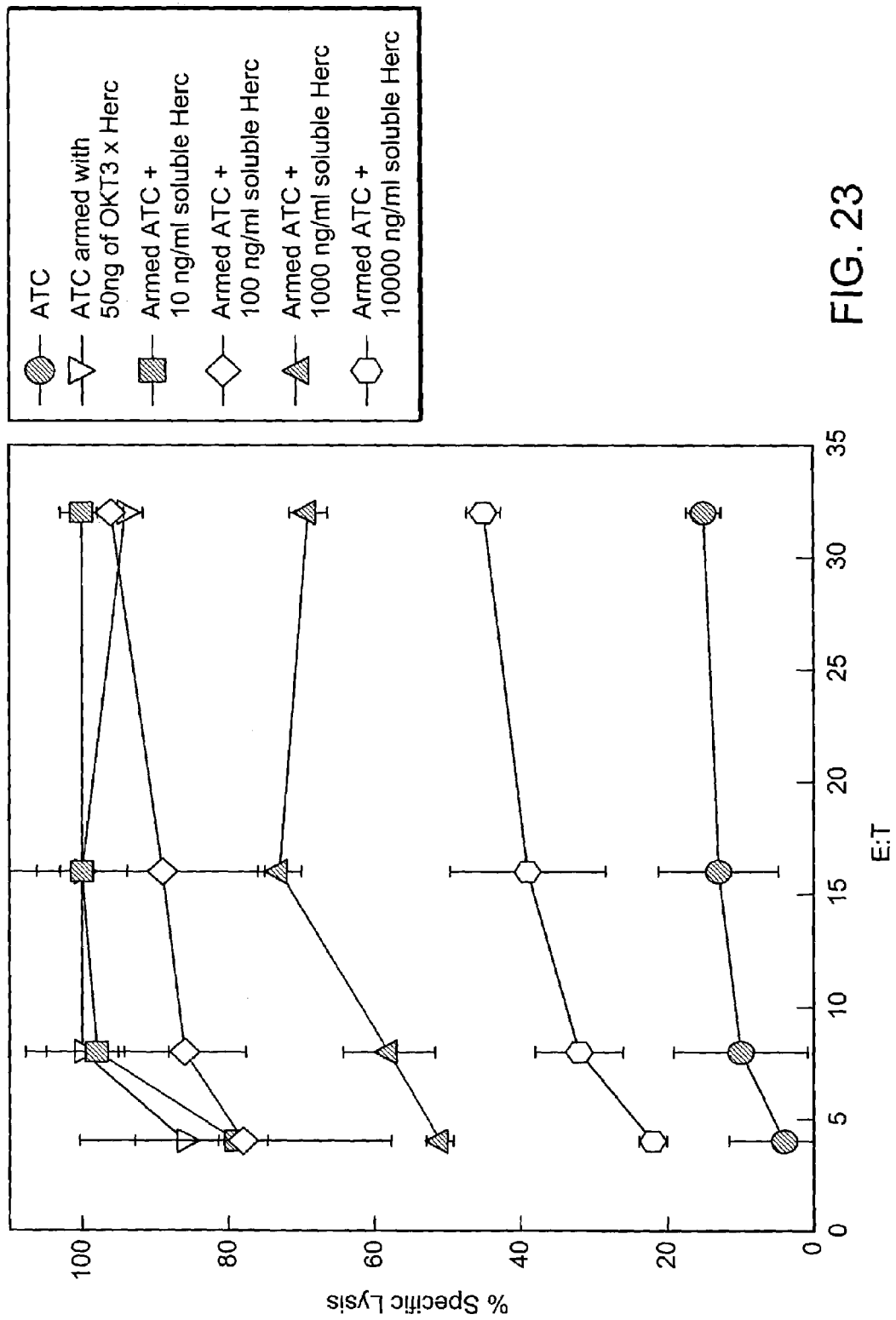
FIG. 23 is a graph illustrating that cytotoxicity mediated by ATC armed with OKT3 x Herc is not inhibited by soluble Herceptin®.

FIG. 23 shows that cytotoxicity mediated by ATC armed with OKT3 x Herc is not inhibited by soluble Herceptin®. Increasing concentrations of anti-Her2 antibody (0.5, 5, 50, 100, 500, 1000, 5000 ng of Herceptin® did not block cytotoxicity mediated by Her2i armed ATC until 1000 ng/ml was reached. Therefore, circulating Herceptin® would not inhibit target killing by Her2Bi armed ATC. On the other hand, prebinding of tumor targets with Her2Bi prior to the addition of unarmed ATC did not form rosettes or enhance specific cytotoxicity (data not shown). In other words, pretreatment of a patient with Her2Bi would not provide enough binding for unarmed ATC to bind via CD3 to the tumor. The error bars indicate ±1 SD.

Example 19

In vivo Efficacy and Cytotoxicity

Figure 25:
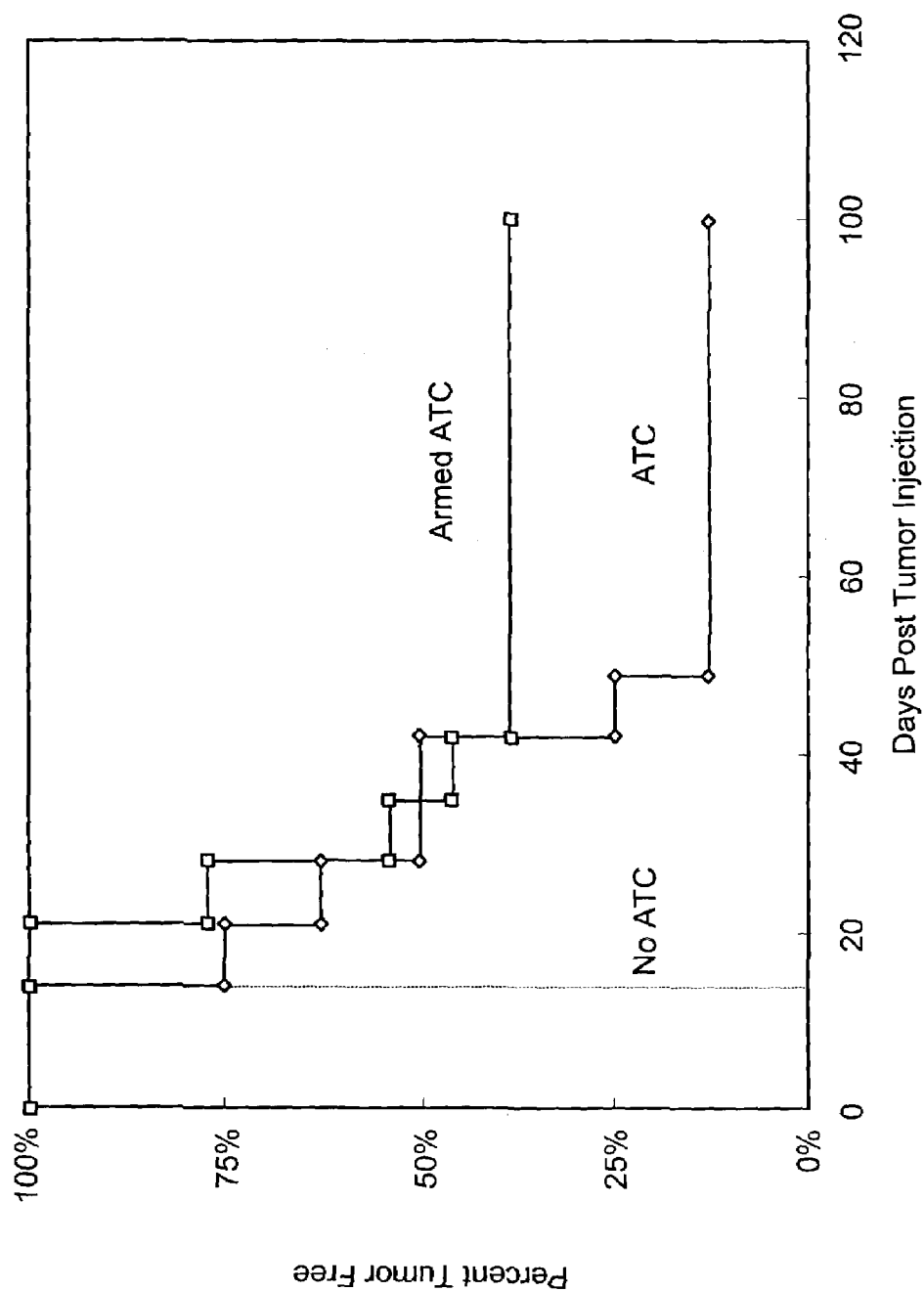
FIG. 25 is a graph illustrating that subcutaneous coinjections of armed ATC ($20 \times 10^6$) and CEA+LS174 ($1 \times 10^6$) colon carcinoma cell line (Winn Assay) prevented tumor progression and death in 40% of the mice that received armed ATC whereas only 10% of the mice that receive ATC alone survived more than 100 days.

Multiple intravenous injections or intraperitoneal injections of 20 to 50×10$^6$ ATC armed with 50 ng of OKT3 x anti-CEA were not toxic to SCID mice. Subcutaneous coinjections of armed ATC (20×10$^6$) and CEA+LS174 (1×10$^6$) colon carcinoma cell line (Winn Assay) prevented tumor progression and death in 40% of the mice that received armed ATC whereas only 10% of the mice that receive ATC alone survived more than 100 days (FIG. 25). The SCID mice received 3 Gy of total body irradiation to eliminate NK cells to assure engraftment of tumor cells 1×10$^6$ LS 174T. All of the control SCID (tumor without ATC) mice died of tumor progression by day 22 (tumor size>22 mm).

Example 20

Cytokine Secretion by Normal ATC Armed with Her2Bi or OKT3 x Herc Induced by Binding to PC-3.

Figure 26:
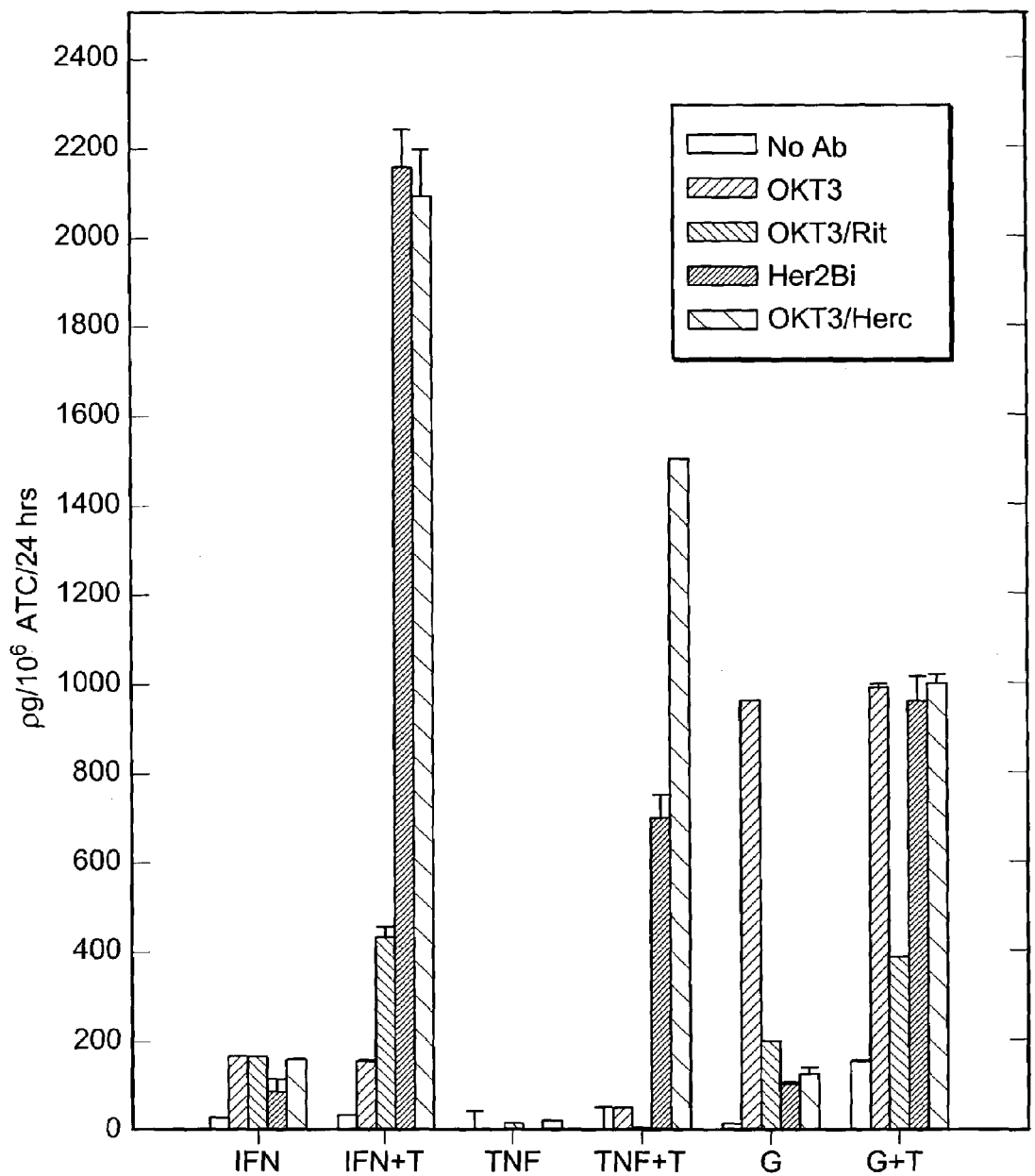
FIG. 26 is a bar graph illustrating cytokine secretion by normal ATC armed with Her2Bi or OKT3 x Herc induced by binding to PC-3.

Tumor cells (200,000) are plated as described supra and incubated overnight. The next day unarmed or armed ATC (2×10$^6$/well) are co-cultured with tumor cells (T) for 24 hours. Culture supernatants are pooled and tested for IFNγ, TNFα and GM-CSF (G) as described above. The results indicate that in the absence of tumor, ATC or ATC armed with OKT3 or OKT3/Rit, there were low levels of IFNγ produced. When normal ATC armed with 50 ng of Her2Bi or OKT3 x Herc were co-cultured with PC-3 (FIG. 26), the ATC markedly increased their production of IFNγ, TNFα and GM-CSF (error bars indicate±1 SD).

Figure 27:
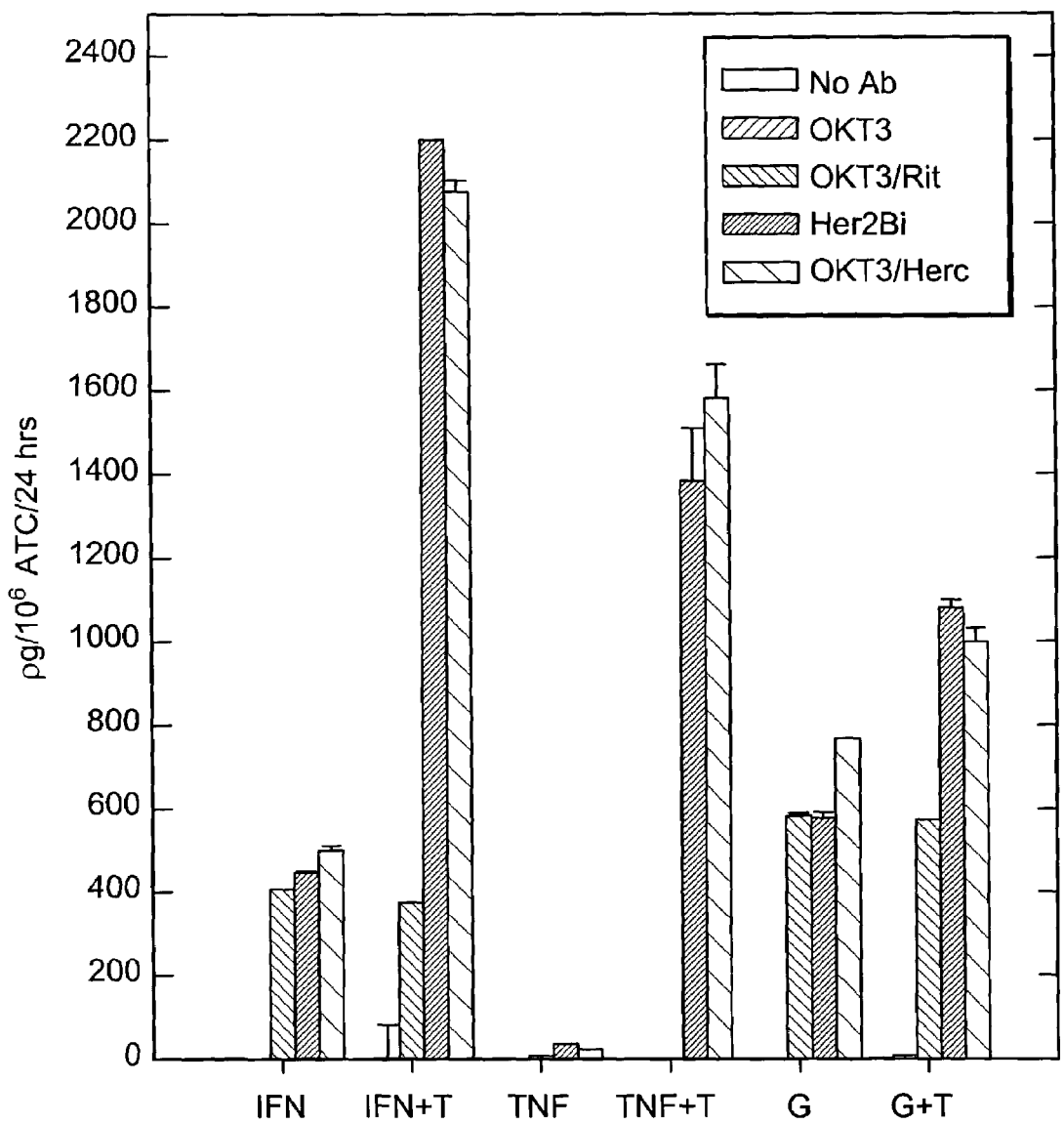
FIG. 27 is a bar graph illustrating cytokine secretion by armed T cells from patients who have received multiple cycles of chemotherapy.

FIG. 27 shows the results for T cells from a patient that were armed with Her2Bi or OKT3 x Herc. ATC were grown from a blood sample after a patient with Ewing's Sarcoma had already undergone 5 cycles of ifosfamide and etoposide chemotherapy. Binding of Her2Bi armed ATC with PC-3 induced 5 marked fold increases in IFNγ and TNFα synthesis. Although GM-CSF synthesis in the absence of PC-3 was higher, there was a 2 fold increase in GM-CSF production by patient ATC. These data show that ATC from patients who have received multiple cycles of chemotherapy are still capable of producing cytokines after arming with Her2Bi.

In retroviral gene transduction of ATC, the results indicate that both IL-2 transgene and endogenous cytokine IFNγ levels had become quiescent a week or more after transduction of the retroviral vector containing IL-2. However, exposing OKT3 x anti-CEA (T84.66) armed ATC to CEA+LS174T induced secretion of IL-2 and IFNγ.[157] Altogether, these data show that the triggering of cytokine secreting occurs using different tumors bearing Her2 receptors as well as in a different model using a different BiAb and colon carcinoma cell target.

Example 21

Clinical Scale-up of Arming Doses Needed for Specific Cytotoxicity.

Figure 28:
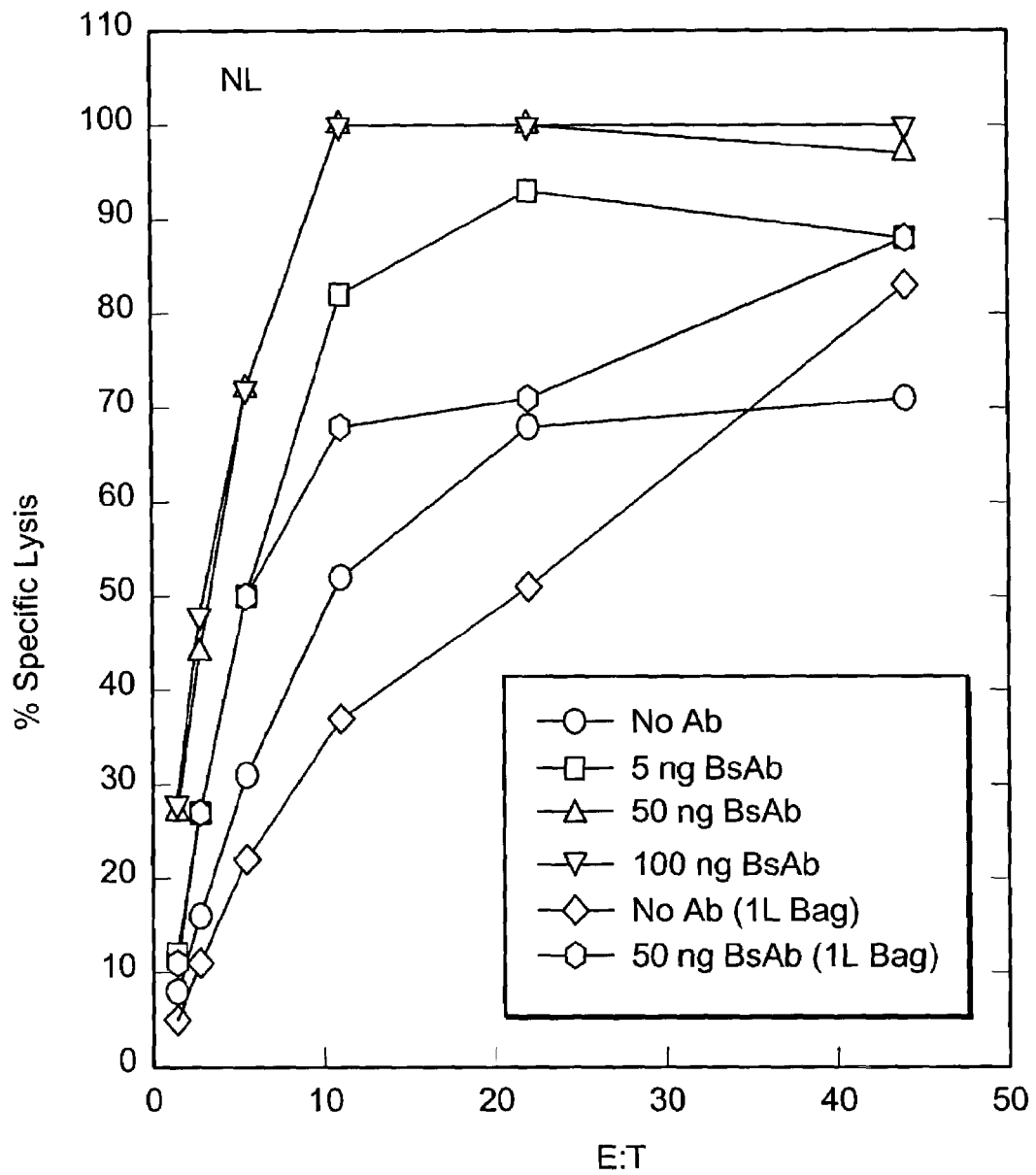
FIGS. 28 and 29 are graphs illustrating the clinical results of arming doses needed for specific cytotoxicity.
Figure 29:
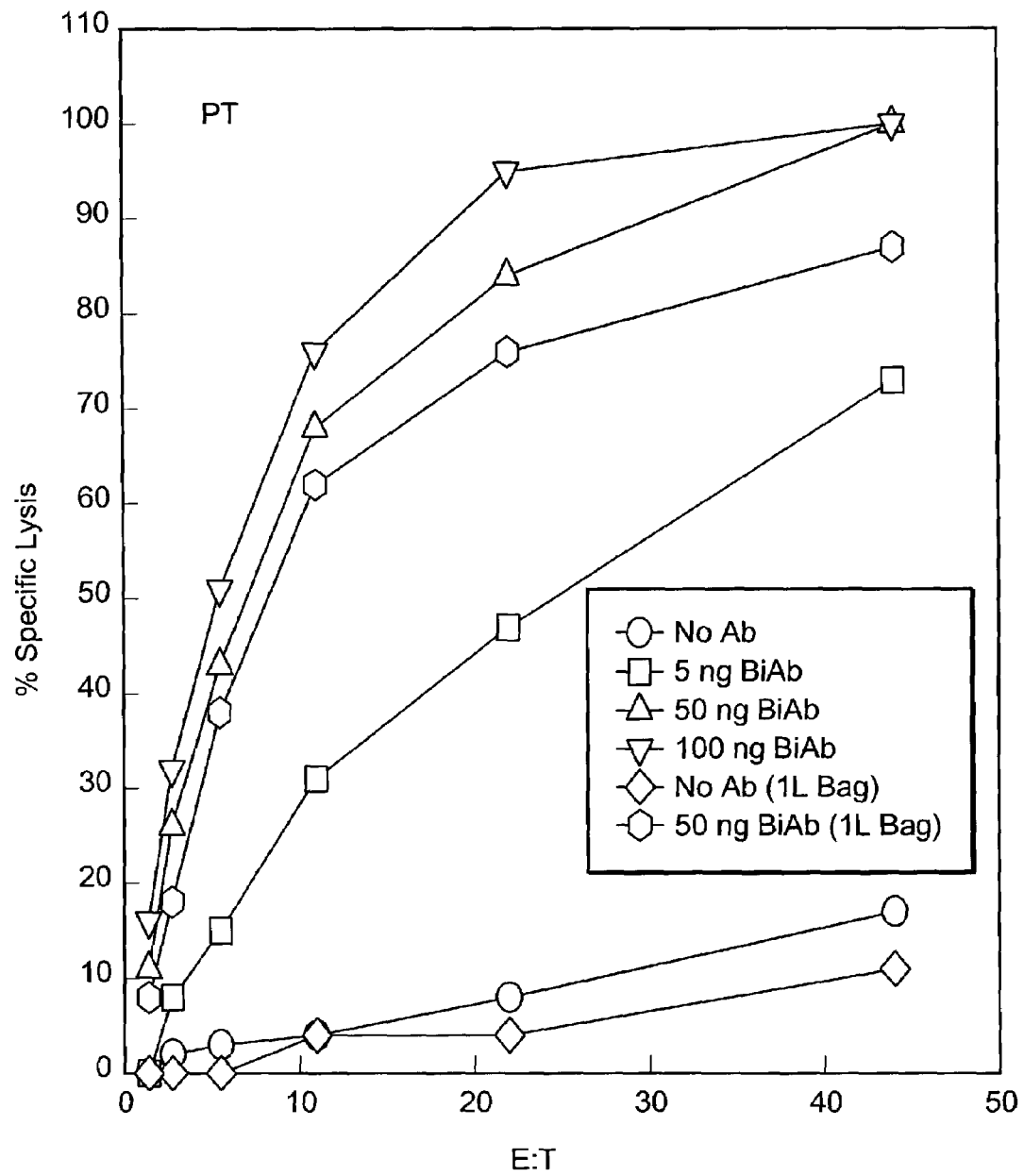

Arming 1 billion ATC was performed at a dose of 0 ng and the cytotoxicity directed at MCF-7 were compared to a series of dose titration curves ranging from 0.1 to 500 ng. FIG. 28 shows the data for the normal (NL) and FIG. 29 shows the data for the patient (PT).

One billion ATC were armed with 50 ng/million ATC by adding 50 micrograms to one billion ATC in an Ethox 3L bag in plasmanate. The doses used to arm ATC in tubes are indicated in figure legend.

Figure 30:
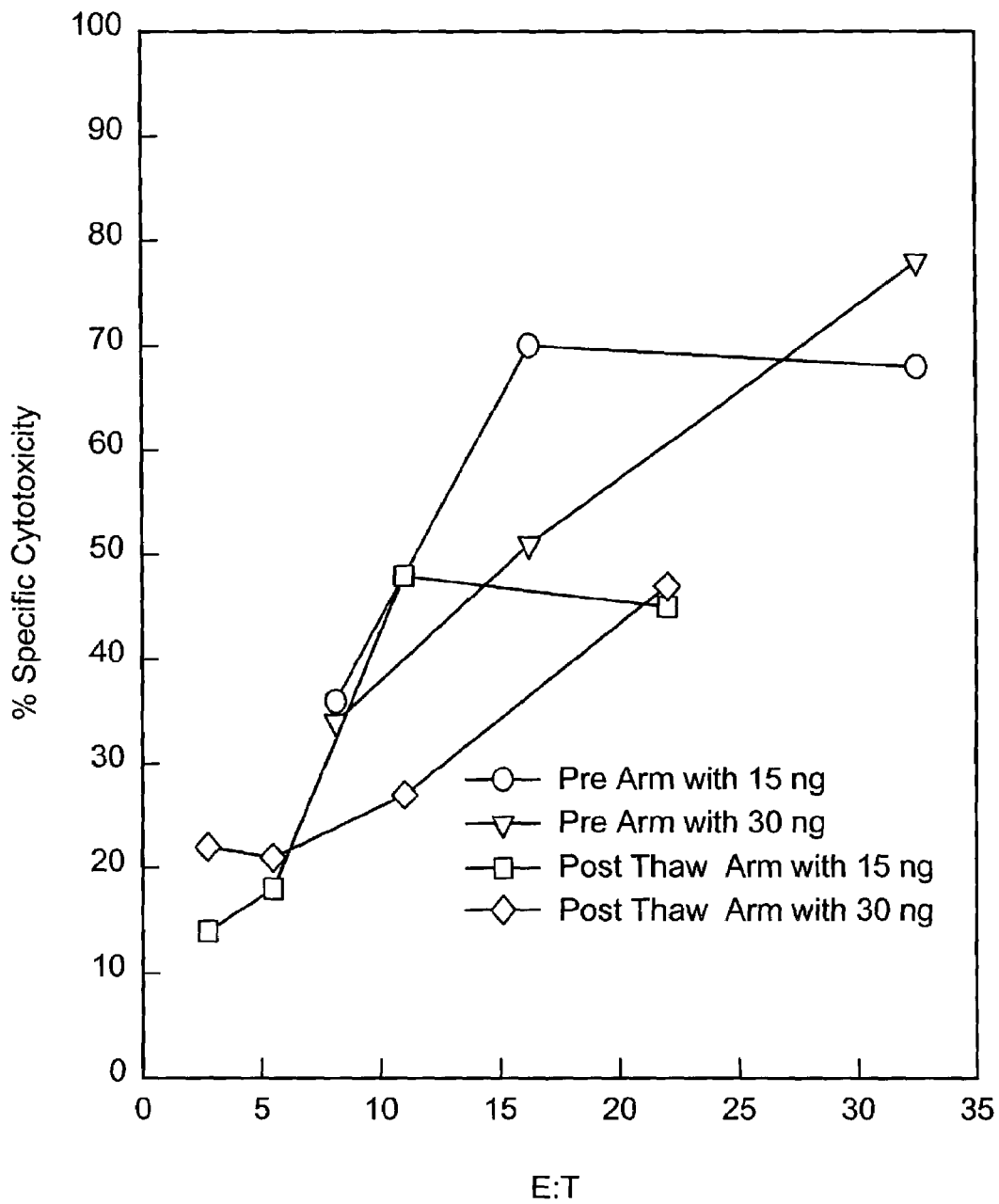
FIG. 30 is a graph illustrating that cryopreservation had little affect on ATC specific cytotoxicity directed at Her2+ MCF-7 targets.

Cryopreservation had little affect on specific cytotoxicity directed at Her2+ MCF-7 targets. FIG. 30 shows the two aliquots are comparable in functional cytotoxic activity. In order to test the effects of freezing/thawing on redirected cytotoxicity, an aliquot of normal ATC was compared to aliquot of the same ATC that were cryopreserved, thawed, and then armed with 15 or 30 ng of Her2Bi, respectively. The right panel of FIG. 30 shows specific lysis for ATC that were frozen, thawed and then armed with OKT3 x Herc.

Example 22

Arming of Anti-CD3/Anti-CD28 Coactivated T Cells (COACTS) with Her2Bi (OKT3 x 9184 or OKT3 x Herc).

Figure 31:
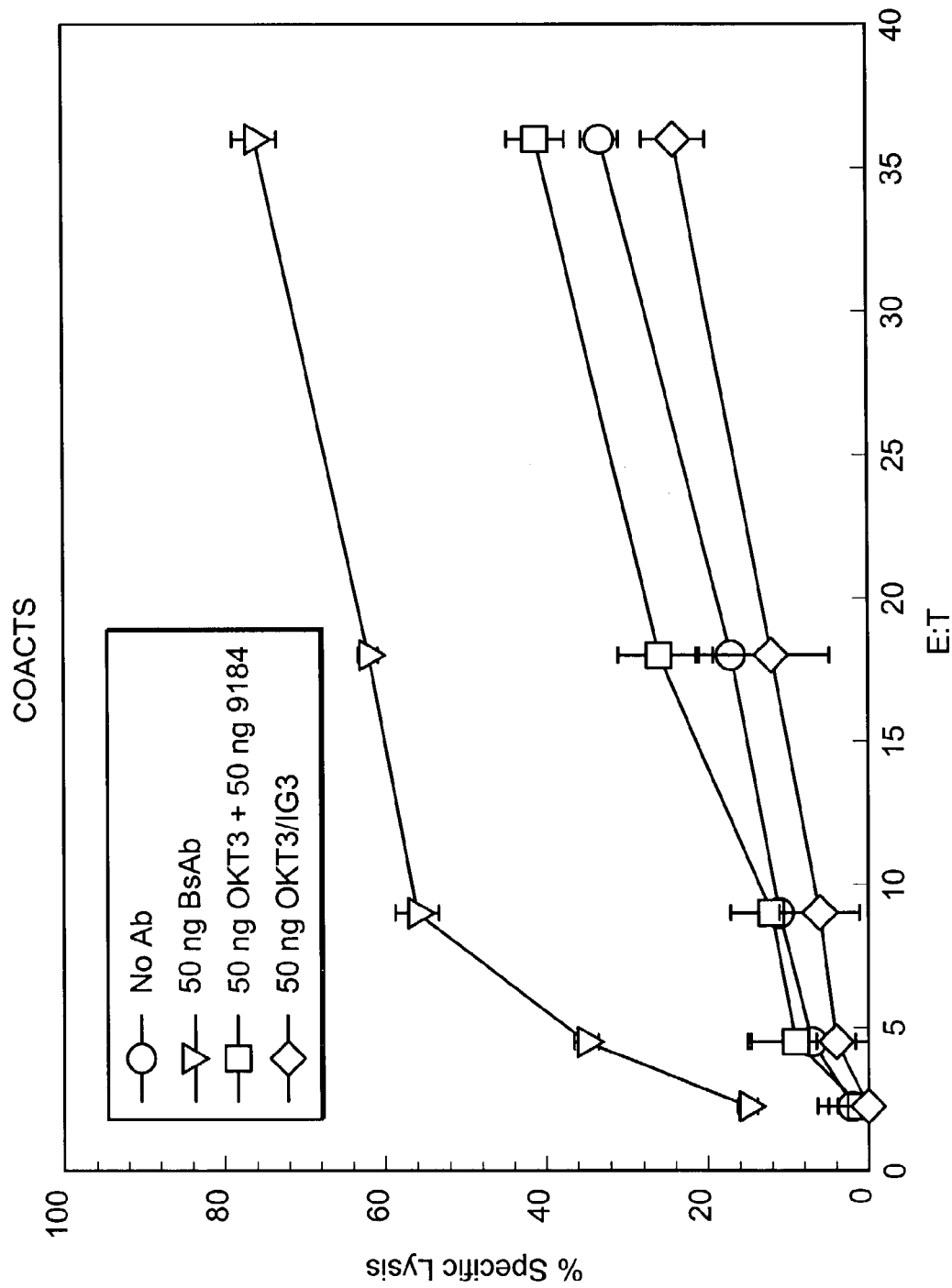
FIG. 31 is a graph illustrating the cytotoxic ability of T cells by arming of anti-CD3/anti-CD28 coactivated T cells (CO-ACTS) with Her2Bi (OKT3 x 9184 or OKT3 x Herc).
Figure 32B:
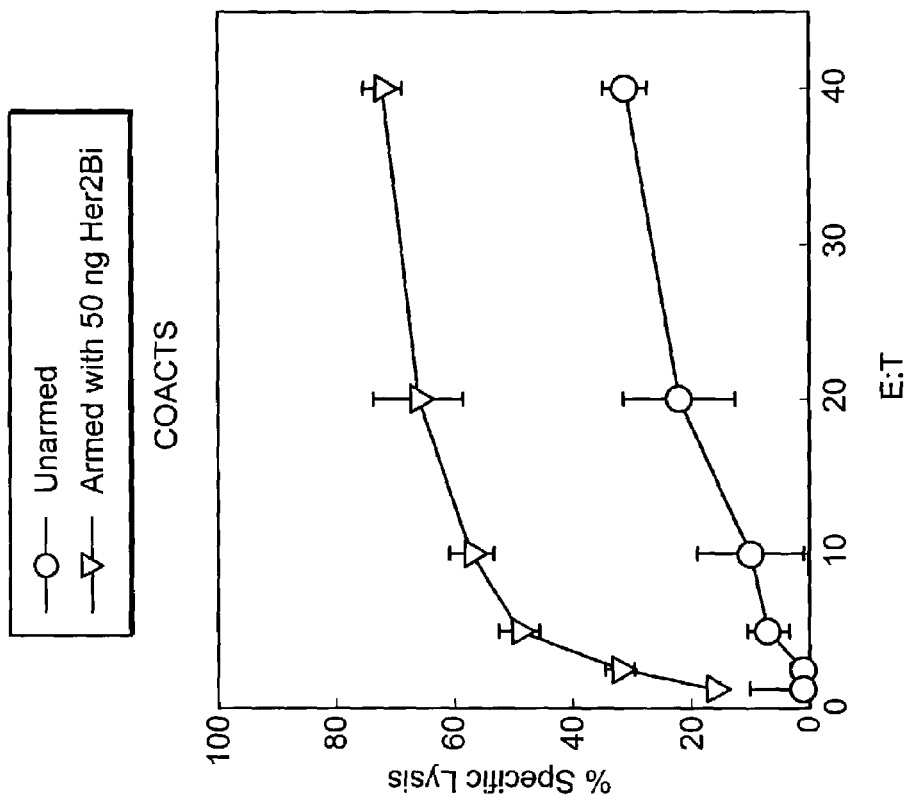
FIG. 32 is a graph illustrating the clinical data using cancer patients' COACTS and ATC armed with OKT3 x 9184. COACTS and ATC have comparable specific cytotoxicity activity against MCF-7 targets. Panels P1, P2, and P3 show the ability of unarmed and armed COACTS and ATC to mediate specific cytotoxicity.
Figure 32A:
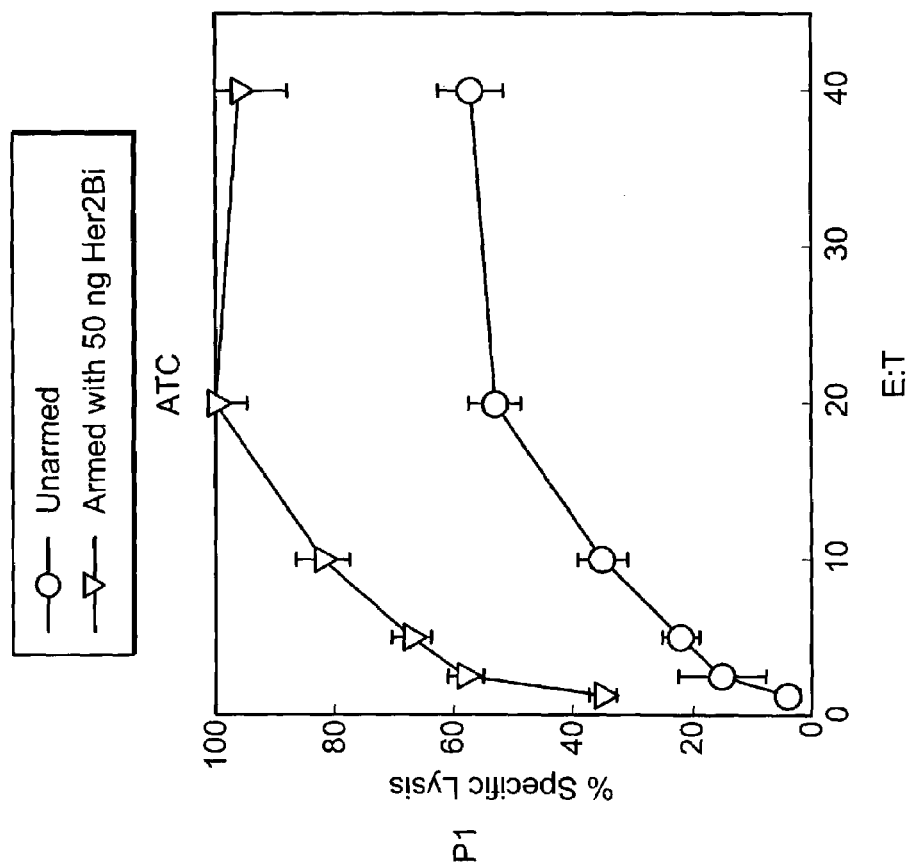
Figure 32D:
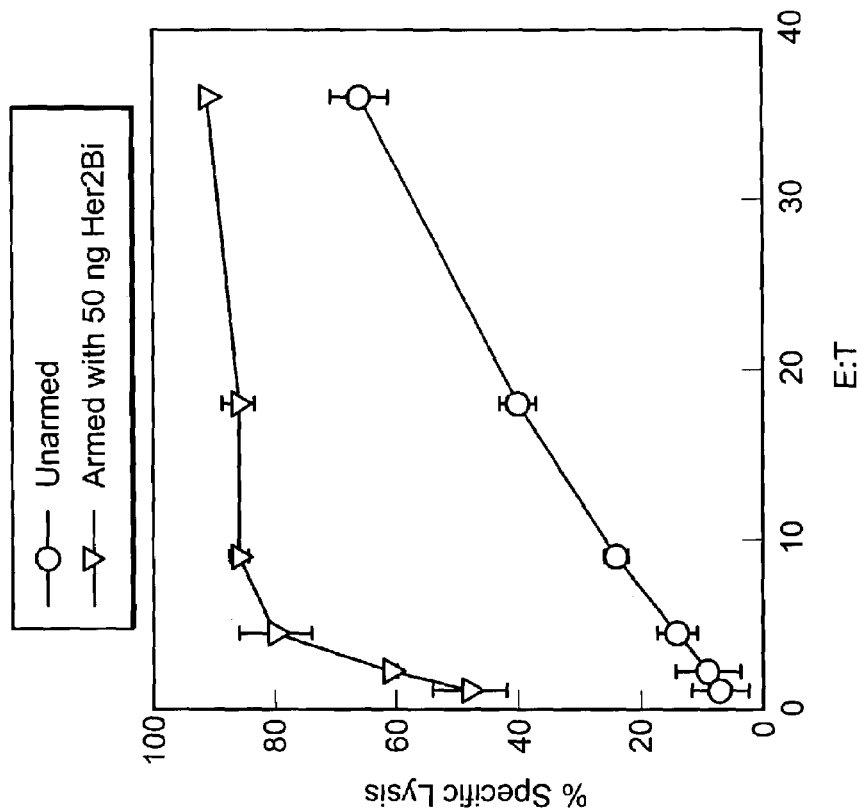
Figure 32C:
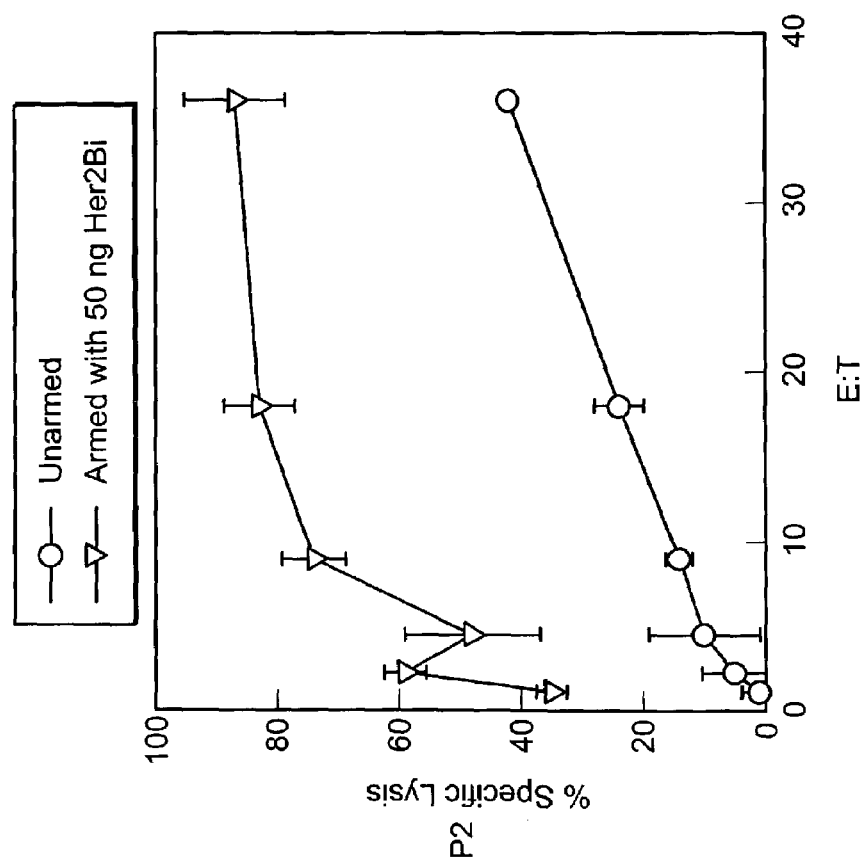
Figure 32F:
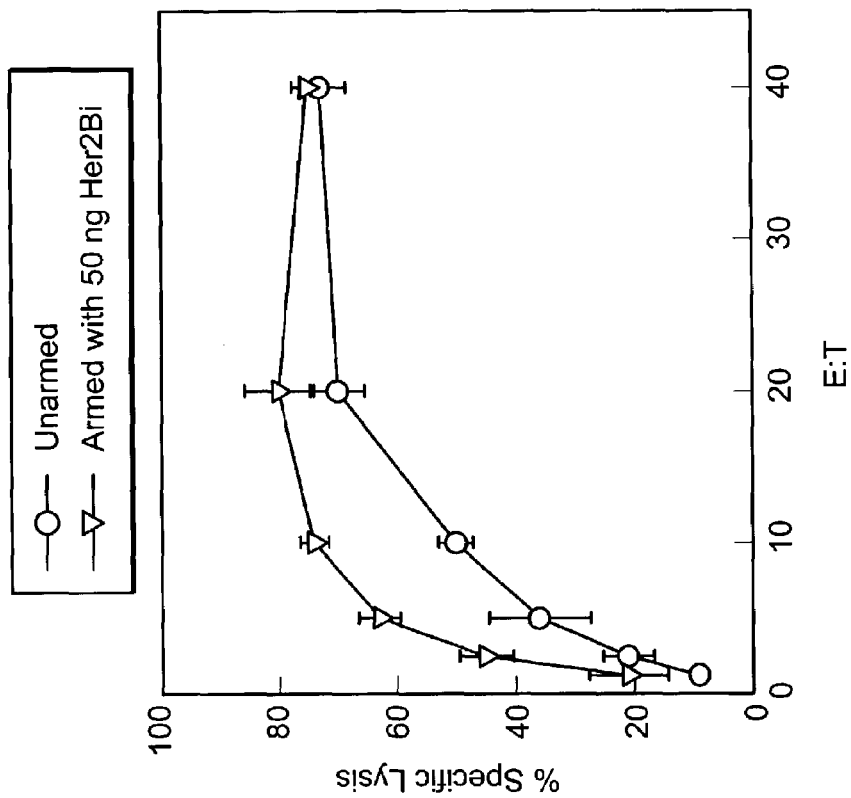
Figure 32E:
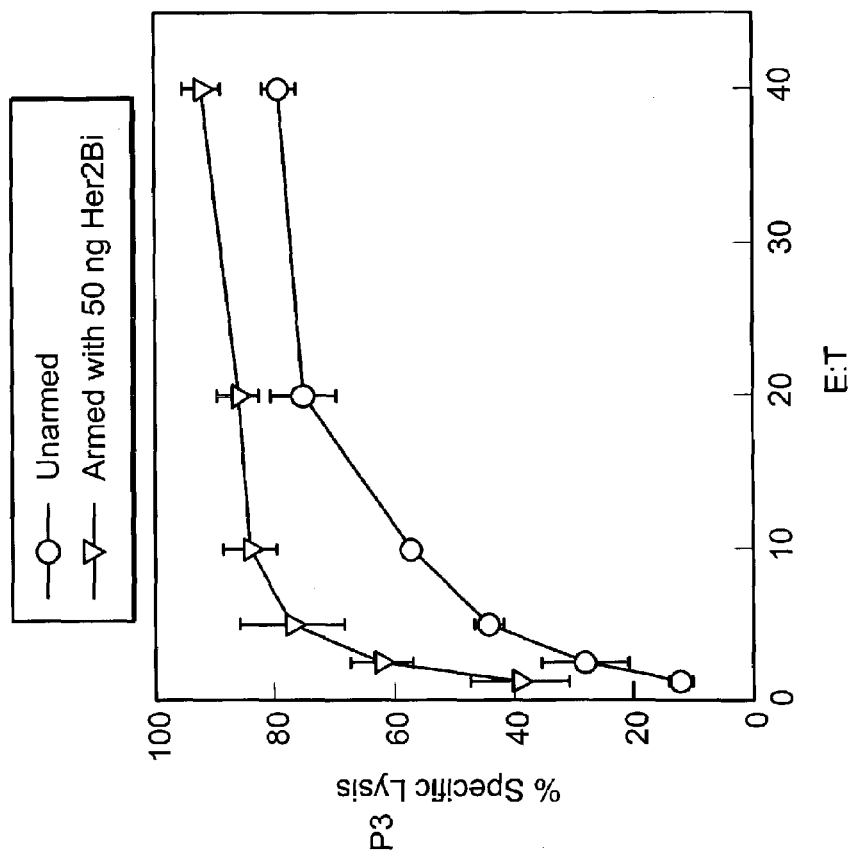

COACTS were left unarmed or armed with 50 ng of OKT3 x 9184, 50 ng of 9184 alone, or 50 ng of OKT3 x IG3 and tested at the indicated E/T ratios for cytotoxicity directed at MCF-7. FIG. 31 shows that COACTS can be armed and lyse MCF-7 targets.

Cancer patients COACTS and ATC armed with OKT3 x 9184 have comparable specific cytotoxicity activity against MCF-7 targets. COACTS and ATC were produced over a 14 day culture period from the same blood samples from three cancer patients. Armed COACTS or ATC from each patient was tested against MCF-7 targets. Panel P1,P2, and P3 of FIG. 32 show the ability of unarmed and armed COACTS and ATC to mediate specific cytotoxicity.

A phase I dose-escalation study, was completed, using infusions of autologous ex vivo expanded COACTS for the treatment of refractory cancer patients.[95] The technical limits of ex vivo COACTS expansion, the in vivo localization and trafficking of COACTS, and immune effects induced by COACTS infusions in the patients were evaluated. Infusions of COACTS were safe, induced detectable, serum levels IFNγ, GM-CSF, and TNFα, and significantly enhanced the ability of freshly isolated PBMC to secrete IFNγ and GM-CSF upon in vitro anti-CD3/anti-CD28 costimulation. These data suggest that the immune systems of these patients were modulated by COACTS infusions. Follow-up studies are in progress to evaluate COACTS in combination with chemotherapy and biologic response modifiers.

Example 23

BiAb Targeting Reactivation of Gene-Transduced T Cells Enhances Both Endogenous Cytokine Production and Secretion of the Transgene Cytokine Product Expression.

In order to circumvent transgene downregulation, OKT3 x T84.66 (anti-CD3 x anti-carcinoembryonic antigen) was used to bind and retarget IL-1α gene transduced ATC. 157 ATC had been modified with a IL-1α retroviral vector and armed with anti-CD3 x T84.66 and mixed with LS174T (CEA+colon carcinoma line). Binding of armed ATC to LS174T cells led to the induction of both endogenous IFN γ secretion and IL-1α secretion. These data further support the use of armed ATC.

Example 24

Treatment of Human Patient with Armed ATC Specific for Pancreatic Cancer.

The patient (AR), with pancreatic cancer, was leukopheresed for a starting population of $9.8 \times 10^9$ mononuclear cells with 58% CD3+ cells, 43% CD4+, and 14% CD8+ cells. The ATC were harvested and armed 10 days later with a total harvest of $61.8 \times 10^9$ ATC consisting of 94% CD3+, 83% CD4+, and 12% CD8+ cells. The patient has received multiple doses of $2.5 \times 10^9$ ATC armed with a dose of 50 ng OKT3 x Herceptin bispecific antibody over two weeks without and dose limiting toxicities.

Table 3 below shows a summary of male patients with hormone refractory prostate cancer (HRPC) who were/are being treated with armed ATC and their clinical toxicities using OKT3 x 9184. Although the bispecific antibody contains another anti-HER2/neu monoclonal antibody, the toxicities are similar.

It is clear that there are no dose limiting toxicities at the doses that have been given to the 4 patients with prostate cancer (Table I), 1 patient with Stage II breast cancer, and the first patient with pancreatic cancer. All of the infusions were completed on an outpatient basis.

Table 4 summarizes the expansion of ATC prior to arming and phenotyping data of the product that was infused into the men with hormone refractory prostate cancer.

TABLE 4

Summary of Product Expansion (Cells x $10^9$)

| Pt | Starting MNC | Days of Culture | % CD3 Pre | % CD4 Pre | % CD8 Pre | Total Harvest | Viability | CD3 Harvest | CD4 Harvest | CD8 Harvest |
|---|---|---|---|---|---|---|---|---|---|---|
| 1 | 9.4 | 11 | 15 | 8 | 7 | 40 | 95 | 38 | 34 | 2.8 |
| 2 | 14.7 | 16 | 37 | 28 | 9 | 32 | 90 | 31 | 28 | 2.2 |
| 3 | 15.1 | 13 | 36 | 24 | 12 | 35 | 95 | 34.3 | 20 | 12 |
| 4 | 15.3 | 14 | 17 | — | — | 38 | 95 | 35.3 | 28.5 | 8.36 |

Example 25

Confirmation of Specific Cytotoxicity Directed at HER2/neu Positive Pancreatic Cell Lines Mediated by ATC from an Additional Normal Subject and Two Patients with Cancer.

Figure 33:
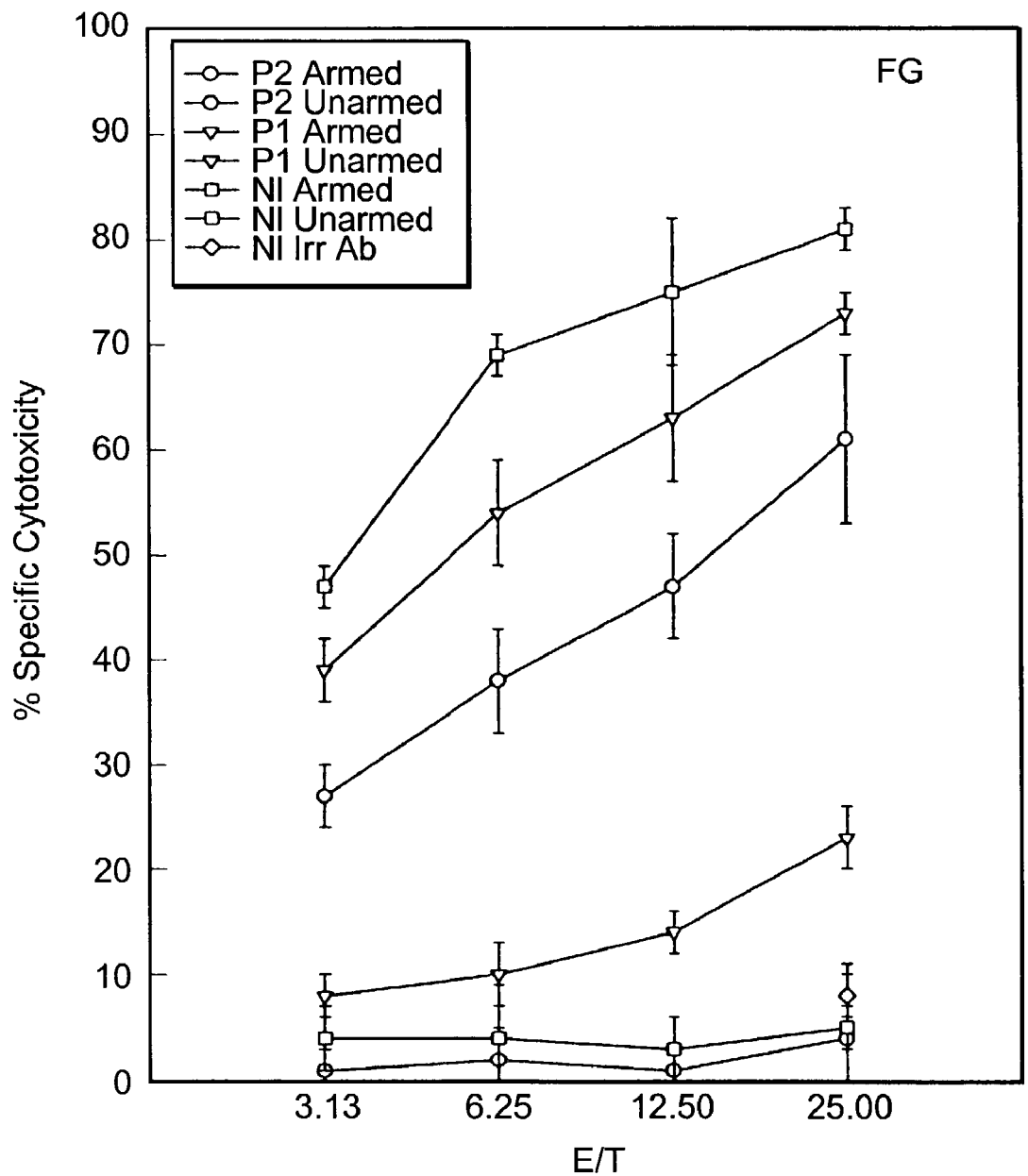
FIG. 33 is a graph showing specific cytotoxicity for one normal subject and two patients with prostate cancer at effector to target ratios from 3.13 to 25.00.

Additional data were obtained using ATC armed with 50 ng of OKT3 x Herceptin per million ATC. The FG pancreatic cell line was plated the night before, radiolabeled with $^{51}$Cr, and unarmed ATC, ATC armed with OKT3 x Herceptin or ATC armed with irrelevant BiAb OKT3 x Rituxan were plated and $^{51}$Cr release was assessed after 18 hrs of co-culture. Specific cytotoxicity for one normal subject and two patients with prostate cancer at effector to target ratios from 3.13 to 25.00 are shown in FIG. 33. Arming of the ATC from the two patients and normal clearly augmented specific cytotoxicity at all effector to target ratios (E:T).

Figure 34:
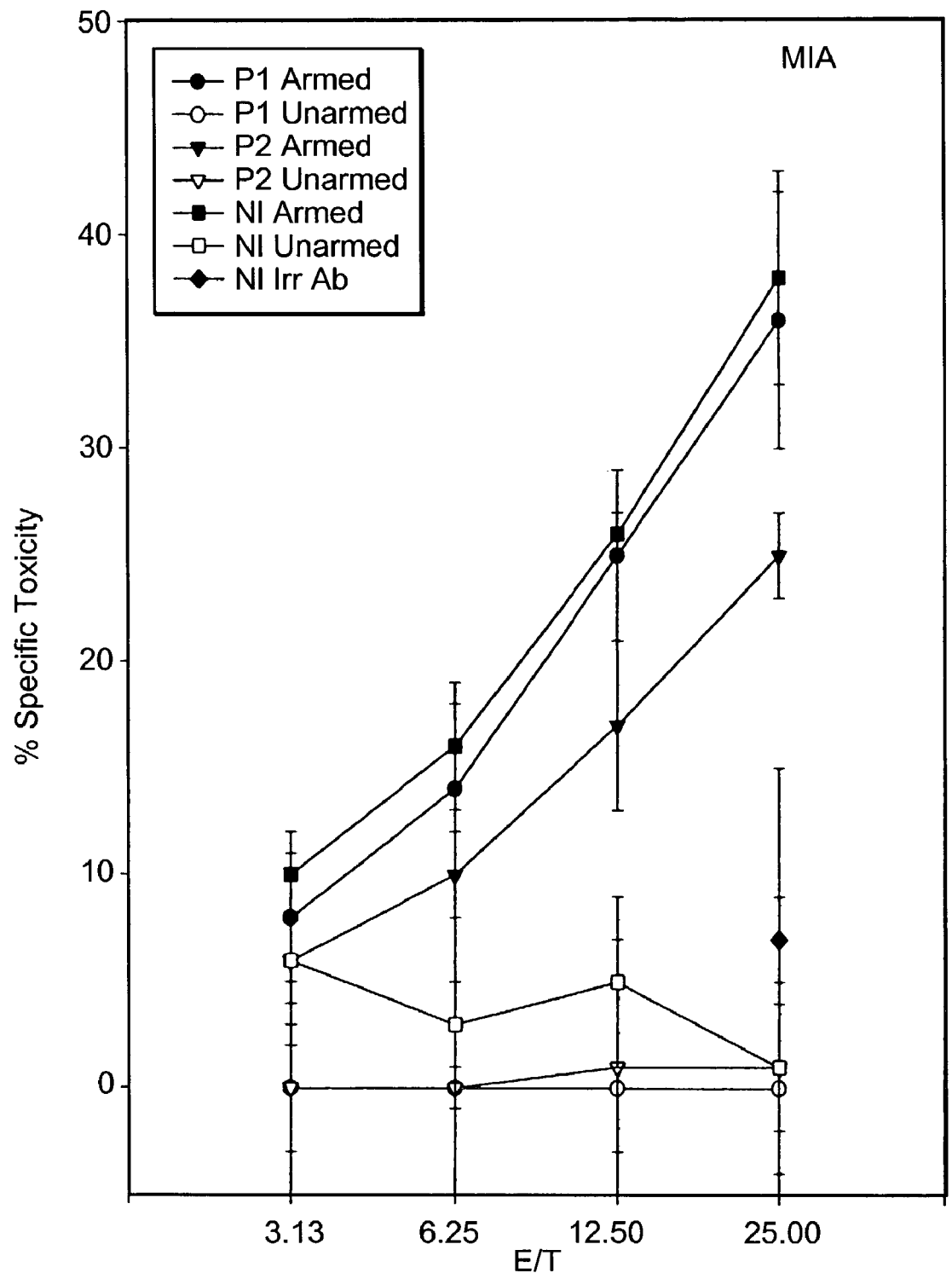
FIG. 34 is a graph showing that armed ATC were able to kill MIA targets, a pancreatic cell line.
Figure 35A:
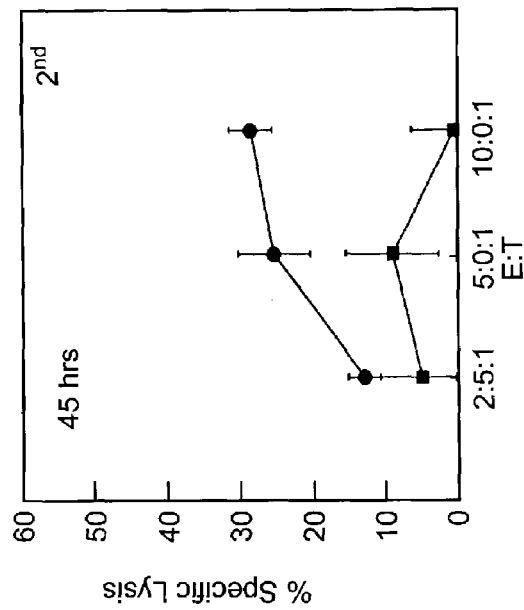
FIG. 35 is a graph showing the $1^{st}$ cytotoxicity assay mediated by an aliquot of armed T cells and an aliquot of unarmed ATC tested at time zero. After 48 hrs of incubation with the first set of targets, the unarmed and armed ATC were harvested and aliquots of each were replated onto a second set of targets for a second culture and $2^{nd}$ cytotoxicity assay at 45 hrs. After the replated unarmed (ATC) or armed ATC (aATC) were co-cultured with SK-BR-3 between 48 hrs and 96 hrs, the unarmed and armed ATC were harvested and aliquots of each were replated onto a third set of targets for a third culture and a $3^{rd}$ cytotoxicity assay at 96 hrs. Finally, the unarmed and armed ATC that had been co-cultured with SK-BR-3 from 96 hrs to 215 hrs were harvested and aliquots of each were replated onto a fourth set of targets in a $4^{th}$ cytotoxicity assay at 215 hrs.
Figure 35B:
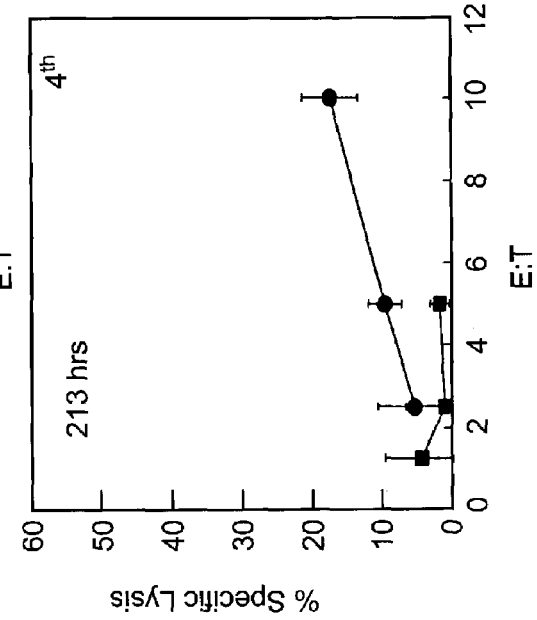
Figure 35C:
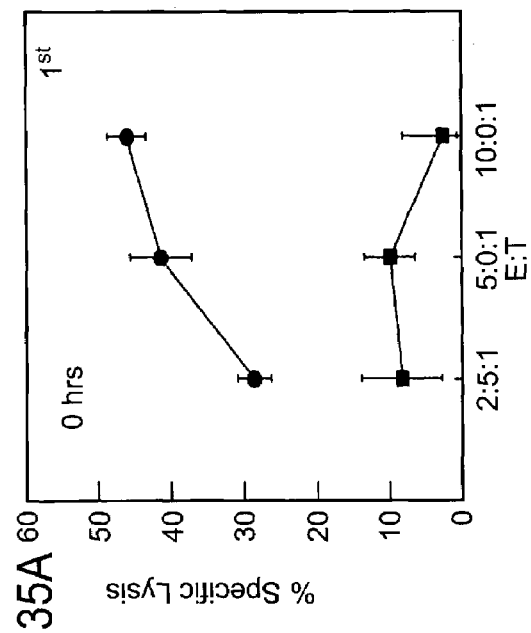
Figure 35D:
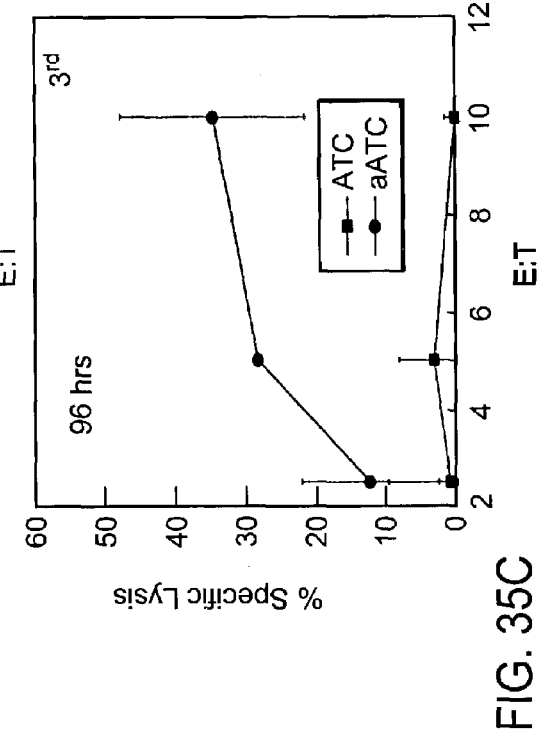
Figure 37A:
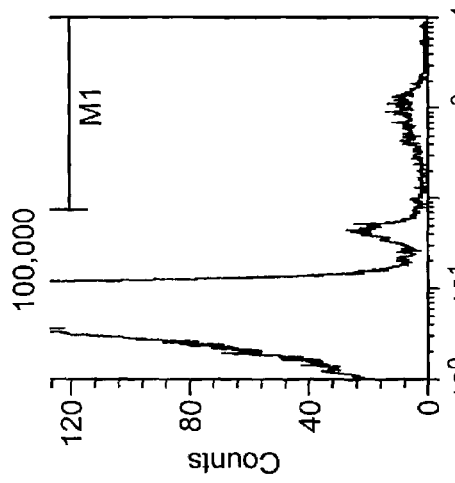
FIG. 37 are graphs from flow cytometry data showing survival or trafficking in patients by detecting IgG2a bearing armed ATC.
Figure 37B:
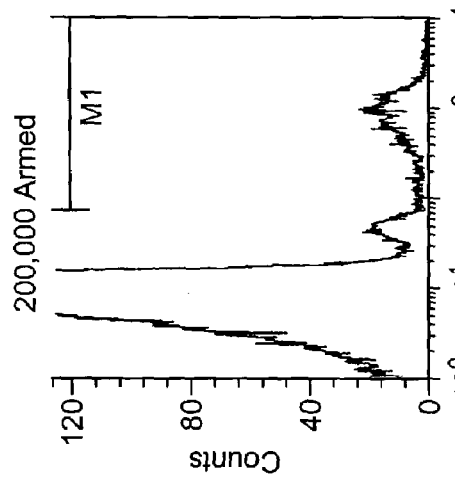
Figure 37C:
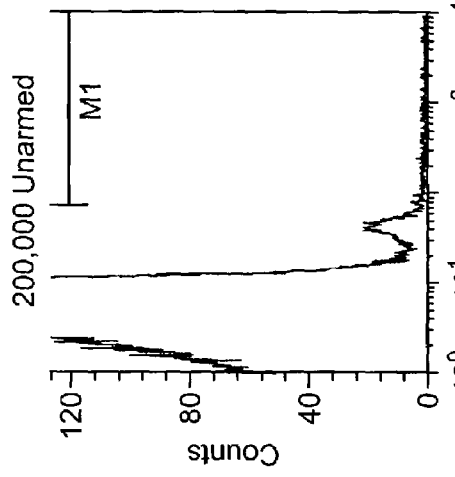
Figure 37D:
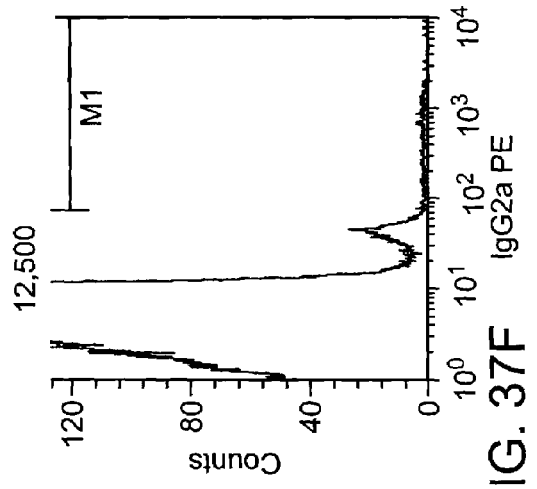
Figure 37E:
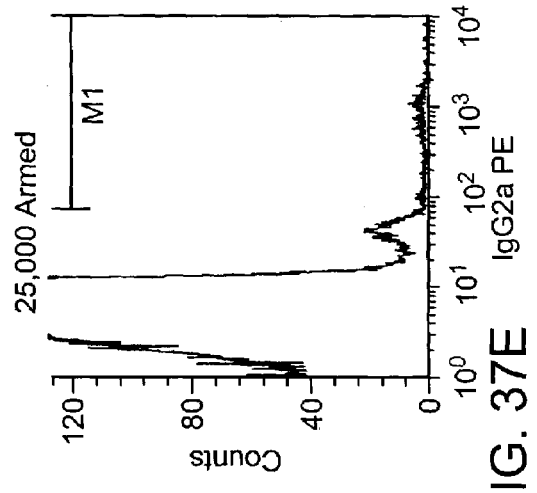
Figure 37F:
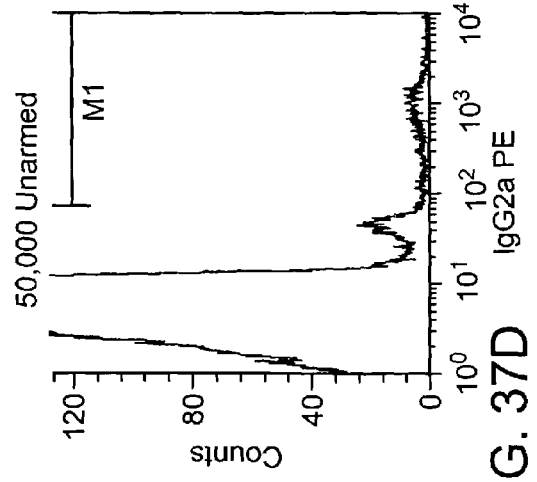

In order to confirm cytotoxicity in a second pancreatic cell line, an additional cell line, MIA was purchased from ATCC and tested in the same assay. FIG. 34 shows that armed ATC

TABLE 3

Summary of Treatment of Patients HRPC Prostate Cancecr

| | Patient Initials | MRU # | Age | Treatment Started | Survival Disease Status | Course Completed | Dose Delivered (x $10^9$) | ≥ Grade 3 Toxicity |
|---|---|---|---|---|---|---|---|---|
| 1 | RG | 975929 | 65 | Aug. 05, 2001 | Oct. 13, 2001 Died of Progression | Yes | 20 | Chills |
| 2 | TN | 0982204 | 81 | Sep. 12, 2001 | Died of Progression | Yes | 20 | Chills |
| 3 | PP | 523902 | 75 | Feb. 8, 2002 | Alive, No response so far | Yes | 20 | Chills |
| 4 | EM | 1008188 | 85 | May 7, 2002 | Alive, Not evaluable | 6$^{th}$ Infusion | 12 | Chills | were able to kill MIA targets. Western blotting of the MIA cell line confirmed the expression of HER2/neu receptors on the cell line.

Example 26

ATC Armed with OKT3 x Herceptin can Kill Multiple Times.

In order to determine whether armed ATC could kill tumor cells multiple times, a series of parallel cultures that contained unarmed, armed with HER2Bi, and armed with OKT3 x Rituxan, was set up. SK-BR-3 breast cancer target cells were plated overnight prior to each of the cytotoxicity assays. Before arming of the ATC, the ATC were marked with 5(6) carboxyfluorescein diacetate N-succinimidyl ester (CFDA-SE) dye so that the dye could be used to evaluate the number of cell divisions that occur and be detected by gating for green fluorescence using flow cytometry. Effector: Target ratios ranging from 2.5 to 10:1 were setup on the day of the cytotoxicity assay by performing cold counts of the plated target cells after each radiolabeling. This maneuver accounts for cell losses and provides the actual number of targets in each well prior to the addition of effector T cells. Panel A of FIG. 35 shows the $1^{st}$ cytotoxicity assay mediated by an aliquot of armed T cells and an aliquot of unarmed ATC tested at time zero. After 48 hrs of incubation with the first set of targets, the unarmed and armed ATC were harvested and aliquots of each were replated onto a second set of targets for a second culture and $2^{nd}$ cytotoxicity assay at 45 hrs. After the replated unarmed (ATC) or armed ATC (aATC) were co-cultured with SK-BR-3 between 48 hrs and 96 hrs, the unarmed and armed ATC were harvested and aliquots of each were replated onto a third set of targets for a third culture and a $3^{rd}$ cytotoxicity assay at 96 hrs. Finally, the unarmed and armed ATC that had been co-cultured with SK-BR-3 from 96 hrs to 215 hrs were harvested and aliquots of each were replated onto a fourth set of targets in a $4^{th}$ cytotoxicity assay at 215 hrs. Since repeated cytotoxicity was observed, the data show that the ATC were still "armed" with OKT3 x Herceptin. Flow cytometry on the armed ATC at 213 hrs clearly showed persistence of OKT3 (murine IgG2a) on the surface of the ATC. Viability was consistently greater than 80% by propidium iodide and by trypan blue exclusion.

Example 27

Cell Division Occurs in the ATC Population Mediating Cytotoxicity.

The experiment shown in FIG. 35, was conducted to determine whether the cells would divide after binding to HER2/neu antigen on the surface of SK-BR-3 target cells. The flow cytometry data in FIG. 36, showed that there was evidence for several cell divisions during the multiple rounds of tumor antigen exposure as exhibited by the detection of cells exhibiting decreased amounts of CFDA-SE fluorescence. Panels A and B show armed ATC 3 hrs and 48 hrs after mixing of the armed ATC with SK-BR-3 targets, Panels C and D show unarmed ATC at 3 hrs and 48 hrs after mixing with SK-BR-3 targets. Panels E and F show armed ATC alone without exposure to targets. Panel B shows that nearly all of the population has shifted downwards from the mean fluorescence intensity (MFI) of the original peaks of MFI's 30 and 18 on Panel A compared to peaks with MFI's of 30, ~20, ~10, and ~5 on Panel B. Unarmed ATC (Panel D) mixed with targets have divided at roughly the doubling time seen for ATC in culture with nearly all of the cells synchronized at point 2. Armed ATC in Panel F have started to divide and there is a large population of cells that have divided (MFI ~20) a smaller population that divided twice at a MFI of ~9. In contrast, unarmed ATC in the presence of SK-BR-3 do not proliferate, and armed ATC without targets exhibit some proliferative shifts as a result of "low" level activation induced by the arming process with a small population with a MFI of ~35 representing cells that had not divided. It is anticipated that arming provides a low level restimulation to ATC. In summary, Panel B with armed and targeted ATC shows 4 cell populations identified by the arrows that originated from populations #1 and #2 in Panel A.

Example 28

CD4$^+$ or CD8$^+$ T Cell Subsets Preferentially Proliferate

All of the ATC, were marked with CFDA-SE prior to arming with HER2Bi or irrelevant (control) OKT3 x Rituxan, phycoerythrin labeled monoclonal antibodies directed at human CD$^+$ and CD8$^+$ were used to determine the proportion of CD4+ and CD8+cells that occurred within the whole population of CFDA-SE positive ATC.

FIG. 36 presents a combination overlay from another experiment that shows the numbers of CFDA-SE$^+$ cells within the CD4$^+$ or CD8$^+$ subsets that had been armed with OKT3 x Herceptin, OKT3 x Rituxan, or left unarmed. The key point is that the CD4$^+$ cell population showed evidence of cell division with a very distinct population of cells that had divided and showed reduce intensity whereas the CD4$^+$ cells armed with OKT3 x Rituxan and unarmed ATC did not show as many cells that had divided and exhibited half as much staining intensity.

Example 29

| No. Armed ATC spiked | % of WBC Gate | Abs Count of spiked ATC | FIG. 6 Panel |
|---|---|---|---|
| 200,000 | 4.70 | 131 | B |
| 100,000 | 2.00 | 53 | C |
| 50,000 | 1.19 | 27 | D |
| 25,000 | 0.69 | 18 | E |
| 12,500 | 0.40 | 11? | F |

Trafficking and Detection of Circulating Armed ATC After Infusion.

The survival or trafficking of circulating armed ATC after infusion were monitored in patients using a newly developed flow cytometry assay to detect IgG2a bearing armed ATC. In order to determine-what the sensitivity of flow cytometry for detecting T cells bearing membrane bound IgG2a (the OKT3 portion of the BiAb or OKT3 alone), increasing known amounts of ATC armed with 50 ng/million ATC, were added to fresh heparinized blood and tested the whole blood for cells bearing mouse IgG2a with a PE conjugated polyclonal goat anti mouse-IgG2a antibody.

The six panels of FIG. 37 show that as few as 12,500 armed ATC per ml mixed with 5.58 million normal white cells in the gate (total WBC 5.58×10$^3$/mm$^3$ from the CBC) can be detected by flow cytometry using this method.

In FIG. 37, Panel F, the data show that as low as 0.4% ATC armed with OKT3 x Herceptin/million could be detected in whole blood. Based on these sensitivity studies, we tested several random samples of blood and phenotyped the blood for murine IgG$_{2a}$ bearing T cells. Up to 1.5% positive cells in the WBC gate (corrected for isotype control) were detected in the peripheral blood of Patient MRU #523902 up to 8 days after his sixth infusion of armed ATC.

Example 30

In vivo Survival of Armed ATC Following the First Infusion of Armed ATC

Based on the detection of persistent $IgG_{2a}$ bearing cells, a kinetic study to determine the survival of armed ATC following the first infusion of armed ATC was performed. Phenotyping on the peripheral blood was obtained Pre, 10 mins, 30 mins, 1 hr, 4 hrs, 10 hrs, and 24 hrs after an infusion of $2.0 \times 10^9$ OKT3 x 9184 (anti-HER2/neu, a gift from Nexell) armed ATC. The kinetic study showed that armed ATC can be detected at approximately as 1% of the total WBC gate as soon as 30 mins after infusion. The armed ATC could not be detected around 4 hrs, but detection and persistence in the patient's circulation occurred between 10 hrs and 24 hrs after the infusion.

Example 31

Long-Term Survival of Engrafted Human T Cells in Beige/SCID Mice.

Follow-up studies on mice engrafted with human T cells went into remission after 11 or 12 intra-tumoral injections of $50 \times 10^6$ armed ATC. Phenotyping of the spleen and bone marrow revealed 5.5% $CD3^+$ cells. The control mice had no detectable human $CD3^+$ cells. The data show that the directly injected armed ATC, killed tumor cells and outnumbered the total number of injected armed ATC (600 million). The increase in number of in vivo armed ATC is due to the fact that armed ATC divide at least once or more after engaging the tumor in vivo. It is important to note that no IL-2 was given to the mice after their tumors regressed.

Example 32

Trafficking of ATC in vivo and Accumulation at Tumor Sites.

Blood phenotyping and biopsies of accessible metastatic lesions are obtained. The biopsied tissue is used in indirect immunofluorescence assays using anti-$IgG_{2a}$ antibodies to detect the OKT3 component of OKT3 x Herceptin®. The clinical protocol incorporates biopsies when they are obtained. For example, peripheral blood mononuclear cells (PBMCs) can be obtained from a subject and isolated by density gradient centrifugation, e.g., with Ficoll/Hypaque. Specific cell populations can be depleted or enriched using standard methods. For example, monocytes/macrophages can be isolated by adherence on plastic. T cells or B cells can be enriched or depleted, for example, by positive and/or negative selection using antibodies to T cell or B cell surface markers, for example by incubating cells with a specific primary monoclonal antibody (mAb), followed by isolation of cells that bind the mAb using magnetic beads coated with a secondary antibody that binds the primary mAb. Peripheral blood or bone marrow derived hematopoietic stem cells can be isolated by similar techniques using stem cell-specific mAbs (e.g., anti-CD34 mAbs). Specific cell populations can also be isolated by fluorescence activated cell sorting according to standard methods. Monoclonal antibodies to cell-specific surface markers known in the art and many are commercially available.

Example 33

Prevention of Tumor Re-Growth

To prevent tumor growth, irradiated female Beige/SCID mice (the kind gift of Dr. Ray Frackelton) were co-injected subcutaneously in the hip with $10^6$ PC-3 tumor cells and either: IL-2 alone, $10^7$ unarmed ATC and IL-2, $10^7$ armed ATC and IL-2, or $2 \times 10^7$ armed ATC and IL-2. IL-2 was given in the dose of 10 IU/g bodyweight. 50 ng of OKT3 x Herceptin BiAb was used to arm ATC. Once injected, mice were given no further treatment but were monitored for weight and length by width tumor dimensions every two to four days. Length by width dimensions were used to calculate tumor volume with a standard hemi-elipsoid formula: (length × $width^2$)/2. Animals with 864 $mm^3$ (12×12 mm) tumors were euthanized. Mice were monitored continuously from first sign of tumor development through the $105^{th}$ day following initial co-injection.

In an attempt to prevent established tumors in the Beige/SCID mouse model, irradiated and non-irradiated females were injected subcutaneously in the hip with $10^6$ PC-3 tumor cells and allowed to develop 62.5 $mm^3$ (5×5 mm) tumors. Mice were given direct intratumoral injections twice per week with either: IL-2 alone, $10^7$ armed ATC and IL-2, or $5 \times 10^7$ armed ATC and IL-2. A 10 IU/g bodyweight dose of IL-2 was maintained. 50 ng of OKT3 x Herceptin BiAb was used to arm ATC. As in the previously described Winn (or co-injection) assay, mice were individually tracked for length by width tumor dimensions and animal weight every two to four days. Mice with 864 $mm^3$ (12×12 mm) tumors were sacrificed. Mice were monitored continuously until tumor remissions were induced, then periodically thereafter to track relapse.

Statistical Analysis

Specific cytotoxicity was calculated as the mean of triplicate wells±standard deviation using Excel (Microsoft Office). ELISA values for cytokine and chemokine secretion were calculated as the mean of duplicate wells using Excel. All graphical representations of in vitro data were created using SigmaPlot (Jandel Corporation, San Rafael, Calif.).

For all animal experiments, Kaplan-Meier curves were generated. Tumor growth delay models were also generated, testing statistical differences between the growth curves of each group with the non-parametric Kruskal-Wallis test followed by Dunn's multiple comparisons test. All statistical analyses were performed using the Prism statistical program (GraphPad, San Diego, Calif.).

Flow Cytometry

Following tumor relapse in two animals that had undergone remission and two untreated, tumor-free control mice, bone marrow, spleen, and peripheral blood samples were harvested. Human CD3, CD4, CD8, CD16, CD45RO, CD45RA, and CD56 expression were evaluated by flow cytometry on a FACSCalibur System (BD Biosciences, San Jose, Calif.).

Results

Armed Activated T-Cells Bind and Lyse $HER2^+$ Tumor Cells

OKT3 x Herceptin BiAb armed ATC exhibit enhanced specificity over unarmed or irrelevant (OKT3 x Rituxan) BiAb armed ATC, resulting in high levels of PC-3 prostate cancer cell lysis. Using an irrelevant BiAb to crosslink CD3 proteins of an ATC without engaging tumor antigen fails to induce cytotoxicity above the level of unarmed ATC in the presence of tumor targets.

Figure 38:
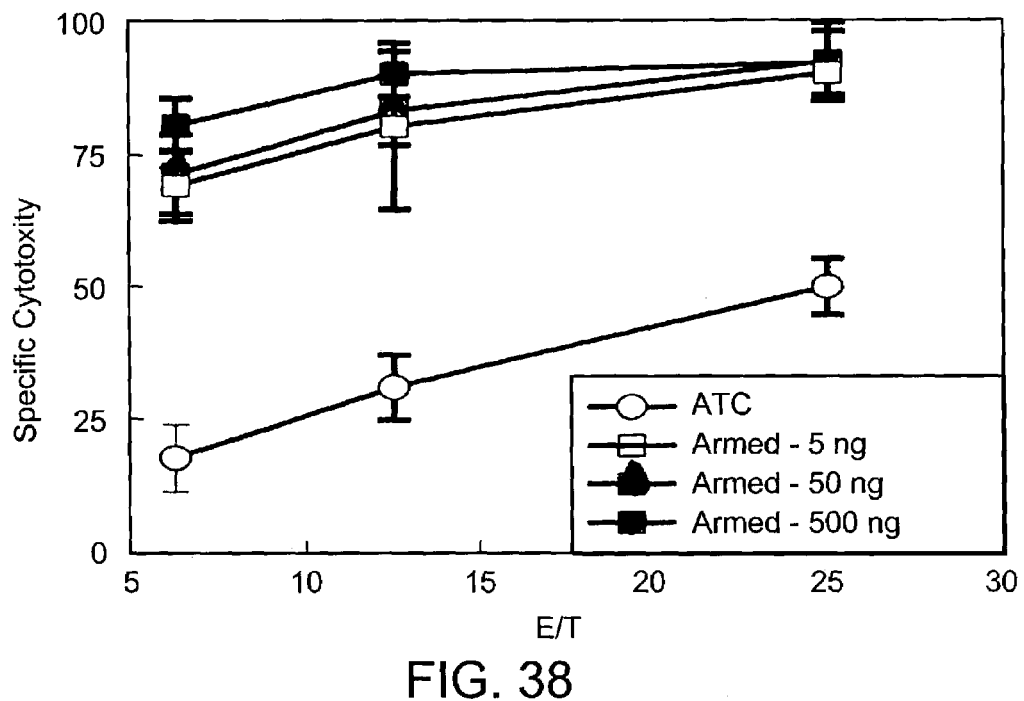
FIG. 38 is a graph showing Percent specific cytotoxicity toward PC-3 tumor targets is elevated through the arming of activated T-cells with BiAb. Cytotoxicity is measured here with three E/T ratios of 6.25, 12.5, and 25:1. The % standard error of the mean (SEM) is depicted with error bars at each E/T ratio. Unarmed ATC (●) kill less than half of all tumor targets at the highest E/T, while ATC armed with 5 ng (□), 50 ng (▲), and 500 ng (■) are capable of almost 100% tumor cell lysis at a 25:1 E/T.

BiAb doses between 5 and 500 ng per $10^6$ ATC can double to triple the % specific cytotoxicity observed with unarmed T-cells (FIG. 38). BiAb doses of 5 to 500 ng are optimal to redirect cytotoxicity of all ATC, since smaller doses of BiAb result in reduced levels of killing and addition of more BiAb does not increase tumor cell lysis. Arming with BiAb enhances cytokine and chemokine secretion by activated T-cells.

Figure 39:
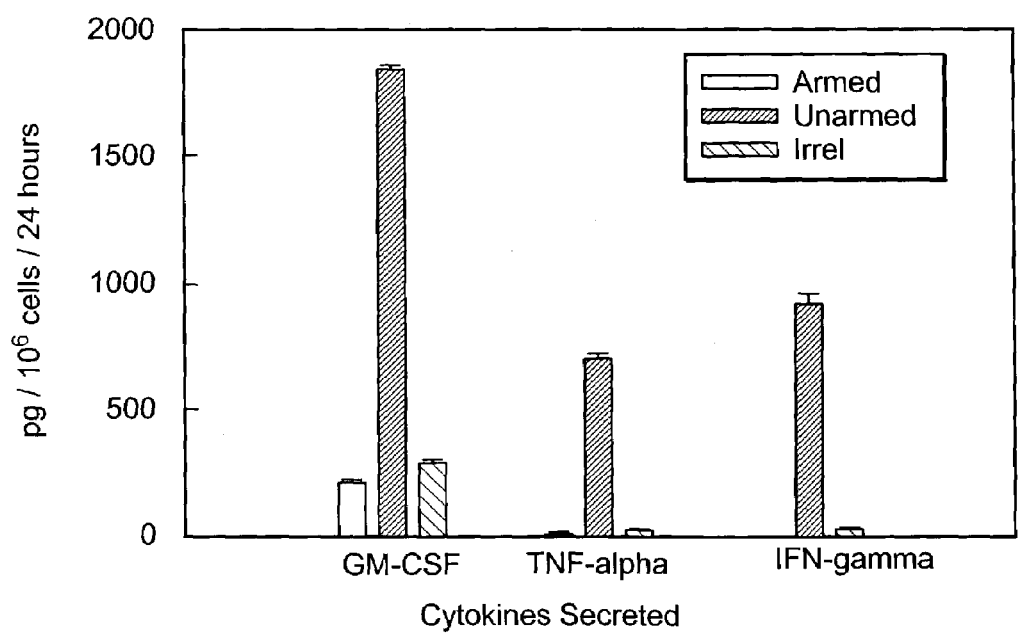
FIG. 39 is a graph showing A comparison of unarmed ( ), armed (■), and irrelevant BiAb armed ATC reveals that armed ATC exhibit markedly elevated levels of cytokine and chemokine secretion over the controls. Unarmed ATC cytokine secretion of TNF-α and IFN-γ was too minimal for representation in this chart. T-cells and PC-3 targets were plated at a 10:1 E/T ratio and incubated overnight at 37° C.

Since GM-CSF, TNF-α and IFN-γ are known to produce anti-tumor effects (ELISA assays booklets, other reference), cell culture supernatants were measured after overnight incubation at 37° C. at a 10:1 E/T ratio. Armed ATC exhibit a distinct increase in GM-CSF, TNF-α and IFN-γ when compared with irrelevant armed or activated T-cells (FIG. 39). MIP-1α and RANTES chemokines may improve trafficking of armed ATC to tumor sites. For this reason, cell culture supernatants were tested by ELISA to quantify chemokine secretion. Elevated levels of MIP-1α and RANTES chemokine secretion were seen from armed ATC exposed to PC-3 tumor targets. As was comparable with cytokine secretion, irrelevant armed or ATC alone showed much lower levels of chemokine secretion.

Example 34

Figure 40:
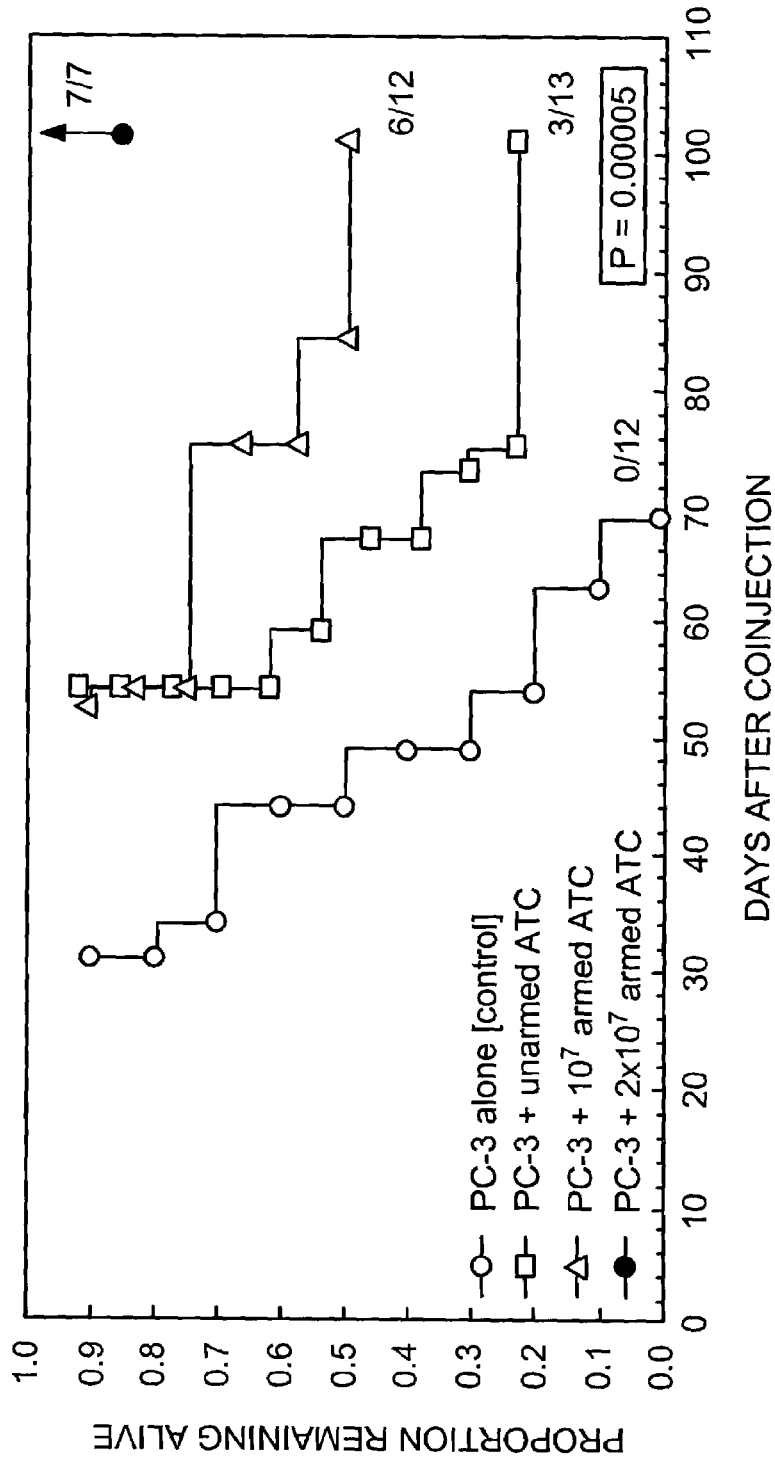
FIG. 40 is a Kaplan-Meier plot showing The tumor-free survival proportion is greatest among mice given the highest dose ($2 \times 10^7$) of armed ATC (orange line). Survival is improved above the rate of the control (O) first in mice receiving the lower dose ($10^7$) of armed ATC (▲), then in mice receiving the same dose ($10^7$) of unarmed ATC (■).

Co-Injection of Armed Activated T-cells and Prostate Cancer Cells can Prevent Tumors in Mice Control mice receiving only PC-3 tumor cells and 10 IU/g IL-2 were all sacrificed due to tumor burden by day 70. Three (n=13) mice receiving only 10 ATC for every PC-3 tumor target (dose of $10^7$ ATC with IL-2) never developed tumor, while a fourth mouse was still alive with reduced tumor burden of 108 mm³ (6×6 mm) by day 105. Co-injecting with 10 armed ATC per target (dose of $10^7$ ATC with IL-2) prevented tumors in 6 of 12 mice. A seventh mouse was still alive by day 105 with reduced tumor burden of 108 mm³ (6×6 mm). The highest dose of armed ATC ($2\times10^7$ ATC with IL-2) co-injected with PC-3 targets was sufficient to completely prevent tumor development in the entire group (n=7), p=0.00005. The Kaplan-Meier survival curves of FIG. 40 represent the proportion of mice, which have no subcutaneous tumor burden after co-injection.

Figure 41:
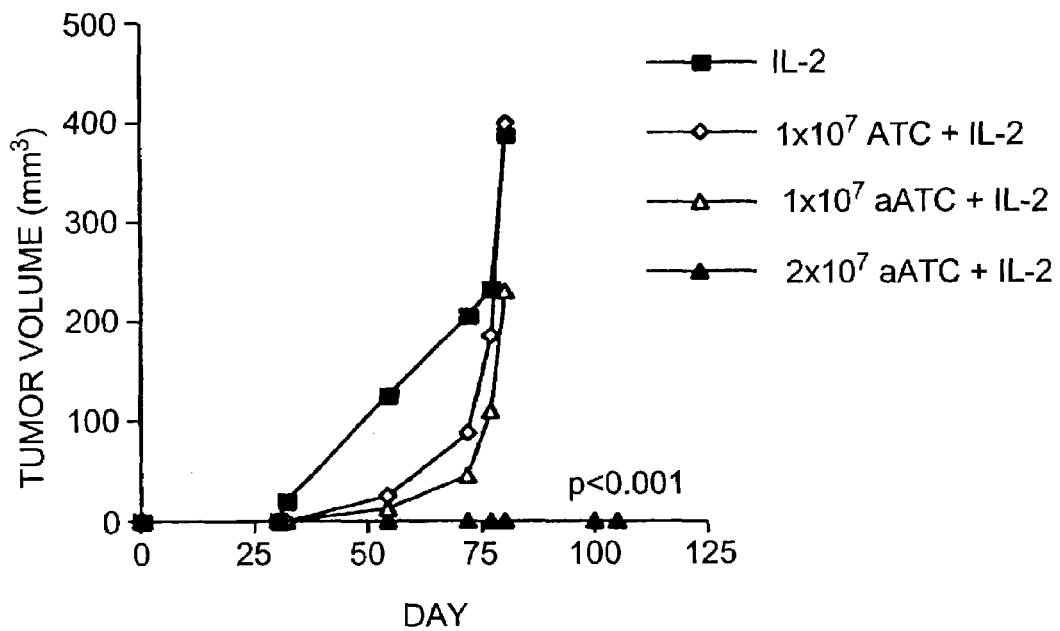
FIG. 41 is a graph showing tumor growth delay curves depicting efficacy of unarmed and armed ATC in preventing PC-3 tumors. The highest dose of armed ATC ($2 \times 10^7$) (▲) is completely effective in delaying tumor growth by day 105, whereas treatment with $10^7$ armed ATC will not prevent but can delay tumor growth (Δ). Although not as effective as the equivalent dose of armed ATC in delaying tumor growth, $10^7$ unarmed ATC (♦) also delayed tumor growth above the rate of the control (■).

FIG. 41 represents the relative efficacy of unarmed and armed ATC in delaying tumor growth among the groups of mice. A high dose of $2\times10^7$ armed ATC can completely prevent tumor growth in all mice by day 105, and is statistically significant when compared with the control (p<0.001). 50% fewer armed or unarmed ATC (107) only delay tumor growth above the rate of the control (p<0.01).

Example 35

Figure 42:
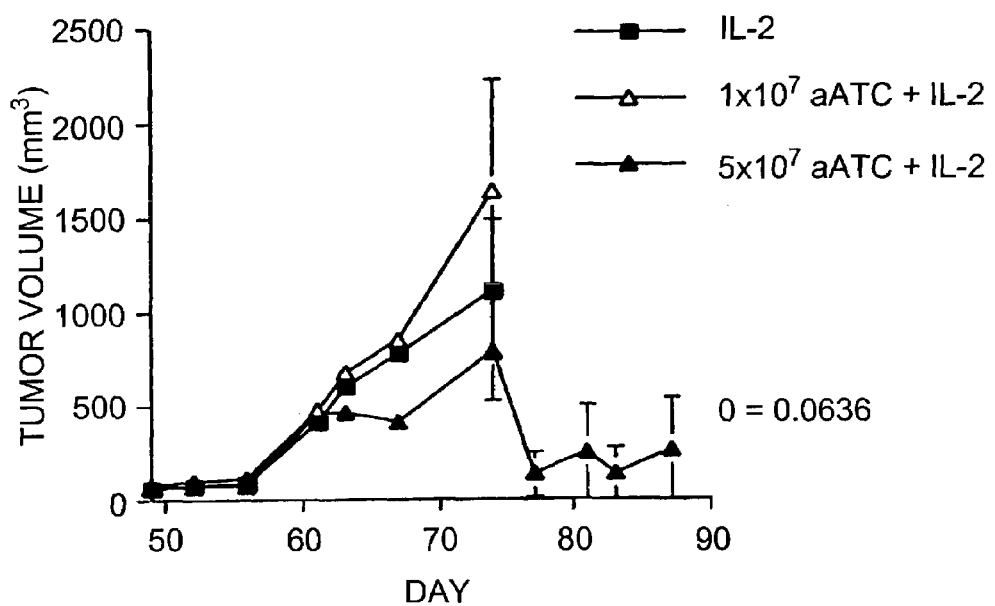
FIG. 42 is a graph showing tumor growth delay. The highest dose ($5 \times 10^7$) of armed ATC plus IL-2 (▲) delays tumor growth out to day 90 when compared with the IL-2 control group (■), p=0.0636. The low dose of $10^7$ aATC (Δ) is not effective in delaying tumor growth when compared with control mice.
Figure 43:
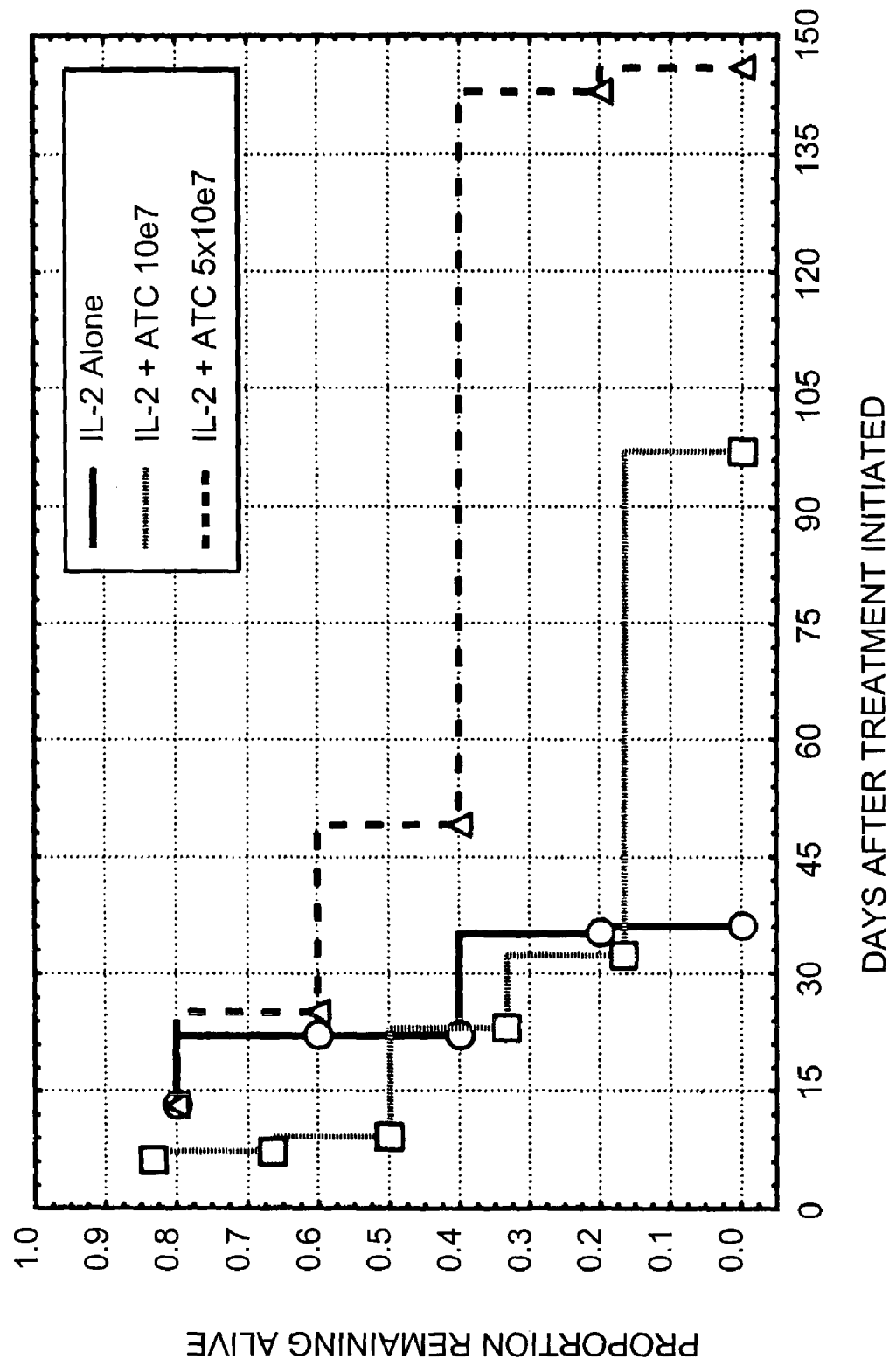
FIG. 43 is a Kaplan-Meier plot showing that sufficient numbers of armed ATC induce long remissions in mice with established tumors. Tumors disappeared after 6 weeks of treatment in 2 of 5 mice (40%) given $5 \times 10^7$ armed ATC plus IL-2, twice per week (Δ). Tumors disappeared in 1 of 6 mice (17%) after 6 weeks of treatment with $10^7$ armed ATC plus IL-2 (□). All control mice (given IL-2 alone) were sacrificed due to tumor burden within six weeks of primary injection with tumor targets (O). Treatment with armed ATC plus IL-2 or IL-2 alone was not initiated until established tumors reached 5×5 mm in dimension.

Treating Established Tumors with Armed Activated T-Cells can Eradicate Tumors in Mice Once subcutaneous hip tumors reached a volume of 62.5 mm³ (5×5 mm), direct tumor injections were initiated. Throughout the injection schedule (twice per week until remission was induced) established tumors in both treatment groups, $10^7$ and $2\times10^7$ aATC plus 10 IU/g IL-2, and control mice, only 10 IU/g IL-2, were observed to continue growing. While all control mice were sacrificed due to tumor volumes of >864 mm³ within six weeks of injection with tumor cells, remissions in both treatment groups were observed. Tumor growth in mice given the low dose treatment of $10^7$ ATC gave similar results as compared to control mice (FIG. 42), with the exception of a single mouse whose tumor volume reached 666 mm³ before gradually decreasing to 224 mm³ and disappearing 4 days later. This mouse was given 6 weeks of treatment only and subsequently maintained tumor remission for 7 weeks without further treatment or IL-2, at which time relapse occurred and the mouse was sacrificed. Treating mice with $5\times10^7$ ATC appeared to improve survival within the first six weeks of treatment, when compared with low dose ATC or IL-2 treatment. In addition, similar remission results were observed in two mice given high dose aATC after 6 weeks of treatment. Two mice with tumor volumes approaching 864 mm³ simply "lost" their tumors within 2-4 days and maintained tumor remission for 12 weeks without further treatment or IL-2. Although these 2 mice relapsed after 12 weeks and survival curves were not statistically significant (p=0.195), the animals were sacrificed for engraftment analyses by flow cytometry.

Tumor growth delay analysis revealed only the highest dose of armed ATC was effective when compared with the control, although the data were not statistically significant (p=0.0636).

Example 36

Long-Term Human T-Cell Engraftment is Indicated with Tumor Remission

Two female beige/SCID mice receiving no injections of tumor, ATC treatment, or IL-2 were used as negative controls to evaluate human T-cell engraftment in treated female beige/SCID mice. No detectable (<1%) human lymphocytes were observed in the bone marrow, spleen, and peripheral blood of both control mice.

Flow cytometry of the first treated mouse ($5\times10^7$ ATC) revealed approximately 3% CD45RA+ and 1% CD45RO+ human cells in the bone marrow, nearly 5% CD4+ and possible 5% CD3+, CD45RA and RO+ populations in the peripheral blood, and no detectable human cells in the spleen. Results from the second treated mouse (same dose) revealed approximately 2.5% CD4+, 2% CD8+, and up to 2.5% CD45RA and RO+ populations in the bone marrow, approximately 4% of each CD45RA and RO+, up to 3% CD8+, and 5.5% CD3+ populations in the spleen, and no detectable human cells in the peripheral blood.

Example 37

Phenotyping of Armed ATC to Determine Survival and Trafficking.

In order to determine the kinetics of armed ATC after infusions, blood is drawn for phenotyping before the $1^{st}$ infusion and 30 mins, 1 hr, 4 hrs, 8 hrs, 24 hrs, 48 hrs, and 72 hrs (just prior to the 2nd infusion). Based on the kinetics that are observed, additional studies are done to define the decay rate or accumulation of armed ATC during the multiple infusions. After the $1^{st}$ infusion, samples are tested just prior to and 1 hr after each infusion. PE conjugated polyclonal goat anti-mouse IgG2a is used to detect OKT3 monomers or OKT3 dimers or multimers on the surface of ATC. These studies will be coordinated with the $^{111}$Indium labeled trafficking studies.

Clinical Correlates/Analyses.

The number of IFN ELISPOTS from fresh unstimulated PBMC from men before and after infusions of armed ATC at the various time points are compared. The number of IFNγ ELISPOTS at each time point are compared with the pretreatment number of ELISPOTS to look for differences in the precursor frequency. The tests applied will determine whether: 1) baseline IFNγ ELISPOTS responses of men with HRPC without stimulation are different than normal age-matched men; 2) the induction of IFN ELISPOTS responses is different in the same men before and after infusions of armed ATC and how long they remain elevated; 3) the responses are specific or nonspecific to HER2 receptors; 4) the circulating amount of HER2 receptors decreases as a result of a clinical response; and 5) each of the immunologic or serum assays will be collated on a laboratory database and correlated with the clinical response database to look for in vivo/in vitro correlates.

Example 38

Comparison of Immunologic Changes Between Baseline and Each Pre-Determined Time Point After Receiving Armed ATC Treatment.

A total of 28 patients are used to detect a difference of about 0.53 standard deviation in proliferation, in ELISPOTS, or in the amount of cytokine produced between baseline and after armed ATC treatment at each time point. A total of 28 patients provide a two-sided 95% confidence interval for the estimate of the proportion change in particular phenotype within 11% if the true change in this population is 10%. Paired t-test or Wilcoxon signed rank test is used to compare the difference between baseline and after armed ATC treatment in proliferation, ELISPOTS, and the amount of cytokine produced to identify the time point when the change becomes significant. To examine the time effect on these immune responses, data from different study time point (including baseline) is analyzed using mixed model for repeated measurements data.

The number of IFNγ ELISPOTS from fresh unstimulated PBMC from men before and after infusions of armed ATC at the various time points is compared to test if in vivo lysis of tumors by the armed ATC induce memory T cells capable of responding to PC-3 when exposed in vitro to tumor (a recall response) and to look for differences in the precursor frequency. Paired t-test or Wilcoxon signed rank test is used in these comparisons. Similarly, anti-CD3 stimulated cells will be compared before and after immunotherapy. Further comparisons will be made after stimulations with HER2+ and HER2-cell lines. The results from these stimulations will be normalized to the responses of the PBMC from age-matched men as controls. The means, medians and standard deviations are calculated for the number of IFNγ ELISPOTS. Student's t-test are used to examine whether the number of IFNγ ELISPOTS at baseline of men with HRPC without stimulation are different from normal age-matched men. Mean changes in the induction of IFNγ ELISPOTS responses before and after immunotherapy are plotted over time to explore how long they can remain elevated. Mixed model for repeated measurements data is used to examine the time effect on the induction of IFNγ ELISPOTS in this study population. Mixed model for repeated measurements data is used to examine the time effect on the circulating amount of HER2 receptors. Logistic regression model and Cox's proportional hazard regression model is used to evaluate each of the in vivo or in vitro immunological or serum assays (e.g. HAMA) as predictors of clinical responses (complete response/partial response) and progression-free survival, respectively.

Example 39

Multiple Exposure of the Anti-CD3 Activated Polyclonal T Cell Population Induces the Development of HER2/neu Specific T Cell Clones.

The data shown in FIG. 44 show the number of IFN gamma ELISPOTS from ATC (unarmed activated T cells that had been exposed 3 times to SK-BR-3), unarmed ATC that were exposed to a human EBV-driven B cell lines (a B cell line would not express HER2/neu receptors; only the final time), and aATC (armed ATC that were exposed to SK-BR-3 three times and then exposed a fourth time in this assay). The assay was performed on day 20 after arming. No additional arming was performed from the initial arming with 50 ng/million. Without wishing to be bound by theory, subpopulations of armed ATC were primed to HER2/neu and have become memory cells as measured by their ability to respond vigorously to rechallenge to HER2/neu antigen on the SK-BR-3 cells. Furthermore, the results suggest that multiple exposure of the anti-CD3 activated polyclonal T cell population has selected or induced the development of HER2/neu specific T cell clones.

This may be a new method for producing antigen specific clones directed at a specific tumor antigen as well as antigens on the tumor that are yet undefined and unknown. One advantage of this type of immunization is that it would immunize the patient with his/her own antigens without an actual definition. This could happen in vivo as well as in our in vitro model.

A new concept: Since there are no dendritic cells in the culture system, one very real possibility is that activated T cells can act professional antigen presenting cells since they upregulate class II upon activation and may act together with the crosslinked tumor antigen in the presence of cytokine and chemokines producted by the reactivation process to induce antigen specific CTL. Class II upregulation may provide the necessary help from CD4 helper cells in the polyclonal mixed to provide the signals needed to induce antigen-specific CTL. Our next experiments will use dendritic cells and purified activated T cell subsets to address the question.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The following references are herein incorporated in their entirety.

REFERENCES

1. Grimm, E. A., A. Mazumder, H. Z. Zhang, and S. A. Rosenberg. 1982. J. Exp. Med. 155:1823-1841.

2. Grimm, E. A., K. M. Ramsey, A. Mazumder, D. J. Wilson, J. Y. Djeu, and S. A. Rosenberg. 1983. J. Exp. Med. 157:884-897.

3. Hersey, P., G. Bindon, A. Edwards, E. Murray, G. Phillips, and W. H. McCarthy. 1981. Int. J. Cancer 28:685-703.

4. Lotze, M. T., E. A. Grimm, A. Mazumder, J. L. Strausser, and S. A. Rosenberg. 1981. Cancer Res. 41:4420-4425.

5. Lanier, L. L., A. M. Le, J. H. Phillips, N. L. Warner, and G. F. Babcock. 1983. J. Immunol. 131:1789-1796.

6. Hercend, T., J. D. Griffin, A. Bensussan, R. E. Schmidt, M. A. Edson, A. Brennan, C. Murray, J. F. Daley, S. F. Schlossman, and J. Ritz. 1985. J. Clin. Invest. 75:932-943.

7. Lotzova, E. and R. B. Herberman. Immunobiology of natural killer cells. CRC Press, Boca Raton.

8. Lotzova, E. and K. B. McCredie. 1978. Cancer Immunol. Immunother. 4:215.

9. Rosenberg, S. A., M. T. Lotze, L. M. Muul, A. E. Chang, F. P. Avis, S. Leitman, W. M. Linehan, C. N. Robertson, R. E.

Lee, J. T. Rubin, C. A. Seipp, C. G. Simpson, and D. E. White. 1987. N. Engl. J. Med. 316:889-897.

10. Mule, J. J., S. Shu, and S. A. Rosenberg. 1985. J. Immunol. 135:646-652.

11. Mule, J. J., J. Yang, S. Shu, and S. A. Rosenberg. 1986. J. Immunol. 136:3899-3909.

12. Thompson, J. A., D. J. Peace, J. P. Klarnet, D. E. Kern, P. D. Greenberg, and M. A. Cheever. 1986. J. Immunol. 137:3675-3680.

13. Mazumder, A., T. J. Eberlein, E. A. Grimm, D. J. Wilson, A. M. Keenan, R. Aamodt, and S. A. Rosenberg. 1984. Cancer 53:896-905.

14. Rosenberg, S. A., M. T. Lotze, L. M. Muul, S. Leitman, A. E. Chang, S. E. Ettinghausen, Y. L. Matory, J. M. Skibber, E. Shiloni, J. T. Vetto, C. A. Seipp, C. Simpson, and C. M. Reichert. 1985. N. Engl. J. Med. 313:1485-1492.

15. Rosenberg, S. A., M. T. Lotze, J. C. Yang, P. M. Aebersold, W. M. Linehan, C. A. Seipp, and D. E. White. 1989. Ann. Surg. 210:474-485.

16. Aebersold, P., C. Hyatt, S. Johnson, K. Hines, L. Korack, M. Sanders, M. T. Lotze, S. Topalian, J. Yang, and S. A. Rosenberg. 1991. J. Natl. Cancer Inst. 83:932-937.

17. Fisher, R. I., C. A. J. Coltman, J. H. Doroshow, A. A. Rayner, M. J. Hawkins, J. W. Miar, P. Wiernik, J. D. McMannis, G. R. Weiss, K. A. Margolin, B. T. Gemlo, D. F. Hoth, D. R. Parkinson, and E. Paietta. 1988. Ann. Intern. Med. 108:518-523.

18. Thompson, J. A., K. L. Shulman, M. C. Benyunes, C. G. Lindgren, C. Collins, P. H. Lange, W. H. Bush, Jr., L. A. Benz, and A. Fefer. 1992. J. Clin. Oncol. 10:960-968.

19. Rosenberg, S. A., P. Spiess, and R. Lafreniere. 1986. Science 233:1318-1321.

20. Griffith, K. D., E. J. Read, and C. S. Carrasquillo. 1989. J. Natl. Cancer Inst. 81:1709-1717.

21. Taneja, S. S., W. Pierce, R. Figlin, and A. Belldegrun. 1995. Urology 45:911-924.

22. Topalian, S. L., D. Solomon, F. P. Avis, A. E. Chang, D. L. Freerksen, W. M. Linehan, M. T. Lotze, C. N. Robertson, C. A. Seipp, P. Simon, C. G. Simpson, and S. A. Rosenberg. 1988. J. Clin. Oncol. 6:839-853.

23. Rosenberg, S. A., B. S. Packard, P. M. Aebersold, D. Solomon, S. L. Topalian, S. T. Toy, P. Simon, M. T. Lotze, J. C. Yang, C. A. Seipp, C. G. Simpson, C. Carter, S. Bock, D. Schwartzentruber, J. P. Wei, and D. E. White. 1988. N. Engl. J. Med. 319:1676-1680.

24. Rosenberg, S. A., P. Aebersold, K. Cometta, A. Kasid, R. A. Morgan, R. Moen, E. M. Karson, M. T. Lotze, J. C. Yang, S. L. Topalian, M. J. Merino, K. Culver, A. D. Miller, R. M. Blaese, and W. F. Anderson. 1990. N. Engl. J. Med. 323:570-578.

25. Goedegebuure, P. S., L. M. Douville, H. Li, G. C. Richmond, D. D. Schoof, M. Scavone, and T. J. Eberlein. 1995. J. Clin. Oncol. 13:1939-1949.

26. Peace, D. J. and M. A. Cheever. 1989. J. Exp. Med. 169:161-173.

27. Lotze, M. T., Y. L. Matory, S. E. Ettinghausen, A. A. Rayner, S. O. Sharrow, C. A. Seipp, M. C. Custer, and S. A. Rosenberg. 1985. J. Immunol. 135:2865-2875.

28. Higuchi, C. M., J. A. Thompson, F. B. Petersen, C. D. Buckner, and A. Fefer. 1991. Blood 77:2561-2568.

29. Rosenberg, S. A. 1984. J. Biol. Response Mod. 3:501-511.

30. Ikarashi, H., K. Fujita, K. Takakuwa, S. Kodama, A. Tokunaga, T. Takahashi, and K. Tanaka. 1994. Cancer Res. 54:190-196.

31. Ikarashi, H., F. Fujita, S. Kodama, K. Tanaka, A. Tokunaga, and T. Takahashi. 1995. Jpn. J. Cancer Res. 83:1359-1992.

32. 1992. Long-term results of a randomized trial comparing cisplatin with cisplatin and cyclophosphamide with cisplatin, cyclophosphamide, and adriamycin in advanced ovarian cancer. GICOG (Gruppo Interregionale Cooperativo Oncologico Ginecologia), Italy. Gynecol. Oncol. 45:115-117.

33. Yoshizawa, H., A. E. Chang, and S. Shu. 1991. J. Immunol. 147:729-737.

34. Chang, A. E. and S. Shu. 1996. Crit. Rev. Oncol. Hematol. 22:213-228.

35. Chang, A. E., A. Aruga, M. J. Cameron, V. K. Sondak, D. P. Normolle, B. A. Fox, and S. Shu. 1997. J. Clin. Oncol. 15:796-807.

36. Riddell, S. R. and P. D. Greenberg. 1990. J. Immunol. Methods 128:189-201.

37. Melief, C. J. 1993. Semin. Hematol. 30:32-33.

38. Schultze, J. L., S. Michalak, M. J. Seamon, G. Dranoff, K. Jung, J. Daley, J. C. Delgado, J. G. Gribben, and L. M. Nadler. 1997. J. Clin. Invest. 100:2757-2765.

39. Schulz, M., P. Aichele, R. Schneider, T. H. Hansen, R. M. Zinkernagel, and H. Hengartner. 1991. Eur. J. Immunol. 21:1181-1185.

40. Riddell, S. R. and P. D. Greenberg. 1995. Cancer Treat. Res. 76:337-369.

41. Riddell, S. R., K. S. Watanabe, J. M. Goodrich, C. R. Li, M. E. Agha, and P. D. Greenberg. 1992. Science 257:238-241.

42. Gedde-Dahl, T., III, B. Fossum, J. A. Eriksen, E. Thorsby, and G. Gaudernack. 1993. Eur. J. Immunol. 23:754-760.

43. Schlichtholz, B., Y. Legros, d. Gillet, C. Gaillard, M. Marty, D. Lane, F. Calvo, and T. Soussi. 1992. Cancer Res. 52:6380-6384.

44. Houbiers, J. G., H. W. Nijman, S. H. van der Burg, J. W. Drijfhout, P. Kenemans, C. J. van de Velde, A. Brand, F. Momburg, W. M. Kast, and C. J. Melief 1993. Eur. J. Immunol. 23:2072-2077.

45. Noguchi, Y., Y.-T. Chen, and L. J. Old. 1994. Proc. Natl. Acad. Sci. USA 91:3171-3175.

46. Yanuck, M., D. P. Carbone, C. D. Pendleton, T. Tsukui, S. F. Winter, J. D. Minna, and J. A. Berzofsky. 1993. Cancer Res. 53:3257-2361.

47. Nijman, H. W., J. G. Houbiers, S. H. van der Burg, M. P. Vierboom, P. Kenemans, W. M. Kast, and C. J. Melief. 1993. J. Immunother. 14:121-126.

48. Smith, C. A., C. Y. C. Ng, H. E. Heslop, M. S. Holladay, S. Richardson, E. V. Turner, S. K. Loftin, C. Li, and M. K. Brenner. 1995. J. Hematother. 4:73-79.

49. Papadopoulos, E. B., M. Ladanyi, D. Emanuel, S. Mackinnon, F. Boulad, M. H. Carabasi, H. Castro-Malaspina, B. H. Childs, A. P. Gillio, T. N. Small, J. W. Young, N. A. Kernan, and R. J. O'Reilly. 1994. N. Engl. J. Med. 330:1185-1191.

50. Osband, M. E., P. T. Lavin, R. K. Babayan, S. Graham, D. L. Lamm, B. Parker, I. S. Sawczuk, S. Ross, and R. J. Krane. 1990. Lancet 335:994-998.

51. Gold, J. E. and M. E. Osband. 1994. Clin. Immunol. Immunopathol. 71:325-332.

52. Gold, J. E. and M. E. Osband. 1994. Eur. J. Cancer 30A:1871-1882.

53. Lavin, P. T., R. Maar, M. Franklin, S. Ross, J. Martin, and M. E. Osband. 1992. Transplant. Proc. 24:3059-3064.

54. Van Wauwe, J. P., J. R. De Mey, and J. G. Gooseens. 1980. J. Immunol. 124:2708-2713.

55. Meuer, S. C., J. C. Hodgdon, R. E. Hussey, J. P. Protentis, S. F. Schlossman, and E. L. Reinherz. 1983. J. Exp. Med. 158:988-993.

56. Meuer, S. C., R. E. Hussey, D. A. Cantrell, J. C. Hodgdon, S. F. Schlossman, K. A. Smith, and E. L. Reinherz. 1984. Proc. Natl. Acad. Sci. USA 81:1509-1513.

57. Weiss, A. and J. B. Imboden. 1987. Adv. Immunol. 41:1-38.

58. Loeffler, C. M., J. L. Platt, P. M. Anderson, E. Katsanis, J. B. Ochoa, W. J. Urba, D. L. Longo, A. S. Leonard, and A. C. Ochoa. 1991. Cancer Res. 51:2127-2132.

59. Murphy, W. J., K. C. Conlon, T. J. Sayers, R. H. Wiltrout, T. C. Back, J. R. Ortaldo, and D. L. Longo. 1993. J. Immunol. 150:3634-3642.

60. Yun, Y. S., M. E. Hargrove, and C. Ting. 1989. Cancer Res. 49:4770-4774.

61. Katsanis, E., Z. Xu, P. M. Anderson, B. B. Dancisak, M. A. Bausero, D. J. Weisdorf, B. R. Blazar, and A. C. Ochoa. 1994. Bone Marrow Transplant. 14:563-572.

62. Ochoa, A. C., G. Gromo, B. J. Alter, P. M. Sondel, and F. H. Bach. 1987. J. Immunol. 138:2728-2733.

63. Anderson, P. M., F. H. Bach, and A. C. Ochoa. 1988. Cancer Immunol. Immunother. 27:82-88.

64. Chen, B. P., M. Malkovsky, J. A. Hank, and P. M. Sondel. 1987. Cell Immunol. 110:282-293.

65. Lotzova, E., C. A. Savary, R. B. Herberman, K. B. McCredie, M. J. Keating, and E. J. Freireich. 1987. Nat. Immun. Cell Growth Regul. 6:219-223.

66. Yang, S. C., K. D. Fry, E. A. Grimm, and J. A. Roth. 1990. Arch. Surg. 125:220-225.

67. Ueda, M., I. D. Joshi, M. Dan, J. P. Uberti, T.-H. Chou, L. L. Sensenbrenner, and L. G. Lum. 1993. Transplantation 56:351-356.

68. Uberti, J. P., I. Joshi, M. Ueda, F. Martilotti, L. L. Sensenbrenner, and L. G. Lum. 1994. Clin. Immunol. Immunopathol. 70:234-240.

69. Anderson, P. M., B. R. Blazar, F. H. Bach, and A. C. Ochoa. 1989. J. Immunol. 142:1383-1394.

70. Anderson, P. M., A. C. Ochoa, N. K. C. Ramsay, D. Hasz, and D. Weisdorf. 1992. Blood 80:1846-8153.

71. Ting, C. -C., M. E. Hargrove, and Y. S. Yun. 1988. J. Immunol. 141:741-748.

72. Ochoa, A. C., D. E. Hasz, R. Rezonzew, P. M. Anderson, and F. H. Bach. 1989. Cancer Res. 49:963-968.

73. Sosman, J. A., K. R. Oettel, J. A. Hank, P. Fisch, and P. M. Sondel. 1989. Transplantation 48:486.

74. Sosman, J. A., Oettel, K. R., Hank, J. A., and Sondel, P. M. FASEB Journal 3(Pt 1), A506. 1989. Ref Type: Abstract 75. Massaia, M., C. Attisano, S. Peola, L. Montacchini, P. Omede, P. Corradini, D. Ferrero, M. Boccadoro, A. Bianchi, and A. Pileri. 1993. Blood 82:1787-1797.

76. Curti, B. C., D. L. Longo, A. C. Ochoa, K. C. Conlon, J. W. Smith, II, W. G. Alvord, S. P. Creekmore, R. G. Fenton, B. L. Gause, J. Holmlund, J. E. Janik, J. Ochoa, P. A. Rice, W. H. Sharfinan, M. Sznol, and W. J. Urba. 1993. J. Clin. Oncol. 11:652-660.

77. Saxton, M. L., D. L. Longo, H. E. Wetzel, H. Tribble, W. G. Alvord, L. W. Kwak, A. S. Leonard, C. D. Ullmann, B. D. Curti, and A. C. Ochoa. 1997. Blood 89:2529-2536.

78. Curti, B. D., A. C. Ochoa, G. C. Powers, W. C. Kopp, W. G. Alvord, J. E. Janik, B. L. Gause, B. Dunn, M. S. Kopreski, R. Fenton, A. Zea, C. Dansky-Ullmann, S. Strobl, L. Harvey, E. Nelson, M. Sznol, and D. L. Longo. 1998. J. Clin. Oncol. 16:2752-2760.

79. June, C. H., J. A. Ledbetter, P. S. Linsley, and C. B. Thompson. 1990. Immunol. Today 11:211-216.

80. Costello, R., C. Cerdan, C. Pavon, H. Brailly, C. Hurpin, C. Mawas, and D. Olive. 1993. Eur. J. Immunol. 23:608-613.

81. June, C. H., J. A. Bluestone, L. M. Nadler, and C. B. Thompson. 1994. Immunol. Today 15:321-331.

82. Jenkins, M. K. and J. G. Johnson. 1993. Curr. Opin. Immunol. 5:361-367.

83. Schwartz, R. H. 1992. Cell 71:1065-1068.

84. Thompson, C. B., T. Lindsten, J. A. Ledbetter, S. L. Kunkel, H. A. Young, S. G. Emerson, J. M. Leiden, and C. H. June. 1989. Proc. Natl. Acad. Sci. USA 86:1333-1337.

85. Rosenberg, E. S., J. M. Billingsley, A. M. Caliendo, S. L. Boswell, P. E. Sax, S. A. Kalams, and B. D. Walker. 1997. Science 278:1447-1450.

86. Garlie, N. K., A. V. LeFever, R. E. Siebenlist, B. L. Levine, C. H. June, and L. G. Lum. 1999. J. Immunother. 4:335-345.

87. Levine, B. L., Y. Ueda, N. Craighead, M. L. Huang, and C. H. June. 1995. Int. Immunol. 7:891-904.

88. Boise, L. H., A. J. Minn, M. A. Accavitti, C. H. June, T. Lindsten, and C. B. Thompson. 1995. Immunity 3:87-98.

89. Boise, L. H., P. J. Noel, and C. B. Thompson. 1995. Curr. Opin. Immunol. 7:620-625.

90. Harada, M., T. Okamoto, K. Omoto, K. Tamada, M. Takenoyama, C. Hirashima, O. Ito, G. Kimura, and K. Nomoto. 1996. Immunology 87:447-453.

91. Shibuya, T. H., Wei, W. Z., Johnson, R. D., Zormeier, M., Meleca, R. H., Mathog, R. H., June, C. H., and Lum, L. G. Anti-CD3/CD28 bead costimulation overcomes regional immunosuppression in HNSCC (head and neck squamous cell carcinoma) patients. ARO Abstracts (Assn for Reseach in Otolaryngology], #659. 1998. Ref Type: Abstract 92. Cayota, A., F. Vuillier, J. Siciliano, and G. Dighiero. 1994. Int. Immunol. 6:611-621.

93. Harding, F. A., J. G. McArthur, J. A. Gross, D. H. Raulet, and J. P. Allison. 1992. Nature 356:607-609.

94. Guinan, E. C., J. G. Gribben, V. A. Boussiotis, G. J. Freeman, and L. M. Nadler. 1994. Blood 84:3261-3282.

95. Lum, L. G., LeFever, A. V., Treisman, J. S., Hanson, J. P., Jr., Garlie, N. K., Kistler, A. M., Yuille, D. L., Levine, B. L., and June, C. H. Phase I study of anti-CD3/anti-CD23 coactivated T cells (COACTS) in cancer patients: enhanced TH1 responses in vivo. Experimental Hematology 26, 772. 1998. Ref Type: Abstract 96. Renner, C. and M. Pfreundschuh. 1995. Immunol. Rev. 145:179-209.

97. Raso, V. and T. Griffin. 1981. Cancer Res. 41:2073-2078.

98. Titus, J. A., P. Perez, A. Kaubisch, M. A. Garrido, and D. M. Segal. 1987. J. Immunol. 139:3153-3158.

99. Perez, P., J. A. Titus, M. T. Lotze, F. Cuttitta, D. L. Longo, E. S. Groves, H. Rabin, P. J. Durda, and D. M. Segal. 1986. J. Immunol. 137:2069-2072.

100. Segal, D. M., M. A. Garrido, P. Perez, J. A. Titus, D. A. Winkler, D. B. Ring, A. Kaubisch, and J. R. Wunderlich. 1988. Mol. Immunol. 25:1099-1103.

101. Bonino, L. D., L. B. De Monte, G. C. Sapnoli, R. Vola, M. Mariani, D. Barone, A. M. Moro, P. Riva, M. R. Niotra, P. G. Natali, and F. Malavasi. 1995. Int. J. Cancer 61:509-515.

102. Kaneko, T., Y. Fusauchi, Y. Kakui, M. Masuda, M. Akahoshi, M. Termura, T. Motoji, K. Okumura, H. Mizoguchi, and K. Oshimi. 1993. Blood 81:1333-1341.

103. Katayose, Y., T. Kudo, M. Suzuki, M. Shinoda, S. Saijyo, N. Sakurai, H. Saeki, K. Fukuhara, K. Imai, and S. Matsuno. 1996. Cancer Res. 56:4205-4212.

104. Mack, M., R. Gruber, S. Schmidt, G. Riethmüller, and P. Kufer. 1997. J. Immunol. 158:3965-3970.

105. Lamers, C. H. J., R. J. van de Griend, E. Braakman, C. P. M. Ronteltap, J. Bénard, and G. Stoter. 1992. Int. J. Cancer 51:973-979.

106. Canevari, S., D. Mezzanzanica, A. Mazzoni, D. R. M. Negri, V. Ramakrishna, R. L. H. Bohuis, M. I. Colnaghi, and G. Bolis. 1995. J. Hematother. 4:423-427.

107. Canevari, S., G. Stoter, F. Arienti, G. Bolis, M. I. Colnaghi, E. M. Di Re, A. M. M. Eggermont, S. H. Goey, J. W. Gratama, C. H. J. Lamers, M. A. Nooy, G. Parmiani, F. Raspagliesi, F. Ravagnani, G. Scarfone, J. B. Trimbos, S. O. Wamaar, and R. L. H. Bolhuis. 1995. J. Natl. Cancer Inst. 87:1463-1469.

108. Bolhuis, R. L. H., C. H. J. Lamers, S. H. Goey, A. M. M. Eggermont, J. B. M. Z. Trimbos, G. Stoter, A. Lanzavecchia, E. di Re, S. Mioth, F. Raspagliesi, L. Rivoltini, and M. I. Colnaghi. 1992. Int. J. Cancer 78-81.

109. Haas, C., G. Strauss, G. Moldenhauer, R. M. Iorio, and V. Schirrmacher. 1998. Clin. Cancer Res. 4:721-730.

110. Zhu, Z., T. Ghose, S. H. Lee, L. A. Fernandez, L. A. Kerr, J. H. Donohue, and D. J. McKean. 1994. Cancer Lett. 86:127-134.

111. Van Dijk, J., S. 0. Warnaar, J. D. van Eendenburg, M. Thienpont, E. Braakman, J. H. Boot, G. J. Fleuren, and R. L. Bolhuis. 1989. Int. J. Cancer 43:344-349.

112. Tahara, H. and M. T. Lotze. 1995. Gene Ther. 2:96-106.
113. Kroesen, B. J., A. ter Haar, P. Willemse, D. T. Sleijfer, E. G. E. de Vries, N. H. Mulder, H. H. Berendsen, P. C. Limburg, H. T. The, and L. de Leij. 1993. Cancer Immunol. Immunother. 37:401-407.

114. Demanet, C., J. Brissinck, J. De Jong, and K. Thielemans. 1996. Blood 87:4390-4398.

115. Bohlen, H., T. Hopff, O. Manzke, A. Engert, D. Kube, P. D. Wickramanayake, V. Diehl, and H. Tesch. 1993. Blood 82:1803-1812.

116. Bohlen, H., O. Manzke, B. Patel, G. Moldenhauer, B. Dörken, V. von Fliedner, V. Diehl, and H. Tesch. 1993. Cancer Res. 43:4310-4314.

117. Anderson, P. M., W. Crist, D. Hasz, A. J. Carroll, D. E. Myers, and F. M. Uckun. 1992. Blood 80:2826-2834.

118. Bejeck, B. E., D. Wang, E. Berven, C. A. Pennell, S. C. Peiper, S. Poppema, F. M. Uckun, and J. H. Kersey. 1995. Cancer Res. 55:2346-2351.

119. de Gast, G. C., I. -A. Haagen, A. A. van Houten, S. C. Klein, A. J. Duits, R. A. de Weger, T. M. Vroom, M. R. Clark, J. Phillips, A. J. G. van Dijk, W. B. M. de Lau, and B. J. E. G. Bast. 1995. Cancer Immunol. Immunother. 40:390-396.

120. Klein, S. C., L. H. Boer, R. A. de Weger, G. C. de Gast, and E. J. E. G. Bast. 1997. Scand. J. Immunol. 46:452-458.

121. Chapoval, A. I., H. Nelson, and C. Thibault. 1995. J. Immunol. 155:1296-1303.

122. Kuwahara, M., M. Kuroki, F. Arakawa, T. Senba, Y. Matsuoka, T. Hideshima, Y. Yamashita, and H. Kanda. 1997. Anticancer Res. 16:2661-2668.

123. Brossart, P., G. Stuhler, T. Flad, S. Stevanovic, H. -G. Rammensee, L. Kanz, and W. Brugger. 1998. Cancer Res. 58:732-736.

124. Renner, C., W. Jung, U. Sahin, R. Denfeld, C. Pohl, L. Trümper, F. Hartmann, V. Diehl, R. van Lier, and M. Pfreundschuh. 1994. Science 264:833-835.

125. Renner, C., S. Bauer, U. Sahin, W. Jung, R. van Lier, G. Jacobs, G. Held, and M. Pfreundschuh. 1996. Blood 87:2930-2937.

126. Pohl, C., R. Denfeld, C. Renner, W. Jung, H. Bohlen, U. Sahin, A. Hombach, R. van Lier, M. Schwonzen, V. Diehl, and M. Pfreundschuh. 1993. Int. J. Cancer 54:820-827.

127. Hayden, M. S., P. S. Linsley, M. A. Gayle, J. Bajorath, W. A. Brady, N. A. Norris, H. P. Fell, J. A. Ledbetter, and L. K. Gilliland. 1994. Therapeut. Immunol. 1:3-15.

128. Alvarez-Vallina, L. and R. E. Hawkins. 1996. Eur. J. Immunol. 26:2304-2309.

129. Renner, C., W. Jung, U. Sahin, R. van Lier, and M. Pfreundschuh. 1995. Eur. J. Immunol. 25:2027-2033.

130. Mazzoni, A., D. Mezzanzanica, G. Jung, H. Wolf, M. I. Colnaghi, and S. Canevari. 1996. Cancer Res. 56:5443-5449.

131. Hombach, A., T. Tillmann, M. Jensen, C. Heuser, R. Sircar, V. Diehl, W. Kruis, and C. Pohl. 1997. Clin. Exp. Immunol. 108:352-357.

132. Hayden, M. S., L. S. Grosmaire, N. A. Norris, L. K. Gilliland, G. Winberg, D. Tritschler, T. T. Tsu, P. S. Linsley, R. S. Mittler, P. D. Senter, H. P. Fell, and J. A. Ledbetter. 1996. Tissue Antigens 48:242-254.

133. Michon, J., S. Moutel, J. Barbet, J. -L. Romet-Lemonne, Y. M. Deo, W. H. Fridman, and J.-L. Teillaud. 1995. Blood 86:1124-1130.

134. Weiner, L. M., J. I. Clark, M. Davey, W. S. Li, I. G. de Palazzo, D. B. Ring, and R. K. Alpaugh. 1995. Cancer Res. 55:4586-4593.

135. Valone, F. H., P. A. Kaufman, P. M. Guyre, L. D. Lewis, V. Memoli, Y. Deo, R. Graziano, J. L. Fisher, L. Meyer, and M. Mrozek-Orlowski. 1995. J. Clin. Oncol. 13:2281-2292.

136. James, N., P. Atherton, A. Koletsky, N. Tchekmedyian, and R. Curnow. 1998. Proc. Am. Soc. Clin. Oncol. 17:436a.

137. Shalaby, M. R., H. M. Shepard, L. Presta, M. L. Rodrigues, P. C. L. Beverley, M. Feldmann, and P. Carter. 1992. J. Exp. Med. 175:217-225.

138. Zhu, Z., G. D. Lewis, and P. Carter. 1995. Int. J. Cancer 62:319-324.

139. Nakamura, Y., Y. Tokuda, M. Iwasawa, H. Tsukamoto, M. Kidokoro, N. Kobayashi, S. Kato, T. Mitomi, S. Habu, and T. Nishimura. 1992. [Comment in: Br. J. Cancer 1993; 67:865-7]. Br. J. Cancer 66:20-26.

140. Dawson, N, Moul, J., and Higano, C. Hormone-refractory prostate cancer: Current issues and treatment options. 1-8. 1999. Physicians & Scientists Publishing Co., Inc. Ref Type: Pamphlet 141. Waselenko, J. K. and N. A. Dawson. 1997. Oncology 11:1551-1567.

142. Watanabe, M., T. Nakada, and H. Yuta. 1999. Int. Urol. Nephrol. 31:61-73.

143. Schwartz, S. Jr., Caceres, C., Morote, J., de Torres, I., Rodriguez-Vallejo, J. M., Gonzalez, J., and Reventos, J. Int. J. Oncol. 14(2), 367-371. 1999. Ref Type: Journal (Full)

144. Morote, J., I. de Torres, C. Caceres, C. Vallejo, S. Jr. Schwartz, and J. Reventos. 1999. Int. J. Cancer 84:421-425.

145. Ullrich, A. and J. Schlessinger. 1990. Cell 61:203-212.

146. Disis, M. L. and M. A. Cheever. 1997. Adv. Cancer Res. 71:343-371.

147. Mark, D. F., L. Feldman, S. Das, H. Kye, S. Mark, C. L. Sun, and M. Samy. 1999. Exp. Mol. Pathol 66:170-178.

148. Bubendorf, L., J. Kononen, P. Koivisto, P. Schraml, H. Moch, T. C. Gasser, N. Willi, G. Sauter, and O. P. Kallioniemi. 1999. Cancer Res. 59:803-806.

149. Eshhar, Z., T. Waks, G. Gross, and D. G. Schindler. 1993. Proc. Natl. Acad. Sci. USA 90:720-724.

150. Hwu, P., G. E. Shafer, J. S. Treisman, D. G. Schindler, G. Gross, R. Cowherd, S. A. Rosenberg, and Z. Eshhar. 1993. J. Exp. Med. 178:361-366.

151. Hwu, P., J. C. Yang, R. Cowherd, J. S. Treisman, G. E. Shafer, Z. Eshhar, and S. A. Rosenberg. 1995. Cancer Res. 55:3369-3373.

152. Eshhar, Z., N. Bach, C. J. Fitzer-Attas, G. Gross, J. Lustgarten, T. Waks, and D. G. Schindler. 1996. Springer Semin. Immunopathol. 18:199-209.

153. Altenschmidt, U., D. Moritz, and B. Groner. 1997. J. Mol. Med. 75:259-266.

154. Fitzer-Attas, C. J. and Z. Eshhar. 1998. Adv. Drug Delivery Rev. 31:171-182.

155. Plavec, I., M. Agarwal, K. E. Ho, M. Pineda, J. Auten, J. Baker, H. Matsuzaki, S. Escaich, M. Bonyhadi, and E. Bohnlein. 1997. Gene Ther. 4:128-139.

156. Quinn, E. R., L. G. Lum, and K. T. Trevor. 1998. Hum. Gene Ther. 9:1457-1467.

157. Trevor, K. T., E. R. Quinn, M. Sen, D. Wankowski, K. Knox, and L. G. Lum. 2000. Bispecific antibody reactivation of gene-transduced T cells: Implications for cancer immunotherapy and gene therapy. Tumor Targeting (In press).

158. Stockmeyer, B., T. Valerius, R. Repp, I. A. F. M. Heijnen, H.-J. Bühring, Y. M. Deo, J. R. Kalden, M. Gramatzki, and J. G. J. van de Winkel. 1997. Cancer Res. 57:696-701.

159. Baselga, J., L. Norton, J. Albanell, Y. M. Kim, and J. Mendelsohn. 1998. Cancer Res. 58:2825-2831.

160. Jones, R. J., G. B. Vogelsang, A. D. Hess, E. R. Farmer, R. B. Mann, R. B. Geller, S. Piantadosi, and G. W. Santos. 1989. Lancet 1:754-757.

161. Baselga, J., D. Tripathy, J. Mendelsohn, S. A. Baughman, C. C. Benz, L. Dantis, N. T. Sklarin, A. D. Seidman, C. A. Hudis, J. Moore, P. P. Rosen, T. Twaddell, I. C. Henderson, and L. Norton. 1996. J. Clin. Oncol. 14:737-744.

162. Lum, L. G., Treisman, J. S., Taylor, R. F., and LeFever, A. V. Phase I/II trial of activated T cells (ATC), IL-2, and GM-CSF after PBSC transplant for stage IIIb or IV breast cancer. Blood 90(Suppl), 381b. 1997. Ref Type: Abstract 163. Thakur, M. L., R. E. Coleman, and M. J. Welch. 1977. J. Lab. Clin. Med. 89:217-228.

164. Beightol, R. W. and W. J. Baker. 1980. Am. J. Hosp. Pharm. 37:847-850.

What is claimed is:

1. A method for treatment of a patient suffering from cancer, said method comprising the steps of:
    (a) isolating a sample of blood mononuclear cells, comprising T cells;
    (b) activating one or more of said T cells by ex vivo stimulation with soluble anti-CD3 monoclonal antibody, and growth of said activated T cells in the presence of between 100 IU/ml to 500 IU/ml of IL-2;
    (c) arming of said activated T cells with bispecific antibodies capable of binding to a T cell receptor complex of a T cell, and to tumor-associated antigens on a tumor cell, under conditions wherein;
        (i) said bispecific antibody binds to said T cells and tumor cells, and/or Fc-receptor positive cells and tumor cells,
        (ii) said bispecific antibody binds to the tumor target and said antibody binding to the tumor target activates said T cells,
        (iii) said bispecific antibody redirects said T cells and/or Fc-receptor positive cells to said tumor cells,
        (iv) said activated and armed T cells destroy said tumor cells; and,
    (d) reinfusing a composition of cells comprising said activated T cell armed with said bispecific antibody into the patient as treatment for the patient, and either:
        (i) contacting T cells specific for different epitopes on the tumor cell, with the composition of cells and inducing proliferation of the T cells specific for different epitopes on the tumor cell, or
        (ii) targeting and contacting multiple target cells with the armed T cell to which the bispecific antibody remains bound and killing said multiple target cells.

2. The method of claim 1, wherein said method further comprises co-infusing intravenously or co-injecting into a tumor arterial supply or tumor site a composition of dendritic cells, and said activated T cells armed with bispecific antibody;
    wherein said dendritic cells and said activated T cells are autologous to the patient, and
    said dendritic cells are cultured in IL-4 and GM-CSF for at least about 7 days, with or without TNFα for at least about an additional 2 days.

3. The method of claim 2, wherein a composition of autologous cells comprising said activated T cells armed with said bispecific antibody with or without IL-2, IL-12, GM-CSF or other immune augmenting cytokines are reinfused into a patient in need of such therapy.

4. The method of claim 1, further comprising co-infusing intravenously or co-injecting into a tumor arterial supply or tumor site a composition of dendritic cells, and said activated T cells armed with bispecific antibody;
    wherein said dendritic cells and activated T cells armed with bispecific antibody are derived from an allogeneic donor and wherein a composition of allogeneic cells comprising said activated T cells armed with said bispecific antibody with or without IL-2, IL-12, GM-CSF or other immune augmenting cytokines are reinfused into the patient in need of such therapy.

5. The method according to any one of claim 1, 2, 3, or 4, wherein the bispecific antibody is comprised of two monoclonal antibodies.

6. The method according to any one of claim 1, 2, 3, or 4, wherein each of the specificities of said bispecific antibody are directed to a tumor antigen and the T cell receptor complex.

7. The method according to any one of claim 1, 2, 3, or 4, wherein the monoclonal antibodies are chemically heteroconjugated to form the bispecific antibody.

8. The method according to any one of claim 1, 2, 3, or 4, wherein the bispecific antibody is comprised of monoclonal antibodies directed to any tumor associated antigen.

9. The method according to any one of claim 1, 2, 3, or 4, wherein the anti T cell receptor monoclonal antibody component of said bispecific antibody is directed against CD3 of the T cell receptor complex.

10. The method according to any one of claim 1, 2, 3, or 4, wherein the patient is immunosuppressed.

11. The method according to any one of claim 1, 2, 3, or 4, wherein the patient is susceptible to, or suffering from diseases associated with abnormal cellular proliferation or growth.

12. The method of any one of claim 1, 2, 3, or 4, wherein said method further comprises freezing and thawing the armed T cell prior to reinfusing the armed T cell into the patient in need of such therapy.

13. The method of any one of claim 1, 2, 3, or 4, wherein the T cell is armed with a bispecific antibody dose of about 0.5 ng per million T cells to about 500 ng per million T cells.

14. The method of claim 13, wherein the arming dose is optimized for each individual patient by titrating a thawed aliquot of the activated T cells to achieve a percent specific cytotoxicity level at an effector to target ratio from about 25:1 to at least about 30% against the tumor target.

15. The method of claim 14, wherein the infusing dose is at least about 2 billion armed T cells.

16. The method of claim 14, wherein the patient receives at least about four infusions.

17. The method of claim 1, wherein the T cell is a CD3/CD8 positive cell.

18. The method of claim 1, wherein the T cell is a CD3/CD4 positive cell.

19. The method of any one of claim 1, 2, 3, or 4, wherein the armed T cell is co-administered with other forms of therapy and/or immunocompetent naïve T cells, and immunocompetent naïve B cells.

20. A method of treatment of a patient suffering from cancer, said method comprising the steps of:
   (a) isolating a sample of peripheral blood mononuclear cells, comprising T cells;
   (b) co-activating of one or more of said T cells by ex vivo stimulation with anti-CD3 and anti-CD28 monoclonal antibodies, soluble or immobilized on a solid support, and growth of said activated T cells in the presence of about 100 IU/ml to about 500 IU/ml of IL-2;
   (c) arming of said co-activated T cells with bispecific antibodies capable of binding to a T cell receptor complex of a T cell, to tumor-associated antigens on a tumor cell, and to Fc-receptors of accessory cells via the Fc part of the antibody, under conditions that allow,
      (i) binding of said bispecific antibody to said T cells, tumor cells, and Fc-receptor cells recruited to the site targeted by said armed T cell,
      (ii) co-activation of said T cells by said antibody binding,
      (iii) binding of said Fc-receptor positive cells to the Fc-region of said bispecific antibody, and;
   (d) reinfusing a composition of cells comprising said activated T cell armed with a bispecific antibody, immunocompetent naïve T cells, and immunocompetent naïve B cells, into the patient as treatment of the patient, wherein:
      (i). the composition of cells induce the proliferation of T cells specific for different epitopes on the tumor cell, or
      (ii) the bispecific antibody remains bound to the armed T cell allowing the armed T cell to target and kill multiple tumor cells.

21. The method of claim 20, further comprising co-infusing intravenously or co-injecting into a tumor arterial supply or tumor site a composition of dendritic cells, and said activated T cells armed with bispecific antibody; wherein, said dendritic cells and said activated T cells are autologous to the patient, and
   wherein said dendritic cells are cultured in IL-4 and GM-CSF for at least about 7 days, with or without TNFα for at least about an additional 2 days.

22. The method of claim 20, further comprising co-infusing intravenously or co-injecting into a tumor arterial supply or tumor site a composition of dendritic cells, and said activated T cells armed with bispecific antibody;
   wherein said dendritic cells and activated T cells armed with bispecific antibody are derived from an allogeneic donor and
   wherein said dendritic cells are cultured in IL-4 and GM-CSF for at least about 7 days, with or without TNF for at least about an additional 2 days.

23. The method of claim 21, wherein a composition of autologous cells comprising said activated T cells armed with a bispecific antibody are reinfused into a patient in need of such therapy in the presence or absence of IL-2, IL-12, GM-CSF or other immune augmenting cytokines and chemokines.

24. The method of claim 22, wherein a composition of allogeneic cells comprising said activated T cells armed with a bispecific antibody are reinfused into a patient in need of such therapy in the presence or absence of IL-2, GM-CSF or other immune augmenting cytokines.

25. The method of claim 21 or 22, wherein the T cells are coactivated by monoclonal antibodies directed against the CD3 and CD 28 immobilized on beads or any other solid support.

26. The method according to any one of claim 1, 2, 3, 4, or 21, or 22, wherein the cellular composition reinfused into patients is free of soluble bispecific antibody.

27. The method of claim 21 or claim 22, wherein said co-activated T cell is armed with a bispecific antibody dose of about 0.5 ng per million T cells to about 100 ng per million T cells.

28. The method of claim 27, wherein the arming dose is optimized for each individual patient by titrating a thawed aliquot of said patient's activated T cells to achieve a percent specific cytotoxicity level at an effector to target ratio of about 25:1 to about 30% against a tumor target.

29. The method of claim 21 or 22, wherein the infusing dose is at least about 2 billion armed T cells.

30. The method of claim 29, wherein said patient receives at least about four infusions.

31. The method of claim 25, wherein said T cell is CD3/CD8 positive cell.

32. The method of claim 25, wherein said T cell is a CD3/CD4 positive cell.

33. The method of claim 25, wherein said armed T cells can be co-administered with other forms of therapy.

34. The method of any one of claim 1, 2, 3, 4, or 20, wherein the tumor is selected from the group consisting of prostate cancer, breast cancer, leukemia, colon cancer, brain cancer, lung cancer, ovarian cancer and neck cancer.

35. The method of any one of claim 1, 2, 3, 4, or 20, wherein said activated T cells produce cytokines that promote an immune response in the patient.

36. The method of claim 35, wherein the cytokines produced by said activated T cells comprise an interferon, granulocyte-macrophage colony stimulating factor, interleukin 2, or another interleukin, TNFα, RANTES, or MIP-α.

37. The method of claim 36, wherein the cytokines produced by said activated T cells recruit naïve T and B cells, NK cells, monocytes, or other immune response cells, to the site whereby said activated T cells are targeted.

38. The method of any one of claim 1, 2, 3, 4, or 20, wherein the armed activated T cells by-pass major histocompatibility restriction via the retargeting of the tumor specific antigen portion of the bispecific antibody to the tumor.

39. The method of any one of claim 1, 2, 3, 4, or 20, wherein said method further comprises said composition of cells stimulating or inducing the development of antigen-specific memory T helper cells from naïve immune cells in said patient after reinfusing said composition of cells into said patient.

40. The method of claim 39, wherein the antigen-specific memory T helper cells are Th1.

41. The method of claim 40, wherein the antigen-specific memory T cells are directed to abnormal or tumor antigens.

42. The method of claim 41, wherein the abnormal or tumor antigens are HER2/neu.

43. The method of any one of claim 1, 2, 3, 4, or 20, wherein said method further comprises said composition of cells stimulating or inducing the development of antigen-specific cytotoxic T cells from naïve immune cells in said patient after reinfusing said composition of cells into said patient.

44. The method of claim 43, wherein the antigen-specific cytotoxic T cells are specific for abnormal or tumor antigens and where the antigen-specific cytotoxic T cells comprise Tc1 or Tc2.

45. The method of claim 44, wherein said abnormal or tumor antigens are HER2/neu.

46. The method of claim 39, wherein said method further comprises said composition of cells inducing or stimulating the development of antigen-specific T cells directed to antigens other than the antigen targeted by the bispecific antibody in said patient after reinfusing said composition of cells into said patient.

47. The method of any one of claim 1, 2, 3, 4, or 20, wherein said method further comprises said composition of cells stimulating or inducing the development of antigen-specific memory B cells from naïve immune cells in said patient after reinfusing said composition of cells into said patient.

48. The method of claim 47, wherein said method further comprises producing antibody specific for abnormal or tumor antigens in said B cells.

49. The method of claim 48, wherein said antigens are HER2/neu.

50. The method of claim 47, wherein said method further comprises said composition of cells inducing or stimulating the development of antigen-specific B cells directed to antigens expressed on the patient's tumor or abnormal cells after reinfusing said composition of cells into said patient.

51. The method of any one of claim 1, 2, 3, 4, or 20, wherein said method further comprises said composition of cells increasing the precursor frequency of antigen specific T cells after reinfusing said composition of cells into said patient.

52. The method of claim 51, wherein said T cells are T helper cells.

53. The method of claim 51, wherein said T cells are cytotoxic T cells.

54. The method of claim 51, wherein said T cells are specific for HER2/neu antigen.

55. The method of claim 51, wherein said T cells are specific for abnormal or tumor antigens other than HER2/neu antigens.

56. The method of any one of claim 1, 2, 3, 4, or 20, wherein the bispecific antibodies are humanized monoclonal antibodies, human phage display library derived human antibodies or genetically engineered antibodies.

57. The method of claim 21, wherein the patient is immunosuppressed.

58. The method of any one of claim 1, 2, 3, 4, or 20, wherein autologous or allogeneic T cells are transduced with vectors coding for chemokines or cytokines.

59. The method of claim 56, wherein said antibodies are capable of inducing an immune response, the method further comprising at least one of the following:
 a said composition of cells stimulating or inducing the development of antigen-specific memory T helper cells from naïve immune cells in said patient after reinfusing said composition of cells into said patient;
 b the antigen-specific memory T helper cells are Th1 or Th2;
 c the antigen-specific memory T cells are directed to abnormal or tumor antigens;
 d the abnormal tumor antigens are HER2/neu;
 e said composition of cells stimulating or inducing the development of antigen-specific cytotoxic T cells from naïve immune cells in said patient after reinfusing said composition of cells into said patient;
 f the antigen specific cytotoxic T cells, Tc1 and Tc2, are specific for abnormal or tumor antigens;
 g said abnormal or tumor antigens are HER2/neu;
 h said composition of cells inducing or stimulating the development of antigen-specific T cells directed to antigens other than the antigen targeted by the bispecific antibody after reinfusing said composition of cells into said patient;
 i said composition of cells stimulating or inducing the development of antigen-specific memory B cells from naïve immune cells after reinfusing said composition of cells into said patient;
 j said B cells produce antibody specific for abnormal or tumor antigens;
 k said antigens are HER2/neu;
 l said composition of cells inducing or stimulating the development of antigen-specific B cells directed to antigens expressed on the patient's tumor or abnormal cells after reinfusing said composition of cells into said patient;
 m said composition of autologous cells increasing the precursor frequency of antigen specific T cells in said patient after reinfusing said composition of cells into said patient;
 n said T cells are T helper cells;
 o said T cells are cytotoxic T cells;
 p said T cells are specific for HER2/neu antigen; or
 q said T cells are specific for abnormal or tumor antigens other than HER2/neu antigens.

60. The method of any one of claim 1, 2, 3, 4, or 20, wherein the antigen-specific armed T cells survive, proliferate and give rise to memory T cells after contact with abnormal or tumor antigens.

61. The method of claim 60, wherein said memory T cells are T helper cells.

62. The method of claim 60, wherein said memory T cells are cytotoxic T cells.

63. The method of any one of claim 1, 2, 3, 4, or 20, wherein the patient is a mammal.

64. The method of any one of claim 1, 2, 3, 4, or 20, wherein the patient is suffering from, or susceptible to disease characterized by abnormal cell growth and proliferation.

65. The method of claim 1, wherein said method further comprises the armed T cells undergoing cell division.

66. The method of claim 1, wherein said method further comprises the armed T cells undergoing multiple cycles of antigen specific tumor cell killing.

67. A method for treatment of a patient suffering from cancer, said method comprising the steps of:
 (a) isolating a sample of peripheral blood mononuclear cells, comprising T cells, from a patient suffering from cancer;
 (b) activating of one or more of said T cells by ex vivo stimulation with soluble anti-CD3 monoclonal antibody, and growth of said activated T cells in the presence of about 100 IU/ml to about 500 IU/ml of IL-2;
 (c) arming of said activated T cells with bispecific antibodies capable of binding to the T cell receptor complex of a T cell, and to tumor-associated antigens on a tumor cell, under conditions wherein;
  (i) said bispecific antibody binds to said T cells, tumor cells, and Fc receptor positive cells, (ii) said antibody binds to the tumor target and said antibody binding to said tumor target activates said T cells, (iii) said antibody redirects said T cells and Fc-receptor positive cells to said tumor cells, (iv) said activated and armed T cells destroy said tumor cells; and, (d) reinfusing, into the patient, a composition of autologous cells comprising said activated T cell armed with a bispecific antibody as treatment of the patient wherein:

(i) contacting T cells specific for different epitopes on the tumor cell with the autologous cells and including proliferation of the T cells specific for different epitopes on the tumor cells, or targeting and contacting multiple target cells with the armed T cell to which the bispecific antibody remains bound, and killing said multiple target cells.

68. The method according to claim 67, wherein a composition of autologous cells comprising said activated T cells armed with a bispecific antibody with or without IL-2, IL-12, GM-CSF or other immune augmenting cytokines are reinfused into a patient in need of such therapy.

69. The method according to claim 68, wherein the bispecific antibody is comprised of two monoclonal antibodies.

70. The method according to claim 69, wherein each of the specificities of said bispecific antibody are directed to a tumor antigen and the T cell receptor complex.

71. The method of any one of claim 1, 20 or 67, wherein the method further comprises targeting and contacting multiple target cells, which the armed T cell, to which the bispecific antibody remains bound, recognizes by recognizing the desired antigens on the target cells, and killing said multiple target cells.

72. A method of treatment, comprising:

(a) providing a formulation comprising:

(i) a pharmaceutically acceptable excipient; and (ii) T-cells having bound thereto a bispecific antibody with a binding specificity for a T-cell antigen, selected from the group consisting of CD28 and CD3, and a binding specificity for a HER2 antigen present on a surface of a cancer cell, wherein the bispecific antibody has a binding specificity of about $10^{-8}$ moles/liter or higher;

(b) infusing said formulation into a human patient suffering from cancer;

(c) binding the bispecific antibodies to cancer cells in the patient;

(d) contacting the cancer cells in the patient with the T cells and lysing the cancer cells in the patient;

(e) creating a T cell memory in the patient's endogenous T cells; and (f) contacting cancer cells in the patient with the patient's endogenous T cells and lysing said cancer cells.

73. The method of claim 72, further comprising:

infusing a cytokine into the patient wherein the cytokine is chosen from IL-2, IL-12, and GM-CSF.

74. The method of claim 39, wherein the antigen-specific memory T helper cells are Th2.

75. The method of claim 43, wherein the method further comprises inducing or stimulating the development of antigen-specific T cells directed to antigens other than the antigen targeted by the bispecific antibody, after reinfusing said composition or autologous cells into said patient.

76. The method of claim 72, wherein said method further comprises:

(i) contacting T cells specific for different epitopes on the cancer cells, with the formulation and inducing proliferation of the T cells specific for different epitopes on the tumor cell, or (ii) targeting and contacting multiple cancer cells with the T cell to which the bispecific antibody remains bound, and killing said multiple cancer cells.

77. The method of claim 72, wherein said method further comprises contacting natural killer cells with the formulation and inducing proliferation of the natural killer cells.

78. The method of claim 72, wherein said T cells secrete immune activating cytokines and chemokines.

79. The method of claim 72, wherein said T cells secrete MIP-1α or RANTES.

80. The method of any one of claim 1, 20, 67, or 72, wherein the bispecific antibody is directed against CD3 or HER2.

81. The method of any one of claim 1, 20, 67, or 72, wherein the anti-CD3 antibody comprises OKT3.

* * * * *